(12) United States Patent
Fuchs et al.

(10) Patent No.: US 11,046,942 B2
(45) Date of Patent: *Jun. 29, 2021

(54) DNASE THERAPY FOR INTRAVASCULAR ACCUMULATION OF EXTRACELLULAR DNA

(71) Applicant: Neutrolis, Inc., Cambridge, MA (US)

(72) Inventors: Tobias A. Fuchs, Wellesley, MA (US); Miguel Jiménez-Alcázar, Madrid (ES); Josephine Göbel, Reinbek (DE); Hanna Englert, Hamburg (DE)

(73) Assignee: NEUTROLIS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/018,642

(22) Filed: Sep. 11, 2020

(65) Prior Publication Data

US 2020/0399622 A1    Dec. 24, 2020

Related U.S. Application Data

(63) Continuation of application No. 16/929,980, filed on Jul. 15, 2020, now Pat. No. 10,801,019, which is a continuation of application No. 16/856,943, filed on Apr. 23, 2020, now abandoned, which is a continuation of application No. 16/530,141, filed on Aug. 2, 2019, now Pat. No. 10,696,956, which is a continuation of application No. PCT/US2018/047084, filed on Aug. 20, 2018.

(60) Provisional application No. 62/611,166, filed on Dec. 28, 2017, provisional application No. 62/547,220, filed on Aug. 18, 2017.

(51) Int. Cl.
| | |
|---|---|
| *A61K 48/00* | (2006.01) |
| *C12N 15/86* | (2006.01) |
| *C12N 9/22* | (2006.01) |
| *C07K 14/435* | (2006.01) |

(52) U.S. Cl.
CPC ............. *C12N 9/22* (2013.01); *A61K 48/00* (2013.01); *A61K 48/0075* (2013.01); *C07K 14/435* (2013.01); *C07K 2319/02* (2013.01); *C07K 2319/31* (2013.01); *C07K 2319/80* (2013.01); *C07K 2319/91* (2013.01); *C12Y 301/21001* (2013.01)

(58) Field of Classification Search
CPC .. A61K 48/00; A61K 48/0075; A61K 38/465; C12N 15/86

See application file for complete search history.

(56) References Cited

U.S. PATENT DOCUMENTS

| | | | |
|---|---|---|---|
| 6,270,989 B1 * | 8/2001 | Treco | C12N 9/16 435/69.1 |
| 6,482,626 B2 | 11/2002 | Baker et al. | |
| 6,656,685 B2 | 12/2003 | Utermohlen et al. | |
| 7,612,032 B2 | 11/2009 | Genkin et al. | |
| 8,388,951 B2 | 3/2013 | Genkin et al. | |
| 8,431,123 B2 | 4/2013 | Genkin et al. | |
| 8,535,663 B2 | 9/2013 | Genkin et al. | |
| 8,796,004 B2 | 8/2014 | Genkin et al. | |
| 8,916,151 B2 | 12/2014 | Genkin et al. | |
| 9,072,733 B2 | 7/2015 | Genkin et al. | |
| 9,149,513 B2 | 10/2015 | Bartoov et al. | |
| 9,198,957 B2 | 12/2015 | Ratner et al. | |
| 9,205,133 B2 | 12/2015 | Dawson et al. | |
| 9,248,166 B2 | 2/2016 | Gerkin et al. | |
| 9,402,884 B2 | 8/2016 | Burns | |
| 9,642,822 B2 | 5/2017 | Wagner | |
| 9,770,492 B2 | 9/2017 | Genkin et al. | |
| 9,845,461 B2 | 12/2017 | Genkin et al. | |
| 9,867,871 B2 | 1/2018 | Jain | |
| 10,617,743 B2 | 4/2020 | Genkin et al. | |
| 10,696,956 B2 | 6/2020 | Fuchs et al. | |
| 2004/0138156 A1 | 7/2004 | Schneider et al. | |
| 2009/0010966 A1 | 1/2009 | Davis et al. | |
| 2013/0149749 A1 | 6/2013 | Holliger et al. | |
| 2013/0236945 A1 | 9/2013 | Song et al. | |
| 2014/0199329 A1 | 7/2014 | Wagner et al. | |
| 2016/0251638 A1 | 9/2016 | Posada et al. | |
| 2016/0376366 A1 | 12/2016 | Chang et al. | |

(Continued)

FOREIGN PATENT DOCUMENTS

| | | |
|---|---|---|
| WO | 2011053982 | 5/2011 |
| WO | 2011131772 | 10/2011 |
| WO | 2015066550 | 5/2015 |

(Continued)

OTHER PUBLICATIONS

Bassi et al. 2012; Regenerative therapies for diabetic microangiopathy. Experimental Diabetes Research. Article ID 916560, pp. 1-11.*
Hattori et al. 2018; Nucleic-acid based gene therapy approaches for sepsis. European Journal of Pharmacology. 833: 403-410.*
Al-Mayouf et al., Loss-of-function variant in DNASE1L3 causes a familial form of systemic lupus erythematosus, Nature Genetics, 2011, vol. 43, No. 12, pp. 1186-1188.

(Continued)

*Primary Examiner* — Karen Cochrane Carlson
(74) *Attorney, Agent, or Firm* — Morgan, Lewis & Bockius LLP

(57) ABSTRACT

The present invention provides engineered DNase proteins (including DNase1-like 3 and DNase1) that are useful for treating conditions characterized by neutrophil extracellular trap (NET) accumulation and/or release. In some aspects, the invention provides compositions and methods for preventing or treating vascular occlusion involving NETs. As demonstrated herein, NETs participate in a non-canonical mechanism for vascular occlusion, which is not dependent on fibrin or platelets.

22 Claims, 43 Drawing Sheets

Specification includes a Sequence Listing.

(56) References Cited

U.S. PATENT DOCUMENTS

| | | |
|---|---|---|
| 2017/0196945 A1 | 7/2017 | Wagner et al. |
| 2020/0024585 A1 | 1/2020 | Fuchs et al. |

FOREIGN PATENT DOCUMENTS

| | | |
|---|---|---|
| WO | 2016139659 | 9/2016 |
| WO | 2018015474 | 1/2018 |
| WO | 2018064681 | 5/2018 |
| WO | 2018134403 | 7/2018 |
| WO | 2018134419 | 7/2018 |

OTHER PUBLICATIONS

Andersen et al. 2014; Extending serum half-life of albumin by engineering neonatal Fc receptor (FcRn) binding. Journal of Biological Chemistry. 289(19): 13492-13502.
Barnes et al. "Targeting potential drivers of COVID-19: Neutrophil extracellular traps", J. Exp. Med., 2020, vol. 217, pp. 1-7.
Baron et al., Cloning and characterization of an actin-resistant DNase I-like endonuclease secreted by macrophages, 3ene, 1998, vol. 215 pp. 291-301.
Berntsson et al., "Structural insight into DNA binding and oligomerization of the multifunctional Cox protein of bacteriophage P2", Nucleic Acids Research, vol. 42, No. 4, 2014, pp. 2725-2735.
Bruschi et al., Neutrophil extracellular traps (NET) induced by different stimuli: A comparative proteomic analysis, PLOS ONE, 2019, pp. 1-18.
Carbonella et al., An autosomal recessive DNASE1L3-related autoimmune disease with unusual clinical presentation mimicking systemic lupus erythematosus, Lupus, 2017, vol. 26, pp. 768-772.
Hakkim et al., "Impairment of neutrophil extracellular trap degradation is associated with lupus nephritis", PNAS, vol. 107, No. 21, 2010, pp. 9813-9818.
International Search Report and Written Opinion for International Application No. PCT/US2018/047084, dated Feb. 15, 2019, 23 pages.
Jimenez-Alcazar et al., "Host DNases prevent vascular occlusion by neutrophil extracellular traps," Science 358, pp. 1202-1206 (2017).
Keyel, "Dnases in health and disease", Developmental Biology, vol. 429, 2017, pp. 1-11.
Kobayashi et al., "Synchronous Growth of Pichia Pastoris for a High-Rate Production of DNaseI at Microquantities", Department of Chemical Engineering. Toyko Institute of Technology. On-Line No. 833, 2004 pp. 1-6.
Landhuis, "Spider-Man Immune Response May Promote Severe COVID-19", Sci. Am., 2020, pp. 1-7.
Napirei et al. 2009; Murine serum nucleases-contrasting effects of plasmin and heparin on the activities of DNase1 and DNase1-lie 3 (DNase1l3). FEBS Journal. 276: 1059-1073.
Onuora, "DNASE1L3 prevents anti-DNA responses", Nature Rev. Rheumatol., 2016, vol. 12 No. 437, 1 page.
Ozgakar et al., DNASEIL3 Mutations in Hypocomplementemic Urticarial Vasculitis Syndrome, Arthritis & Rheumatism, 2013, vol. 65, No. 8, pp. 2183-2189.
Perini et al., "Topical application of Acheflan on rat skin injury accelerates wound healing: a histopathological, Immunohistochemical and biochemical study", BMC Complementary and Alternative Medicine, 2015, vol. 15, No. 203, pp. 1-8.
Piccolo et al., "Intrapleural Tissue Plasminogen Activator and Deoxyribonuclease for Pleural Infection; An Effective and Safe Alternative to Surgery", AnnalsATS, vol. 11, No. 9, 2014, pp. 1419-1425.
Reizis, "Project 3: The role of DNASEIL3 and its DNA substrate in lupus", National Institute of Health (NIH), 2015, 5 pages.
Saito et al., Apoptotic DNA endonuclease (DNase-$\gamma$) gene transfer induces cell death accompanying DNA fragmentation in human glioma cells, Journal of Neuro-Oncology, 2003, vol. 63, pp. 25-31.
Shiokawa et al. 1998; Molecular cloning and expression of a cDNA encoding an apoptotic endonuclease DNase gamma. Biochem. J. 332: 713-720.
Shiokawa et al. 2003; Identification of two functional nuclear localization signals in DNase gamma and their roles in its apoptotic DNase activity. Biochem. J. 376: 377-381.
Sisirak et al., "Digestion of Chromatin in Apoptotic Cell Microparticles Prevents Autoimmunity", Cell vol. 166, 2016, pp. 88-101.
Wang et al., "Targeting the extracellular scavenger DNASEIL3 on SLE", J Xiangya Med, 2017, 3 pages.
Wilber et al., "Deoxyribonuclease I-like III Is an Inducible Macrophage Barrier to Liposomal Transfection", MolecularTherapy, vol. 6, No. 1, 2002, pp. 35-42.
Brill, et al., "Neutrophil extracellular traps promote deep vein thrombosis in mice", J Thromb Haemost. Jan. 2012 ; 10(1): 136-144.
Brinkmann, et all., "Neutrophil extracellular traps: Is immunity the second function of chromatin?", J. Cell Biol. vol. 198 No. 5 773-783.
CORDIS_project_628264_en, Degradation of Neutrophil Extracellular Traps and its impact on thrombolysis, https://cordis.europa.eu/project/id/628264, 2016, 3 pages.
Fuchs, et al., "Extracellular DNA traps promote thrombosis," PNAS, 2010, vol. 107, No. 36, pp. 15880-15885.
Fuchs, et al., "NET impact on deep vein thrombosis," Arterioscler Thromb Vasc Biol. Aug. 2012 ; 32(8): 1777-1783.
Koyama, et al., "DNase $\gamma$, DNase I, and caspase-activated DNase cooperate to degrade dead cells," Genes to Cells 21, 1150-1163 (2016).
Varjú, et al., Fibrinolysis at the Interface of Thrombosis and Inflammation—The Role of Neutrophil Extracellular Traps, Hungarian Scientific Research Fund, Department of Medical Biochemistry, Semmelweis University, Budapest, Hungary, 2014, p. 1-59.
Boettcher et al. "Therapeutic targeting of extracellular DNA improves the outcome of intestinal ischemic reperfusion injury in neonatal rats," Scientific Reports, Nov. 13, 2017.
Branden et al., "Prediction, Engineering, and •Design of Protein Structures", Introduction to Protein Structure, Garland Publishing Inc., New York, p. 247, 1991.
Chica et al., Semi-rational approaches to engineering enzyme activity: combining the benefits of directed evolution and rational design. Curr. Opi. Biotechnol., 2005, vol. 16: 378-384.
De Meyer et al. "Extracellular Chromatin Is an Important Mediator of Ischemic Stroke in Mice," Arteriosclerosis, Thrombosis, and Vascular Biology, May 24, 2012 (May 24, 2012), vol. 32, No. 8, pp. 1884-1891. entire document.
Parsiegla et al., The Structure of Human DNase I Bound to Magnesium and Phosphate Ions Points to a Catalytic Mechanism Common to Members of the DNase I-like Superfamily, Biochemistry, 2012, vol. 51, pp. 10250-10258.
Rodriguez et al., Gen Bank accession No. 013609 Sep. 27, 2017.
Sadowski et al., "The sequence-structure relationship and protein function prediction", Current Opinion in Structural Biology 19:357-362, 2009.
Seffernick, et al., "Melamine deaminase and Atrazine Chlorohydrolase: 98 Percent Identical but Functionally Different", Journal of Bacteriology, 2001, pp. 2405-2410.
Shiokawa et al., "Characterization of Human DNase I Family Endonucleases and Activation of DNase $\gamma$ during Apoptosis", Biochemistry 2001, 40, pp. 143-152.
Tang et al., "Identification of Dehalobacter Reductive Dehalogenases that Catalyse Dechlorination of Chloroform, 1,1,1-trichloroethane and 1,1-dichloroethane", Phil Trans R Soc B, 368, Mar. 18, 2012, 1-10, 2013.
"Whisstock et al. Quaterly Reviews of Biophysics, 2003, ""Prediction of protein function from protein sequence and structure""", 36(3): 307-340."
Witkowski et al., "Conversion of a β-Ketoacyl Synthase to a Malonyl Decarboxylase by Replacement of the Active-Site Cysteine with Glutamine", Biochemistry 1999, 38, pp. 11643-11650.

* cited by examiner

Fig. 1A
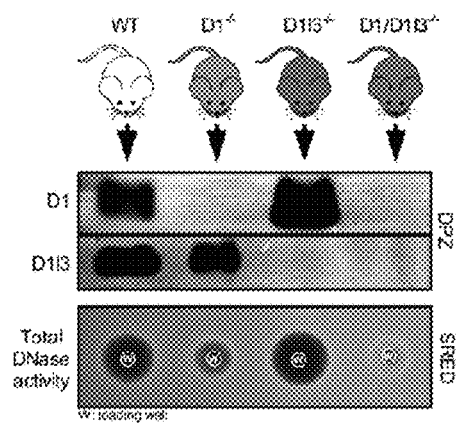
Fig. 1B
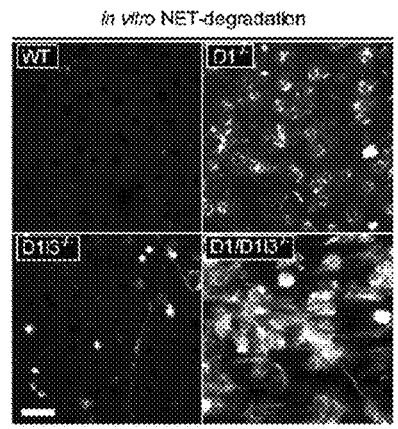
Fig. 1C
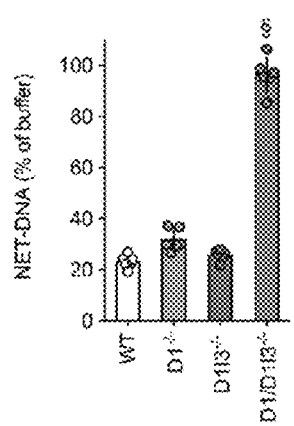
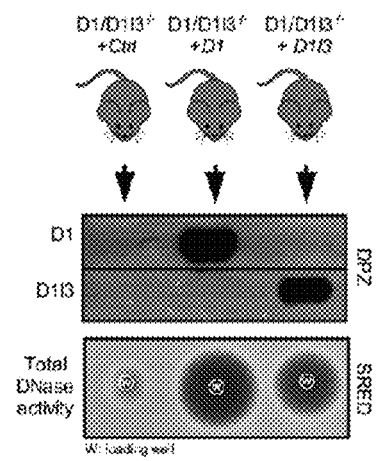
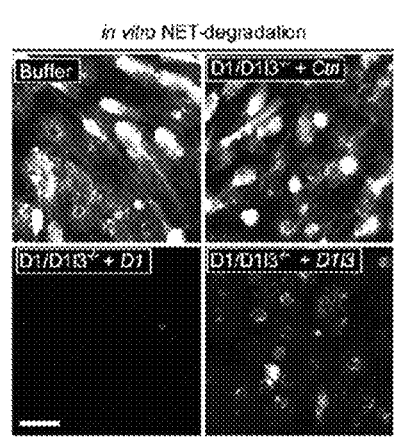
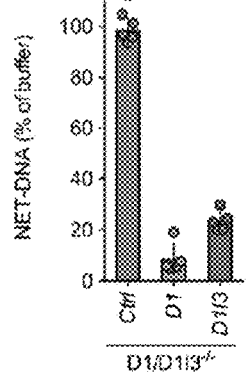
Fig. 1D
Fig. 1E
Fig. 1F

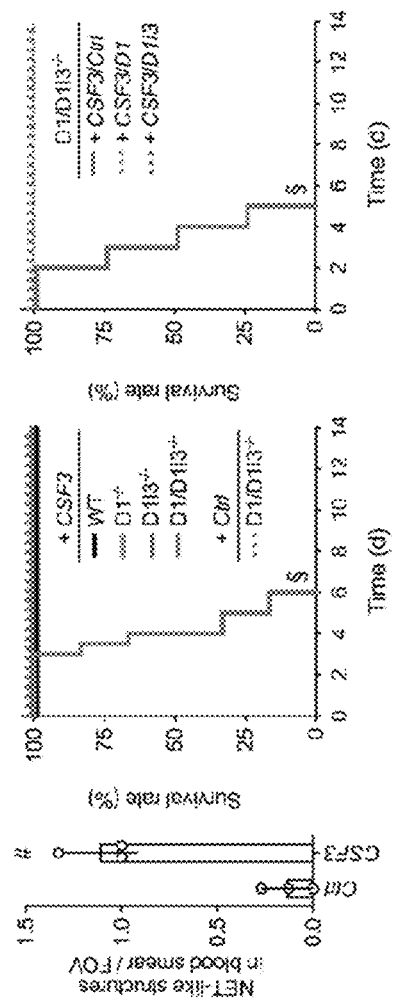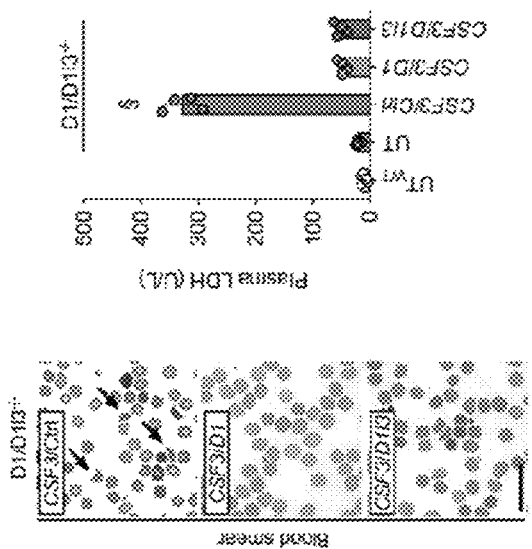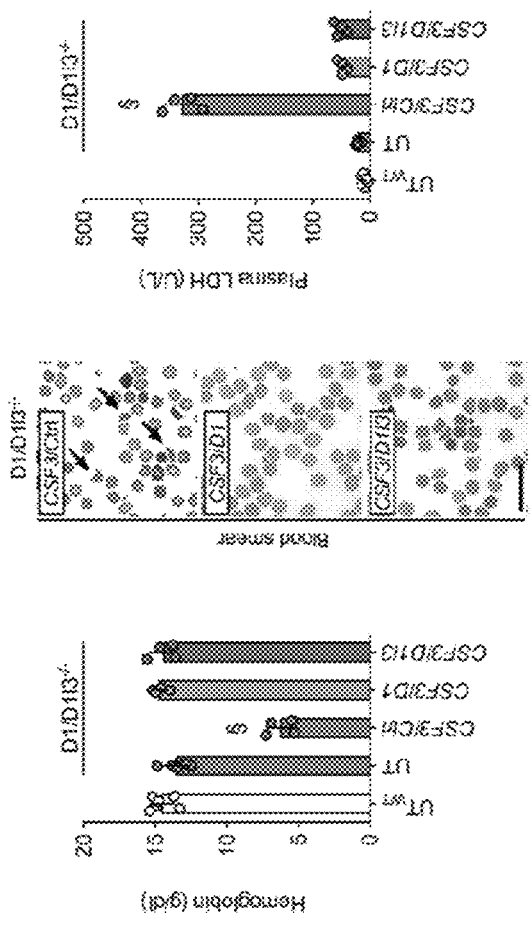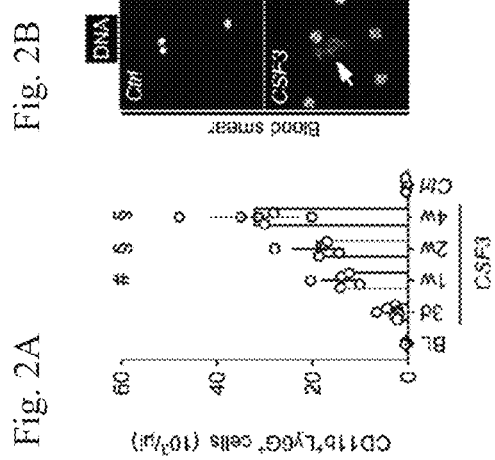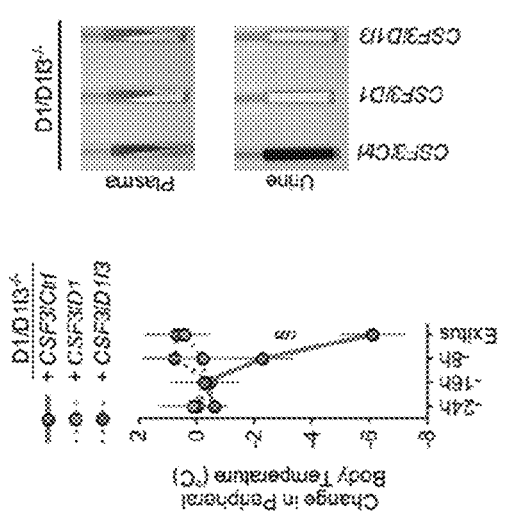

Fig. 3A
Fig. 3B
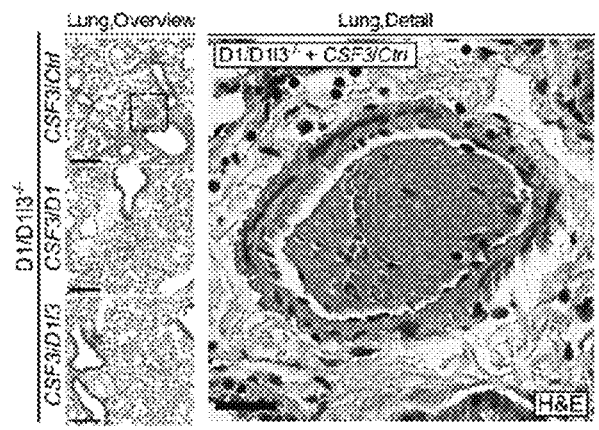
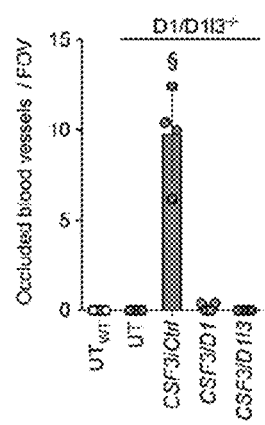
Fig. 3C
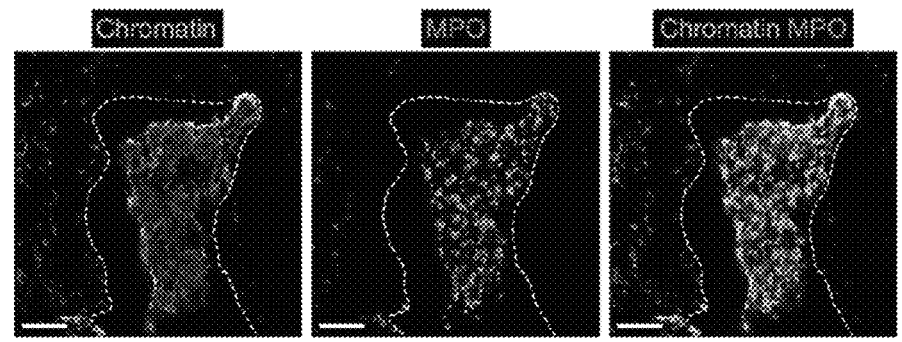
Fig. 3D
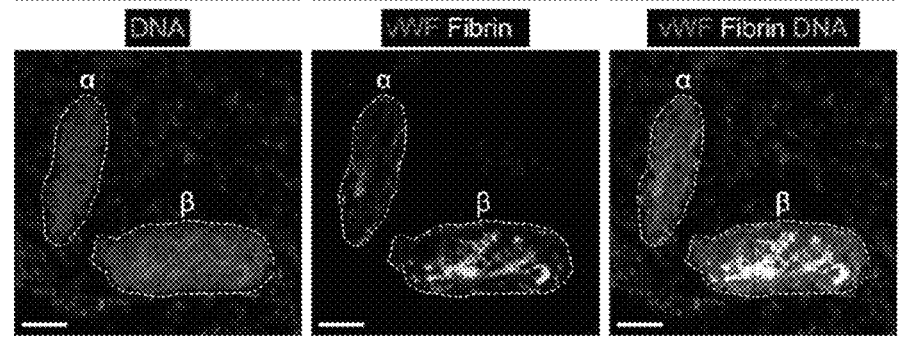
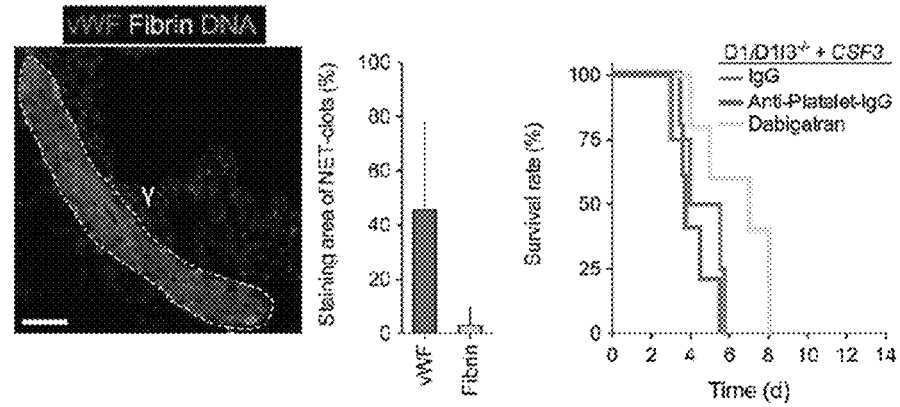
Fig. 3E
Fig. 3F
Fig. 3G

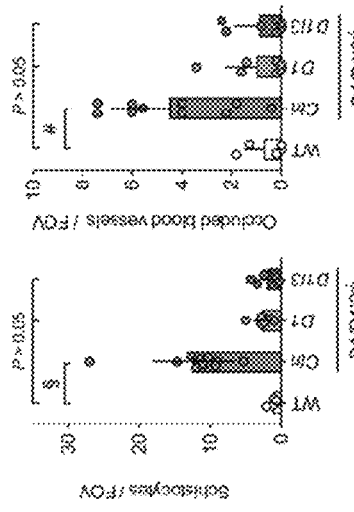
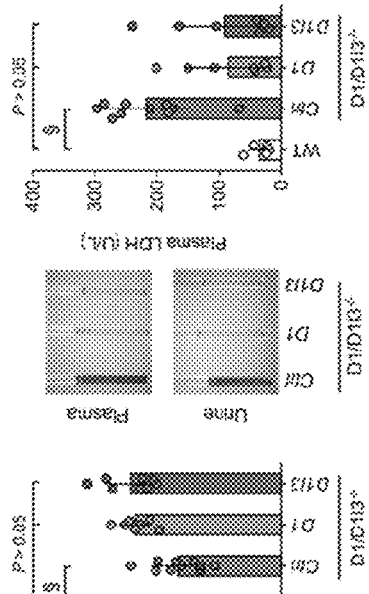
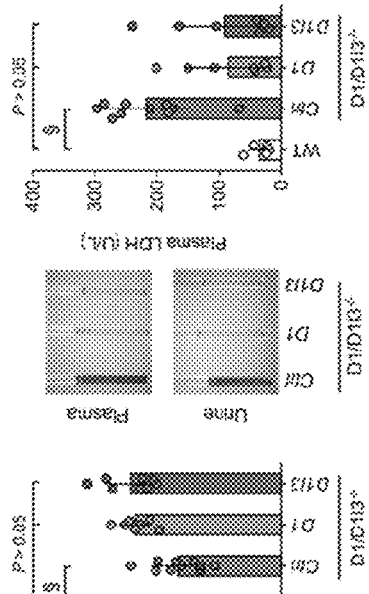
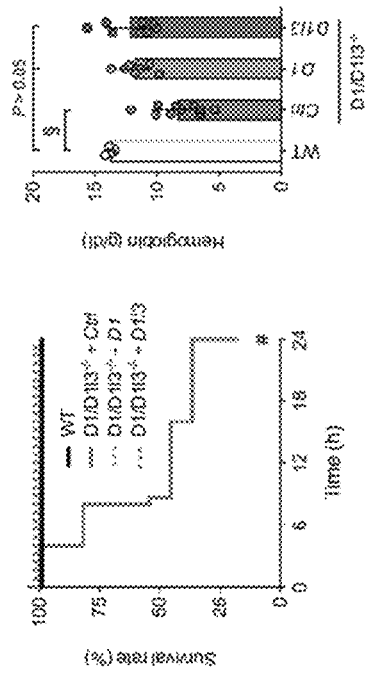
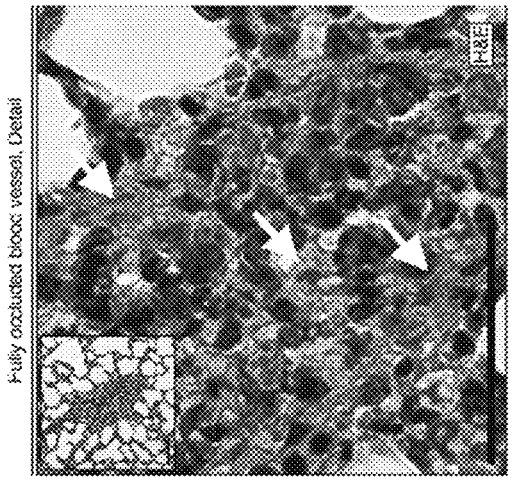
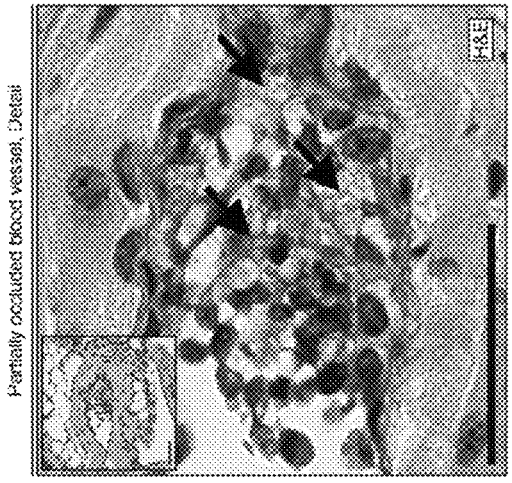
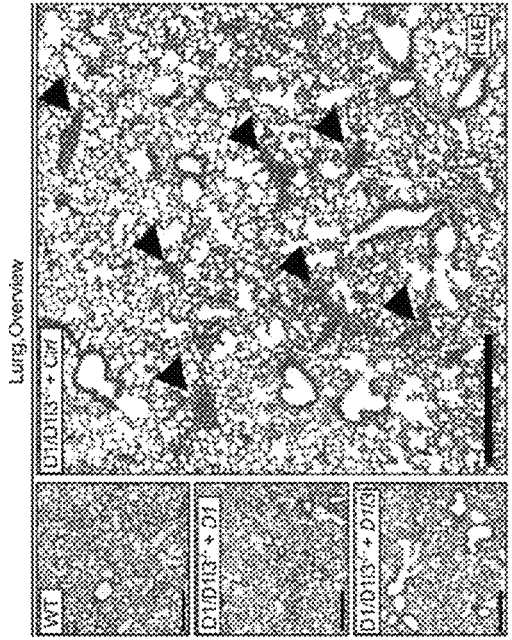

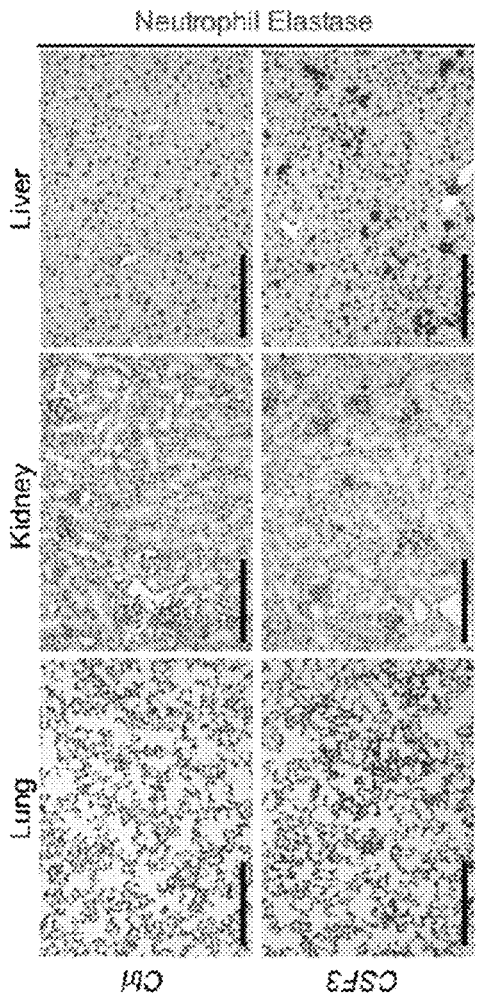
Fig. 5A
Fig. 5B
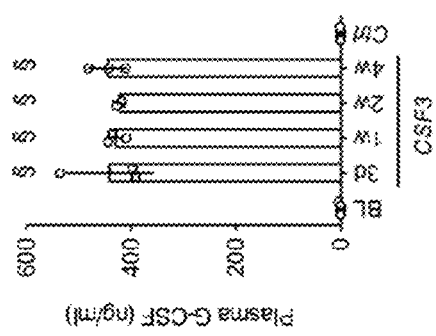
Fig. 5C
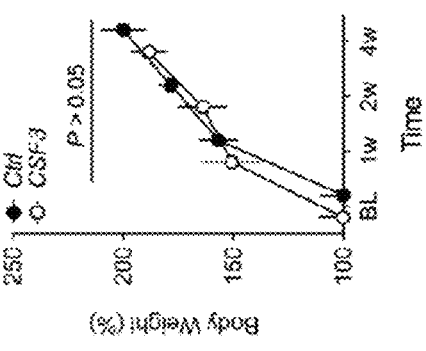
Fig. 5D
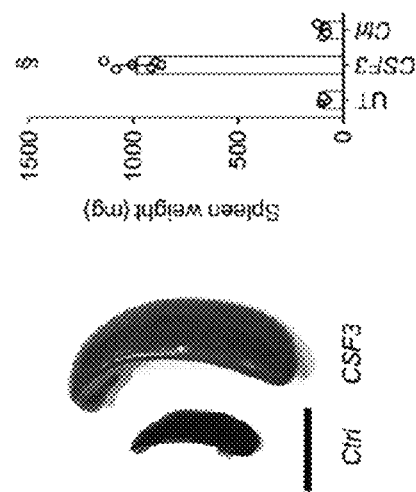
Fig. 5E

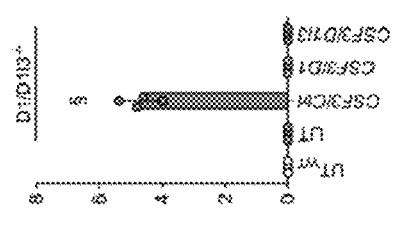
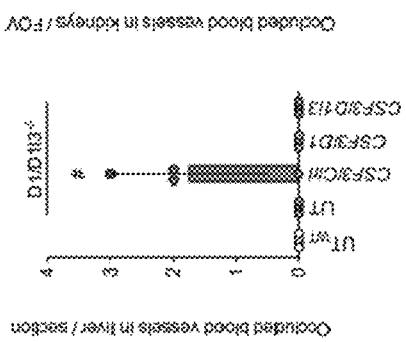
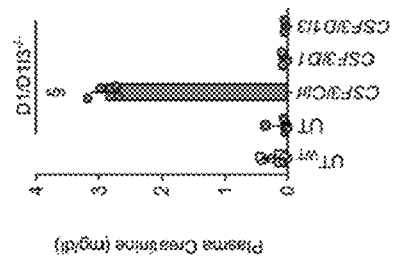
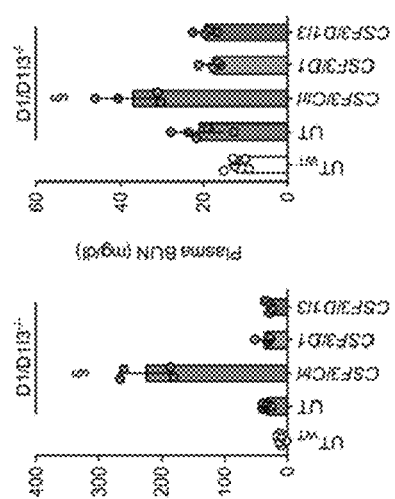
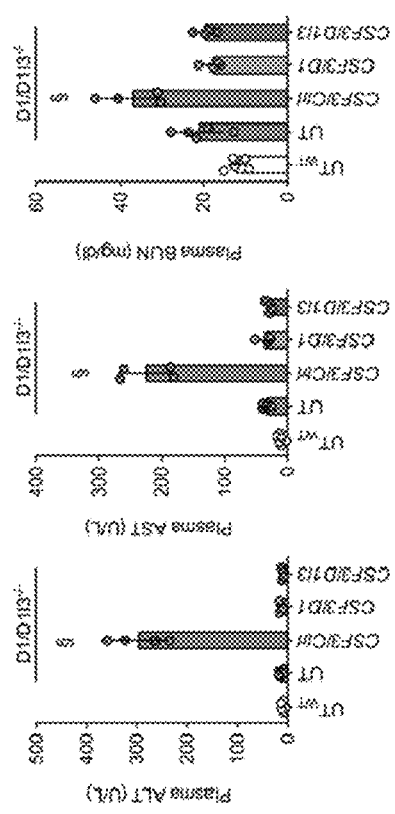
Fig. 6A  Fig. 6B  Fig. 6C
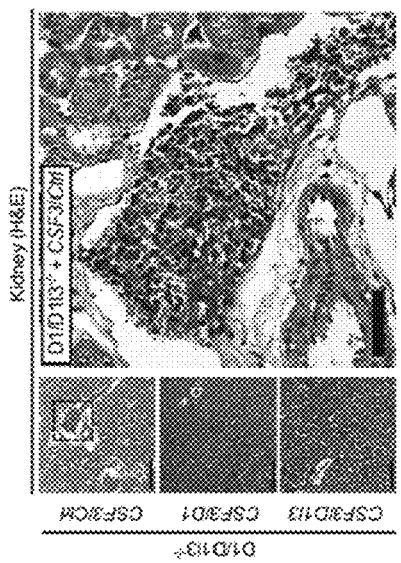
Fig. 6D

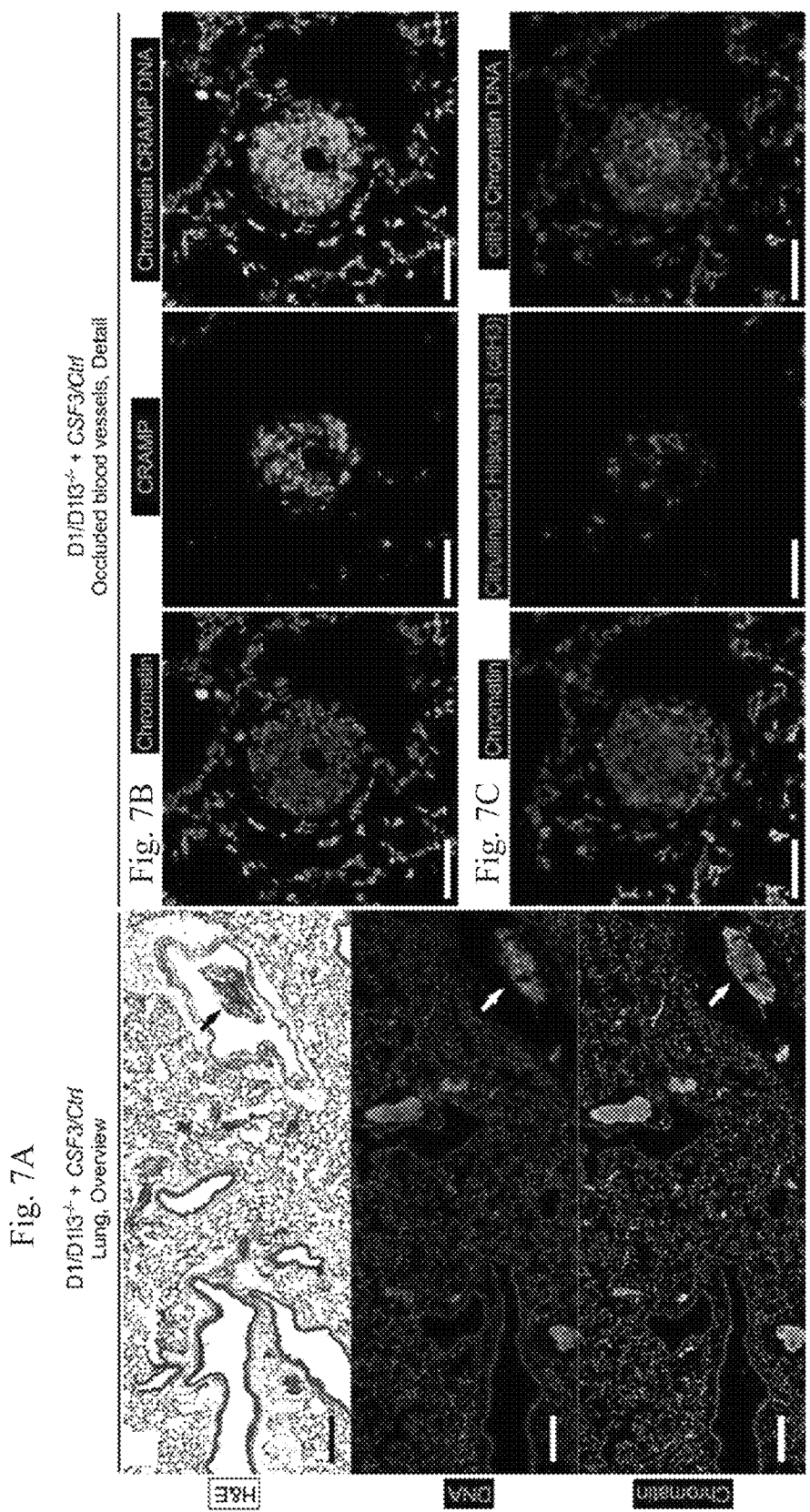

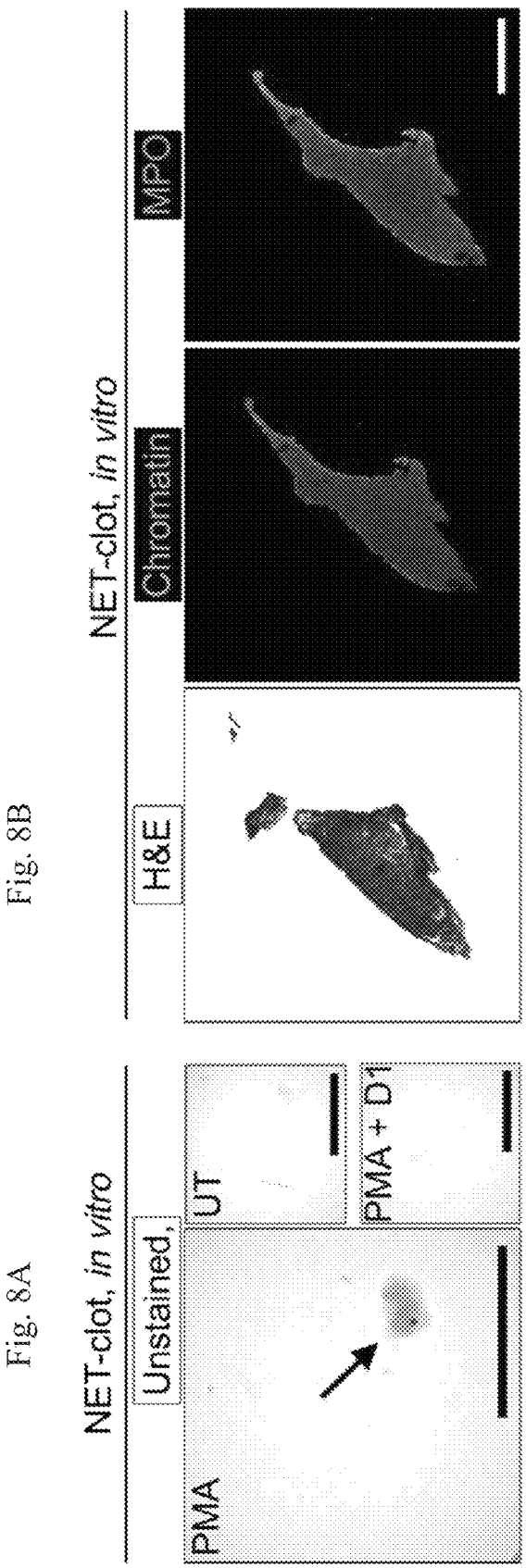

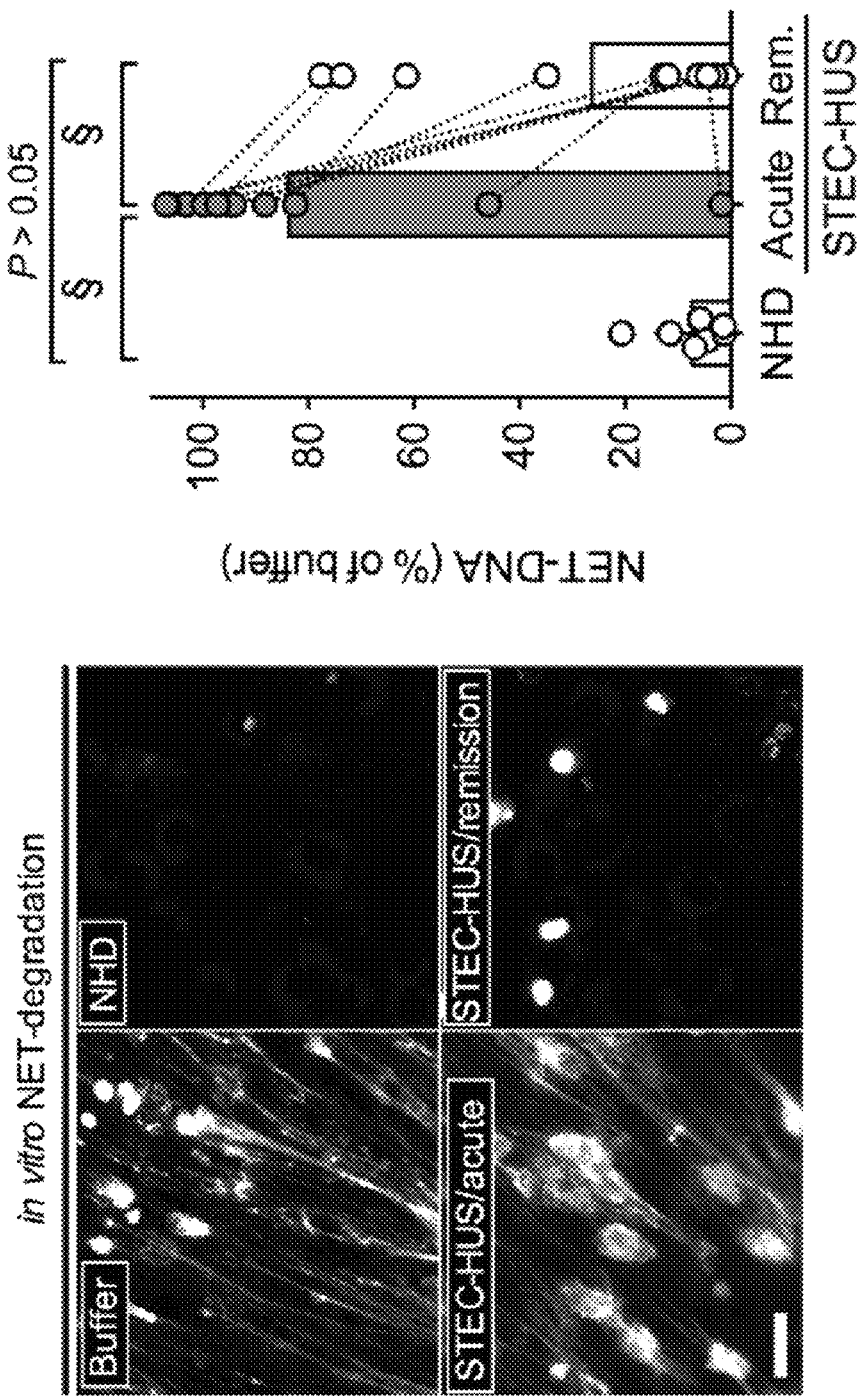

FIG. 10

| # | Cause of death | Sex | Age | Tissue | Hematoxylin-rich clots | Chromatin & MPO-positive | Localization |
|---|---|---|---|---|---|---|---|
| 1 | ARDS | M | 84 | Lung | Yes | Yes | Bronchus |
| 2 | Septic cardiovascular failure + ARDS | F | 63 | Lung | No | Not applicable | Not applicable |
| 3 | ARDS | F | 67 | Lung | No | Not applicable | Not applicable |
| 4 | Septic multi-organ failure + ARDS | M | 72 | Lung | Yes | Yes | Bronchus |
| 5 | Septic cardiovascular failure + ARDS | F | 75 | Lung | No | Not applicable | Not applicable |
| 6 | Septic multi-organ failure | M | 80 | Lung | Yes | Yes | Blood vessel |
| 7 | Septic cardiovascular failure | F | 76 | Lung | Yes | Yes | Blood vessel |
| 8 | ARDS | F | 68 | Lung | No | Not applicable | Not applicable |

Fig. 11A
Fig. 11B
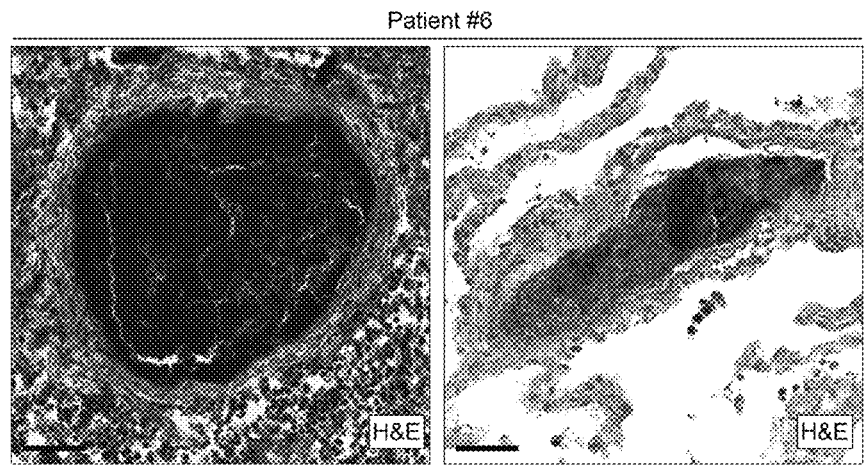
Fig. 11C
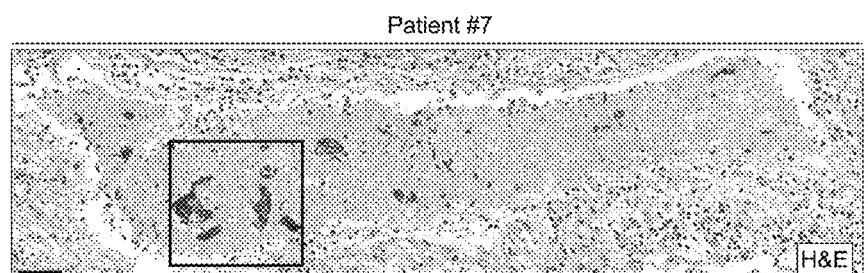
Fig. 11D
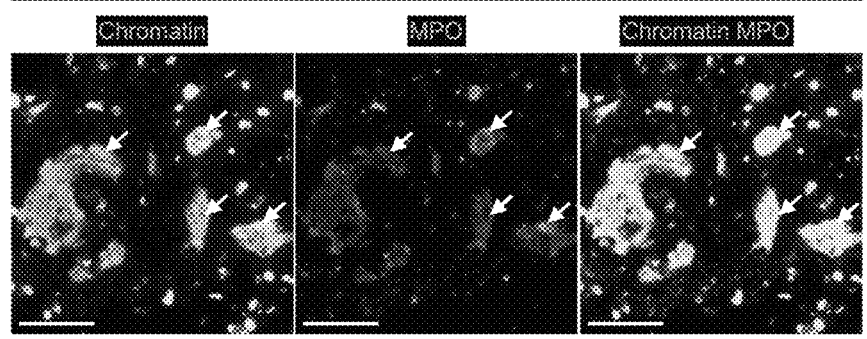

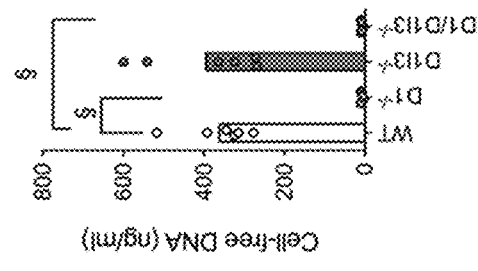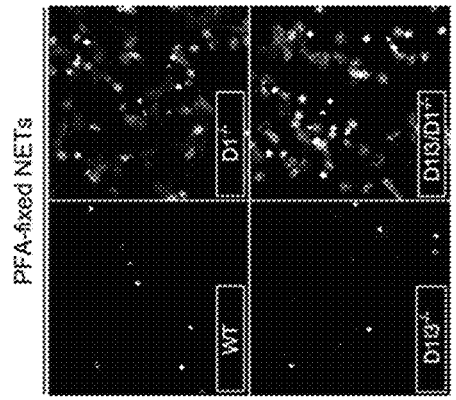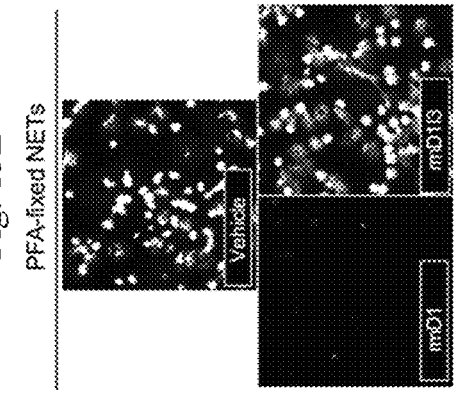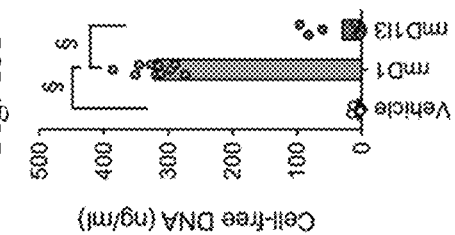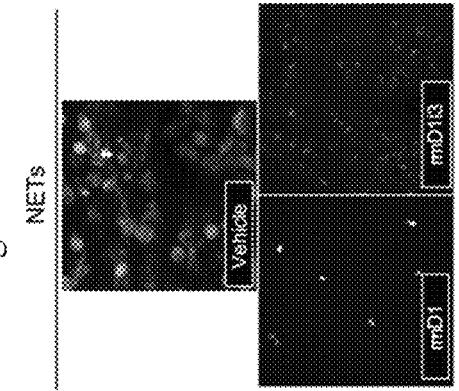

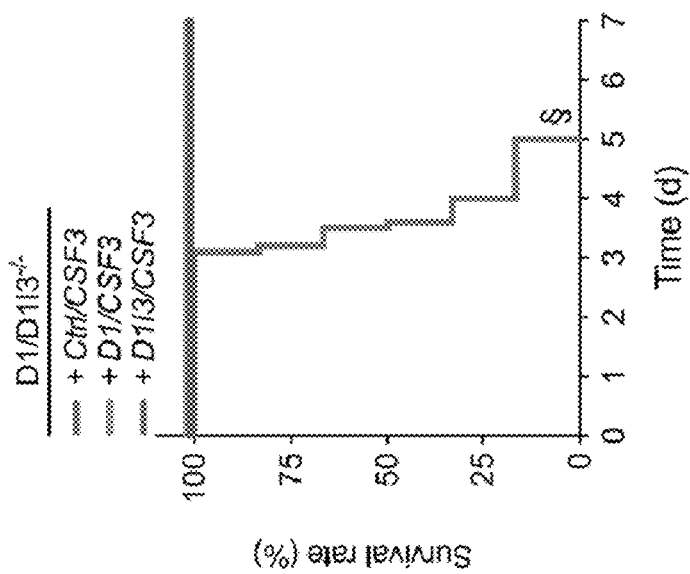
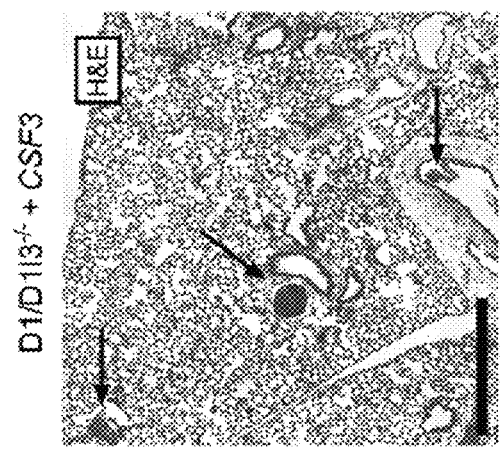
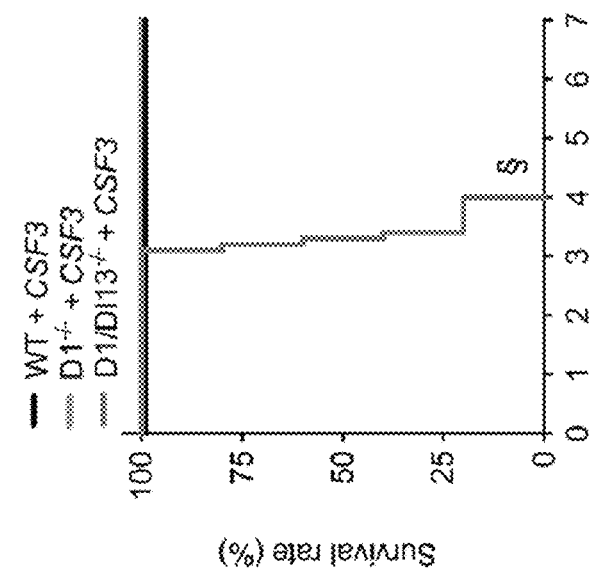

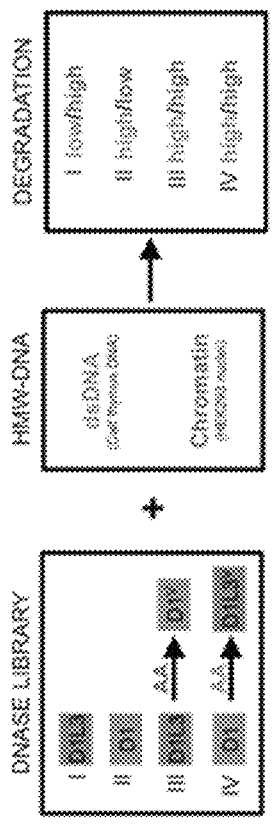
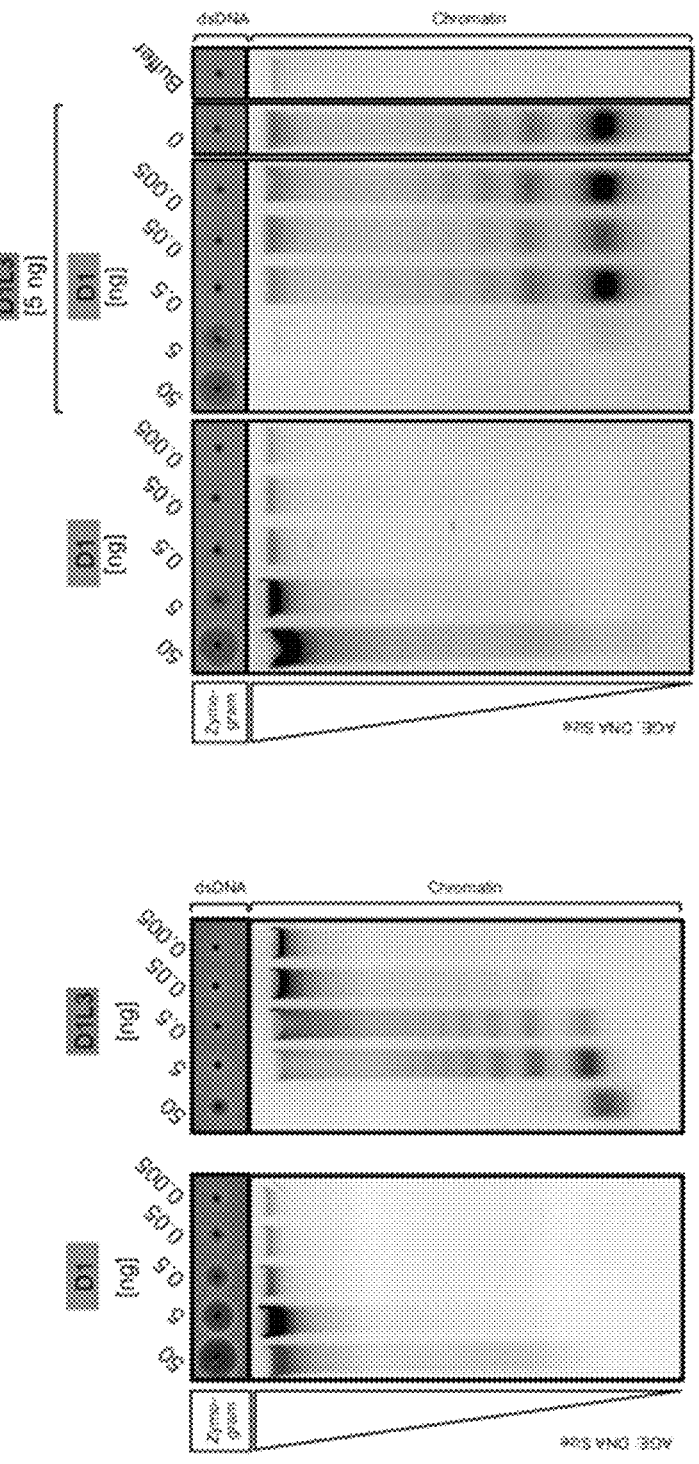
Fig. 16A
Fig. 16B

*FIG. 18*

| # | DNase1L3 | DNase1 | Mutation in DNase1 | Analyzed in this application |
|---|---|---|---|---|
| 1 | R29 (R9) | Q31 (Q9) | Q31R (Q9R) | + |
| 2 | K39 (R19) | A41 (A19) | A41K (A19K) | - |
| 3 | K47 (K27) | Q49 (Q27) | Q49K (Q27K) | + |
| 4 | K50 (K30) | S52 (S30) | S52K (S30K) | - |
| 5 | R66 (R46) | T68 (T46) | T68R (T46R) | - |
| 6 | K74 (K54) | N76 (N54) | N76K (N54K) | + |
| 7 | R77 (R57) | Q79 (Q57) | Q79R (Q57R) | + |
| 8 | R80 (R60) | - | D80_A81insR (D60_A61insR) | + |
| 9 | R81 (R61) | A81 (A59) | A81R (A61R) | + |
| 10 | R92 (R72) | P92 (P70) | P92R (P70R) | + |
| 11 | K109 (K89) | D109 (D87) | D109K (D87K) | + |
| 12 | K114 (K94) | V114 (V92) | V114K (V92) | + |
| 13 | R115 (K95) | D115 (D93) | D115R (D92R) | + |
| 14 | K163 (K143) | A164 (A142) | A164K (A142K) | + |
| 15 | K176 (K156) | Q177 (Q155) | Q177K (Q115K) | + |
| 16 | K180 (K160) | G181 (G159) | G181K (G159K) | + |
| 17 | K199 (K179) | P200 (P178) | P200K (P178K) | - |
| 18 | K200 (K180) | S201 (S179) | S201K (S179K) | + |
| 19 | K203 (K183) | S204 (S182) | S204K (S182K) | + |
| 20 | R208 (R188) | W209 (W187) | W209R (W187R) | + |
| 21 | R212 (R192) | T213 (T191) | T213R (T191R) | + |
| 22 | K226 (K206) | - | A226_T227insK (A204_T205insK) | + |
| 23 | K227 (K207) | T227 (T205) | T227K (T205K) | + |
| 24 | R239 (R219) | A239 (A217) | A239R (A217R) | + |
| 25 | K250 (K230) | D250 (D228) | D250K (D228K) | + |
| 26 | K259 (K239) | A259 (A237) | A259K (A237K) | - |
| 27 | K262 (K262) | G262 (G240) | G262K (G240K) | - |
| 28 | K280 (K260) | M280 (M258) | M280K (M258K) | + |
| 29 | R285 (K265) | - | - | - |
| 30 | K291 (K271) | - | - | - |
| 31 | K292 (K272) | - | - | - |
| 32 | R297 (K277) | - | - | - |
| 33 | K298 (K278) | - | - | - |
| 34 | K299 (K279) | - | - | - |
| 35 | K301 (K281) | - | - | - |
| 36 | K303 (K283) | - | - | - |
| 37 | R304 (K284) | - | - | - |

*FIG. 29*
BUILDING BLOCK-ENGINEERING OF HOMOLOGOUS PROTEINS
I. AMINO ACID SEQUENCE ALIGNMENT OF HOMOLOGOUS ENZYMES
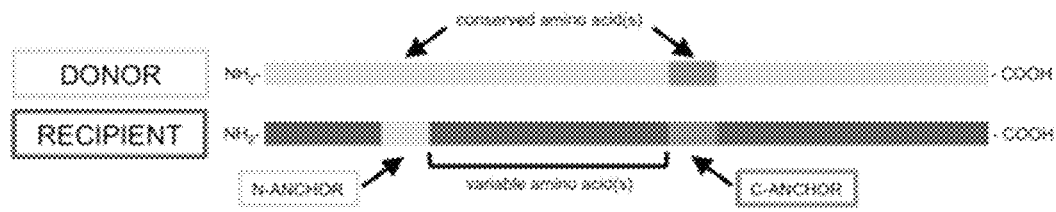
II. EXCISION OF CDNA CODING FOR VARIABLE AMINO ACIDS IN DONOR ENZYME
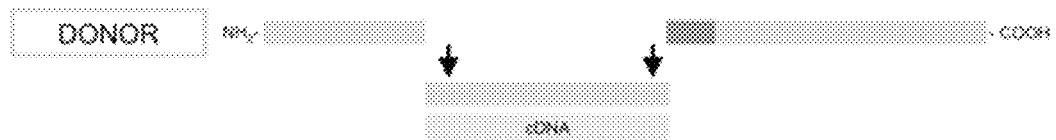
III. DELETION OF CDNA CODING FOR VARIABLE AMINO ACIDS IN RECIPIENT ENZYME
IV. TRANSFER OF CDNA FROM DONOR TO RECIPIENT ENZYME
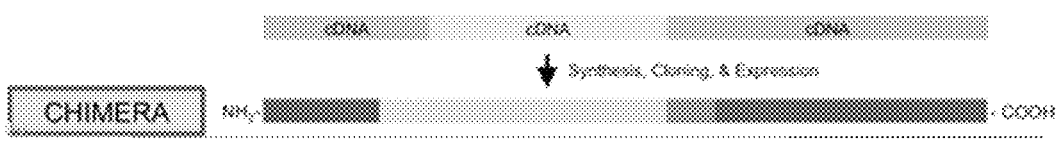

Example of Building Block Engineering: human DNase1 (D1) variants with Building Blocks from human DNase1L3 (D1L3)

Example of Building Block Engineering: human DNase1L3 (D1L3) variants with Building Blocks from human DNase1 (D1)

| BB # | D1L3 N-Anchor Conserved AA in D1 | D1L3 C-Anchors Conserved AA in D1 | D1L3 Building Blocks Variable AA in D1L3 | D1 Building Blocks Variable AA in D1 | Building Block Mutations of D1L3 variants | BB Cluster |
|---|---|---|---|---|---|---|
| 0 | N/A | N/A | 1-20 (MSRELAPLLLLLSIHSALA) | 1-22 (MRGMKLL GALLALAALLQGAVS) | M1_A22delinsMRGMKLLGALLALA ALLQGAVS | BB$_0$ |
| 1 | Signal peptide | F2N,N27 | 21-25 (MRICS) | 23-27 (LKIAA) | M21_S25delinsLKIAA | BB$_{0-1}$ |
| 2 | F2N,N27 | F31,G32 | 28-30 (VRS) | 26-30 (QQT) | V28_S30delinsIQT | |
| 3 | F31,G34 | K35 | 33-34 (ES) | 33-36 (FT) | E33_S34delinsFT | |
| 4 | | | | | | BB$_{?}$ |
| 5 | Y46 | R51 | 47-50 (RVRK) | 49-52 (QILS) | K47_K50delinsQILS | BB$_{0-2}$ |
| 6 | R51 | D53 | 52 (Q) | 54 (V) | Q52V | |
| 7 | D53 | E59 | 54-58 (ILVM) | 56-60 (ALVQ) | I54_M58delinsALVQ | |
| 8 | E59 | D62 | 65-61 (K) | 62-63 (VR) | I60_K61delinsVR | BB$_{0-3}$ |
| 9 | D62 | L71 | 63-70 (SNMRICPI) | 65-72 (SHLTAVGK) | S63_P70delinsSHLTAVGK | |
| 10 | L71 | L75,N78 | 72-74 (MER) | 74-76 (LDN) | M72_R74delinsLDN | |
| 11 | L75,N78 | Y85 | 77-84 (RNSRAGIT) | 79-84 (QDAPDT) | R77_T84delinsQDAPDT | |
| 12 | Y85 | Y87 | 86 (N) | 86 (H) | N86H | |
| 13 | Y87 | S95 | 88-90 (VI) | 88-90 (VV) | V88_I90delinsVV | BB$_{0-4}$ |
| 14 | S95 | L98,G94,R95 | 91-92 (SR) | 91-92 (EP) | S91_R92delinsEP | |
| 15 | L98,G94,R95 | Y98,K99,E100 | 96-97 (NT) | 96-97 (NS) | N96_T97delinsNS | |
| 16 | Y98,K99,E100 | Y102 | 101 (Q) | 101 (R) | Q101R | BB$_{0-2}$ |
| 17 | Y102 | F104 | 103 (A) | 103 (L) | A103L | |
| 18 | F104 | Y106 | 105 (I) | 105 (V) | L105V | |
| 19 | Y106 | Y111/S112 | 107-110 (KEKL) | 107-110 (RPDQ) | K107_L110delinsRPDQ | |
| 20 | Y111/S112 | Y117 | 113-116 (VKRS) | 113-116 (AVDS) | V113_S116delinsAVDS | |
| 21 | Y117 | Y119 | 118 (H) | 118 (Y) | H118Y | |
| 22 | Y119 | D121 | 120 (H) | 120 (D) | H120D | |
| 23 | | | | | | |
| 24 | | | | | | BB$_{?}$ |
| 25 | | | | | | BB$_{?}$ |
| 26 | R132/E133/P134 | V137 | 135-136 (FV) | 136-137 (AI) | I35F_136delinsAI | BB$_{0-5}$ |
| 27 | V137 | F139 | 139 (K) | 139 (R) | V138_139delinsRF | |
| 28 | F139 | T144 | 140-143 (QSPH) | 141-144 (FSRF) | Q140_H143delinsFSRF | |
| 29 | T144 | F149 | 145-148 (AVKD) | 146-149 (EVRE) | A145_D148delinsAVKD | |
| 30 | F149 | I151 | 150 (V) | 151 (A) | V150A | |
| 31 | I151 | P153,I154/H155 | 152 (I) | 153 (V) | I152A | |
| 32 | P153,I154/H155 | P157 | 156-157 (TT) | 157-159 (AA) | T156_T157delinsAA | |
| 33 | P157 | V162 | 158-161 (ETG) | 160-162 (GDA) | E159_S161delinsGDA | |
| 34 | V162 | E164/H165/D166 | 163 (K) | 164 (A) | K163A | |

Fig. 31B (continued)

| BB # | DLL3 N-Anchor Conserved AA in DLL3 | DLL3 C-Anchors Conserved AA in DLL3 | DLL3 Building Blocks Variable AA in DLL3 | D1 Building Blocks Variable AA in D1 | Building Block Mutations of DLL3 variants | BB Cluster |
|---|---|---|---|---|---|---|
| 25 | E164/I165/D166 | L168 | 167 (E) | 168 (A) | E167A | BB_set_37 |
| 26 | | V171/Y172 | 169-170 (VE) | 170-171 (YD) | V169_E172delinsYD | |
| 27 | V

*FIG. 32*
BUILDING BLOCK CLUSTER-ENGINEERING
I. AMINO ACID SEQUENCE ALIGNMENT OF HOMOLOGOUS ENZYMES
II. TANSFER OF BUILDING BLOCK CLUSTERS
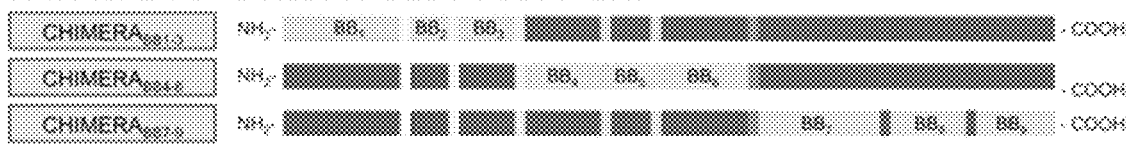
III. TANSFER OF INDIVIDUAL BUILDING BLOCKS (OPTIONAL)
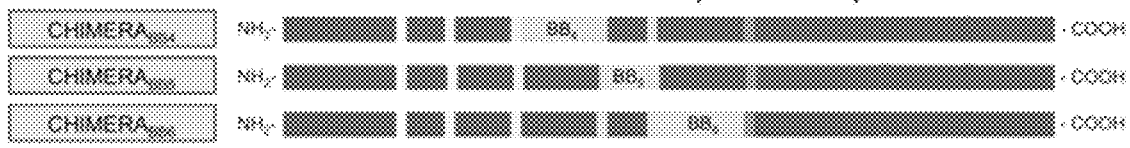
IV. TANSFER OF INDIVIDUAL AMINO ACID RESIDUES (OPTIONAL)
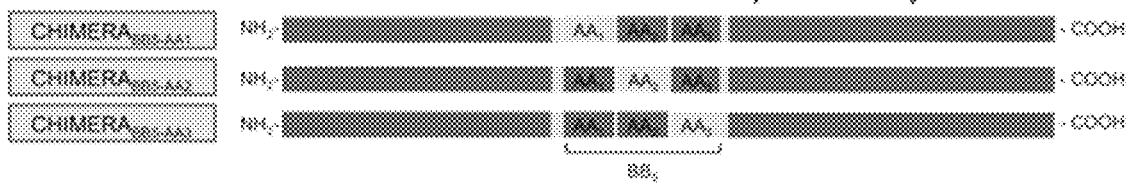

Fig. 36A
NET-clot in cardiac chamber
Fig. 36B
NET-mediated death
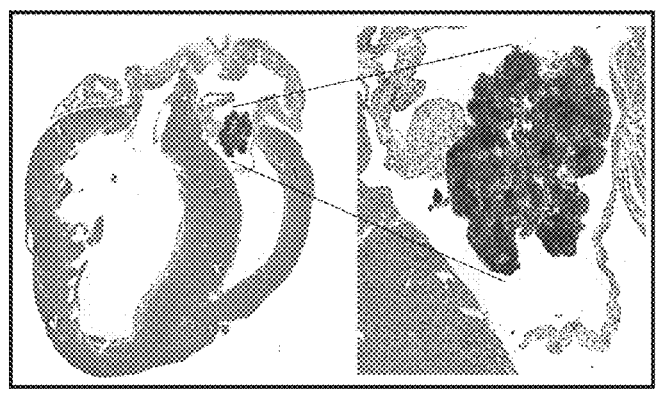
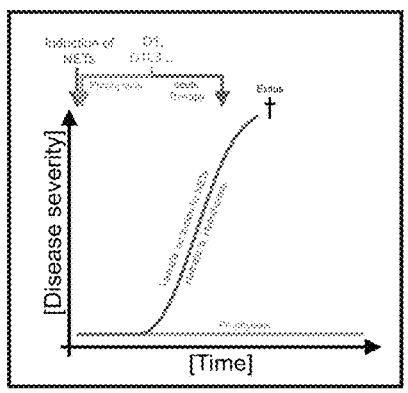
Fig. 36C Experimental design: Acute anti-NET therapy
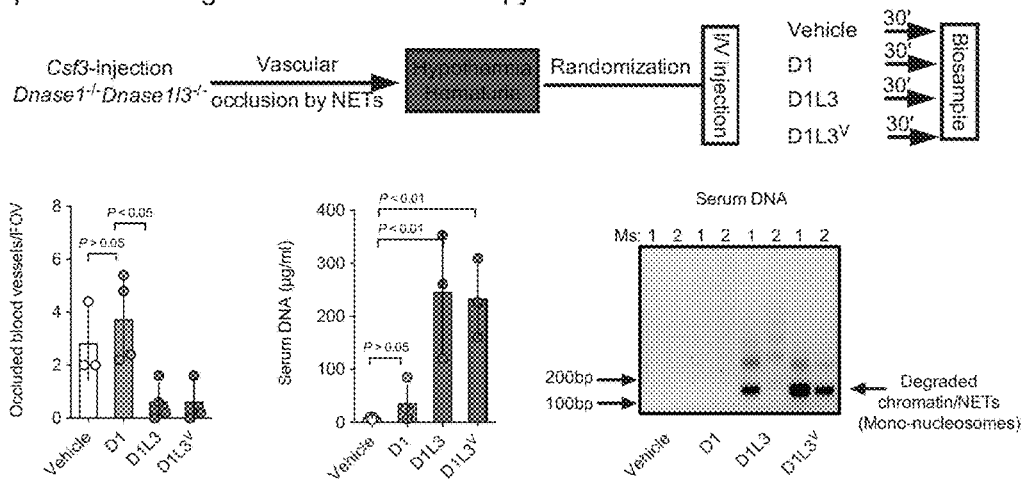
Fig. 36D     Fig. 36E     Fig. 36F Fig. 37A Experimental design: Ischemia-reperfusion injury therapy
Fig. 37B
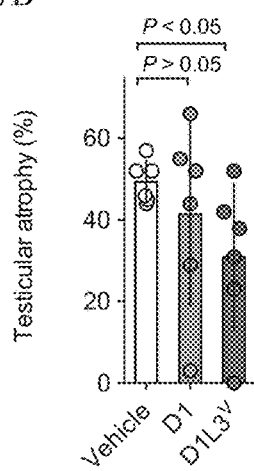
Fig. 37C
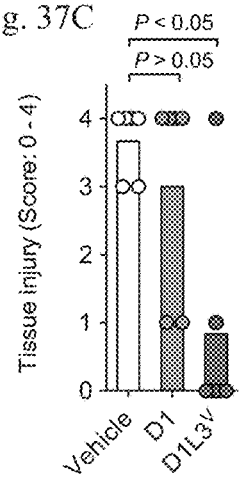
Tissue injury score:
(0) > 95% healthy
(1) > 75% healthy
(2) > 50% healthy
(3) > 25% healthy
(4) < 25% healthy
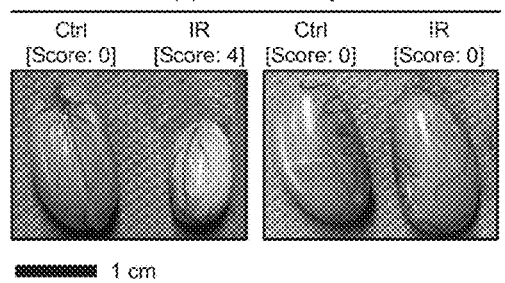

Chinese Hamster Ovary (CHO) cells

Pichia pastoris

*FIG. 39*

| SEQ ID NO | Description | Mutation (Mature protein without signal peptide) | Building Block Engineering | Parental SEQ ID NO |
|---|---|---|---|---|
| 5 | DNase1 variant | Q31R/Q49K/Q79K/W209K (Q28R/Q27K/Q57K/W187K) | - | 1 |
| 6 | DNase1 variant | Q31R/Q49K/Q79K/Q177K/W209K/G262K (Q9R/Q27K/Q57K/Q155K/W187K/G240K) | - | 1 |
| 7 | DNase1 variant | Q31R/A136F/T227K (Q9R/A114F/T205K) | - | 1 |
| 8 | DNase1 variant | A136F/A164K (A114F/A142K) | - | 1 |
| 9 | DNase1 variant | Q79_T84delinsRNSRRGIT (Q57_T62delinsRNSRRGIT) | + (BB1-1) | 1 |
| 10 | DNase1 variant | H86N/V88_V89delinsVH/E91_P92delinsSR (H64N/V66_V67delinsVH/E69_P70delinsSR) | + (BB2-3+4) | 1 |
| 11 | DNase1 variant | A136_I137delinsFV (A114_I115delinsFV) | + (BB5-3) | 1 |
| 12 | DNase1 variant | R199_Q202delinsPKKA/S204_S205delinsKN/W209R/S211D/T213R/Q215V | | 1 |
| 13 | DNase1 variant | P219G/S221_A222delinsQE | | |
| 14 | DNase1 variant | (R177_Q180delinsPKKA/S182_S183delinsKN/W187R/S189D/T191R/Q193V/ P197G/S199_A200delinsQE) | + (BB8-4) | |
| 15 | DNase1 variant | A226_P228delinsVKKS (A204_P206delinsVKKS) | + (BB9-3) | 1 |
| 16 | DNase1 variant | Q79_T84delinsRNSRRGIT/H86N/V88_V89delinsVH/E91_P92delinsSR/ A136_I137delinsFV/ R199_Q202delinsPKKA/S204_S205delinsKN/W209R/S211D/ T213R/Q215V/P219G/S221_A222delinsQE/A226_P228delinsVKKS (Q57_T62delinsRNSRRGIT/H64N/V66_V67delinsVH/E69_P70delinsSR/ A114_I115delinsFV/R177_Q180delinsPKKA/S182_S183delinsKN/W187R/S189D/ T191R/Q193V/P197G/S199_A200delinsQE/A204_P206delinsVKKS) | + (BB1-1, BB2-3+4, BB5-3, BB8-4, BB9-3) | 1 |
| 17 | DNase1L3 variant | F275Y/F279_K280delinsVM/Q282_S305delinsK (F255Y/F259_K260delinsVM/Q262_S285delinsK) | + (BBx-y) | 2 |
| 19 | DNase1L3 variant | Q36_I45delinsMSNATLVSY1 (Q16_I25delinsMSNATLVSY1) | + (BBz-2) | 2 |
| 20 | DNase1L3 variant | Y122_A127delinsGCEPCGN/V129T/S131N (Y102_A107delinsGCEPCGN/V109T/S111N) | + (BDyy-3) | 2 |

SEQUENCE LISTING

```
<160> NUMBER OF SEQ ID NOS: 39

<210> SEQ ID NO 1
<211> LENGTH: 282
<212> TYPE: PRT
<213> ORGANISM: Homo sapiens

<400> SEQUENCE: 1

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
    130                 135                 140
```

-continued

```
Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
                260                 265                 270

Asp His Tyr Pro Val Glu Val Met Leu Lys
                275                 280

<210> SEQ ID NO 2
<211> LENGTH: 305
<212> TYPE: PRT
<213> ORGANISM: Homo sapiens

<400> SEQUENCE: 2

Met Ser Arg Glu Leu Ala Pro Leu Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
```

```
                225                 230                 235                 240
        Gln Glu Ile Val Ser Ser Val Val Pro Lys Ser Asn Ser Val Phe Asp
                        245                 250                 255

Phe Gln Lys Ala Tyr Lys Leu Thr Glu Glu Ala Leu Asp Val Ser
                        260                 265                 270

Asp His Phe Pro Val Glu Phe Lys Leu Gln Ser Ser Arg Ala Phe Thr
                    275                 280                 285

Asn Ser Lys Lys Ser Val Thr Leu Arg Lys Lys Thr Lys Ser Lys Arg
                    290                 295                 300

Ser
        305

<210> SEQ ID NO 3
<211> LENGTH: 284
<212> TYPE: PRT
<213> ORGANISM: Mus musculus

<400> SEQUENCE: 3

Met Arg Tyr Thr Gly Leu Met Gly Thr Leu Leu Thr Leu Val Asn Leu
1               5                   10                  15

Leu Gln Leu Ala Gly Thr Leu Arg Ile Ala Ala Phe Asn Ile Arg Thr
                20                  25                  30

Phe Gly Glu Thr Lys Met Ser Asn Ala Thr Leu Ser Val Tyr Phe Val
            35                  40                  45

Lys Ile Leu Ser Arg Tyr Asp Ile Ala Val Ile Gln Glu Val Arg Asp
        50                  55                  60

Ser His Leu Val Ala Val Gly Lys Leu Leu Asp Glu Leu Asn Arg Asp
65                  70                  75                  80

Lys Pro Asp Thr Tyr Arg Tyr Val Val Ser Glu Pro Leu Gly Arg Lys
                85                  90                  95

Ser Tyr Lys Glu Gln Tyr Leu Phe Val Tyr Arg Pro Asp Gln Val Ser
            100                 105                 110

Ile Leu Asp Ser Tyr Gln Tyr Asp Asp Gly Cys Glu Pro Cys Gly Asn
        115                 120                 125

Asp Thr Phe Ser Arg Glu Pro Ala Ile Val Lys Phe Phe Ser Pro Tyr
    130                 135                 140

Thr Glu Val Gln Glu Phe Ala Ile Val Pro Leu His Ala Ala Pro Thr
145                 150                 155                 160

Glu Ala Val Ser Glu Ile Asp Ala Leu Tyr Asp Val Tyr Leu Asp Val
                165                 170                 175

Trp Gln Lys Trp Gly Leu Glu Asp Ile Met Phe Met Gly Asp Phe Asn
            180                 185                 190

Ala Gly Cys Ser Tyr Val Thr Ser Ser Gln Trp Ser Ser Ile Arg Leu
        195                 200                 205

Arg Thr Ser Pro Ile Phe Gln Trp Leu Ile Pro Asp Ser Ala Asp Thr
    210                 215                 220

Thr Val Thr Ser Thr His Cys Ala Tyr Asp Arg Ile Val Val Ala Gly
225                 230                 235                 240

Ala Leu Leu Gln Ala Ala Val Val Pro Asn Ser Ala Val Pro Phe Asp
                245                 250                 255

Phe Gln Ala Glu Tyr Gly Leu Ser Asn Gln Leu Ala Glu Ala Ile Ser
            260                 265                 270

Asp His Tyr Pro Val Glu Val Thr Leu Arg Lys Ile
        275                 280
```

<210> SEQ ID NO 4
<211> LENGTH: 284
<212> TYPE: PRT
<213> ORGANISM: Artificial Sequence
<220> FEATURE:
<223> OTHER INFORMATION: Artificial synthetic polypeptide sequence

<400> SEQUENCE: 4

```
Met Arg Tyr Thr Gly Leu Met Gly Ile Leu Leu Thr Leu Val Asn Leu
1               5                   10                  15

Leu Gln Leu Ala Ala Thr Leu Arg Ile Ala Ala Phe Asn Ile Arg Thr
            20                  25                  30

Phe Gly Asp Thr Lys Met Ser Asn Ala Thr Leu Ser Ser Tyr Ile Val
        35                  40                  45

Lys Ile Leu Ser Arg Tyr Asp Ile Ala Val Val Gln Glu Val Arg Asp
    50                  55                  60

Thr His Leu Val Ala Val Gly Lys Leu Leu Asp Glu Leu Asn Arg Asp
65                  70                  75                  80

Ile Pro Asp Asn Tyr Arg Tyr Ile Ile Ser Glu Pro Leu Gly Arg Lys
                85                  90                  95

Ser Tyr Lys Glu Gln Tyr Leu Phe Val Tyr Arg Pro Ser Gln Val Ser
            100                 105                 110

Val Leu Asp Ser Tyr His Tyr Asp Asp Gly Cys Glu Pro Cys Gly Asn
        115                 120                 125

Asp Thr Phe Ser Arg Glu Pro Ala Ile Val Lys Phe Phe Ser Pro Tyr
    130                 135                 140

Thr Glu Val Arg Glu Phe Ala Ile Val Pro Leu His Ser Ala Pro Thr
145                 150                 155                 160

Glu Ala Val Ser Glu Ile Asp Ala Leu Tyr Asp Val Tyr Leu Asp Val
                165                 170                 175

Arg Gln Lys Trp Gly Leu Glu Asp Ile Met Phe Met Gly Asp Phe Asn
            180                 185                 190

Ala Gly Cys Ser Tyr Val Thr Ser Ser Gln Trp Ser Ser Ile Arg Leu
        195                 200                 205

Arg Thr Ser Pro Ile Phe Gln Trp Leu Ile Pro Asp Ser Ala Asp Thr
    210                 215                 220

Thr Ala Thr Ser Thr His Cys Ala Tyr Asp Arg Ile Val Val Ala Gly
225                 230                 235                 240

Ala Leu Leu Gln Ala Ala Val Val Pro Ser Ser Ala Val Pro Phe Asp
                245                 250                 255

Phe Gln Ala Glu Tyr Arg Leu Thr Asn Gln Met Ala Glu Ala Ile Ser
            260                 265                 270

Asp His Tyr Pro Val Glu Val Thr Leu Arg Lys Thr
        275                 280
```

<210> SEQ ID NO 5
<211> LENGTH: 282
<212> TYPE: PRT
<213> ORGANISM: Artificial Sequence
<220> FEATURE:
<223> OTHER INFORMATION: Artificial synthetic polypeptide sequence

<400> SEQUENCE: 5

```
Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Arg Thr
            20                  25                  30
```

Phe Gly Glu Thr Lys Met Ser Asn Ala Thr Leu Val Ser Tyr Ile Val
            35                  40                  45

Lys Ile Leu Ser Arg Tyr Asp Ile Ala Leu Val Gln Glu Val Arg Asp
 50                  55                  60

Ser His Leu Thr Ala Val Gly Lys Leu Leu Asp Asn Leu Asn Arg Asp
 65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
            115                 120                 125

Asp Thr Phe Asn Arg Glu Pro Ala Ile Val Arg Phe Phe Ser Arg Phe
 130                 135                 140

Thr Glu Val Arg Glu Phe Ala Ile Val Pro Leu His Ala Ala Pro Gly
 145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
            195                 200                 205

Arg Thr Ser Pro Thr Phe Gln Trp Leu Ile Pro Asp Ser Ala Asp Thr
 210                 215                 220

Thr Ala Thr Pro Thr His Cys Ala Tyr Asp Arg Ile Val Val Ala Gly
 225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
            275                 280

<210> SEQ ID NO 6
<211> LENGTH: 282
<212> TYPE: PRT
<213> ORGANISM: Artificial Sequence
<220> FEATURE:
<223> OTHER INFORMATION: Artificial synthetic polypeptide sequence

<400> SEQUENCE: 6

Met Arg Gly Met Lys Leu Leu Gly Ala Leu Leu Ala Leu Ala Ala Leu
 1                   5                  10                  15

Leu Gln Gly Ala Val Ser Leu Lys Ile Ala Ala Phe Asn Ile Arg Thr
                20                  25                  30

Phe Gly Glu Thr Lys Met Ser Asn Ala Thr Leu Val Ser Tyr Ile Val
            35                  40                  45

Lys Ile Leu Ser Arg Tyr Asp Ile Ala Leu Val Gln Glu Val Arg Asp
 50                  55                  60

Ser His Leu Thr Ala Val Gly Lys Leu Leu Asp Asn Leu Asn Arg Asp
 65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

```
Ala Val Asp Ser Tyr Tyr Asp Asp Gly Cys Glu Pro Cys Gly Asn
            115                 120                 125

Asp Thr Phe Asn Arg Glu Pro Ala Ile Val Arg Phe Phe Ser Arg Phe
        130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
            165                 170                 175

Lys Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
            195                 200                 205

Arg Thr Ser Pro Thr Phe Gln Trp Leu Ile Pro Asp Ser Ala Asp Thr
        210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
            245                 250                 255

Phe Gln Ala Ala Tyr Lys Leu Ser Asp Gln Leu Ala Gln Ala Ile Ser
            260                 265                 270

Asp His Tyr Pro Val Glu Val Met Leu Lys
            275                 280
```

<210> SEQ ID NO 7
<211> LENGTH: 282
<212> TYPE: PRT
<213> ORGANISM: Artificial Sequence
<220> FEATURE:
<223> OTHER INFORMATION: Artificial synthetic polypeptide sequence

<400> SEQUENCE: 7

```
Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Arg Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
            85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
            115                 120                 125

Asp Thr Phe Asn Arg Glu Pro Phe Ile Val Arg Phe Phe Ser Arg Phe
        130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
            165                 170                 175

Gln Glu Lys Trp Gly Leu Glu Asp Val Met Leu Met Gly Asp Phe Asn
            180                 185                 190
```

```
Ala Gly Cys Ser Tyr Val Arg Pro Ser Gln Trp Ser Ser Ile Arg Leu
            195                 200                 205

Trp Thr Ser Pro Thr Phe Gln Trp Leu Ile Pro Asp Ser Ala Asp Thr
    210                 215                 220

Thr Ala Lys Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
            245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
            275                 280

<210> SEQ ID NO 8
<211> LENGTH: 282
<212> TYPE: PRT
<213> ORGANISM: Artificial Sequence
<220> FEATURE:
<223> OTHER INFORMATION: Artificial synthetic polypeptide sequence

<400> SEQUENCE: 8

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Arg Thr
            20                  25                  30

Phe Gly Glu Thr Lys Met Ser Asn Ala Thr Leu Val Ser Tyr Ile Val
            35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
            85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
            115                 120                 125

Asp Thr Phe Asn Arg Glu Pro Ala Ile Val Arg Phe Phe Ser Arg Phe
        130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
            165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
            195                 200                 205

Trp Thr Ser Pro Thr Phe Gln Trp Leu Ile Pro Asp Ser Ala Asp Thr
    210                 215                 220

Thr Ala Lys Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
            245                 250                 255

Phe Gln Ala Ala Tyr Gly Leu Ser Asp Gln Leu Ala Gln Ala Ile Ser
            260                 265                 270
```

Asp His Tyr Pro Val Glu Val Met Leu Lys
        275                 280

<210> SEQ ID NO 9
<211> LENGTH: 282
<212> TYPE: PRT
<213> ORGANISM: Artificial Sequence
<220> FEATURE:
<223> OTHER INFORMATION: Artificial synthetic polypeptide sequence

<400> SEQUENCE: 9

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Gln Val Ser
            100                 105                 110

Ala Val Asp Ser Tyr Tyr Tyr Asp Asp Gly Cys Glu Pro Cys Gly Asn
            115                 120                 125

Asp Thr Phe Asn Arg Glu Pro Phe Ile Val Arg Phe Phe Ser Arg Phe
    130                 135                 140

Thr Glu Val Arg Glu Phe Ala Ile Val Pro Leu His Ala Ala Pro Gly
145                 150                 155                 160

Asp Ala Val Lys Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
        275                 280

<210> SEQ ID NO 10
<211> LENGTH: 284
<212> TYPE: PRT
<213> ORGANISM: Artificial Sequence
<220> FEATURE:
<223> OTHER INFORMATION: Artificial synthetic polypeptide sequence

<400> SEQUENCE: 10

Met Arg Gly Met Lys Leu Leu Gly Ala Leu Leu Ala Leu Ala Ala Leu

-continued

```
             1               5                  10                 15
           Leu Gln Gly Ala Val Ser Leu Lys Ile Ala Ala Phe Asn Ile Gln Thr
                            20                 25                 30

Phe Gly Glu Thr Lys Met Ser Asn Ala Thr Leu Val Ser Tyr Ile Val
                       35                 40                 45

Gln Ile Leu Ser Arg Tyr Asp Ile Ala Leu Val Gln Glu Val Arg Asp
                  50                 55                 60

Ser His Leu Thr Ala Val Gly Lys Leu Leu Asp Asn Leu Asn Arg Asn
            65                 70                 75                 80

Ser Arg Arg Gly Ile Thr Tyr His Tyr Val Val Ser Glu Pro Leu Gly
                            85                 90                 95

Arg Asn Ser Tyr Lys Glu Arg Tyr Leu Phe Val Tyr Arg Pro Asp Gln
                           100                105                110

Val Ser Ala Val Asp Ser Tyr Tyr Tyr Asp Asp Gly Cys Glu Pro Cys
                           115                120                125

Gly Asn Asp Thr Phe Asn Arg Glu Pro Ala Ile Val Arg Phe Phe Ser
           130                135                140

Arg Phe Thr Glu Val Arg Glu Phe Ala Ile Val Pro Leu His Ala Ala
           145                150                155                160

Pro Gly Asp Ala Val Ala Glu Ile Asp Ala Leu Tyr Asp Val Tyr Leu
                           165                170                175

Asp Val Gln Glu Lys Trp Gly Leu Glu Asp Val Met Leu Met Gly Asp
                           180                185                190

Phe Asn Ala Gly Cys Ser Tyr Val Arg Pro Ser Gln Trp Ser Ser Ile
                           195                200                205

Arg Leu Trp Thr Ser Pro Thr Phe Gln Trp Leu Ile Pro Asp Ser Ala
                   210                215                220

Asp Thr Thr Ala Thr Pro Thr His Cys Ala Tyr Asp Arg Ile Val Val
           225                230                235                240

Ala Gly Met Leu Leu Arg Gly Ala Val Val Pro Asp Ser Ala Leu Pro
                           245                250                255

Phe Asn Phe Gln Ala Ala Tyr Gly Leu Ser Asp Gln Leu Ala Gln Ala
                           260                265                270

Ile Ser Asp His Tyr Pro Val Glu Val Met Leu Lys
                           275                280
```

<210> SEQ ID NO 11
<211> LENGTH: 282
<212> TYPE: PRT
<213> ORGANISM: Artificial Sequence
<220> FEATURE:
<223> OTHER INFORMATION: Artificial synthetic polypeptide sequence

<400> SEQUENCE: 11

```
           Met Arg Gly Met Lys Leu Leu Gly Ala Leu Leu Ala Leu Ala Ala Leu
            1               5                  10                 15

Leu Gln Gly Ala Val Ser Leu Lys Ile Ala Ala Phe Asn Ile Gln Thr
                            20                 25                 30

Phe Gly Glu Thr Lys Met Ser Asn Ala Thr Leu Val Ser Tyr Ile Val
                       35                 40                 45

Gln Ile Leu Ser Arg Tyr Asp Ile Ala Leu Val Gln Glu Val Arg Asp
                  50                 55                 60

Ser His Leu Thr Ala Val Gly Lys Leu Leu Asp Asn Leu Asn Gln Asp
            65                 70                 75                 80

Ala Pro Asp Thr Tyr Asn Tyr Val Ile Ser Ser Arg Leu Gly Arg Asn
```

```
                     85                  90                  95
Ser Tyr Lys Glu Arg Tyr Leu Phe Val Tyr Arg Pro Asp Gln Val Ser
                100                 105                 110

Ala Val Asp Ser Tyr Tyr Tyr Asp Asp Gly Cys Glu Pro Cys Gly Asn
            115                 120                 125

Asp Thr Phe Asn Arg Glu Pro Ala Ile Val Arg Phe Phe Ser Arg Phe
        130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
        275                 280

<210> SEQ ID NO 12
<211> LENGTH: 282
<212> TYPE: PRT
<213> ORGANISM: Artificial Sequence
<220> FEATURE:
<223> OTHER INFORMATION: Artificial synthetic polypeptide sequence

<400> SEQUENCE: 12

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
                100                 105                 110

Ala Val Asp Ser Tyr Tyr Tyr Asp Asp Gly Cys Glu Pro Cys Gly Asn
            115                 120                 125

Asp Thr Phe Asn Arg Glu Pro Phe Val Arg Phe Phe Ser Arg Phe
        130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
```

Gln Glu Lys Trp Gly Leu Glu Asp Val Met Leu Met Gly Asp Phe Asn
                180                 185                 190

Ala Gly Cys Ser Tyr Val Arg Pro Ser Gln Trp Ser Ser Ile Arg Leu
            195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
            275                 280

<210> SEQ ID NO 13
<211> LENGTH: 282
<212> TYPE: PRT
<213> ORGANISM: Artificial Sequence
<220> FEATURE:
<223> OTHER INFORMATION: Artificial synthetic polypeptide sequence

<400> SEQUENCE: 13

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
                20                  25                  30

Phe Gly Glu Thr Lys Met Ser Asn Ala Thr Leu Val Ser Tyr Ile Val
            35                  40                  45

Gln Ile Leu Ser Arg Tyr Asp Ile Ala Leu Val Gln Glu Val Arg Asp
        50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Pro Lys Lys Ala Trp Lys Asn Ile Arg Leu
        195                 200                 205

Arg Thr Asp Pro Arg Phe Val Trp Leu Ile Gly Asp Gln Glu Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn

```
                    245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
        275                 280

<210> SEQ ID NO 14
<211> LENGTH: 283
<212> TYPE: PRT
<213> ORGANISM: Artificial Sequence
<220> FEATURE:
<223> OTHER INFORMATION: Artificial synthetic polypeptide sequence

<400> SEQUENCE: 14

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
50                  55                  60

Ser His Leu Thr Ala Val Gly Lys Leu Leu Asp Asn Leu Asn Gln Asp
65                  70                  75                  80

Ala Pro Asp Thr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
210                 215                 220

Thr Val Lys Lys Ser Thr His Cys Ala Tyr Asp Arg Ile Val Val Ala
225                 230                 235                 240

Gly Met Leu Leu Arg Gly Ala Val Val Pro Asp Ser Ala Leu Pro Phe
                245                 250                 255

Asn Phe Gln Ala Ala Tyr Gly Leu Ser Asp Gln Leu Ala Gln Ala Ile
            260                 265                 270

Ser Asp His Tyr Pro Val Glu Val Met Leu Lys
        275                 280

<210> SEQ ID NO 15
<211> LENGTH: 285
<212> TYPE: PRT
<213> ORGANISM: Artificial Sequence
<220> FEATURE:
<223> OTHER INFORMATION: Artificial synthetic polypeptide sequence
```

<400> SEQUENCE: 15

```
Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Arg Asn
65                  70                  75                  80

Ser Arg Arg Gly Ile Thr Tyr Asn Tyr Val Ile Ser Ser Arg Leu Gly
                85                  90                  95

Arg Asn Ser Tyr Lys Glu Arg Tyr Leu Phe Val Tyr Arg Pro Asp Gln
            100                 105                 110

Val Ser Ala Val Asp Ser Tyr Tyr Tyr Asp Gly Cys Glu Pro Cys
        115                 120                 125

Gly Asn Asp Thr Phe Asn Arg Glu Pro Phe Val Arg Phe Phe Ser
130                 135                 140

Arg Phe Thr Glu Val Arg Glu Phe Ala Ile Val Pro Leu His Ala Ala
145                 150                 155                 160

Pro Gly Asp Ala Val Ala Glu Ile Asp Ala Leu Tyr Asp Val Tyr Leu
                165                 170                 175

Asp Val Gln Glu Lys Trp Gly Leu Glu Asp Val Met Leu Met Gly Asp
            180                 185                 190

Phe Asn Ala Gly Cys Ser Tyr Val Pro Lys Lys Ala Trp Lys Asn Ile
        195                 200                 205

Arg Leu Arg Thr Asp Pro Arg Phe Val Trp Leu Ile Gly Asp Gln Glu
210                 215                 220

Asp Thr Thr Val Lys Lys Ser Thr His Cys Ala Tyr Asp Arg Ile Val
225                 230                 235                 240

Val Ala Gly Met Leu Leu Arg Gly Ala Val Val Pro Asp Ser Ala Leu
                245                 250                 255

Pro Phe Asn Phe Gln Ala Ala Tyr Gly Leu Ser Asp Gln Leu Ala Gln
            260                 265                 270

Ala Ile Ser Asp His Tyr Pro Val Glu Val Met Leu Lys
        275                 280                 285
```

<210> SEQ ID NO 16
<211> LENGTH: 305
<212> TYPE: PRT
<213> ORGANISM: Artificial Sequence
<220> FEATURE:
<223> OTHER INFORMATION: Artificial synthetic polypeptide sequence

<400> SEQUENCE: 16

```
Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60
```

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
            115                 120                 125

Asp Thr Phe Asn Arg Glu Pro Ala Ile Val Arg Phe Phe Ser Arg Phe
        130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Phe Pro Val Glu Phe Lys Leu Gln Ser Ser Arg Ala Phe Thr
        275                 280                 285

Asn Ser Lys Lys Ser Val Thr Leu Arg Lys Lys Thr Lys Ser Lys Arg
            290                 295                 300

Ser
305

<210> SEQ ID NO 17
<211> LENGTH: 282
<212> TYPE: PRT
<213> ORGANISM: Artificial Sequence
<220> FEATURE:
<223> OTHER INFORMATION: Artificial synthetic polypeptide sequence

<400> SEQUENCE: 17

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
                20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
        50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

```
Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Tyr Pro Val Glu Val Met Leu Lys
        275                 280

<210> SEQ ID NO 18
<211> LENGTH: 305
<212> TYPE: PRT
<213> ORGANISM: Artificial Sequence
<220> FEATURE:
<223> OTHER INFORMATION: Artificial synthetic polypeptide sequence

<400> SEQUENCE: 18

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
                20                  25                  30

Glu Ser Lys Gln Glu Asn Lys Thr Ala Met Asp Val Ile Val Lys Val
            35                  40                  45

Ile Lys Arg Cys Asp Ile Ile Leu Val Met Glu Ile Lys Asp Ser Asn
50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Asn Asp
        115                 120                 125

Thr Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190
```

```
Gly Cys Ser Tyr Val Pro Lys Lys Ala Trp Lys Asn Ile Arg Leu Arg
            195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Val Val Pro Lys Ser Asn Ser Val Phe Asp
            245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
    275                 280                 285

Asn Ser Lys Lys Ser Val Thr Leu Arg Lys Lys Thr Lys Ser Lys Arg
    290                 295                 300

Ser
305

<210> SEQ ID NO 19
<211> LENGTH: 305
<212> TYPE: PRT
<213> ORGANISM: Artificial Sequence
<220> FEATURE:
<223> OTHER INFORMATION: Artificial synthetic polypeptide sequence

<400> SEQUENCE: 19

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Met Ser Asn Ala Thr Leu Val Ser Tyr Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
            85                  90                  95

Thr Tyr Lys Glu Gln Tyr Ala Phe Leu Tyr Lys Glu Lys Leu Val Ser
        100                 105                 110

Val Lys Arg Ser Tyr His Tyr His Asp Tyr Gln Asp Gly Asp Ala Asp
    115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
            165                 170                 175

His Arg Trp Lys Ala Glu Asn Phe Ile Phe Met Gly Asp Phe Asn Ala
        180                 185                 190

Gly Cys Ser Tyr Val Pro Lys Lys Ala Trp Lys Asn Ile Arg Leu Arg
    195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240
```

```
Gln Glu Ile Val Ser Ser Val Val Pro Lys Ser Asn Ser Val Phe Asp
            245                 250                 255

Phe Gln Lys Ala Tyr Lys Leu Thr Glu Glu Ala Leu Asp Val Ser
        260                 265                 270

Asp His Phe Pro Val Glu Phe Lys Leu Gln Ser Ser Arg Ala Phe Thr
            275                 280                 285

Asn Ser Lys Lys Ser Val Thr Leu Arg Lys Lys Thr Lys Ser Lys Arg
        290                 295                 300

Ser
305

<210> SEQ ID NO 20
<211> LENGTH: 306
<212> TYPE: PRT
<213> ORGANISM: Artificial Sequence
<220> FEATURE:
<223> OTHER INFORMATION: Artificial synthetic polynucleotide sequence

<400> SEQUENCE: 20

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Gly Cys Glu Pro Cys Gly Asn
        115                 120                 125

Asp Thr Phe Asn Arg Glu Pro Phe Val Val Trp Phe Gln Ser Pro His
130                 135                 140

Thr Ala Val Lys Asp Phe Val Ile Ile Pro Leu His Thr Thr Pro Glu
145                 150                 155                 160

Thr Ser Val Lys Glu Ile Asp Glu Leu Val Glu Val Tyr Thr Asp Val
                165                 170                 175

Lys His Arg Trp Lys Ala Glu Asn Phe Ile Phe Met Gly Asp Phe Asn
            180                 185                 190

Ala Gly Cys Ser Tyr Val Pro Lys Lys Ala Trp Lys Asn Ile Arg Leu
        195                 200                 205

Arg Thr Asp Pro Arg Phe Val Trp Leu Ile Gly Asp Gln Glu Asp Thr
210                 215                 220

Thr Val Lys Lys Ser Thr Asn Cys Ala Tyr Asp Arg Ile Val Leu Arg
225                 230                 235                 240

Gly Gln Glu Ile Val Ser Ser Val Val Pro Lys Ser Asn Ser Val Phe
                245                 250                 255

Asp Phe Gln Lys Ala Tyr Lys Leu Thr Glu Glu Ala Leu Asp Val
            260                 265                 270

Ser Asp His Phe Pro Val Glu Phe Lys Leu Gln Ser Ser Arg Ala Phe
        275                 280                 285
```

Thr Asn Ser Lys Lys Ser Val Thr Leu Arg Lys Lys Thr Lys Ser Lys
            290                 295                 300

Arg Ser
305

<210> SEQ ID NO 21
<211> LENGTH: 282
<212> TYPE: PRT
<213> ORGANISM: Artificial Sequence
<220> FEATURE:
<223> OTHER INFORMATION: Artificial synthetic polypeptide sequence

<400> SEQUENCE: 21

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Ser Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Ser
        115                 120                 125

Asp Thr Phe Asn Arg Glu Pro Ala Ile Val Arg Phe Phe Ser Arg Phe
    130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
        275                 280

<210> SEQ ID NO 22
<211> LENGTH: 846
<212> TYPE: DNA
<213> ORGANISM: Artificial Sequence
<220> FEATURE:
<223> OTHER INFORMATION: Artificial synthetic polynucleotide sequence

<400> SEQUENCE: 22

```
atgagaggta tgaagctcct tggtgccctc ctggctctcg ctgctctcct ccaaggagca    60
gtttctctaa agattgctgc tttcaatatt caaacctttg gcgagactaa aatgtcctcg   120
gcaacattag tatcttacat tgttcagatc ctttctcgtt acgacatagc tttggtccag   180
gaggttagag actcccactt gactgccgtc ggtaagctgc tagacaatct taaccaagac   240
gcacctgaca cctaccacta cgttgttagt gagcctctcg gtagaaactc ctacaaggag   300
agatacctat ttgtctaccg tccagatcag gtgtctgctg tggactctta ctactatgac   360
gacggttgtg aaccttgtgg ttcagacacc ttcaacagag aaccagctat cgttagattt   420
ttctccagat tcaccgaggt cagagagttc gccatcgttc cattgcacgc tgcgcctgga   480
gatgcagtgg ccgaaattga cgctctctat gatgtctacc tggacgttca ggaaaaatgg   540
ggtctagaag atgttatgct gatgggagac ttcaacgctg gttgctctta cgttaggcca   600
tctcaatggt caagcatcag actatggact cccccaacgt tccaatggct tattcctgac   660
tccgctgata ctaccgccac tcccactcat tgtgcatatg acagaattgt tgtcgctggt   720
atgctactgc gtggagctgt cgtaccagat tctgctctgc catttaactt ccaagccgca   780
tatggtcttt ctgaccaact ggctcaagcc atctctgatc actaccctgt ggaagttatg   840
cttaag                                                               846

<210> SEQ ID NO 23
<211> LENGTH: 282
<212> TYPE: PRT
<213> ORGANISM: Artificial Sequence
<220> FEATURE:
<223> OTHER INFORMATION: Artificial synthetic polypeptide sequence

<400> SEQUENCE: 23

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Arg Thr
            20                  25                  30

Phe Gly Glu Thr Lys Met Ser Ser Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Ser
        115                 120                 125

Asp Thr Phe Asn Arg Glu Pro Phe Ile Val Arg Phe Phe Ser Arg Phe
    130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205
```

Trp Thr Ser Pro Thr Phe Gln Trp Leu Ile Pro Asp Ser Ala Asp Thr
    210                 215                 220

Thr Ala Lys Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
            275                 280

<210> SEQ ID NO 24
<211> LENGTH: 846
<212> TYPE: DNA
<213> ORGANISM: Artificial Sequence
<220> FEATURE:
<223> OTHER INFORMATION: Artificial synthetic polynucleotide sequence

<400> SEQUENCE: 24
atgagaggta tgaagctcct tggtgccctc ctggctctcg ctgctctcct ccaaggagca      60
gtttctctaa agattgctgc tttcaatatt agaacctttg gcgagactaa aatgtcctcg     120
gcaacattag tatcttacat tgttcagatc ctttctcgtt acgacatagc tttggtccag     180
gaggttagag actcccactt gactgccgtc ggtaagctgc tagacaatct taaccaagac     240
gcacctgaca cctaccacta cgttgttagt gagcctctcg gtagaaactc ctacaaggag     300
agataccatt ttgtctaccg tccagatcag gtgtctgctg tggactctta ctactatgac     360
gacggttgtg aaccttgtgg ttcagacacc ttcaacagag aaccattcat cgttagattt     420
ttctccagat tcaccgaggt cagagagttc gccatcgttc cattgcacgc tgcgcctgga     480
gatgcagtgg ccgaaattga cgctctctat gatgtctacc tggacgttca ggaaaaatgg     540
ggtctagaag atgttatgct gatgggagac ttcaacgctg ttgctctta cgttaggcca     600
tctcaatggt caagcatcag actatggact cccccaacgt tccaatggct tattcctgac     660
tccgctgata ctaccgccaa gcccactcat tgtgcatatg acagaattgt tgtcgctggt     720
atgctactgc gtggagctgt cgtaccagat tctgctctgc catttaactt ccaagccgca     780
tatggtcttt ctgaccaact ggctcaagcc atctctgatc actaccctgt ggaagttatg     840
cttaag                                                                846

<210> SEQ ID NO 25
<211> LENGTH: 915
<212> TYPE: DNA
<213> ORGANISM: Artificial Sequence
<220> FEATURE:
<223> OTHER INFORMATION: Artificial synthetic polynucleotide sequence

<400> SEQUENCE: 25
atgtctagag agcttgctcc actcctccta ctccttctta gtatccactc tgcactcgcc      60
atgagaattt gtagcttcaa tgtaagatcc ttcggtgaat ctaagcagga ggacaaaaac     120
gctatggacg ttattgtgaa ggtcattaag agatgtgata tcattctagt tatggagatc     180
aaggactcta caacagaatt gccccatcc cttatggaaa agctgaatag aaactctaga     240
agaggaatta cttacaacta cgttatctct ctaggctgg gtagaaacac ttacaaggag     300
caatatgcat tctatacaa ggaaaagcta gtttccgtta gcgttcttta ccactatcat     360
gactaccaag acggcgatgc tgacgttttt c tccagagaac cattcgttgt ttggtttcag     420

```
tctcctcaca ccgctgttaa ggacttcgtg attatcccac tacacactac gccagaaacc        480
tctgtcaagg aaatagatga acttgttgaa gtttacaccg acgtgaagca cagatggaag        540
gccgagaatt tcattttcat gggtgatttc aacgccggat gctcatatgt ccctaaaaag        600
gcttggaaaa acatccgttt gagaaccgat cctagatttg tctggctcat cggtgaccaa        660
gaggacacca cagtcaaaaa gtctaccaac tgtgcttacg acagaattgt tctgcgtggt        720
caggagattg tttcatctgt tgtcccaaag tccaactccg tctttgattt ccaaaaggct        780
tacaaactga ctgaggagga agctttagac gtgtccgacc acttccctgt agagtttaag        840
ctgcaatcct ccagagcatt cactaactct aaaaagtcag tcactttgcg taaaaagact        900
aagtctaaga gatcg                                                        915

<210> SEQ ID NO 26
<211> LENGTH: 846
<212> TYPE: DNA
<213> ORGANISM: Artificial Sequence
<220> FEATURE:
<223> OTHER INFORMATION: Artificial synthetic polynucleotide sequence

<400> SEQUENCE: 26
atgtctagag agcttgctcc actcctccta ctccttctta gtatccactc tgcactcgcc         60
atgagaattt gtagcttcaa tgtaagatcc ttcggtgaat ctaagcagga ggacaaaaac        120
gctatggacg ttattgtgaa ggtcattaag agatgtgata tcattctagt tatggagatc        180
aaggactcta acaacagaat ttgccccatc cttatggaaa agctgaatag aaactctaga        240
agaggaatta cttacaacta cgttatctct tctaggctgg gtagaaacac ttacaaggag        300
caatatgcat ttctatacaa ggaaaagcta gtttccgtta gcgttcttta ccactatcat        360
gactaccaag acggcgatgc tgacgttttc tccagagaac cattcgttgt ttggtttcag        420
tctcctcaca ccgctgttaa ggacttcgtg attatcccac tacacactac gccagaaacc        480
tctgtcaagg aaatagatga acttgttgaa gtttacaccg acgtgaagca cagatggaag        540
gccgagaatt tcattttcat gggtgatttc aacgccggat gctcatatgt ccctaaaaag        600
gcttggaaaa acatccgttt gagaaccgat cctagatttg tctggctcat cggtgaccaa        660
gaggacacca cagtcaaaaa gtctaccaac tgtgcttacg acagaattgt tctgcgtggt        720
caggagattg tttcatctgt tgtcccaaag tccaactccg tctttgattt ccaaaaggct        780
tacaaactga ctgaggagga agctttagac gtgtccgacc actaccctgt agaggtcatg        840
ttgaag                                                                  846

<210> SEQ ID NO 27
<211> LENGTH: 20
<212> TYPE: DNA
<213> ORGANISM: Artificial Sequence
<220> FEATURE:
<223> OTHER INFORMATION: Artificial synthetic polynucleotide sequence

<400> SEQUENCE: 27
gtcgacatgc ggtacacagg                                                    20

<210> SEQ ID NO 28
<211> LENGTH: 26
<212> TYPE: DNA
<213> ORGANISM: Artificial Sequence
<220> FEATURE:
<223> OTHER INFORMATION: Artificial synthetic polynucleotide sequence
```

<400> SEQUENCE: 28
ctcgagtcag atttttctga gtgtca                                          26

<210> SEQ ID NO 29
<211> LENGTH: 24
<212> TYPE: DNA
<213> ORGANISM: Artificial Sequence
<220> FEATURE:
<223> OTHER INFORMATION: Artificial synthetic polynucleotide sequence

<400> SEQUENCE: 29
gaagtcccag gaattcaaag atgt                                            24

<210> SEQ ID NO 30
<211> LENGTH: 22
<212> TYPE: DNA
<213> ORGANISM: Artificial Sequence
<220> FEATURE:
<223> OTHER INFORMATION: Artificial synthetic polynucleotide sequence

<400> SEQUENCE: 30
gcgtgatacc cgggagcgat tg                                              22

<210> SEQ ID NO 31
<211> LENGTH: 29
<212> TYPE: DNA
<213> ORGANISM: Artificial Sequence
<220> FEATURE:
<223> OTHER INFORMATION: Artificial synthetic polynucleotide sequence

<400> SEQUENCE: 31
agtcgactcc cggccaccat gtccctgca                                       29

<210> SEQ ID NO 32
<211> LENGTH: 29
<212> TYPE: DNA
<213> ORGANISM: Artificial Sequence
<220> FEATURE:
<223> OTHER INFORMATION: Artificial synthetic polynucleotide sequence

<400> SEQUENCE: 32
tgcagggaca tggtggccgg gagtcgact                                       29

<210> SEQ ID NO 33
<211> LENGTH: 23
<212> TYPE: PRT
<213> ORGANISM: Artificial Sequence
<220> FEATURE:
<223> OTHER INFORMATION: Artificial synthetic polypeptide sequence

<400> SEQUENCE: 33

Ser Ser Arg Ala Phe Thr Asn Ser Lys Lys Ser Val Thr Leu Arg Lys
1               5                   10                  15

Lys Thr Lys Ser Lys Arg Ser
            20

<210> SEQ ID NO 34
<211> LENGTH: 310
<212> TYPE: PRT
<213> ORGANISM: Artificial Sequence
<220> FEATURE:
<223> OTHER INFORMATION: Artificial synthetic polypeptide sequence

<400> SEQUENCE: 34

Met Ser Leu His Pro Ala Ser Pro Arg Leu Ala Ser Leu Leu Leu Phe

```
                1               5              10              15
        Ile Leu Ala Leu His Asp Thr Leu Ala Leu Arg Leu Cys Ser Phe Asn
                       20              25              30

Val Arg Ser Phe Gly Ala Ser Lys Lys Glu Asn His Glu Ala Met Asp
                       35              40              45

Ile Ile Val Lys Ile Ile Lys Arg Cys Asp Leu Ile Leu Leu Met Glu
                50              55              60

Ile Lys Asp Ser Ser Asn Asn Ile Cys Pro Met Leu Met Glu Lys Leu
        65                     70              75                      80

Asn Gly Asn Ser Arg Arg Ser Thr Thr Tyr Asn Tyr Val Ile Ser Ser
                       85              90              95

Arg Leu Gly Arg Asn Thr Tyr Lys Glu Gln Tyr Ala Phe Val Tyr Lys
                       100             105             110

Glu Lys Leu Val Ser Val Lys Thr Lys Tyr His Tyr His Asp Tyr Gln
                       115             120             125

Asp Gly Asp Thr Asp Val Phe Ser Arg Glu Pro Phe Val Val Trp Phe
                       130             135             140

His Ser Pro Phe Thr Ala Val Lys Asp Phe Val Ile Val Pro Leu His
        145                     150             155                     160

Thr Thr Pro Glu Thr Ser Val Lys Glu Ile Asp Glu Leu Val Asp Val
                       165             170             175

Tyr Thr Asp Val Arg Ser Gln Trp Lys Thr Glu Asn Phe Ile Phe Met
                       180             185             190

Gly Asp Phe Asn Ala Gly Cys Ser Tyr Val Pro Lys Lys Ala Trp Gln
                       195             200             205

Asn Ile Arg Leu Arg Thr Asp Pro Lys Phe Val Trp Leu Ile Gly Asp
                       210             215             220

Gln Glu Asp Thr Thr Val Lys Lys Ser Thr Ser Cys Ala Tyr Asp Arg
        225                     230             235                     240

Ile Val Leu Cys Gly Gln Glu Ile Val Asn Ser Val Val Pro Arg Ser
                       245             250             255

Ser Gly Val Phe Asp Phe Gln Lys Ala Tyr Asp Leu Ser Glu Glu Glu
                       260             265             270

Ala Leu Asp Val Ser Asp His Phe Pro Val Glu Phe Lys Leu Gln Ser
                       275             280             285

Ser Arg Ala Phe Thr Asn Asn Arg Lys Ser Val Ser Leu Lys Lys Arg
                       290             295             300

Lys Lys Gly Asn Arg Ser
        305                     310

<210> SEQ ID NO 35
<211> LENGTH: 310
<212> TYPE: PRT
<213> ORGANISM: Mus musculus

<400> SEQUENCE: 35

1               5              10              15
        Met Ser Leu Tyr Pro Ala Ser Pro Tyr Leu Ala Ser Leu Leu Leu Phe

Ile Leu Ala Leu His Gly Ala Leu Ser Leu Arg Leu Cys Ser Phe Asn
                       20              25              30

Val Arg Ser Phe Gly Glu Ser Lys Lys Glu Asn His Asn Ala Met Asp
                       35              40              45

Ile Ile Val Lys Ile Ile Lys Arg Cys Asp Leu Ile Leu Leu Met Glu
                50              55              60
```

```
Ile Lys Asp Ser Asn Asn Ile Cys Pro Met Leu Met Glu Lys Leu
 65                  70                  75                  80

Asn Gly Asn Ser Arg Arg Ser Thr Thr Tyr Asn Tyr Val Ile Ser Ser
             85                  90                  95

Arg Leu Gly Arg Asn Thr Tyr Lys Glu Gln Tyr Ala Phe Leu Tyr Lys
            100                 105                 110

Glu Lys Leu Val Ser Val Lys Ala Lys Tyr Leu Tyr His Asp Tyr Gln
            115                 120                 125

Asp Gly Asp Thr Asp Val Phe Ser Arg Glu Pro Phe Val Val Trp Phe
            130                 135                 140

Gln Ala Pro Phe Thr Ala Ala Lys Asp Phe Val Ile Val Pro Leu His
145                 150                 155                 160

Thr Thr Pro Glu Thr Ser Val Lys Glu Ile Asp Glu Leu Ala Asp Val
                165                 170                 175

Tyr Thr Asp Val Arg Arg Trp Lys Ala Glu Asn Phe Ile Phe Met
                180                 185                 190

Gly Asp Phe Asn Ala Gly Cys Ser Tyr Val Pro Lys Lys Ala Trp Lys
            195                 200                 205

Asn Ile Arg Leu Arg Thr Asp Pro Asn Phe Val Trp Leu Ile Gly Asp
210                 215                 220

Gln Glu Asp Thr Thr Val Lys Lys Ser Thr Ser Cys Ala Tyr Asp Arg
225                 230                 235                 240

Ile Val Leu Arg Gly Gln Glu Ile Val Asn Ser Val Val Pro Arg Ser
                245                 250                 255

Ser Gly Val Phe Asp Phe Gln Lys Ala Tyr Glu Leu Ser Glu Glu Glu
            260                 265                 270

Ala Leu Asp Val Ser Asp His Phe Pro Val Glu Phe Lys Leu Gln Ser
            275                 280                 285

Ser Arg Ala Phe Thr Asn Ser Arg Lys Ser Val Ser Leu Lys Lys Lys
            290                 295                 300

Lys Lys Gly Ser Arg Ser
305                 310

<210> SEQ ID NO 36
<211> LENGTH: 282
<212> TYPE: PRT
<213> ORGANISM: Artificial Sequence
<220> FEATURE:
<223> OTHER INFORMATION: Artificial synthetic polypeptide sequence

<400> SEQUENCE: 36

Met Arg Ser Met Lys Leu Leu Gly Ala Leu Ala Leu Ala Ala Leu
 1               5                  10                  15

Leu Gln Gly Ala Val Ser Leu Lys Ile Ala Ala Phe Asn Ile Gln Thr
             20                  25                  30

Phe Gly Glu Thr Lys Met Ser Asn Ala Thr Leu Val Ser Tyr Ile Val
             35                  40                  45

Gln Ile Leu Ser Arg Tyr Asp Ile Ala Leu Val Gln Glu Val Arg Asp
         50                  55                  60

Ser His Leu Thr Ala Val Gly Lys Leu Leu Asp Asn Leu Asn Gln Asp
 65                  70                  75                  80

Ala Pro Asp Thr Tyr His Tyr Val Val Ser Glu Pro Leu Gly Arg Asn
                 85                  90                  95

Ser Tyr Lys Glu Arg Tyr Leu Phe Val Tyr Arg Pro Asp Gln Val Ser
            100                 105                 110
```

```
Ala Val Asp Ser Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Arg Thr Ser Pro Ala Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Gln Gly Ala Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
        275                 280
```

<210> SEQ ID NO 37
<211> LENGTH: 305
<212> TYPE: PRT
<213> ORGANISM: Artificial Sequence
<220> FEATURE:
<223> OTHER INFORMATION: Artificial synthetic polypeptide sequence

<400> SEQUENCE: 37

```
Met Ser Arg Glu Leu Thr Pro Leu Leu Leu Leu Leu Ser Ile His
1               5                   10                  15

Ser Thr Leu Ala Leu Arg Ile Cys Ser Phe Asn Val Arg Ser Phe Gly
            20                  25                  30

Glu Ser Lys Gln Glu Asp Gln Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190
```

```
Gly Cys Ser Tyr Val Pro Lys Lys Ala Trp Lys Asn Ile Arg Leu Arg
            195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Val Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
    275                 280                 285

Asn Ser Lys Lys Ser Val Thr Leu Arg Lys Lys Thr Lys Ser Lys Arg
    290                 295                 300

Ser
305

<210> SEQ ID NO 38
<211> LENGTH: 302
<212> TYPE: PRT
<213> ORGANISM: Homo sapiens

<400> SEQUENCE: 38

Met His Tyr Pro Thr Ala Leu Leu Phe Leu Ile Leu Ala Asn Gly Ala
1               5                   10                  15

Gln Ala Phe Arg Ile Cys Ala Phe Asn Ala Gln Arg Leu Thr Leu Ala
            20                  25                  30

Lys Val Ala Arg Glu Gln Val Met Asp Thr Leu Val Arg Ile Leu Ala
        35                  40                  45

Arg Cys Asp Ile Met Val Leu Gln Glu Val Val Asp Ser Ser Gly Ser
    50                  55                  60

Ala Ile Pro Leu Leu Leu Arg Glu Leu Asn Arg Phe Asp Gly Ser Gly
65                  70                  75                  80

Pro Tyr Ser Thr Leu Ser Ser Pro Gln Leu Gly Arg Ser Thr Tyr Met
                85                  90                  95

Glu Thr Tyr Val Tyr Phe Tyr Arg Ser His Lys Thr Gln Val Leu Ser
            100                 105                 110

Ser Tyr Val Tyr Asn Asp Glu Asp Val Phe Ala Arg Glu Pro Phe
        115                 120                 125

Val Ala Gln Phe Ser Leu Pro Ser Asn Val Leu Pro Ser Leu Val Leu
    130                 135                 140

Val Pro Leu His Thr Thr Pro Lys Ala Val Glu Lys Glu Leu Asn Ala
145                 150                 155                 160

Leu Tyr Asp Val Phe Leu Glu Val Ser Gln His Trp Gln Ser Lys Asp
                165                 170                 175

Val Ile Leu Leu Gly Asp Phe Asn Ala Asp Cys Ala Ser Leu Thr Lys
            180                 185                 190

Lys Arg Leu Asp Lys Leu Glu Leu Arg Thr Glu Pro Gly Phe His Trp
        195                 200                 205

Val Ile Ala Asp Gly Glu Asp Thr Thr Val Arg Ala Ser Thr His Cys
    210                 215                 220

Thr Tyr Asp Arg Val Val Leu His Gly Glu Arg Cys Arg Ser Leu Leu
225                 230                 235                 240

His Thr Ala Ala Ala Phe Asp Phe Pro Thr Ser Phe Gln Leu Thr Glu
                245                 250                 255
```

```
Glu Glu Ala Leu Asn Ile Ser Asp His Tyr Pro Val Glu Val Glu Leu
            260                 265                 270

Lys Leu Ser Gln Ala His Ser Val Gln Pro Leu Ser Leu Thr Val Leu
            275                 280                 285

Leu Leu Leu Ser Leu Leu Ser Pro Gln Leu Cys Pro Ala Ala
            290                 295                 300

<210> SEQ ID NO 39
<211> LENGTH: 299
<212> TYPE: PRT
<213> ORGANISM: Homo sapiens

<400> SEQUENCE: 39

Met Gly Gly Pro Arg Ala Leu Leu Ala Ala Leu Trp Ala Leu Glu Ala
1               5                   10                  15

Ala Gly Thr Ala Ala Leu Arg Ile Gly Ala Phe Asn Ile Gln Ser Phe
            20                  25                  30

Gly Asp Ser Lys Val Ser Asp Pro Ala Cys Gly Ser Ile Ile Ala Lys
            35                  40                  45

Ile Leu Ala Gly Tyr Asp Leu Ala Leu Val Gln Glu Val Arg Asp Pro
50                  55                  60

Asp Leu Ser Ala Val Ser Ala Leu Met Glu Gln Ile Asn Ser Val Ser
65                  70                  75                  80

Glu His Glu Tyr Ser Phe Val Ser Ser Gln Pro Leu Gly Arg Asp Gln
            85                  90                  95

Tyr Lys Glu Met Tyr Leu Phe Val Tyr Arg Lys Asp Ala Val Ser Val
            100                 105                 110

Val Asp Thr Tyr Leu Tyr Pro Asp Pro Glu Asp Val Phe Ser Arg Glu
            115                 120                 125

Pro Phe Val Val Lys Phe Ser Ala Pro Gly Thr Gly Glu Arg Ala Pro
            130                 135                 140

Pro Leu Pro Ser Arg Arg Ala Leu Thr Pro Pro Leu Pro Ala Ala
145                 150                 155                 160

Ala Gln Asn Leu Val Leu Ile Pro Leu His Ala Ala Pro His Gln Ala
            165                 170                 175

Val Ala Glu Ile Asp Ala Leu Tyr Asp Val Tyr Leu Asp Val Ile Asp
            180                 185                 190

Lys Trp Gly Thr Asp Asp Met Leu Phe Leu Gly Asp Phe Asn Ala Asp
            195                 200                 205

Cys Ser Tyr Val Arg Ala Gln Asp Trp Ala Ala Ile Arg Leu Arg Ser
            210                 215                 220

Ser Glu Val Phe Lys Trp Leu Ile Pro Asp Ser Ala Asp Thr Thr Val
225                 230                 235                 240

Gly Asn Ser Asp Cys Ala Tyr Asp Arg Ile Val Ala Cys Gly Ala Arg
            245                 250                 255

Leu Arg Arg Ser Leu Lys Pro Gln Ser Ala Thr Val His Asp Phe Gln
            260                 265                 270

Glu Glu Phe Gly Leu Asp Gln Thr Gln Ala Leu Ala Ile Ser Asp His
            275                 280                 285

Phe Pro Val Glu Val Thr Leu Lys Phe His Arg
            290                 295
```

DNASE THERAPY FOR INTRAVASCULAR ACCUMULATION OF EXTRACELLULAR DNA

PRIORITY

This Application is a continuation of U.S. application Ser. No. 16/929,980, filed Jul. 15, 2020, which is a continuation of U.S. application Ser. No. 16/856,943, filed Apr. 23, 2020, which is a continuation of U.S. application Ser. No. 16/530,141, filed Aug. 2, 2019 (now U.S. Pat. No. 10,696,956), which is a continuation of PCT/US2018/047084, filed Aug. 20, 2018, and which claims the benefit of, and priority to, US Provisional Application Nos. 62/611,166 filed Dec. 28, 2017 and 62/547,220 filed Aug. 18, 2017, each of which is hereby incorporated by reference in its entirety.

BACKGROUND OF THE INVENTION

Inflammation is an essential host response to control invading microbes and heal damaged tissues. Uncontrolled and persistent inflammation causes tissue injury in a plethora of inflammatory disorders. Neutrophils are the predominant leukocytes in acute inflammation. During infections neutrophils generate neutrophil extracellular traps (NETs), lattices of DNA-filaments decorated with toxic histones and enzymes that immobilize and neutralize bacteria. The relevance of NETs in host defense is illustrated by the fact that extracellular DNases serve as virulence factors in several pathogenic bacteria. However, inappropriately released NETs may harm host cells due to their cytotoxic, proinflammatory, and prothrombotic activity. Indeed, NETs are frequently associated with inflammatory or ischemic organ damage and the therapeutic infusion of DNases limits host injury in various animal models.

Extracellular trap (ET) formation is not limited to neutrophils as other leukocytes, namely monocytes, macrophages, basophils, eosinophils, and mast cells release ETs as well. Furthermore, cancer cells, including acute promyelocytic leukemia (APL) cells, and injured endothelial cells can expose DNA-filaments, which have ET-like features.

How the host degrades NETs in vivo to limit tissue damage during episodes of inflammation is poorly understood. DNase1 (D1) in serum has been shown to digest the DNA-backbone of NETs in vitro. Other extracellular DNases have been identified, including DNase1-like 3 (D1L3) in circulation, which can digest extracellular microparticle-associated chromatin.

D1 and D1L3 form along with DNase1-like 1 (D1L1) and DNase1-like 2 (D1L2) the DNase1-protein family, a group of homologous secreted DNase enzymes that are expressed in humans and provide drug candidates for NET-associated diseases. However, the physical, enzymatic, and pharmacokinetic properties of these enzymes are not ideal for therapy.

The present invention provides engineered DNases, including DNase1-like 3 and DNase1, for therapy, including for preventing or treating vascular occlusions that can result from release of NETs during acute inflammatory episodes.

SUMMARY OF THE INVENTION

The present invention provides engineered DNase proteins (including DNase1-like 3 and DNase1) that are useful for treating conditions characterized by neutrophil extracellular trap (NET) accumulation and/or release. In some aspects, the invention provides compositions and methods for preventing or treating vascular occlusion involving NETs. As demonstrated herein, NETs participate in a non-canonical mechanism for vascular occlusion, which is not dependent on fibrin and platelets.

In some aspects, the invention provides DNase1-like 3 (D1L3) variants engineered to have physical, pharmacodynamic, and/or enzymatic properties more suitable for therapy, for example, to reduce or prevent NET accumulation in a subject. In some embodiments, the D1L3 enzyme has advantages in manufacturing, providing for production of the recombinant enzyme suitable for use in therapy. In various embodiments, the invention provides a recombinant D1L3 variant comprising one or more amino acid alterations resulting in one or more glycosylations, inactivation of a nuclear localization signal, and/or deletion of all or part of a C-terminal tail.

In various embodiments, the D1L3 protein variant has increased protein stability, increased resistance towards inhibition by proteases, increased bioavailability, and substantially the same or better DNA and/or chromatin and/or NET-degrading activity (in vitro or in vivo) as compared to wild-type D1L3 protein. In various embodiments, the D1L3 variant comprises one or more of the following properties relative to wild type D1L3 (e.g., SEQ ID NO:2): the same or substantially the same (or higher) protein-free DNA (naked DNA) degradation activity, the same or substantially the same (or higher) chromosomal DNA (chromatin) degradation activity, protease resistance, an increased circulatory half-life, and higher production levels with in vitro expression systems (e.g. Chinese hamster ovary cells and/or *Pichia pastoris*).

In some embodiments, the D1L3 variant includes one or a plurality of block substitutions from human DNase1 (SEQ ID NO:1), described herein as building block substitutions.

In some aspects, the invention provides DNase1 (D1) variants engineered to have physical, pharmacodynamic, and/or enzymatic properties more suitable for therapy, for example, to reduce or prevent NET accumulation in a subject. In some embodiments, the D1 enzyme has advantages in manufacturing, providing for production of the recombinant enzyme suitable for use in therapy. In various embodiments, the engineered D1 variant comprises an amino acid sequence that is at least 80% identical to the mature enzyme of amino acid sequence of SEQ ID NO:1, with one or more amino acid substitutions, additions (including insertions), or deletions resulting in one or more of a mutated DNA binding site, a mutated chromatin binding site, a mutated actin binding site, a mutated glycosylation site, addition of a nuclear localization signal (e.g., having similarity or identity to NLS1 or NLS2 of D1L3), and/or a C-terminal domain similar to or identical to the C-terminal tail of D1L3.

In various embodiments, the D1 variant is engineered to comprise one or more of the following characteristics relative to the wild type enzyme: the same or higher protein-free DNA (naked DNA) degradation activity, higher chromosomal DNA (chromatin) degradation activity, similar or improved protease resistance, actin resistance, similar or improved penetration from blood into urine and/or bile, and higher production levels in vitro expression systems (e.g. Chinese hamster ovary cells and/or *Pichia pastoris*).

D1 variants described herein may have a combination of point mutations, including addition of cationic residues, and/or may comprise one or more block substitutions from D1L3 (SEQ ID NO:2). Such block substitutions are described herein, and termed "building block substitutions."

In some aspects, the invention provides pharmaceutical compositions comprising the D1L3 and/or D1 variants, or polynucleotides or vectors encoding the same, and a pharmaceutically acceptable carrier. In various embodiments, the composition is formulated for parenteral or pulmonary administration. In some embodiments, the composition is formulated for intravenous, intraarterial, intraperitoneal, intraarticular, intramuscular, topical, or subcutaneous administration. In some embodiments, the composition comprises both D1L3 and D1, which are each optionally engineered variants described herein. In some embodiments, the composition comprises a chimeric protein containing block sequences from both D1 and D1L3. Exemplary block substitutions between D1 and D1L3 are shown in FIG. 31.

In still other aspects, the invention provides a process for DNase enzyme engineering, by producing chimeric sequences. For example, in these aspects the method comprises providing a protein-protein alignment of donor and recipient DNase enzymes; identifying variable amino acid sequences for transfer ("building block"). The variable amino acid or amino acids are flanked by one or more conserved amino acids in the donor and recipient DNase enzymes (upstream and downstream of the building block). These building blocks can be swapped between recipient and donor proteins. The chimeric enzyme is then produced recombinantly.

In still other aspects, the invention provides a method of making a pharmaceutical composition for reducing or preventing neutrophil extracellular trap (NET) accumulation. In these embodiments, the invention employs a genetically modified mouse deficient in D1 and D1L3 activity, and heterologous expression of G-CSF polynucleotide (e.g., in hepatocyte cells) or inducing a sustained endogenous G-CSF expression (e.g. via repetitive administration of microbial compounds). This mouse model accumulates NETs and rapidly develops NET-related vascular occlusions. In these embodiments, the invention comprises administering a candidate NET inhibitor or candidate DNase enzyme (including a D1L3 or D1 variant in accordance with this disclosure) to the genetically-modified mouse, and selecting a NET inhibitor or DNase enzyme that reduces the accumulation of NETs. The selected inhibitor or enzyme is formulated for administration to a human patient.

In some aspects, the invention provides a method for treating a subject in need of neutrophil extracellular trap (NET) degradation. The method comprises administering a therapeutically effective amount of a D1L3 and/or D1, and/or variants thereof according to this disclosure. The D1L3 or D1 variant may be administered as pharmaceutical compositions comprising the recombinant protein, or in some embodiments the encoding DNA or RNA, or in some embodiments, vectors comprising the same.

In various embodiments, the present invention pertains to the treatment of diseases or conditions characterized by the presence or accumulation of NETs. Such diseases or conditions include, but are not limited to, diseases associated with chronic neutrophilia (e.g., an increase in the number of neutrophils), neutrophil aggregation and leukostasis, thrombosis and vascular occlusion (e.g. sickle cell disease), ischemia-reperfusion injury (e.g. midgut volvulus, testicular torsion, limb ischemia reperfusion, vital organ ischemia-reperfusion, organ transplantation), surgical and traumatic tissue injury, an acute or chronic inflammatory reaction or disease, an autoimmune disease (e.g. systemic lupus erythematosus (SLE), lupus nephritis, rheumatoid arthritis, vasculitis, systemic sclerosis), cardiovascular disease (e.g., myocardial infarction, stroke, atherosclerosis, venous thromboembolism, including thrombolytic therapy), metabolic disease (e.g., diabetes), systemic inflammation (e.g., systemic inflammatory response syndrome (SIRS), sepsis, septic shock, disseminated intravascular coagulation (DIC), and thrombotic microangiopathy (TMA)), inflammatory diseases of the respiratory tract (e.g. cystic fibrosis, chronic obstructive pulmonary disease (COPD), acute lung injury (ALI), smoke induced lung injury, transfusion induced lung injury (TRALI), acute respiratory distress syndrome (ARDS), and asthma, atelectasis, bronchitis, empyema), renal inflammatory diseases (acute and chronic kidney diseases, including acute kidney injury (AKI) and chronic kidney disease (CKD), inflammatory diseases related to transplanted tissue (e.g. graft-versus-host disease) and cancer (e.g. leukemia, tumor metastasis, and solid tumors).

In some embodiments, the subject has or is at risk of a ductal occlusion in a ductal system. Non-limiting examples of a ductal system or an organ or tissue containing a ductal system include bile duct, tear duct, lactiferous duct, cystic duct, hepatic duct, ejaculatory duct, parotid duct, submandicular duct, major sublingual duct, bartholin's duct, cerebral aqueduct, pancreas, mammary gland, vas deferens, ureter, urinary bladder, gallbladder, and liver. As such, the present invention is useful for treating a subject who has pancreatitis, cholangitis, conjunctivitis, mastitis, dry eye disease, an obstruction of the vas deferens, or renal disease.

In other embodiments, the subject has or is at risk of NETs accumulating on endothelial surfaces (e.g., surgical adhesions), the skin (e.g., wounds/scarring, uclers), or in synovial joints (e.g., gout, arthritis). For instance, NETs may contribute to surgical adhesions, e.g., after an invasive medical procedure. The present invention can be administered during surgery to prevent or inhibit the formation of surgical adhesions. In some instances, D1, D1L3 (including variants thereof), or the combination of D1 and D1L3 (or variants thereof) as outlined herein can be administered topically to the skin to prevent or treat wounds and/or scarring. In other instances, D1, D1L3, or variants, or the combinations thereof as outlined herein can be administered to synovial joints to prevent or treat gout and arthritis.

In some embodiments, the subject has or is at risk of a vascular occlusion comprising NETs.

In various embodiments, the present invention pertains to the treatment of diseases that are treatable with DNase enzyme, including D1 and streptodornase. Such diseases or conditions include thrombosis, stroke, sepsis, lung injury, atherosclerosis, viral infection, sickle cell disease, myocardial infarction, ear infection, wound healing, liver injury, endocarditis, liver infection, pancreatitis, primary graft dysfunction, limb ischemia reperfusion, kidney injury, blood clotting, alum-induced inflammation, hepatorenal injury, pleural exudations, hemotorax, intrabiliary blood clots, post pneumatic anemia, ulcers, otolaryngological conditions, oral infections, minor injuries, sinusitis, post-operative rhinoplasties, infertility, bladder catheter, wound cleaning, skin reaction test, pneumococcal meningitis, gout, leg ulcers, cystic fibrosis, Kartegener's syndrome, asthma, lobar atelectasis, chronic bronchitis, bronchiectasis, lupus, primary ciliary dyskinesia, bronchiolitis, empyema, pleural infections, cancer, dry eyes disease, lower respiratory tract infections, chronic hematomas, Alzheimer's disease, and obstructive pulmonary disease.

In still other embodiments, the invention provides a method for recombinant production of D1 or D1L3, or variants thereof, using a non-mammalian expression system, such as *Pichia pastoris*. In some embodiments, the *Pichia pastoris* encodes the DNase enzyme with the native signal peptide allowing for secretion from host cells.

Other objects, embodiments and advantages of the present invention are apparent in the Detailed Description below.

BRIEF DESCRIPTION OF THE DRAWINGS

FIG. 1A-FIG. 1F illustrate that DNase1 and DNase1l3 in circulation degrade NETs in vitro, and characterize DNA-degrading activity of sera from WT, DNase1−/− (D1−/−), DNase1l3−/− (D1L3−/−), DNase1/DNase1l3−/− (D1/D1L3−/−) mice. FIG. 1A provides detection of DNase1 (D1), DNase1l3 (D1L3), and total DNse activity by the zymographic assays DPZ and SRED. FIG. 1B provide images and FIG. 1C provide quantification of DNA-stainings of NETs generated in vitro after incubation with sera from indicated genotypes (N=6). Scale bar: 50 μm. FIG. 1C shows DPZ and SRED analysis of sera from D1/D1L3−/− mice stably expressing a plasmid with DNase1 (D1), DNase1l3 (D1L3), or a control plasmid (Ctrl). FIG. 1E shows images and FIG. 1F shows quantification of DNA-staining of NETs generated in vitro after incubation with buffer or sera from D1/D1L3−/− mice expressing D1, D1L3, or Ctrl (N=5). Scale bar: 50 μm. Images are representative of two or more independent experiments. Statistics: (FIG. 1C and FIG. 1F) one-way ANOVA followed by Bonferroni's multiple comparisons post test; § P<0.001 vs. all other groups.

FIG. 2A-FIG. 2I illustrate that DNase1 or DNase1l3 is required to tolerate chronic neutrophilia. Chronic neutrophilia was induced by injection of a G-CSF-expression plasmid (CSF3). Controls received an empty plasmid (Ctrl). FIG. 2A shows blood neutrophil count of WT mice and controls after 2 weeks (N=3-6). FIG. 2B shows NET-like structures (arrow) in DNA-stainings of blood smears from WT mice after 1 week (N=3). Scale bar: 20 μm. FIG. 2C shows survival of WT (N=7), DNase1−/− (D1−/−, N=6), DNase1l3−/− (D1L3−/−, N=6), DNase1/DNase1l3−/− mice (D1/D1L3−/−, N=6) and controls (Ctrl, N=4). FIG. 2D shows survival of D1/D1L3−/− mice co-expressing CSF3 with DNase1 (CSF3/D1, N=5), DNase1l3 (CSF3/D1L3, N=6), and controls (CSF3/Ctrl, N=4). FIGS. 2E-2I characterizes mortality during chronic neutrophilia (N=4). FIG. 2E shows change in peripheral body temperature. FIG. 2F provides photographs of plasma and urine. FIG. 2G provides concentration of hemoglobin in blood. FIG. 2H provides images of blood smears. Arrows point to schistocytes. Scale bar: 20 μm. FIG. 2I shows LDH concentration in plasma. UT: untreated mice (N=5-6). Images are representative of three or more mice. Statistics: (FIGS. 2A, 2H, 2I) one-way and (FIG. 2E) two-way ANOVA followed by Bonferroni's multiple comparisons post test, (FIG. 2B) student's t-test, (FIGS. 2C, 2D) Log-rank test; #P<0.01, § P<0.001 vs. all other groups or baseline (BL).

FIG. 3A-FIG. 3G illustrate that DNase1 and DNase1l3 prevent vascular occlusion by NET-clots during chronic neutrophilia. Histological analysis of DNase1/DNase1l3−/− mice (D1/D1L3−/−) co-expressing CSF3 with DNase1 (CSF3/D1, N=4), DNase1l3 (CSF3/D1L3, N=4), or a control plasmid (CSF3/Ctrl, N=4). FIG. 3A provides hematoxylin and eosin stainings (H&E) of lungs. Scale bars: 500 μm (overview), 25 μm (detail). FIG. 3B shows quantification of blood vessels in lungs occluded by hematoxylin-positive clots per field of view (FOV). Untreated WT mice (UTWT, N=4), untreated D1/D1L3−/− mice (UT; N=4). FIG. 3C shows immunostaining of occluded blood vessels for the neutrophil-marker myeloperoxidase (MPO) and chromatin. FIGS. 3D and 3E show immunostaining for von Willebrand factor (vWF), fibrin, and DNA. Three types of NET-clots were detected (α, vWF+/fibrin−; β, vWF+/fibrin+; γ, vWF−/fibrin−). FIG. 3F provides quantification of vWF and fibrin in NET-clots. Data shown as mean±SD, n=108. FIG. 3G shows survival of D1/D1L3−/− mice expressing CSF3 treated with IgG (N=4), anti-platelet-IgG (N=5), and dabigatran (N=5). Scale bars: 50 μm. Images are representative of three or more mice. (FIGS. 3C, 3D, 3E) dotted line indicates vessel wall. Statistics: (FIG. 3B) one-way ANOVA followed by Bonferroni's multiple comparisons post test; § P<0.001 vs. all other groups, (FIG. 3G) Log-rank test; P>0.05 Anti-Platelet-IgG or Dabigatran vs. IgG.

FIG. 4A-FIG. 4I illustrate that DNase1 and DNase1l3 protect against host injury in septicemia. WT mice (N=5) and mice with a combined deficiency in DNase1 and DNase1l3 (D1/D1L3−/−) expressing DNase1 (D1, N=7), DNase1l3 (D1L3, N=8), or a control plasmid (Ctrl, N=11) were treated with lipopolysaccharide and heat-killed E. coli to induce septicemia. FIG. 4A shows survival time of septic mice. FIG. 4B shows concentration of hemoglobin in blood. FIG. 4C shows photographs of plasma and urine. FIG. 4D provides LDH concentration in plasma. FIG. 4E shows quantification of schistocytes in blood per field of view (FOV). FIG. 4F shows quantification of occluded blood vessels in lungs per FOV. FIG. 4G shows hematoxylin and eosin stainings (H&E) of lungs. Arrowheads point to occluded blood vessels. Scale bars: 500 μm. FIGS. 4H and 4I show H&E staining of partially and fully occluded blood vessel. Arrows point to NETs covering the intercellular space. Inserts are overviews. Scale bars: 50 μm. Statistics: (FIG. 4A) Log-rank test; #P<0.01 vs. all other groups, (FIGS. 4B-4F) one-way ANOVA followed by Bonferroni's multiple comparisons post test; § P<0.001, #P<0.01.

FIG. 5A-FIG. 5E show a murine model of chronic neutrophilia. Four-week old WT mice were injected with a CSF3-expression plasmid (CSF3) or with an empty control plasmid (Ctrl). FIG. 5A shows G-CSF levels in plasma (N=3-6). BL: baseline, before injection; Ctrl: mice expressing the control plasmid without CSF3 for 2 weeks (N=4-5). FIG. 5B shows immunostaining for neutrophil elastase of lungs, kidneys, and livers. Scale bars: 200 μm. FIG. 5C shows photographs and weights of spleens (N=5-6). Scale bar: 1 cm. FIG. 5D shows body weight of mice at indicated times (N=3-5). FIG. 5E shows neutrophil counts in whole blood and plasma levels of ALT, AST, BUN, and creatinine 2 weeks after the injection. Images are representative of three or more mice. Statistics: (FIGS. 5A, 5C) one-way and (FIG. 5D) two-way ANOVA followed by Bonferroni's multiple comparisons post test, and (FIG. 5E) Student's t-test; #P<0.01, § P<0.001 vs. (FIG. 5A) BL, or (FIG. 5C) UT.

FIG. 6A-FIG. 6D show that DNase1 and DNase1l3 prevent the formation of NET-clots and organ injury in liver and kidneys during chronic neutrophilia. Analysis of DNase1/DNase1l3−/− mice (D1/D1L3−/−) co-expressing CSF3 a control plasmid (CSF3/Ctrl, N=4), with DNase1 (CSF3/D1, N=4), or with DNase1l3 (CSF3/D1L3, N=4). Controls include untreated WT mice (UTWT, N=4) and untreated D1/D1L3−/− mice (UT; N=4). FIG. 6A shows plasma levels of alanine and aspartate aminotransferases (ALT, AST). FIG. 6B shows plasma levels of blood urea nitrogen (BUN) and creatinine. FIG. 6C provides quantification of intravascular hematoxylin-rich clots in livers per section and in kidneys per field of view (FOV). FIG. 6D provides H&E stainings of livers and kidneys. Scale bars: 500 μm (overviews), 50 μm (detail). Images are representative of three or more mice. Statistics: (FIGS. 6A, 6B, 6C) one-way ANOVA followed by Bonferroni's multiple comparisons post test; #P<0.01, § P<0.001 vs. all other groups.

FIG. 7A-FIG. 7C show hematoxylin-positive clots are composed of NETs. Analysis of lungs from DNase1/DNase1l3−/− mice (D1/D1L3−/−) with chronic neutrophilia (D1/D1L3−/−+CSF3/Ctrl) shown in FIGS. 3A-3G. FIG. 7A provides staining with hematoxylin and eosin (H&E), for DNA, and for chromatin of consecutive lung sections. Scale bars: 200 µm. FIG. 7B provides immunostaining of occluded blood vessel for chromatin, CRAMP (cathelin-related antimicrobial peptide), and DNA. Scale bars: 50 µm. FIG. 7C provides immunostaining of occluded blood vessel for chromatin, citrullinated histone 3 (citH3), and DNA. Scale bars: 50 µm. Images are representative of three or more mice.

FIG. 8A and FIG. 8B show that human NETs form clots in vitro. FIG. 8A provides a photograph of NET-clot (arrow) generated by PMA-activated human neutrophils in vitro. Untreated neutrophils (UT) or neutrophils activated in the presence of recombinant human DNase1 (PMA+D1) served as controls. Scale bars: 5 mm. FIG. 8B provides hematoxylin and eosin stainings (H&E) and immunostaining for chromatin and the neutrophil-marker myeloperoxidase (MPO) of in vitro generated NET-clots. Scale bars: 200 µm. Images are representative of three or more independent experiments.

FIG. 9A and FIG. 9B show NET-degradation correlates with disease activity in STEC-HUS. FIG. 9A shows images and FIG. 9B shows quantification of DNA-staining of NETs generated in vitro after incubation with buffer, plasma from normal healthy donors (N=7), or plasma collected in the acute disease state (Acute) and in remission (Rem.) of 11 patients with STEC-HUS. Scale bar: 50 µm. Statistics: one-way ANOVA followed by Bonferroni's multiple comparisons post test; § $P<0.001$ vs. all other groups.

FIG. 10 provides a table of descriptions of human tissue from various patients examined, such as patient number, cause of death as indicated in the autopsy report (ARDS, acute respiratory distress syndrome). Sex and age of the patient. Type of analyzed tissue. The tissues was analyzed in a three step procedure: first, identification of hematoxylin-rich clots/aggregates in hematoxylin & eosin stainings; second, identification of NETs in hematoxylin-rich clots by immunostaining for chromatin & myeloperoxidase (MPO); third, identification of the localization of the NET-clots within the lung architecture.

FIG. 11A-FIG. 11D show human NETs form clots in situ. Lung tissue collected at autopsy from two patients with sepsis (Patient #6 and #7 in FIG. 10). FIG. 11A shows H&E staining of two hematoxylin-rich intravascular clots in lung tissue from patient #6. FIG. 11B shows immunostaining of consecutive section for chromatin and myeloperoxidase (MPO) of left blood vessel shown in panel A. FIG. 11C shows H&E staining blood vessel in lung tissue from patient #7 shows hematoxylin-rich intravascular clots. FIG. 11D shows immunostaining of consecutive section for chromatin and MPO. Arrows point to clots of NETs. Scale bar: 50 µm.

FIG. 13A-FIG. 13F shows that DNase1 and DNase1l3 degrade NETs by distinct mechanisms. FIG. 13A provides DNA-stainings of PFA-fixed NETs generated in vitro after incubation with sera from WT, DNase1−/− (D1−/−), DNase1l3−/− (D1L3−/−), DNase1/DNase1l3−/− mice (D1/D1L3−/−). Data are representative of independent experiments. Scale bar: 50 µm. FIG. 13B shows the concentration of cell-free DNA fragments released from PFA-fixed NETs after incubation with sera from WT, D1−/−, D1L3−/−, and D1/D1L3−/− mice. FIG. 13C shows DNA-stainings of non-fixed NETs generated in vitro after incubation with vehicle, recombinant murine DNase1 (rmD1), or recombinant murine DNase1l3 (rmD1L3). FIG. 13D shows the concentration of cell-free DNA fragments released from non-fixed NETs generated in vitro after incubation with vehicle, rmD1, or rmD1L3. FIG. 13E shows DNA-stainings of PFA-fixed NETs generated in vitro after incubation with vehicle, rmD1, or rmD1L3. FIG. 13F shows the concentration of cell-free DNA fragments released from PFA-fixed NETs generated in vitro after incubation with vehicle, rmD1, or rmD1L3. Statistics by one-way ANOVA followed by Bonferroni's multiple comparisons post test; § $P<0.0001$.

FIG. 14A-FIG. 14E show DNase activity in human and murine plasma quantified by SRED. FIG. 14A illustrates supplementation of plasma from normal healthy donors (NHD) with polyclonal antibodies against human DNase1 (α-hDNase1), but not with IgG, blocks the DNA degrading activity in a concentration-dependent manner (*: $p<0.05$ vs. IgG). FIG. 14B shows plasma supplemented with 200 µg/ml α-hDNase1 and heparin, an inhibitor of DNase1l3, blocks residual DNase activity in plasma supplemented with 200 µg/ml α-hDNase1 (*: $p<0.05$ vs. NHD). FIG. 14C-FIG. 14E provide a comparison of DNase activity in serial dilutions of plasma from mice and NHD. FIG. 14C illustrates that total DNase activity of WT mice is approximately 10-times higher than in NHD. FIG. 14D shows DNase1 activity in plasma from DNase1l3−/− mice is approximately 10-fold higher than human plasma supplemented with 500 µg/ml heparin. (E DNase1l3 activity in plasma from DNase1−/− mice is approximately 10-fold higher than human plasma supplemented with 200 µg/ml α-hDNase1. (F, G) In vitro NET-degradation is illustrated in FIG. 14F and FIG. 14G. FIG. 14F shows activated neutrophils incubated with plasma from NHD alone or supplemented with 200 µg/ml α-hDNase1, plasma from TMA patients, and plasma from WT, DNase1−/−, and DKO mice (Scale bars: 200 µm). FIG. 14G shows cell-free DNA in supernatants of activated neutrophils incubated with plasma from indicated sources (§: $p<0.001$ vs. NHD). In vitro NET-degradation by human plasma is dependent on DNase1 as DNase1l3 in human plasma is not sufficient to degrade NETs.

FIG. 15A-FIG. 15C show a lethal course of chronic neutrophilia in an alternative strain of DNase1/DNase1l3−/− mice. An alternative strain of DNase1−/− mice (see Methods of Example 1) was crossed with DNase1l3−/− mice to generate mice with a combined deficiency. FIG. 15A provides survival curves of neutrophilia in WT (N=9), DNase1−/− (D1−/−, N=5), and DNase1/DNase1l3−/− mice (D1/D1L3−/−, N=5). Chronic neutrophilia was induced by injection of a CSF3-expression plasmid (CSF3). FIG. 15B provides hematoxylin and eosin stainings (H&E) of lung sections. Arrow points to hematoxylin positive clots in D1/D1L3−/− mice. Scale bar: 500 µm. FIG. 15C provides survival of D1/D1L3−/− mice coexpressing CSF3 with a control plasmid (CSF3/Ctrl, N=6), with DNase1 (CSF3/D1, N=5), or with DNase1l3 (CSF3/D1L3, N=6). Statistics: Log-rank test; § $P<0.001$.

FIG. 16A-FIG. 16B show the screening approach to identify hyperactive variants of DNase1 and DNase1L3 in vitro. FIG. 16A shows a library of DNases included wild-type DNase1L3 (I, D1L3), wild-type DNase1 (II, D1), and variants thereof. D1 and D1L3 variants were designed by transferring amino acids from D1L3 to D1 (III, D1$^V$) and D1 to D1L3 (IV, D1L3$^V$). DNase activity was tested using the degradation of high-molecular weight (HMW) DNA, dsDNA and chromatin, as a substrate. In FIG. 16B, zymography showed dsDNA degrading activity as dark circles. The dsDNA degrading activity correlates with the diameter. Samples without activity show the loading well as small black spot (e.g. D1, 0.0005 ng). D1 degrades dsDNA approximately 100-fold more efficiently than D1L3. Agarose gel electrophoresis (AGE) of DNA isolated from digested chromatin shows a shift from high-molecular weight DNA to lower or low-molecular weight DNA that correlates with chromatin degrading activity. D1L3 degrades chromatin approximately 100-fold more efficiently than D1. At a ratio of 10:1 or 1:1 (m/m), D1 and D1L3 show synergistic effects in the degradation of chromatin.

FIG. 18 shows a list of arginine- and lysine-residues that are present in DNase1L3 only. The corresponding amino acid in DNase1 and amino acid substitution in DNase1 are indicated. Numbers in brackets are the amino acid position in the mature protein without signal peptide. Arginine- and lysine-residues that are located in the C-terminal tail of D1L3 are shown in lanes 29-37. This application tested 22 of the 37 possible DNase1 variants.

(FIG. 21A) Zymography show dsDNA degrading activity as dark circles. The dsDNA degrading activity correlates with the diameter. Samples without activity show the loading well as small black spot (e.g. Ctrl). Murine DNase1 (mD1) and human DNase1 (D1) show similar levels of dsDNA degrading activity. Agarose gel electrophoresis (AGE) of DNA isolated from digested chromatin shows a shift from high-molecular weight DNA to lower or low-molecular weight DNA that correlates with chromatin degrading activity. Murine DNase1 (mD1) shows more chromatin degrading activity than human DNase1 (D1). (FIG. 21B) Gene therapy with human DNase1 provides only partial protection from lethal vascular occlusion by NETs. Chronic neutrophilia with concomitant intravascular NET-formation was induced as by hepatic expression of Csf3, which encodes with G-CSF. The data show the survival curve of Csf3-expressing Dnase1$^{-/-}$Dnase1l3$^{-/-}$ mice. Animals were injected with Csf3 and an empty control vector (Ctrl, N=6), with a mixture of Csf3 and human DNase1 (hDnase1, N=12), and with Csf3 and murine DNase1 (mDnase1, N=5). P-values were calculated using log-rank test.

(FIG. 20A) Gene therapy with rodent-like DNase1-variants provides full protection from lethal vascular occlusion by NETs. Chronic neutrophilia with concomitant intravascular NET-formation was induced as by hepatic expression of Csf3, which encodes with G-CSF. The data show the survival curve of Csf3-expressing Dnase1$^{-/-}$Dnase1l3$^{-/-}$ mice. Animals were injected with Csf3 and an empty control vector (Ctrl, N=6), with a mixture of Csf3 and human DNase1 (hDnase1, N=12) as shown in FIG. 21. A third group of Dnase1$^{-/-}$Dnase1l3$^{-/-}$ mice received an injection with Csf3 and the gene encoding with murine-like DNase1-variant, which contains 4 amino acid mutations Q31R/Q49K/Q79R/W209R (Q31R/Q49K/Q79R/W209R, N=6). A fourth group of Dnase1$^{-/-}$Dnase1l3$^{-/-}$ mice received an injection with Csf3 and the gene encoding with rat-like DNase1-variant, which contains 6 amino acid mutations Q31R, Q49K, Q79R, Q177K, W209R, and G262K (Q31R/Q49K/Q79R/Q177K/W209R/G262K, N=6). P-values were calculated using log-rank test. (FIG. 22B) Zymography showed dsDNA degrading activity as dark circles. The dsDNA degrading activity correlates with the diameter. Samples without activity show the loading well as small black spot (e.g. Ctrl). Agarose gel electrophoresis (AGE) of DNA isolated from digested chromatin shows a shift from high-molecular weight DNA to lower or low-molecular weight DNA that correlates with chromatin degrading activity. The murine-like variant of human DNase1 (Q31R/Q49K/Q79R/W209R), and the rat-like variant of human DNase1 (Q31R/Q49K/Q79R/Q177K/W209R/G262K) show similar dsDNA but more chromatin degrading activity than wild-type human DNase1.

(FIG. 24A) Culture supernatants of transfected HEK293 cells were analyzed. HEK cells transfected with wild type DNase1 (D1) and DNase1L3 (D1L3) served as controls. Zymography showed dsDNA degrading activity as dark circles. The dsDNA degrading activity correlates with the diameter. Samples without activity show the loading well as small black spot (e.g. Ctrl). Agarose gel electrophoresis (AGE) of DNA isolated from digested chromatin shows a shift from high-molecular weight DNA to lower or low-molecular weight DNA that correlates with chromatin degrading activity. The D1$^V$ that features three amino acid mutations Q31R/T227K/A136F has similar dsDNA degrading activity, but a greater capacity to degrade chromatin than D1 and D1$^V$ featuring Q31R, T227K, A136F, or Q31R/T227K. (FIG. 24B) Gene therapy with a hyperactive D1$^V$ provides full partial protection from lethal vascular occlusion by NETs. Chronic neutrophilia with concomitant intravascular NET-formation was induced as by hepatic expression of Csf3, which encodes with G-CSF. The data show the survival curve of Csf3-expressing Dnase1$^{-/-}$Dnase1l3$^{-/-}$ mice. Animals were injected with Csf3 and an empty control vector (Ctrl, N=6), with a mixture of Csf3 and human DNase1 (hDnase1, N=12) as shown in FIG. 21. In addition, a group of Dnase1$^{-/-}$Dnase1l3$^{-/-}$ mice received an injection with Csf3 and the gene encoding with a human DNase1-variant, which contains the triple amino acid mutation Q31R/T227K/A136F (Q31R/T227K/A136F, N=6). P-values were calculated using log-rank test.

(FIG. 26A) Amino acid sequence alignment of human DNase1 (SEQ ID NO: 1) and human DNase1L3 (SEQ ID NO: 2). Sequence rulers demark the amino acid positions. Critical arginine residues in DNase1L3 are highlighted. Shared amino acids between DNase1 and DNase1L3 are highlighted and serve as anchors to replace the amino acids sequence ATP of DNase1 with VKKS of DNase1L3. (FIG. 26B) Zymography showed dsDNA degrading activity as dark circles. The dsDNA degrading activity correlates with the diameter. Samples without activity show the loading well as small black spot (e.g. Ctrl). The gel was loaded with wild-type DNase1 (D1), DNase1 variants (D1$^V$) that feature the mutations A226_T227insK, T227K, and A226_P228delinsVKKS. A226_T227insK, but not A226_P228delinsVKKS, is associated with a reduced dsDNA degrading activity.

FIG. 29 shows the concept of building block engineering of homologous proteins. The technology transfers single or multiple variable amino acids, which are flanked by conserved single or multiple variable amino acids, between a donor and recipient protein.

Figure 30:
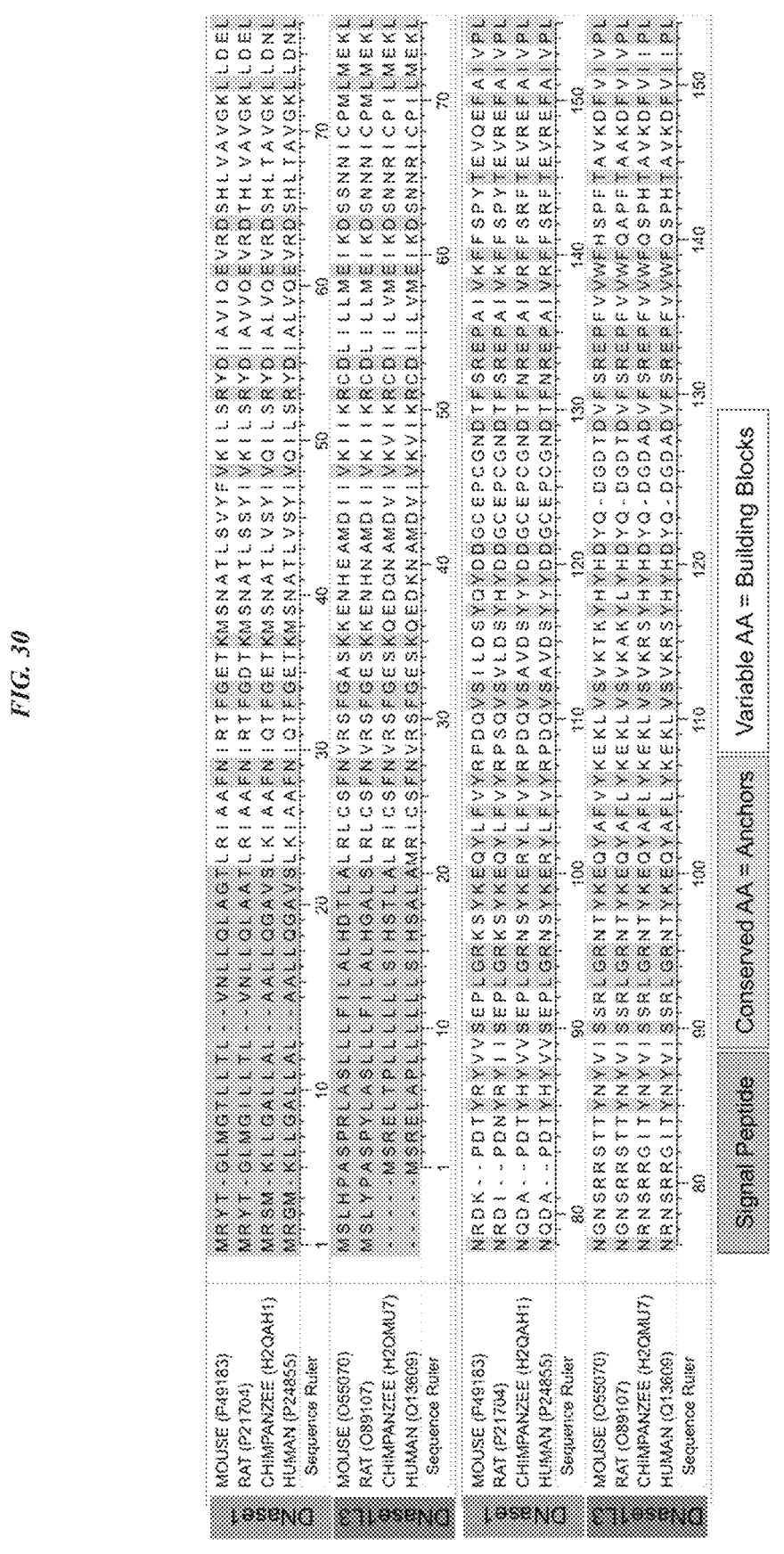
Figure 30:
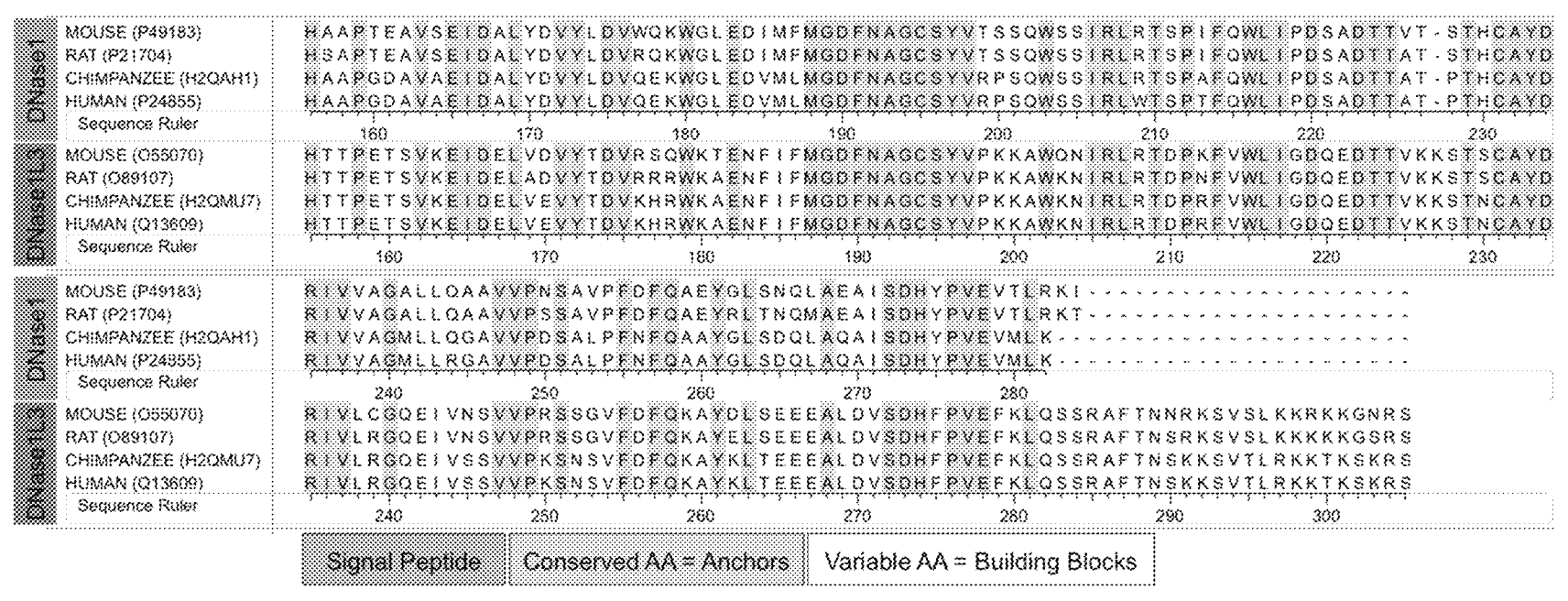

FIG. 30 shows an amino acid sequence alignment of DNase1 and DNase1L3 of mouse (SEQ ID NOS: 3 and 34), rat (SEQ ID NOS: 4 and 35), chimpanzee (SEQ ID NOS: 36 and 37), and human (SEQ ID NOS: 1 and 2). The N-terminal signal peptide and conserved amino acids are highlighted. Variable amino acids are not highlighted and serve as Building Blocks that can be transferred from DNase1 to DNase1L3 and vice versa. Abbreviations: AA, amino acid.

FIG. 31A-FIG. 31B show lists of Building Blocks in human DNase1 (D1) and human DNase1L3 (D1L3). FIG. 31A shows amino acids that are conserved in D1 and D1L3, which serve as N- and C-anchors, respectively. Building blocks are variable amino acids in D1 and D1L3. Mutations that transfer Building Blocks from D1L3 to D1 are shown. FIG. 31B shows N- and C-anchors in D1L3. Mutations that transfer Building Blocks from D1 to D1L3 are listed. AA: amino acid.

FIG. 32 shows an application of the building block engineering of homologous proteins. The application uses as an initial screening step, the transfer of clusters of building blocks between a homologous donor and recipient protein. Additional optional steps are the transfer of individual building blocks, followed by the transfer of individual amino acids. In a final step (not shown), multiple amino acids, building blocks, and building block clusters may be combined to degenerate a chimeric enzyme.

FIG. 34A shows an amino acid sequence alignment of human DNase1 (SEQ ID NO: 1) and human DNase1L3 (SEQ ID NO: 2). Sequence rulers demark the amino acid positions. The C-terminal tail of DNase1L3 is highlighted and its nuclear localization signal is boxed. Shared amino acids between DNase1 and DNase1L3 are indicated. Amino acids located after the conserved SDH motive were exchanged the building block cluster 60-62 between DNase1 and DNase1L3. FIG. 34B shows zymography showing dsDNA degrading activity as dark circles. The dsDNA degrading activity correlates with the diameter. Samples without activity show the loading well as small black spot (e.g. Ctrl). Agarose gel electrophoresis (AGE) of DNA isolated from digested chromatin shows a shift from high-molecular weight DNA to lower or low-molecular weight DNA that correlates with chromatin degrading activity. The gels were loaded with wild-type DNase1 (D1), DNase1 variant (D1$^V$) that features the BB cluster 60-62 from D1, DNase1L3 variant (D1L3$^V$) that features the BB cluster 60-62 from D1, and a D1L3$^V$ with two mutations (K301A, K303A) were made to inactivate the NLS2. D1L3$^V$ with BB cluster 60-62 from D1 showed increased chromatin degrading activity compared to wild-type D1L3.

FIG. 35A shows the amino acid sequence alignment of human DNase1 (SEQ ID NO: 1) and human DNase1L3 (SEQ ID NO: 2). Sequence rulers demark the amino acid positions. The glycosylation motives N40-X-T42 and N128-X-T130 of DNase1 are highlighted. The sites are part of building block (BB) 4 and building block cluster (BB) 23-25. Relevant shared amino acids between DNase1 and DNase1L3 are highlighted. (FIG. 35B) Zymography showed dsDNA degrading activity as dark circles. The dsDNA degrading activity correlates with the diameter. Samples without activity show the loading well as small black spot (e.g. Ctrl). Agarose gel electrophoresis (AGE) of DNA isolated from digested chromatin shows a shift from high-molecular weight DNA to lower or low-molecular weight DNA that correlates with chromatin degrading activity. The gels were loaded with wild-type DNase1L3 (D1L3), DNase1L3 variant (D1L3$^V$) that features BB 4 from D1, and DNase1L3 variant (D1L3$^V$) that features the BB cluster 23-25 from D1. A Western Blot (WB) with antibodies against D1L3 detected that D1L3$^V$ showed increased amounts of larger proteins. Both glycosylated DNase1L3 variants (D1L3$^V$) retained their capacity to degrade chromatin.

FIG. 36A-FIG. 36F shows the therapeutic effect of DNase1L3 (SEQ ID NO: 2) and a variant thereof (SEQ ID NO: 17) against NETs in vivo. FIG. 36A shows an H&E staining of a mouse heart with a hematoxylin-rich and dense clot of NETs within a cardiac chamber. FIG. 36B shows a time line starting with the induction of NETs, leading to vascular occlusion by NETs and death. Hematuria and hypothermia are external signs for in vivo NET-clots. (FIG. 36C) Outline of the experimental design: Csf3 was expressed in DNase1$^{-/-}$Dnase1l3$^{-/-}$ to induce vascular clots of NETs. Mice that showed hematuria and hypothermia were randomized by an injection of vehicle (N=3), dornase alpha (D1, N=3), purified DNase1L3 (D1L3, N=3), or a purified DNase1L3 variant (SEQ ID NO: 17, D1L3$^V$, N=3). After 30 minutes lungs and serum were collected. The therapy with D1L3 or D1L3$^V$, but not saline or D1, significantly reduced vascular occlusion by NETs in lungs (FIG. 36D) and increased the levels of DNA in serum (FIG. 36E). FIG. 36F shows oligo-nucleosomes in the serum from mice receiving the D1L3 therapy. Mice receiving D1L3$^V$ showed smaller mono- and di-nucleosomes. DNA isolates from serum of mice receiving D1 therapy showed faint DNA smears of various sizes, whereas no DNA could be isolated from serum of mice injected with vehicle.

FIG. 37A-FIG. 37C shows the therapeutic effect of a DNase1L3 variant (SEQ ID NO: 17) in a rat model of ischemia-reperfusion (IR) injury. (FIG. 37A) Outline of the experimental design: One testicle of male wild-type rats was subjected to testicular torsion. The procedure causes an ischemic tissue injury. Mice were randomized. A de-torsion of the testicle was performed, followed by an injection of vehicle (N=6), dornase alpha (D1, N=6), or a purified DNase1L3 variant (SEQ ID NO: 17, D1L3$^V$, N=6). The untreated and the ischemic testicle were collected after 7 days. FIG. 37B shows that the therapy with the D1L3$^V$, but not saline or D1, significantly reduced atrophy in the ischemic testicle. FIG. 37C quantified the macroscopic tissue injury. All untreated testicles are brownish and vascularized, indicating healthy tissue (Ctrl, Score: 0). Testicular torsion followed by reperfusion damaged tissue, which appeared whitish (IR, Score: 4). Therapy with the D1L3$^V$, but not saline or D1, substantially reduced the tissue injury and 4/6 testicles showed no signs of injury. Scale bar: 1 cm.

(FIG. 38B) Robust expression of D1L3 and D1L3$^V$ was achieved in *Pichia pastoris*. (FIG. 38C) Zymography showed dsDNA degrading activity as dark circles. The dsDNA degrading activity correlates with the diameter. Samples without activity show the loading well as small black spot (e.g. D1L3, 0.0005 ng). Agarose gel electrophoresis (AGE) of DNA isolated from digested chromatin shows a shift from high-molecular weight DNA to lower or low-molecular weight DNA that correlates with chromatin degrading activity. D1L3$^V$ degrades chromatin approximately 10-fold more efficiently than D1L3.

FIG. 39 illustrates certain DNase variants in accordance with this disclosure. The amino acid mutations in DNase1 and DNase1L3 with signal peptide as well as the mature proteins without signal peptide are listed. Mutations that were generated using Building Block Engineering are marked with "+" and the Building Blocks are indicated in brackets.

DETAILED DESCRIPTION OF THE INVENTION

Figure 12:
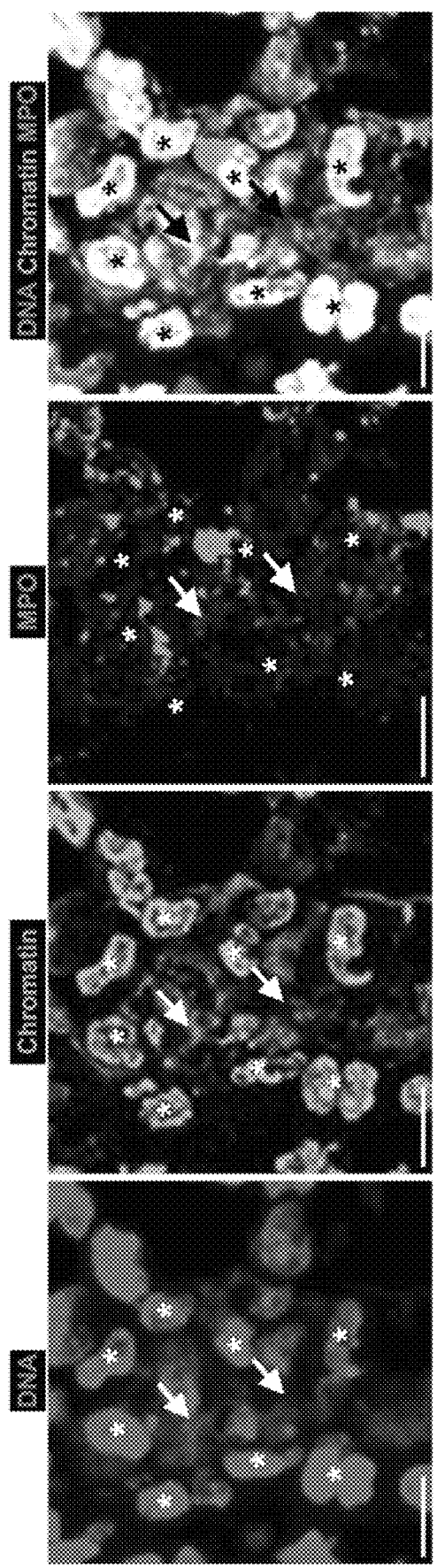
FIG. 12 shows NET-clots occlude blood vessels in septic mice. Immunostaining of fully occluded blood vessel in septic DNase1/DNase1l3−/− mice for DNA, chromatin and myeloperoxidase (MPO). DNA and chromatin stainings of NETs (arrows) appear dimmer than nuclear stainings (asterisks) and cover the intercellular space. Scale bars: 10 µm.

The present invention provides engineered DNase proteins, members of the DNase1-protein family (including DNase1-like 3 and DNase1) that are useful for treating conditions characterized by neutrophil extracellular trap (NET) accumulation and/or release. In some aspects, the invention provides compositions and methods for preventing or treating vascular occlusion involving NETs. As demonstrated herein, NETs participate in a non-canonical mechanism for vascular occlusion, which is not dependent on fibrin and platelets.

As used herein, the term "neutrophil extracellular trap" or "NET" refers to any extracellular trap ("ET") comprising extracellular DNA formed by cells such as, but not limited to, neutrophils, monocytes, macrophages, basophils, eosinophils, mast cells, cancer cells, injured cells (e.g., injured endothelial cells), and the like. Unless the context indicates otherwise, the terms NET and ET are used interchangeably herein.

There are two extracellular DNase enzymes found in the circulation of humans and mice, DNase1 (D1) and DNase1-like 3 (D1L3). These enzymes can be deficient in their ability and mechanism to degrade NETs in vitro and in vivo, and are found at relatively low concentrations in humans and mice. The natural enzymes do not have ideal physical, enzymatic, and/or pharmacodynamic properties for recombinant therapy, and particularly for systemic therapy.

D1 and D1L3 belong, along with DNase1-like 1 (D1L1) and DNase1-like 2 (D1L2), to the DNase1-protein family. D1 and D1L3 are expressed in a variety of species including, humans, primates, and rodents. In humans and mice, D1 and D1L3 show a protein similarity of 49-52%. However, despite their homology, D1 and D1L3 differ in cellular origin, sensitivity towards inhibitors, and substrate affinity. D1 preferentially cleaves protein-free DNA (e.g. bacterial DNA, plasmid DNA), whereas D1L3 targets chromatin, the complex of DNA and histones, which is commonly found in the nucleus of eukaryotic cells. D1 activity is inhibited upon binding to monomeric actin and sensitive to physiological salt concentrations. In addition, D1 is glycosylated at N40 (corresponds to N18 in the mature enzyme without signal peptide) and N128 (N106), which makes the enzyme resistant to inactivation by serum proteases. In contrast, D1L3 lacks glycosylation and actin-binding sites, which causes its susceptibility towards several proteases and resistance towards actin, respectively.

In some aspects, the invention provides D1L3 variants engineered to have physical, pharmacodynamic, and/or enzymatic properties more suitable for therapy, for example, to reduce or prevent NET accumulation in a subject. In various embodiments, the invention provides a recombinant D1L3 protein variant comprising: one or more glycosylations, one or more amino acid alterations resulting in increased substrate affinity, inactivation of a nuclear localization signal, deletion of all or part of a C-terminal tail, pegylation, and fusion to a carrier protein or moiety. In various embodiments, the D1L3 variant has increased protein stability, increased protease-resistance, increased bioavailability, increased half-life in circulation, and/or substantially the same or better DNA and/or chromatin and/or NET-degrading activity, higher production levels with in vitro expression systems (e.g. Chinese hamster ovary cells and/or *Pichia pastoris*) as compared to wild-type D1L3 protein of SEQ ID NO:2.

In various embodiments, the D1L3 variant comprises an amino acid sequence with at least 80% sequence identity to the enzyme defined by the amino acid sequence of SEQ ID NO:2, with one or more amino acid modifications with respect to SEQ ID NO:2 as described herein. In some embodiments, D1L3 variant comprises an amino acid sequence with at least 90%, or at least 95%, or at least 97%, or at least 98% sequence identity with the DNase enzyme defined by SEQ ID NO:2.

As used herein, when referring to sequence identity with wild-type DNase enzymes, and unless stated otherwise, sequences refer to mature enzymes lacking the signal peptide. Further, unless stated otherwise, amino acid positions are numbered with respect to the full translated DNase sequence, including signal peptide, for clarity. Accordingly, for example, reference to sequence identity to the enzyme of SEQ ID NO:2 refers to a percent identity with the mature enzyme having M21 at the N-terminus. Similarly, reference to sequence identity to the enzyme of SEQ ID NO:1 (human D1) refers to a percent identity with the mature enzyme having L23 at the N-terminus.

The similarity of nucleotide and amino acid sequences, i.e. the percentage of sequence identity, can be determined via sequence alignments as known in the art. Such alignments can be carried out with several art-known algorithms, such as with the mathematical algorithm of Karlin and Altschul (Karlin & Altschul (1993) *Proc. Natl. Acad. Sci. USA* 90: 5873-5877), with hmmalign (HMMER package, on the world wide web at hmmer.wustl.edu/) or with the CLUSTAL algorithm (Thompson, J. D., Higgins, D. G. & Gibson, T. J. (1994) Nucleic Acids Res. 22, 4673-80). Exemplary algorithms are incorporated into the BLASTN and BLASTP programs of Altschul et al (1990) *J. Mol. Biol.* 215: 403-410. When utilizing BLAST programs, the default parameters of the respective programs are used.

In some embodiments, the recombinant D1L3 protein variant comprises one or more glycosylation consensus sequences, e.g., NX(T/S). The human wild type enzyme (SEQ ID NO:2) does not contain a consensus glycosylation sequence. However, engineering a glycosylation consensus sequence into D1L3 can provide for glycosylation (and protease resistance) without substantial impact on the enzyme activity. In some embodiments, the glycosylation consensus sequence includes a D38N substitution and an N40T or N40S substitution, and/or an A127N substitution and a V129T or V129S substitution from the wild type sequence (e.g., SEQ ID NO:2). In some embodiments, the recombinant D1L3 enzyme has one, two, three, or four glycosylation sites. The consensus sequence can be introduced into the protein at a location that does not affect its enzymatic activity, and in some embodiments is located near portions of the enzyme that are important for maintaining structure of the enzyme (e.g., such as within amino acids 25 to 289, and in some embodiments, within amino acids 24 to 150).

In some embodiments, the invention provides a DNase enzyme comprising an amino acid sequence that is at least 80% identical to the amino acid sequence of the enzyme defined by SEQ ID NO:2, wherein the enzyme has a substitution of asparagine at the position corresponding to position 38 and/or position 127 of SEQ ID NO:2, and the N38 and/or N127 is glycosylated. In some embodiments, the substitution at position 38 and/or 127 is made via a building block substitution from SEQ ID NO:1 as described herein.

In various embodiments, D1L3 variants having one or more glycosylations exhibit increased resistance to serum protease degradation and/or an increased serum half-life compared to wild-type D1L3 protein (SEQ ID NO:2).

In some embodiments, D1L3 protein variant comprises an inactivation of a nuclear localization signal (NLS). D1L3 features two nuclear localization sites (NLS1, NLS2), which both target the enzyme to the nucleus during apoptosis. Indeed, D1L3 is required for fragmentation of nuclear DNA in apoptotic and necrotic cells in vivo. NLS1 is located near the N-terminus (about amino acid positions 80 to 96 with respect to SEQ ID NO: 2). NLS2 (amino acid positions 291 to 304 with respect to SEQ ID NO: 2) is embedded within a C-terminal tail (amino acid positions 283 to 305 with respect to SEQ ID NO: 2) that is unique to D1L3 and not present in D1. The C-terminal tail is thought to be required for D1L3 to degrade different substrates of extracellular DNA, namely lipid-encapsulated DNA and chromatin within apoptotic bodies. Lipids encapsulate DNA during transfections. In brief, cDNA, protein-free DNA, and cationic lipids form a complex that penetrates through the plasma membrane of target cells. D1L3 interferes with transfections and the C-terminal tail is critical for this function. Physiological substrates of D1L3 are apoptotic bodies, extracellular lipid vesicles filled with chromatin from apoptotic cells. The C-terminal tail enables D1L3 to penetrate through lipid membranes of apoptotic bodies and degrade the chromatin load. The C-terminal tail is also thought to be required for degradation of lipid-free, extracellular chromatin by D1L3. Thus, the C-terminal tail, a molecular feature unique to D1L3, appears to be responsible for the distinct substrate affinities of D1 and D1L3.

Inactivation of one or more NLSs enhances the availability and/or activity of the enzyme in the circulation. In some embodiments, the NLS inactivation is by deletion of all or part of NLS1 and/or NLS2. In some embodiments, the NLS is inactivated by substitution and/or deletion of amino acids within NLS1 and/or NLS2. In some embodiments, NLS2 is deleted, entirely or partially. In some embodiments, the D1L3 protein variant comprises a deletion of all or part of the C-terminal tail, and/or substitution of one or more amino acids in the C-terminal tail.

In certain embodiments, the D1L3 variant contains one or more, e.g., 1, 2, 3, 4, 5, or more amino acid substitutions, additions (e.g., insertions), or deletions in the NLS1 domain. The NLS2 domain or a portion thereof may be deleted. In certain embodiments, the D1L3 protein variant contains one or more, e.g., 1, 2, 3, 4, 5, or more amino acid substitutions, additions, or deletions in the C-terminal tail domain. The C-terminal tail domain or a portion thereof may be deleted. In various embodiments, the D1L3 protein variant contains one or more, e.g., 1, 2, 3, 4, 5, or more amino acid substitutions, additions, or deletions in the NLS2 domain which is located in the C-terminal tail domain. The NLS2 domain or a portion thereof can be deleted in the D1L3 protein variant.

In various aspects, the invention provides a protein engineering technology that is based on a transfer of a single amino acid or multiple-adjacent amino acids, termed "building block", between two members of a protein family, such as DNase1-protein family members to generate enzymatically active variants of DNase1-protein family members (including variant of D1 and D1L3). A "building block" is defined by amino acids that are variable between two or more members of the DNase1-protein family. These variable amino acids are flanked by amino acids that are conserved between two or more members of the DNase1-protein family ("anchors"). The variable single amino acid or multiple contiguous amino acids ("building blocks") are exchanged between members of the DNase1-protein family by implanting them between conserved single amino acid or multiple contiguous amino acids ("anchors").

This approach is referred to herein as "building-block protein engineering." Where three or more amino acids are transferred, up to ⅓ of the amino acids may be further substituted. For example, where three or six amino acids are transferred as a building block, one or up to two resides may be further substituted, respectively. In some embodiments, four or more amino acids are transferred as a building block substitution, and up to 25% of the transferred amino acids are further substituted, e.g., with conservative or non-conservative amino acid modifications. For example, where four, eight, or twelve amino acids are transferred, one, two, or three amino acids (respectively) may be further substituted in the building block substitution.

In various aspects (including in connection with embodiments described above), the D1L3 variant comprises at least one building block substitution from D1. FIG. 31 illustrates 62 building block substitutions between D1 and D1L3.

Exemplary building block substitutions from D1 include one or more of:

substitution of 1-20 (MSRELAPLLLLLLSIHSALA) of SEQ ID NO:2 with 1-22 (MRGMKLLGALLALAALLQGAVS) from SEQ ID NO:1; substitution of 21-25 (MRICS) of SEQ ID NO:2 with 23-27 (LKIAA) from SEQ ID NO:1; substitution of 28-30 (VRS) of SEQ ID NO:2 with 30-32 (IQT) from SEQ ID NO:1; substitution of 33-34 (ES) of SEQ ID NO:2 with 35-36 (ET) from SEQ ID NO:1; substitution of 36-45 (QEDKNAMDVI) of SEQ ID NO:2 with 38-47 (MSNATLVSYI) from SEQ ID NO:1; substitution of 47-51 (KVIK) of SEQ ID NO:2 with 49-53 (QILS) from SEQ ID NO:1; substitution of 52 (C) of SEQ ID NO:2 with 54 (Y) from SEQ ID NO:1; substitution of 54-58 (IILVM) of SEQ ID NO:2 with 56-60 (IALVQ) from SEQ ID NO:1; substitution of 60-61 (IK) of SEQ ID NO:2 with 62-63 (VR) from SEQ ID NO:1; substitution of 63-70 (SNNRICPI) of SEQ ID NO:2 with 65-72 (SHLTAVGK) from SEQ ID NO:1; substitution of 72-74 (MEK) of SEQ ID NO:2 with 74-76 (LDN) from SEQ ID NO:1;

substitution of 77-84 (RNSRRGIT) of SEQ ID NO:2 with 79-84 (QDAPDT) from SEQ ID NO:1; substitution of 86 (N) of SEQ ID NO:2 with 86 (H) from SEQ ID NO:1; substitution of 88-89 (VI) of SEQ ID NO:2 with 88-89 (VV) from SEQ ID NO:1; substitution of 91-92 (SR) of SEQ ID NO:2 with 91-92 (EP) from SEQ ID NO:1; substitution of 96-97 (NT) of SEQ ID NO:2 with 96-97 (NS) from SEQ ID NO:1; substitution of 101 (Q) of SEQ ID NO:2 with 101 (R) from SEQ ID NO:1; substitution of 103 (A) of SEQ ID NO:2 with 103 (L) from SEQ ID NO:1; substitution of 105 (L) of SEQ ID NO:2 with 105 (V) from SEQ ID NO:1; substitution of 107-110 (KEKL) of SEQ ID NO:2 with 107-110 (RPDQ) from SEQ ID NO:1; substitution of 113-116 (VKRS) of SEQ ID NO:2 with 113-116 (AVDS) from SEQ ID NO:1; substitution of 118 (H) of SEQ ID NO:2 with 118 (Y) from SEQ ID NO:1; substitution of 120 (H) of SEQ ID NO:2 with 120 (D) from SEQ ID NO:1; substitution of 122-127 (YQDGDA) of SEQ ID NO:2 with 122-128 (GCEPCGN) from SEQ ID NO:1; substitution of 129 (V) of SEQ ID NO:2 with 130 (T) from SEQ ID NO:1; substitution of 131 (S) of SEQ ID NO:2 with 132 (N) from SEQ ID NO:1; substitution of 135-136 (FV) of SEQ ID NO:2 with 136-137 (AIV) from SEQ ID NO:1; substitution of 138 (W) of SEQ ID NO:2 with 139 (R) from SEQ ID NO:1; substitution of 140-143 (QSPH) of SEQ ID NO:2 with 141-144 (FSRF) from SEQ ID NO:1; substitution of 145-148 (AVKD) of SEQ ID NO:2 with 146-149 (EVRE) from SEQ ID NO:1; substitution of 150 (V) of SEQ ID NO:2 with 151 (A) from SEQ ID NO:1; substitution of 152 (I) of SEQ ID NO:2 with 153 (V) from SEQ ID NO:1; substitution of 156-157 (TT) of SEQ ID NO:2 with 157-158 (AA) from SEQ ID NO:1; substitution of 159-161 (ETS) of SEQ ID NO:2 with 160-162 (GDA) from SEQ ID NO:1; substitution of 163 (K) of SEQ ID NO:2 with 164 (A) from SEQ ID NO:1; substitution of 167 (E) of SEQ ID NO:2 with 168 (A) from SEQ ID NO:1; substitution of 169-170 (VE) of SEQ ID NO:2 with 170-171 (YD) from SEQ ID NO:1; substitution of 173 (T) of SEQ ID NO:2 with 174 (L) from SEQ ID NO:1; substitution of 176-178 (KHR) of SEQ ID NO:2 with 177-179 (QEK) from SEQ ID NO:1; substitution of 180-181 (KA) of SEQ ID NO:2 with 181-182 (GL) from SEQ ID NO:1; substitution of 183-186 (NFIF) of SEQ ID NO:2 with 184-187 (DVML) from SEQ ID NO:1; substitution of 198-201 (PKKA) of SEQ ID NO:2 with 199-202 (RPSQ) from SEQ ID NO:1; substitution of 203-204 (KN) of SEQ ID NO:2 with 204-205 (SS) from SEQ ID NO:1; substitution of 208 (R) of SEQ ID NO:2 with 209 (W) from SEQ ID NO:1; substitution of 210 (D) of SEQ ID NO:2 with 211 (S) from SEQ ID NO:1; substitution of 212 (R) of SEQ ID NO:2 with 213 (T) from SEQ ID NO:1; substitution of 214 (V) of SEQ ID NO:2 with 215 (Q) from SEQ ID NO:1; substitution of 218 (G) of SEQ ID NO:2 with 219 (P) from SEQ ID NO:1; substitution of 220-221 (QE) of SEQ ID NO:2 with 221-222 (SA) from SEQ ID NO:1; substitution of 225-228 (VKKS) of SEQ ID NO:2 with 226-228 (ATP) from SEQ ID NO:1; substitution of 230 (N) of SEQ ID NO:2 with 230 (H) from SEQ ID NO:1; substitution of 238-240 (LRG) of SEQ ID NO:2 with 238-240 (VAG) from SEQ ID NO:1; substitution of 241-246 (QEIVSS) of SEQ ID NO:2 with 241-246 (MLLRGA) from SEQ ID NO:1; substitution of 250 (K) of SEQ ID NO:2 with 250 (D) from SEQ ID NO:1; substitution of 252-254 (NSV) of SEQ ID NO:2 with 252-254 (ALP) from SEQ ID NO:1; substitution of 256 (D) of SEQ ID NO:2 with 256 (N) from SEQ ID NO:1; substitution of 259-260 (KA) of SEQ ID NO:2 with 259-260 (AA) from SEQ ID NO:1; substitution of 262 (K) of SEQ ID NO:2 with 262 (G) from SEQ ID NO:1; substitution of 264-267 (TEEE) of SEQ ID NO:2 with 264-267 (SDQL) from SEQ ID NO:1; substitution of 269-271 (LDV) of SEQ ID NO:2 with 269-271 (QAI) from SEQ ID NO:1; substitution of 275 (F) from SEQ ID NO:2 with 275 (Y) from SEQ ID NO:1; substitution of 279-280 (FK) of SEQ ID NO:2 with 279-280 (VM) from SEQ ID NO:1; and substitution of 282-305 (QSSRAFTNSKKSVTLRKKTKSKRS) of SEQ ID NO:2 with 282 (K) from SEQ ID NO:1.

These building block substitutions from D1 result in variants of D1L3 which feature one or more of the following mutations:
M1_A20delinsMRGMKLLGALLALAALLQGAVS, M21_S25delinsLKIAA, V28_S30delinsIQT, E33_S34delinsET, Q36_I45delinsMSNATLVSYI, K47_K50delinsQILS, C52Y, I54_M58delinsIALVQ, I60_K61delinsVR, S63_I70delinsSHLTAVGK, M72_K74delinsLDN, R77_T84delinsQDAPDT, N86H, V88_I89delinsVV, S91_R92delinsEP, N96_T97delinsNS, Q101R, A103L, L105V, K107_L110delinsRPDQ, V113_S116delinsAVDS, H118Y, H120D, Y122_A127delinsGCEPCGN, V129T, S131N, 135F_136VdelinsAI, W138R, Q140_H143delinsFSRF, A145_D148delinsAVKD, V150A, I152A, T156_T157delinsAA, E159_S161delinsGDA, K163A, E167A, V169_E170delinsYD, T173L, K176_R178delinsQEK, K180_A181delinsGL, N183_F186delinsDVML, P198_A201delinsRPSQ, K203_N204delinsSS, R208W, D210S, R212T, V214Q, G218P, Q220_E221delinsSA, V225_S228delinsATP, N230H, L238_R239delinsVA, Q241_S246delinsMLLRGA, K250D, N252_V254delinsALP, D256N, K259_A260delinsAA, K262G, T264_E267delinsSDQL, L269_V271delinsQAI, F275Y, F279_K280delinsVM, Q282_S305delinsK.

The term "delins" refers to a deletion between and including two indicated amino acids, with an insertion of an amino acid or sequence of amino acids at the site of the deletion. For example, the notation E91_P92delinsSR means that the amino acids from E91 to P92 are deleted and the amino acids SR are inserted at the site of the deletion (e.g., the resulting amino acid sequence will have S91 and R92).

The term "ins" refers to an insertion of amino acids between two indicated amino acids. For example, the notation E91_P92insSR means that the amino acids SR are inserted between E91 and P92, resulting in the sequence E91, S92, R93, and P94.

Multiple mutations in one enzyme are separated by "/" e.g., T227K/A136F or R199_Q202delinsPKKA/ S204_S205delinsKN/W209R/S211D/T213R/Q215V/ P219G/S221_A222delinsQE.

In some embodiments, the D1L3 variant comprises one or more adjacent building block substitutions. For example, the D1L3 variant may comprise with respect to SEQ ID NO:2 the mutation F275Y/F279_K280delinsVM/ Q282_S305delinsK (SEQ ID NO: 17). In some embodiments, the D1L3 variant may comprise with respect to SEQ ID NO:2 the mutation Q36_I45delinsMSNATLVSYI (SEQ ID NO: 19). In some embodiments, the D1L3 variant may comprise with respect to SEQ ID NO:2 the mutation Y122_A127delinsGCEPCGN/V129T/S131N (SEQ ID NO: 20).

In an exemplary embodiment, the D1L3 variant comprises 2 or 3 substitutions selected from the mutations with respect to SEQ ID NO:2: Q36_I45delinsMSNATLVSYI, Y122_A127delinsGCEPCGN/V129T/S131N, F275Y/ F279_K280delinsVM/Q282_S305delinsK.

Thus, in some embodiments, the invention provides a DNase enzyme comprising an amino acid sequence that is at least 80% identical to the amino acid sequence of the enzyme defined by SEQ ID NO:2, and comprises at least one building block substitution from the amino acid sequence of SEQ ID NO:1. Building block substitutions between SEQ ID NOS: 1 and 2 are illustrated and numbered in FIG. 31. For example, in some embodiments, the enzyme comprises the mutation F275Y/F279_K280delinsVM/ Q282_S305delinsK, and which optionally comprises the amino acid sequence of SEQ ID NO: 17. In some embodiments, the enzyme comprises the mutations Q36_I45delinsMSNATLVSYI, Y122_A127delinsGCEPCGN, V129T, or S131N, and optionally has the amino acid sequence of SEQ ID NO: 19 or SEQ ID NO: 20.

Exemplary D1L3 variants include those comprising the amino acid sequence of SEQ ID Nos: 17 to 20. The invention in some embodiments, includes derivatives having from 1 to 10 (e.g., 1 to 5) amino acid insertions, deletions, or substitutions with respect to any one of SEQ ID NOS:17 to 20. In some embodiments, the D1L3 variant comprises one or more additional block amino acid substitutions from a homologous DNase (e.g., from D1). Such block substitutions may replace at least 2, at least 3, at least 4, or at least 5 amino acids. In some embodiments, the block substitutions replace from 2 to 20 amino acids, such as from 3 to 15 amino acids, or from 3 to 10 amino acids, with the comparable building block from the homologous DNase.

The engineered variants of D1L3 protein may comprise one or more additional amino acid substitutions, additions (insertions), deletions, or truncations in the amino acid sequence of human D1L3 (SEQ ID NO: 2). Amino acid substitutions may include conservative and/or non-conservative substitutions.

For example, "conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe. "Conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. As used herein, "non-conservative substitutions" are defined as exchanges of an amino acid by another amino acid listed in a different group of the six standard amino acid groups (1) to (6) shown above.

In some embodiments, the D1L3 protein variant comprises an N-terminal or C-terminal fusion to a half-life extending moiety, such as albumin, transferrin, an Fc, or elastin-like protein. See U.S. Pat. No. 9,458,218, which is hereby incorporated by reference in its entirety. In some embodiments, the D1L3 is dimerized by an immunoglobulin hinge region. For example, the engineered enzymes described herein may also include an Fc-fusion domain (e.g. a hinge and CH2 domains and CH3 domains of an immunoglobulin). In other cases, the engineered D1L3 protein is fused to albumin, e.g., human albumin or a fragment thereof. See WO 2015/066550; U.S. Pat. No. 9,221,896, which are hereby incorporated by reference in its entirety. Albumin can be joined to at the N-terminus or the C-terminus of the engineered D1 protein, and may optionally comprise an amino acid linker. In some embodiments, D1L3 and D1 are together dimerized by an Fc hinge region, creating a dimeric molecule with synergistic functional properties for degrading NETs.

In some embodiments, the recombinant D1L3 protein variant comprises one or more polyethylene glycol (PEG) moieties, which may be conjugated at one or more of positions or the C-terminus. In some embodiments, the native amino acid at that position is substituted with an amino acid having a side chain suitable for crosslinking with hydrophilic moieties, to facilitate linkage of the hydrophilic moiety to the peptide. In other embodiments, an amino acid modified to comprise a hydrophilic group is added to the peptide at the C-terminus. The PEG chain(s) may have a molecular weight in the range of about 500 to about 40,000 Daltons. In some embodiments, the PEG chain(s) have a molecular weight in the range of about 500 to about 5,000 Daltons. In some embodiments, the PEG chain(s) have a molecular weight of about 10,000 to about 20,000 Daltons.

In various embodiments, the D1L3 protein variant has increased protein stability, increased serum availability, and substantially the same or better NET-degrading activity (as determined in vitro or in vivo) as compared to wild-type D1L3 protein. In various embodiments, the D1L3 variant comprises one or more of the following properties relative to wild type D1L3: higher protein-free DNA (naked DNA) degradation activity, the same or substantially the same (e.g., at least 50%) chromosomal DNA degradation activity, protease resistance, an increased half-life, and higher production levels with in vitro expression systems (e.g. Chinese hamster ovary cells and/or *Pichia pastoris*).

DNA fragmentation can be measured using methods known to those skilled in the art such as gel electrophoresis and DNase activity assays. Methods for quantifying NETs, NET degradation, and DNA fragmentation activity are described in, for example, Hakkim et al., *Proc. Natl. Acad. Sci USA,* 2010, 107(21):9813-9818; Napirei et al. *Biochem J,* 2005, 389: 355-364. Fuchs et al., *J Cell Biol,* 2007, 176(2):231-241, Sisirak et al. *Cell,* 2016, 166:88-101, and Jiménez-Alcázar et al. *J Thromb* Haemost, 2015, 13, 732-742.

In some aspects, the invention provides DNase1 (D1) variants engineered to have physical, pharmacodynamic, and/or enzymatic properties more suitable for therapy, for example, to reduce or prevent NET accumulation in a subject. In some embodiments, the variant is more amenable to recombinant expression, thereby providing considerable manufacturing advantages. In various embodiments, the engineered D1 variant comprises an amino acid sequence that is at least 80% identical to the mature enzyme defined by the amino acid sequence of SEQ ID NO:1, with one or more amino acid substitutions, additions, or deletions resulting in one or more of a mutated DNA binding site, addition of a chromatin binding site, a mutated actin binding site, mutation of a glycosylation site, addition of a nuclear localization signal (e.g., having similarity or identity to NLS1 or NLS2 of D1L3), and/or a C-terminal domain similar to the C-terminal tail of D1L3. The D1 variant comprises an amino acid sequence with at least 80% identity to the amino acid sequence of the enzyme defined by SEQ ID NO:1, with one or more amino acid modifications with respect to SEQ ID NO:1 as described herein. In some embodiments, D1L3 variant comprises an amino acid sequence with at least 90%, or at least 95%, or at least 97%, or at least 98% identity with the enzyme of SEQ ID NO:1.

In various embodiments, the D1 variant comprises one or more amino acid substitutions, additions, deletions, or truncations in the amino acid sequence of human D1 (SEQ ID NO: 1). In some embodiments, the amino acid substitutions, and may include conservative and/or non-conservative substitutions as described. For example, the D1 variant may have from 1 to 20 (or from 1 to 10, or from 1 to 5) amino acid substitutions, deletions, or insertions with respect to the enzyme of SEQ ID NO:1.

In some embodiments, the D1 variant comprises one or more additional block amino acid substitutions from a homologous DNase (e.g., from D1L3). Such block substitutions may each replace from 1 to 24 amino acids, such as from 3 to 15 amino acids, or from 3 to 10 amino acids, from the homologous DNase. In some embodiments, the D1 variant comprises from 2 to 5 block substitutions from the homologous DNase (e.g., D1L3). In some embodiments 2 or 3 contiguous building block substitutions are transferred.

In various embodiments, the D1 variant is engineered to comprise one or more of the following characteristics relative to the wild type enzyme: the substantially the same or higher protein-free DNA (naked DNA) degradation activity (e.g., at least 50% or better), higher chromosomal DNA degradation activity, similar or improved protease resistance, actin resistance, an increased serum half-life, improved penetration from blood into urine or bile, or a combination of such properties.

In some embodiments, the engineered D1 enzyme comprises an amino acid sequence comprising at least 50% (or at least 70%, 80%, 90%) sequence identity to the C-terminal domain of wild-type D1L3 protein (e.g., amino acids 283 to 305 of SEQ ID NO:2).

In some embodiments, the D1 enzyme comprises an amino acid sequence having at least 50% or at least 75% sequence identity to the NLS1 of wild-type D1L3 (amino acids 35 to 51 of SEQ ID NO:2), a nuclear localization signal 2 (NLS2) having substantial sequence identity to the NLS2 of wild-type D1L3 protein (amino acids 296 to 304 of SEQ ID NO:2).

In various aspects, the recombinant D1 variant comprises one or more building block substitutions selected from: substitution of 1-22 (MRGMKLLGALLALAALLQGAVS) from SEQ ID NO:1 with 1-20 (MSRELAPLLL LLLSIHSALA) from SEQ ID NO:2; substitution of 23-27 (LKIAA) from SEQ ID NO:1 with 21-25 (MRICS) from SEQ ID NO:2; substitution of 30-32 (IQT) from SEQ ID NO:1 with 28-30 (VRS) from SEQ ID NO:2; substitution of 35-36 (ET) from SEQ ID NO:1 with 33-34 (ES) from SEQ ID NO:2; substitution of 38-47 (MSNATLVSYI) from SEQ ID NO:1 with 36-45 (QEDKNAMDVI) from SEQ ID NO:2; substitution of 49-52 (QILS) from SEQ ID NO:1 with 47-50 (KVIK) from SEQ ID NO:2; substitution of 54 (Y) from SEQ ID NO:1 with 52 (C) from SEQ ID NO:2; substitution of 56-60 (IALVQ) from SEQ ID NO:1 with 54-58 (IILVM) from SEQ ID NO:2; substitution of 62-63 (VR) from SEQ ID NO:1 with 60-61 (IK) from SEQ ID NO:2; substitution of 65-72 (SHLTAVGK) from SEQ ID NO:1 with 63-70 (SNNRICPI) from SEQ ID NO:2; substitution of 74-76 (LDN) from SEQ ID NO:1 with 72-74 (MEK) from SEQ ID NO:2; substitution of 79-84 (QDAPDT) from SEQ ID NO:1 with 77-84 (RNSRRGIT) from SEQ ID NO:2; substitution of 86 (H) from SEQ ID NO:1 with 86 (N) from SEQ ID NO:2; substitution of 88-89 (VV) from SEQ ID NO:1 with 88-89 (VI) from SEQ ID NO:2; substitution of 91-92 (EP) from SEQ ID NO:1 with 91-92 (SR) from SEQ ID NO:2; substitution of 96-97 (NS) from SEQ ID NO:1 with 96-97 (NT) from SEQ ID NO:2; substitution of 101 (R) from SEQ ID NO:1 with 101 (Q) from SEQ ID NO:2; substitution of 103 (L) from SEQ ID NO:1 with 103 (A) from SEQ ID NO:2; substitution of 105 (V) from SEQ ID NO:1 with 105

(L) from SEQ ID NO:2; substitution of 107-110 (RPDQ) from SEQ ID NO:1 with 107-110 (KEKL) from SEQ ID NO:2; substitution of 113-116 (AVDS) from SEQ ID NO:1 with 113-116 (VKRS) from SEQ ID NO:2; substitution of 118 (Y) from SEQ ID NO:1 with 118 (H) from SEQ ID NO:2, substitution of 120 (D) from SEQ ID NO:1 with 120 (H) from SEQ ID NO:2; substitution of 122-128 (GCEPCGN) from SEQ ID NO:1 with 122-127 (YQDGDA) from SEQ ID NO:2, substitution of 130 (TF) from SEQ ID NO:1 with 129 (V) from SEQ ID NO:2; substitution of 132 (N) from SEQ ID NO:1 with 131 (S) from SEQ ID NO:2; substitution of 136-137 (AI) from SEQ ID NO:1 with 135-136 (FV) from SEQ ID NO:2; substitution of 139 (R) from SEQ ID NO:1 with 138 (W) from SEQ ID NO:2; substitution of 141-144 (FSRF) from SEQ ID NO:1 with 140-143 (QSPH) from SEQ ID NO:2; substitution of 146-149 (EVRE) from SEQ ID NO:1 with 145-148 (AVKD) from SEQ ID NO:2; substitution of 151 (A) from SEQ ID NO:1 with 150 (V) from SEQ ID NO:2; substitution of 153 (V) from SEQ ID NO:1 with 152 (I) from SEQ ID NO:2; substitution of 157-158 (AA) from SEQ ID NO:1 with 156-157 (TT) from SEQ ID NO:2; substitution of 160-162 (GDA) from SEQ ID NO:1 with 159-161 (ETS) from SEQ ID NO:2; substitution of 164 (A) from SEQ ID NO:1 with 163 (K) from SEQ ID NO:2; substitution of 168 (A) from SEQ ID NO:1 with 167 (E) from SEQ ID NO:2; substitution of 170-171 (YD) from SEQ ID NO:1 with 169-171 (VE) from SEQ ID NO:2; substitution of 174 (L) from SEQ ID NO:1 with 173 (T) from SEQ ID NO:2; substitution of 177-179 (QEK) from SEQ ID NO:1 with 176-178 (KHR) from SEQ ID NO:2; substitution of 181-182 (GL) from SEQ ID NO:1 with 180-181 (KA) from SEQ ID NO:2; substitution of 184-187 (DVML) from SEQ ID NO:1 with 183-187 (NFIF) from SEQ ID NO:2; substitution of 199-202 (RPSQ) from SEQ ID NO:1 with 198-201 (PKKA) from SEQ ID NO:2; substitution of 204-205 (SS) from SEQ ID NO:1 with 203-204 (KN) from SEQ ID NO:2; substitution of 209 (W) from SEQ ID NO:1 with 208 (R) from SEQ ID NO:2; substitution of 211 (S) from SEQ ID NO:1 with 210 (D) from SEQ ID NO:2; substitution of 213 (T) from SEQ ID NO:1 with 212 (R) from SEQ ID NO:2; substitution of 215 (Q) from SEQ ID NO:1 with 214 (V) from SEQ ID NO:2; substitution of 219 (P) from SEQ ID NO:1 with 218 (G) from SEQ ID NO:2; substitution of 221-222 (SA) from SEQ ID NO:1 with 220-221 (QE) from SEQ ID NO:2; substitution of 226-228 (ATP) from SEQ ID NO:1 with 225-228 (VKKS) from SEQ ID NO:2; substitution of 230 (H) from SEQ ID NO:1 with 230(N) from SEQ ID NO:2; substitution of 238-239 (VA) from SEQ ID NO:1 with 238-239 (LR) from SEQ ID NO:2; substitution of 241-246 (MLLRGA) from SEQ ID NO:1 with 241-246 (QEIVSS) from SEQ ID NO:2; substitution of 250-251 (D) from SEQ ID NO:1 with 250-251 (K) from SEQ ID NO:2; substitution of 252-254 (ALP) from SEQ ID NO:1 with 252-254 (NSV) from SEQ ID NO:2; substitution of 256 (N) from SEQ ID NO:1 with 256 (D) from SEQ ID NO:2; substitution of 259-260 (AA) from SEQ ID NO:1 with 259-260 (KA) from SEQ ID NO:2; substitution of 262 (G) from SEQ ID NO:1 with 262 (K) from SEQ ID NO:2; substitution of 264-267 (SDQ) from SEQ ID NO:1 with 264-267 (TEEE) from SEQ ID NO:2; substitution of 269-271 (QAI) from SEQ ID NO:1 with 269-271 (LDV) from SEQ ID NO:2; substitution of 275 (Y) from SEQ ID NO:1 with 275 (F) from SEQ ID NO:2; substitution of 279-280 (VM) from SEQ ID NO:1 with 279-280 (FK) from SEQ ID NO:2; and substitution of 282 (K) from SEQ ID NO:1 with 282-305 (QSSRAFTNSKKSVTLRKKTKSKRS) from SEQ ID NO:2.

These building block substitutions from D1L3 results in variants of D1, which feature one or more of the following mutations: 1M_S22delinsMSRELAPLLLLLLSIHSALA, L23_A27delinsMRICS, I30_T32delinsVRS, E35_T36delinsES, M38_I47delinsQEDKNAMDVI, Q49_S52delinsKVIK, Y54C, I56_Q60delinsIILVM, V62_R63delinsIK, S65_K72delinsSNNRICPI, L74_N76delinsMEK, Q79_T84delinsRNSRRGIT, H86N, V88_V89delinsVI, E91_P92delinsSR, N96_S97delinsNT, R101Q, L103A, V105L, R107_Q110delinsKEKL, A113_S116delinsVKRS, Y118H, D120H, G122_N128delinsYQDGDA, T130S, N132S, A136_I137delinsFV, R139W, F141_F144delinsQSPH, E146_E149delinsAVKD, A151V, V153I, A157_A158delinsTT, G160_A162delinsETS, A164K, A168E, Y170_D171delinsVE, L174T, Q177_K179delinsKHR, G181_L182delinsKA, D184_L187delinsNFIF, R199_Q202delinsPKKA, S204_S205delinsKN, W209R, S211D, T213R, Q215V, P219G, S221_A222delinsQE, A226_P228delinsVKKS, H230N, V238_A239delinsLR, M241_A246delinsQEIVSS, D250K, A252_P254delinsNSV, N256D, A259_A260delinsKA, G262K, S264_L267delinsTEEE, Q269_I271delinsLDV, Y275F, V279_M280delinsFK, K282delinsQSSRAFTNSKKSVTLRKKTKSKRS.

In some embodiments, a recombinant D1 variant comprises the following modifications with respect to SEQ ID NO:1: Y275F, V279_M280delinsFK, and K282delinsQSSRAFTNSKKSVTLRKKTKSKRS (SEQ ID NO: 16). Such variants comprise a C-terminal tail, and display higher affinity for DNA-lipid complexes.

In some embodiments, a recombinant D1 variant comprises the following amino acid modifications with respect to SEQ ID NO:1: Q79_T84delinsRNSRRGIT (e.g., SEQ ID NO: 10); H86N, and/or, V88_V89delinsVI, and/or E91_P92delinsSR (e.g. SEQ ID NO: 11, which includes all three); A136_I137delinsFV (e.g., SEQ ID NO: 12); R199_Q202delinsPKKA, and/or S204_S205delinsKN, and/or W209R, and/or S211D, and/or T213R, and/or Q215V, and/or P219G, and/or S221_A222delinsQE (e.g., SEQ ID NO: 13, which includes all eight); and A226_P228delinsVKKS (e.g., SEQ ID NO: 14).

In some embodiments, where the D1 variant comprises the substitution H86N, the variant comprises at least one addition modification, such as a building block substitution or other point mutation described herein (such as the addition of a cationic amino acid or substitution that results in resistance to actin).

In some embodiments, the D1 variant comprises at least two adjacent, contiguous, building block substitutions that result in mutations with respect to SEQ ID NO:1 of: H86N/ V88_V89delinsVI (e.g., SEQ ID NO: 11); R199_Q202delinsPKKA/S204_S205delinsKN/W209R/ S211D/T213R/Q215V/P219G/S221_A222delinsQE (e.g., SEQ ID NO: 13); Y275F/V279_M280delinsFK/ K282delinsQSSRAFTNSKKSVTLRKKTKSKRS (SEQ ID NO: 16).

Figure 31A:
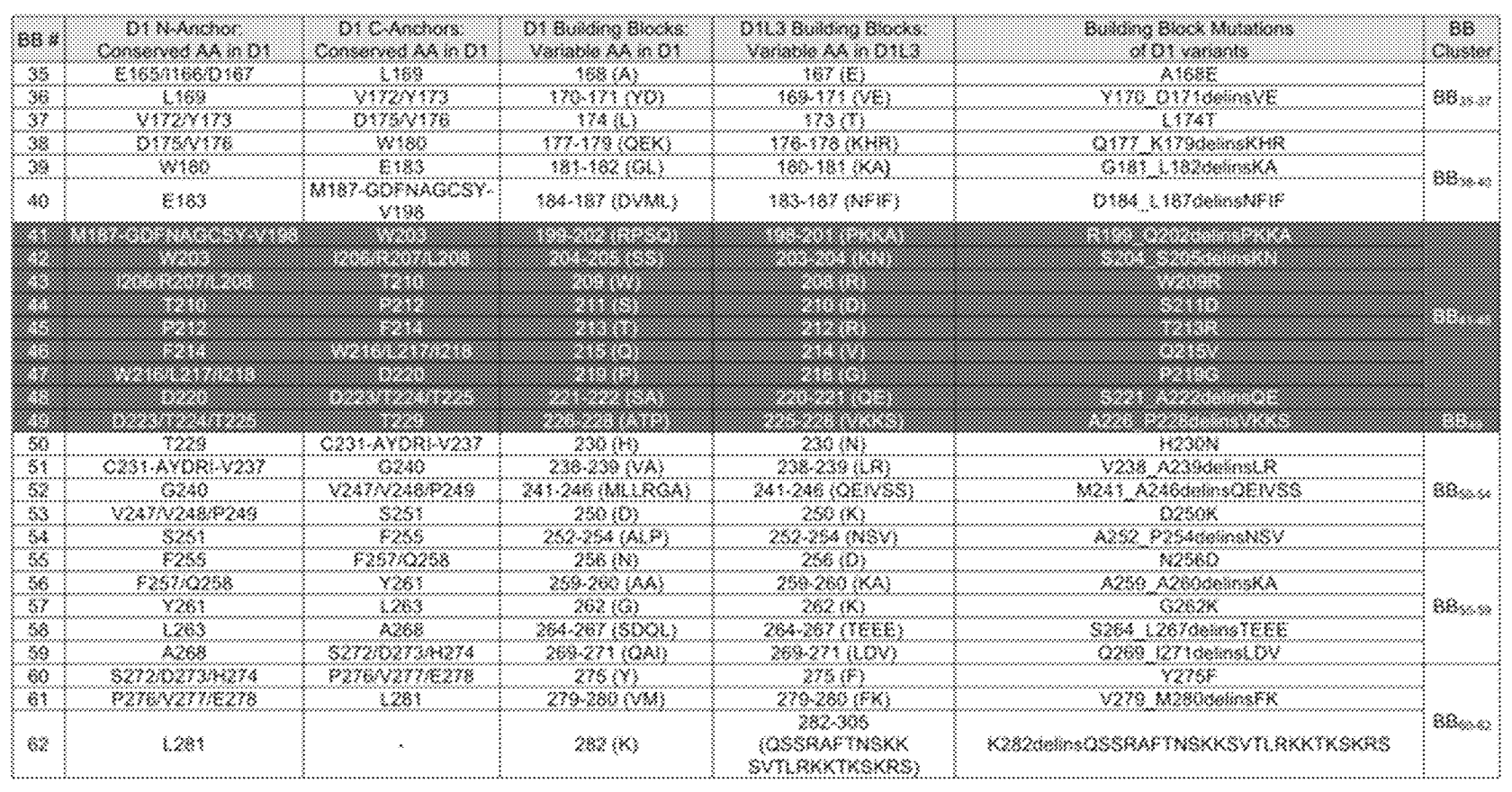

In some embodiments, the invention provides a DNase enzyme comprising an amino acid sequence that is at least 80% identical to the amino acid sequence of the enzyme defined by SEQ ID NO:1, and comprising at least one building block substitution from the amino acid sequence of SEQ ID NO:2, where the DNase enzyme has increased chromatin-degrading activity as compared to the DNase enzyme of SEQ ID NO:1. In some embodiments, the enzyme comprises at least two adjacent building block substitutions from SEQ ID NO:2. Building block substitutions between D1 (SEQ ID NO:1) and D1L3 (SEQ ID NO:2) are illustrated in FIG. 31.

In some embodiments, the enzyme comprises the following modification with respect to SEQ ID NO:1: Q79_T84delinsRNSRRGIT, and optionally comprises the amino acid sequence of SEQ ID NO: 10.

In some embodiments, the enzyme comprises the following modification with respect to SEQ ID NO:1: H86N/V88_V89delinsVI/E91_P92delinsSR, and optionally comprises the amino acid sequence of SEQ ID NO: 11.

In some embodiments, the enzyme comprises the following modifications with respect to SEQ ID NO:1: A136_I137delinsFV, and optionally comprises the amino acid sequence of SEQ ID NO: 12.

In some embodiments, the enzyme comprises two or more of the following modifications with respect to SEQ ID NO:1: R199_Q202delinsPKKA, and/or S204_S205delinsKN, and/or W209R, and/or S211D, and/or T213R, and/or Q215V, and/or P219G, and/or S221_A222delinsQE, and optionally comprises the amino acid sequence of SEQ ID NO: 13 (which comprises all eight).

In some embodiments, the enzyme comprises the following modifications with respect to SEQ ID NO:1: A226_P228delinsVKKS, and optionally comprises the amino acid sequence of SEQ ID NO: 14.

In some embodiments, the enzyme comprises two or more of the following modifications with respect to SEQ ID NO:1: Q79_T84delinsRNSRRGIT, and/or H86N, and/or V88_V89delinsVI, and/or E91_P92delinsSR, and/or A136_I137delinsFV, and/or R199_Q202delinsPKKA, and/or S204_S205delinsKN, and/or W209R, and/or S211D, and/or T213R, and/or Q215V, and/or P219G, and/or S221_A222delinsQE, and/or A226_P228delinsVKKS, and optionally comprises the amino acid sequence of SEQ ID NO: 15.

In some embodiments, the enzyme comprises two or more the following modification with respect to SEQ ID NO:1: Y275F, and/or V279_M280delinsFK, and/or K282delinsQSSRAFTNSKKSVTLRKKTKSKRS, and optionally comprises the amino acid sequence of SEQ ID NO: 16.

Exemplary D1 variants include those comprising the amino acid sequence of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16. The invention in some embodiments, includes derivatives having from 1 to 10 (e.g., 1 to 5) amino acid insertions, deletions, or substitutions with respect to any one of SEQ ID NOS: 5, 6, 7, 8, 9, 10, 11, 12, 13, 14, 15, or 16. In some embodiments, the D1 variant comprises one or more additional block amino acid substitutions from a homologous DNase (e.g., from D1L3). Such block substitutions may replace from 2 to 20 amino acids, such as from 3 to 15 amino acids, or from 3 to 10 amino acids of the D1 variant, with building block amino acids from the homologous DNase (e.g., D1L3, SEQ ID NO:2). Building block substitutions between D1 and D1L3 are illustrated in FIG. 31. In some embodiments, the DNase enzyme comprises an amino acid sequence that is at least 95% or at least 97% identical to SEQ ID NO:15.

In various embodiments, the enzyme exhibits one or more properties selected from: similar or higher affinity for protein-free DNA compared to the enzyme of SEQ ID NO:1, a higher chromatin degradation activity compared to the enzyme of SEQ ID NO:1, an enzymatic activity that is resistant to inhibition by actin compared to the enzyme of SEQ ID NO:1, and a combination thereof.

In some embodiments, the D1 variant comprises an N-terminal or C-terminal fusion to a half-life extending moiety, such as albumin, transferrin, an Fc, or elastin-like protein, as described for D1L3. In some embodiments, the D1 enzyme is dimerized by an immunoglobulin hinge region.

In various embodiments, the D1 variant exhibits one or more properties selected from: the same or higher protein-free DNA (naked DNA) degradation activity, higher chromosomal DNA (chromatin) degradation activity, similar or improved protease resistance, actin resistance, similar or improved penetration from blood into urine and/or bile, and higher production levels in vitro expression systems (e.g. Chinese hamster ovary cells and/or *Pichia pastoris*), and a combination thereof.

In various embodiments, the DNase enzyme comprises an amino acid sequence that is at least 80% identical to the amino acid sequence of the enzyme defined by SEQ ID NO:1, and comprises the substitution, insertion, or addition of one or more arginine and/or lysine residues, wherein the DNase enzyme has increased chromatin-degrading activity as compared to the enzyme of SEQ ID NO:1. In some embodiments, the one or more arginine and/or lysine residues are amino acid substitutions selected from substitutions at positions corresponding to positions 31, 41, 49, 52, 68, 76, 79, 81, 92, 109, 114, 115, 164, 177, 181, 200, 201, 204, 209, 213, 227, 239, 250, 259, 262, and 280 of SEQ ID NO:1. Exemplary modifications at these positions include Q31R, A41K, Q49R, S52K, T68R, N76K, Q79R, D80_A81insR, A81R, P92R, D109K, V114K, D115R, A164K, Q177K, G181K, P200K, S201K, S204R, W209R, T213R, A226_T227insK, T227K, A239R, D250K, A259K, G262K, and K280M. In various embodiments, the enzyme comprises substitution and/or insertion of at least two, or at least three, or at least four, or at least five, or at least six arginine and/or lysine residues. In some embodiments, DNase enzyme comprises an arginine or lysine at one or more positions corresponding to positions 31, 49, 76, 79, 92, 109, 164, 177, 200, 201, 204, 209, 213, and 262 of SEQ ID NO:1, which are optionally selected from Q31R, Q49R, N76K, Q79R, P92R, D109K, A164K, Q177K, P200K, S201K, S204R, W209R, T213R, W209R, and G262K. These positions/substitutions can independently provide better activity, including activity for degrading chromatin.

In various embodiments, if the enzyme comprises a substitution of Q31R or T227K, the enzyme comprises at least two amino acid modifications selected from Q31R, A41K, Q49R, S52K, T68R, N76K, Q79R, D80_A81insR, A81R, P92R, D109K, V114K, D115R, A164K, Q177K, G181K, P200K, S201K, S204R, W209R, T213R, A226_T227insK, T227K, A239R, D250K, A259K, G262K, and K280M. In some embodiments, the amino acid substitutions include Q31R and T227K with respect to SEQ ID NO:1.

In some embodiments, the DNase enzyme has an arginine or lysine at positions corresponding to positions 31, 49, 79, and 209 of SEQ ID NO:1, and may optionally comprise the following amino acid substitutions: Q31R, Q49K, Q79R, and W209R. These positions harbor an arginine or lysine in murine D1, but not wild-type human D1, and can transfer chromatin-degrading activity to human D1.

In some embodiments, the DNase enzyme has an arginine or lysine at positions corresponding to positions 31, 49, 79, 177, 209, and 262 of SEQ ID NO:1, and may optionally comprise the amino acid substitutions Q31R, Q49K, Q79R, A136F, Q177K, W209R, G262K. Four of these positions harbor an arginine or lysine in rat D1, but not wild-type human D1, and together can transfer chromatin degrading activity to human D1.

In some embodiments, the DNase enzyme has a lysine or arginine residue at positions corresponding to positions 31 and 227 of SEQ ID NO:1.

In some embodiments, the DNase enzyme has a lysine or arginine at the position corresponding to position 164 of SEQ ID NO:1, which is optionally lysine (A164K).

In various embodiments, the engineered D1 protein contains one or more amino acid modifications (e.g., substitutions, additions, and deletions) in the actin binding site (e.g. substitution of A136, such as A136F), and thereby hindering or preventing actin binding. As such, the engineered D1 protein can be actin-resistant or substantially actin-resistant. See Ulmer et al., *PNAS USA* Vol. 93, pp 8225-8229 (1996). Thus, in various embodiments, the DNase enzyme comprises an amino acid substitution at position 136 with respect to SEQ ID NO:1, and which is optionally A136F. Mutations to D1 providing for actin resistance, such as mutations at position 136 (e.g., A136F, or substitution of another bulky, hydrophobic, cyclic or aromatic amino acid at this position), may be combined with any other mutation described herein, including addition of cationic residues or building block substitutions.

In some embodiments, the D1 variant is resistant to actin-inhibition and capable of degrading chromatin. For example, the D1 variant may comprise the following amino acid substitutions: Q31R, T227K, and A136F with respect to SEQ ID NO:1. In some embodiments, the DNase enzyme comprises the following amino acid substitutions: A164K and A136F.

In some embodiments, the DNase enzyme comprises a glycosylation consensus sequence that comprises a N40S substitution and/or an N128S substitution with respect to SEQ ID NO:1. For example, in some embodiments the enzyme comprises the amino acid substitutions: Q31R, N40S, A136F, N128S, and T227K with respect to SEQ ID NO:1.

In various embodiments, the D1 variant contains one or more amino acid modifications (e.g., substitutions, additions, insertions, and deletions) in the glycosylation sites, and thereby increasing affinity towards lipid encapsulated DNA. As such, the engineered D1 protein can degrade lipid encapsulated DNA in transfection reactions. See Wilber et al., *Mol Ther* 6, 35-42 (2002).

In various embodiments, the D1 variant is glycosylated, or may be non-glycosylated particularly where long circulating half-life is not needed. The amino acid alterations described herein can be made in the context of glycosylated or non-glycosylated variants.

In some embodiments, D1 variant is resistant to actin-inhibition and capable of degrading chromatin within lipid vescicles. Exemplary D1 variants comprise one or more amino acid modifications selected from: Q31R, T227K, A136F, N40D or N40A, and N128D or N128S, with amino acids numbered according to SEQ ID NO:1. Such variants may lack glycosylation sites, which are beneficial from a manufacturing perspective.

In some embodiments, the D1 variant is resistant to actin-inhibition and capable of degrading chromatin within lipid vesicles, and comprises amino acid modifications Q31R, T227K, A136F, N40D, and N128D with respect to SEQ ID NO:1.

Other modifications to D1 can be as described in Pan et al. *J Biol Chem,* 1998, 273, 11701-11708 and in US 2014/0199329, the entire disclosure of which is hereby incorporated by reference in its entirety.

The engineered D1 variant can have an increased or extended serum half-life compared to the wild-type D1 protein (SEQ ID NO:1). In some embodiments, the engineered D1 comprises an Fc-fusion domain (e.g. a hinge region, and/or and CH2 domains and CH3 domains of an immunoglobulin). In some embodiments, the engineered D1 is fused to albumin, e.g., human albumin or a fragment thereof. Albumin can be joined to at the N-terminus or the C-terminus of the engineered D1 enzyme, optionally through an amino acid a linker.

In some aspects, the invention provides pharmaceutical compositions comprising the recombinant D1L3 and/or D1 variants, or polynucleotides or vectors encoding the same, and a pharmaceutically acceptable carrier. In various embodiments, the recombinant D1L3 protein variant is formulated for parenteral or pulmonary administration. In some embodiments, the composition is formulated for intravenous, intraarterial, intraperitoneal, intraarticular, intramuscular, topical, or subcutaneous administration, or other route described herein. In some embodiments, the composition comprises both D1L3 and D1, which are each optionally engineered variants described herein. In some embodiments, the recombinant D1L3 variant and the recombinant D1 variant are formulated for parenteral or pulmonary administration.

The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

Routes of administration include, for example: intradermal, intramuscular, intraperitoneal, intraarticular, intravenous, subcutaneous, intraarterial, oral, sublingual, pulmonary, or transdermal. In some embodiments, the administering is effected orally or by parenteral injection or infusion. In some embodiments, the route of administration is topical, including as eye drops or mouth wash.

In still other aspects, the invention provides a method of making a pharmaceutical composition for reducing or preventing neutrophil extracellular trap (NET) accumulation. In these embodiments, the invention employs a genetically modified mouse deficient in D1 and D1L3 activity, and heterologous expression of a G-CSF polynucleotide (e.g., in hepatocyte cells) or induction of a sustained endogenous G-CSF expression (e.g., via repetitive administration of microbial compounds). This mouse model accumulates NETs and rapidly develops NET-related vascular occlusions. In these embodiments, the invention comprises administering a candidate NET inhibitor or candidate DNase enzyme (including a D1L3 or D1 variant in accordance with this disclosure) to the genetically-modified mouse, and selecting a NET inhibitor or DNase enzyme that reduces the accumulation of NETs. The selected inhibitor or enzyme is formulated (as described) for administration to a human patient.

One skilled in the art recognizes standard methods for generating double knockout Dnase1$^{-/-}$Dnase1l3$^{-/-}$ mice. Detailed descriptions can be found in, for example, European Application No. EP 17152528.0.

In some aspects, the invention provides a method for treating a subject in need of neutrophil extracellular trap (NET) degradation. The method comprises administering a therapeutically effective amount of D1L3 and/or D1 (which may include variants described herein, or in some embodiments one or more wild type enzymes, including for D1L3 and D1 combination therapy) according to this disclosure. The D1L3 or D1 may be administered as pharmaceutical compositions comprising the recombinant protein, or in some embodiments comprising the encoding DNA or RNA or vectors comprising the same.

In some embodiments, the method comprises administering a therapeutically effective amount of a D1L3 or variant thereof and a D1 or variant thereof. The D1L3 or variant thereof, and the D1 or variant thereof, may be administered in a single pharmaceutical composition or separate pharmaceutical compositions. In some embodiments, the ratio of D1L3 or variant thereof to D1 or variant thereof is in the range of 100:1 to 1:100 by mass, or 10:1 to 1:10 by mass, and is optionally about 1:1.

In some embodiments, the subject exhibits impaired NET degradation and/or exhibits pathological NET accumulation. In some embodiments, the subject has a chronic or acute inflammatory disorder. In some embodiments, the subject has an acute or chronic infection.

In various embodiments, the present invention pertains to the treatment of diseases or conditions characterized by the presence or accumulation of NETs. Such diseases or conditions include, but are not limited to, diseases associated with chronic neutrophilia (e.g., an increase in the number of neutrophils), neutrophil aggregation and leukostasis, thrombosis and vascular occlusion (e.g. sickle cell disease), ischemia-reperfusion injury (e.g. midgut *volvulus*, testicular torsion, limb ischemia reperfusion, vital organ ischemia-reperfusion, organ transplantation), surgical and traumatic tissue injury, an acute or chronic inflammatory reaction or disease, an autoimmune disease (e.g. systemic lupus erythematosus (SLE), lupus nephritis, rheumatoid arthritis, vasculitis, systemic sclerosis), cardiovascular disease (e.g., myocardial infarction, stroke, atherosclerosis, venous thromboembolism, including thrombolytic therapy), metabolic disease (e.g., diabetes), systemic inflammation (e.g., systemic inflammatory response syndrome (SIRS), sepsis, septic shock, disseminated intravascular coagulation (DIC), and thrombotic microangiopathy (TMA)), inflammatory diseases of the respiratory tract (e.g. cystic fibrosis, chronic obstructive pulmonary disease (COPD), acute lung injury (ALI), smoke induced lung injury, transfusion induced lung injury (TRALI), acute respiratory distress syndrome (ARDS), and asthma, atelectasis, bronchitis, empyema), renal inflammatory diseases (acute and chronic kidney diseases, including acute kidney injury (AM) and chronic kidney disease (CKD), inflammatory diseases related to transplanted tissue (e.g. graft-versus-host disease) and cancer (e.g. leukemia, tumor metastasis, and solid tumors).

In some embodiments, the subject has or is at risk of NETs occluding ductual systems. The present invention can be administered to a subject to treat pancreatitis, cholangitis, conjunctivitis, mastitis, dry eye disease, obstructions of vas deferens, or renal diseases. In such embodiments, the method comprises administering a therapeutically effective amount of a D1L3 or variant thereof, and/or a therapeutically effective amount of D1 or a variant thereof. For example, the subject may be administered an enzyme comprising an amino acid sequence having 80% or more sequence identity with the enzyme defined by SEQ ID NO:2, and an enzyme comprising an amino acid sequence having 80% or more sequence identity with the enzyme defined by SEQ ID NO:1. In some embodiments, the enzymes comprise the amino acid sequence of the enzyme defined by SEQ ID NO:2 and the amino acid sequence of the enzyme defined by SEQ ID NO:1.

In some embodiments, the ductal system is bile duct, tear duct, lactiferous duct, cystic duct, hepatic duct, ejaculatory duct, parotid duct, submandicular duct, major sublingual duct, bartholin's duct, cerebral aqueduct, pancreas, mammary gland, vas deferens, ureter, urinary bladder, gallbladder, and liver. For example, the subject may have pancreatitis, cholangitis (e.g., primary sclerosing cholangitis), conjunctivitis, mastitis, dry eye disease, an obstruction of the vas deferens, or renal disease. In some embodiments, the DNase enzyme is administered by intravenous, intraarterial, or intraperitoneal administration. In various embodiments, the DNase when applied, for example, intravenously, will be present in enzymatically active form in various ductal systems, such as in bile fluid.

In some embodiments, the subject has or is at risk of NETs accumulating on endothelial surfaces (e.g. surgical adhesions), the skin (e.g. wounds/scarring), or in synovial joints (e.g. gout and arthritis). The present invention can be administered to a subject to treat a condition characterized by an accumulation of NETs on an endothelial surface such as, but not limited to, a surgical adhesion. In various embodiments, the present invention can be administered to a subject to treat a condition characterized by an accumulation of NETs on skin such as, but not limited to, wounds and scars. In certain embodiments, the present invention can be administered to a subject to treat a condition characterized by an accumulation of NETs in a synovial joint such as, but not limited to, gout and arthritis.

In some embodiments, the subject has or is at risk of a vascular occlusion comprising NETs. In such embodiments, the method comprises administering a therapeutically effective amount of a D1L3 or variant thereof, and/or a therapeutically effective amount of D1 or a variant thereof. For example, the subject may be administered an enzyme comprising an amino acid sequence having 80% or more sequence identity with the enzyme defined by SEQ ID NO:2. In some embodiments, the enzyme comprises the amino acid sequence of the enzyme defined by SEQ ID NO:2. In some embodiments, the subject is further administered an enzyme comprising an amino acid sequence having 80% or more sequence identity with the enzyme defined by SEQ ID NO:1, such as the enzyme defined by SEQ ID NO:1.

In some embodiments, the subject has a condition relating to NETs as described in WO 2016/118476 and U.S. Pat. No. 9,642,822, which are hereby incorporated by reference in its entirety.

In various embodiments, the subject has a disease that is or has been treated with wild-type DNases, including D1 and streptodomase. Such diseases or conditions include thrombosis, stroke, sepsis, lung injury, atherosclerosis, viral infection, sickle cell disease, myocardial infarction, ear infection, wound healing, liver injury, endocarditis, liver infection, pancreatitis, primary graft dysfunction, limb ischemia reperfusion, kidney injury, blood clotting, alum-induced inflammation, hepatorenal injury, pleural exudations, hemotorax, intrabiliary blood clots, post pneumatic anemia, ulcers, otolaryngological conditions, oral infections, minor injuries, sinusitis, post-operative rhinoplasties, infertility, bladder catheter, wound cleaning, skin reaction test, pneumococcal meningitis, gout, leg ulcers, cystic fibrosis, Kartegener's syndrome, asthma, lobar atelectasis, chronic bronchitis, bronchiectasis, lupus, primary cilliary dyskinesia, bronchiolitis, empyema, pleural infections, cancer, dry eyes disease, lower respiratory tract infections, chronic hematomas, Alzheimer's disease, and obstructive pulmonary disease.

In certain embodiments, the present invention pertains to the treatment of diseases or conditions characterized by deficiency of D1, deficiency of D1L3, and deficiency of D1 and D1L3. In some cases, the subject has a mutation in the Dnase1 and/or the Dnase1l3 gene. Such subjects can also have an autoimmune disease (e.g., SLE, systemic sclerosis) or an inflammatory disease. In some cases, the subject has an acquired inhibitor of D1 (e.g., anti-DNase1-antibody and actin) and/or the D1L3 (e.g., anti-DNase1l3-antibody). Such subjects can also have an autoimmune disease (e.g., SLE, systemic sclerosis) or an inflammatory disease (e.g., sepsis and ischemia-reperfusion injury).

In some embodiments, the subject has cystic fibrosis, and the DNase composition is administered by pulmonary delivery.

In various embodiments, for example, where the subject is at risk of, or exhibits symptoms of, NET-related vascular occlusion, the protein or composition (e.g., comprising D1L3, D1, or a variant of D1L3 or D1, including variants described herein) may be administered intravenously, intramuscularly, subcutaneously, or intraarterially.

In various embodiments, the subject is monitored for the NET-degrading activity of blood, plasma, or serum. For example, the subject may be monitored for about one week to about four weeks, to reduce the risk of vascular or ductal occlusion by NETs, or NET-related damage to organs. In some embodiments, the subject may receive from one to four administrations over the course of from one week to one month (or 1-2 weeks), as needed to prevent or reduce intravascular NET accumulation (including NET-related intravascular occlusions) during an acute infection or inflammatory event. In other embodiments, the subject may receive continuous infusion over the course of from one hour to one month (or 1-2 weeks). In some cases, the subject may receive at least one, e.g., 1, 2, 3, 4 or more infusions daily, for example (without limitation), in the case of critical illness such as sepsis, stroke, or myocardial infarction.

The treatment of disease or conditions relating to NETs may involve administration of a D1 variant, a D1L3 variant, or a combination comprising a D1 variant and a D1L3 variant. In some embodiments, two or more of variants of the D1 protein described herein are administered. In some embodiments, two or more of variants of the D1L3 protein described herein are administered.

The present D1 protein variants and D1L3 protein variants can be administered as a prophylactic therapy, such as before the onset of one or more symptoms of the disease or condition.

As used herein, "treatment" or "treating" or "treated" refers to therapeutic treatment wherein the object is to slow (lessen) an undesired physiological condition, disorder or disease, or to obtain beneficial or desired clinical results. Beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as lupus).

In the methods of the invention, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in neutrophil extracellular traps; (2) a reduction in intravascular clots; (3) a reduction in ductral clots; (4) a reduction of accumulation of NETs in synovial joints; (5) an increase in the degradation of neutrophil extracellular traps; (6) an increase in degradation of extracellular protein-free DNA; (7) an increase in degradation of extracellular chromosomal DNA or protein-bound DNA; (8) an increase in the degradation of neutrophil extracellular traps in the presence of autoantibodies; (9) a reduction in tissue/organ inflammation; (10) a reduction in tissue/organ injury; (11) a reduction in tissue/organ atrophy; (12) an increased patient survival rate; and (13) some relief from one or more symptoms associated with the disease or condition.

Positive therapeutic responses in any given disease or condition can be determined by standardized response criteria specific to that disease or condition. Clinical response can be assessed for changes in vascular occlusion and the presence of NETs using screening techniques such as magnetic resonance imaging (MRI) scan, ultrasound scan, histology, and counting of NETs in the circulation. In addition to these positive therapeutic responses, the subject undergoing therapy may experience the beneficial effect of an improvement in the symptoms associated with the disease.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

In various embodiments, the present invention provides an expression vector, comprising a nucleic acid encoding a wild type or D1L3 or D1 variant described herein, which can find use for genetic therapy. Genetic therapy can be useful for chronic illness such as a genetic deficiency of D1L3 and/or D1 (such as a deleterious mutation). In various embodiments, the expression vector comprises DNA or RNA. In various embodiments, the expression vector is a mammalian expression vector.

In some embodiments, expression vectors comprise a nucleic acid encoding the protein variants operably linked to an expression control region, or complement thereof, that is functional in a host cell (e.g., prokaryotic, eukaryotic, or mammalian cell). The expression control region is capable of driving expression of the operably linked blocking and/or stimulating agent encoding nucleic acid such that the blocking and/or stimulating agent is produced in a human cell transformed with the expression vector.

Expression control regions are regulatory polynucleotides (sometimes referred to herein as elements), such as promoters and enhancers, that influence expression of an operably linked nucleic acid. An expression control region of an expression vector of the invention is capable of expressing operably linked encoding nucleic acid in a human cell. In an embodiment, the expression control region confers regulatable expression to an operably linked nucleic acid. A signal (sometimes referred to as a stimulus) can increase or decrease expression of a nucleic acid operably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

Expression systems functional in human cells are well known in the art, and include viral systems. Generally, a promoter functional in a human cell is any DNA sequence capable of binding mammalian RNA polymerase and initiating the downstream (3') transcription of a coding sequence into mRNA. A promoter will have a transcription initiating region, which is usually placed proximal to the 5' end of the coding sequence, and typically a TATA box located 25-30 base pairs upstream of the transcription initiation site. The TATA box is thought to direct RNA polymerase II to begin RNA synthesis at the correct site. A promoter will also typically contain an upstream promoter element (enhancer element), typically located within 100 to 200 base pairs upstream of the TATA box. An upstream promoter element determines the rate at which transcription is initiated and can act in either orientation. Of particular use as promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Flp (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of AAV (Kootstra et al., Ann. Rev. Pharm. Toxicol., 43:413-439, 2003). In addition, direct and targeted genetic integration strategies may be used to insert nucleic acid sequences encoding the chimeric fusion proteins including CRISPR/CAS9, zinc finger, TALEN, and meganuclease gene-editing technologies.

All cited references are herein expressly incorporated by reference in their entirety.

EXAMPLES

Example 1: Host DNases Prevent Vascular Occlusion by Neutrophil Extracellular Traps Platelet and fibrin clots occlude blood vessels in hemostasis and thrombosis. Here we report a non-canonical mechanism for vascular occlusion based on neutrophil extracellular traps (NETs), antimicrobial DNA-fibers released by activated neutrophils. We show that two DNases, DNase1 and DNase1-like 3, degrade NETs in circulation during episodes of murine inflammation. In the absence of both DNases, intravascular NETs form clots that obstruct blood vessels and cause organ damage. Vascular occlusions in patients with severe bacterial infections are associated with a defect to degrade NETs ex vivo and the formation of intravascular NET-clots. DNase1 and DNase1-like 3 are independently expressed and thus provide dual host protection against deleterious effects of NETs in inflammation.

Inflammation is an essential host response to control invading microbes and heal damaged tissues (1). Uncontrolled and persistent inflammation causes tissue injury in a plethora of inflammatory disorders. Neutrophils are the predominant leukocytes in acute inflammation. During infections neutrophils generate extracellular traps (NETs), lattices of DNA-filaments decorated with toxic histones and enzymes that immobilize and neutralize bacteria (2). The relevance of NETs in host defense is illustrated by the fact that extracellular DNases serve as virulence factors in several pathogenic bacteria (3, 4). However, inappropriately released NETs may harm host cells due to their cytotoxic, proinflammatory, and prothrombotic activity (5-7). Indeed, NETs are frequently associated with inflammatory or ischemic organ damage and the therapeutic infusion of DNases limits host injury in various animal models (8, 9).

How the host degrades NETs in vivo to limit tissue damage during episodes of inflammation is poorly understood. Earlier work has shown that DNase1 in serum digests the DNA-backbone of NETs in vitro (10). We analyzed serum from wild type mice by zymography and detected two enzymatically active DNases, DNase1 and DNase1-like 3 [(DNase1l3) (FIG. 1A). Both enzymes are members of the DNase1 protein family, but differ in their origin and substrate affinity. DNase1 is expressed by non-hematopoietic tissues and preferentially cleaves protein-free DNA (11,12). DNase1l3, also known as DNase γ, is secreted by immune cells and targets DNA-protein-complexes, such as nucleosomes (11,13). We generated mice that lacked DNA-degrading activity in serum due to a combined deficiency of DNase1 and DNase1l3 (FIG. 1A). In vitro generated NETs remained intact after exposure to DNase1/DNase1l3−/− sera, whereas sera from wild type, DNase1−/−, and DNase1l3−/− mice degraded NETs (FIG. 1B and FIG. 1C). We used a hepatocyte-specific expression plasmid in conjunction with hydrodynamic gene delivery to stably express the cDNA of DNase1 or DNase1l3 in the liver of DNase1/DNase1l3−/− mice. Given that both enzymes contain a secretory protein signal sequence (11), this approach restored the activity of DNase1 or DNase1l3 in circulation (FIG. 1D) and the capacity of sera from DNase1/

DNase1l3−/− mice to degrade NETs (FIG. 1E and FIG. 1F). Taken together, these data show that two independently expressed host enzymes, DNase1 and DNase1l3, degrade NETs in vitro.

To test the requirement of DNase1 and DNase1l3 for NET-degradation in vivo, we aimed to chronically stimulate wild type, DNase1−/−, DNase1l3−/−, and DNase1/DNase1l3−/− mice with the granulocyte-colony stimulating factor (G-CSF). G-CSF triggers neutrophilia, a hallmark of acute inflammation, and stimulates a subpopulation of neutrophils to spontaneously release NETs ex vivo (14). We cloned the cDNA of CSF3, which encodes G-CSF, into the hepatocyte-specific expression plasmid. Hydrodynamic injection of wild type mice with the CSF3-plasmid resulted in chronically elevated levels of G-CSF in plasma (FIG. 5A). Consequently, the neutrophil blood count steadily increased and spontaneously formed NETs were detected in blood smears (FIG. 2A and FIG. 2B). We furthermore observed an increased number of resident neutrophils in vital organs and splenomegaly (FIG. 5B and FIG. 5C). Importantly, CSF3-injected wild type mice grew normally, did not develop organ injury, and did not show macroscopic signs of distress or abnormal behavior (FIG. 5D and FIG. 5E). Collectively, these data suggest that chronic neutrophilia with concomitant NET formation is well tolerated in wild type mice.

Next, we stably expressed CSF3 in the liver of DNase1−/−, DNase1l3−/−, and DNase1/DNase1l3−/− mice. Mice with a single deficiency in DNase1 or DNase1l3 did not show signs of distress (not shown), whereas all mice with a combined deficiency died within 6 days after CSF3-injection (FIG. 2C). DNase1/DNase1l3−/− mice receiving the control plasmid lacking CSF3 survived without showing any abnormalities (FIG. 2C, not shown). We co-expressed DNase1 or DNase1l3 with CSF3 in DNase1/DNase1l3−/− mice to induce neutrophilia and NETs and simultaneously restore DNase1 or DNase1l3 in circulation. Expression of either DNase was sufficient for DNase1/DNase1l3−/− mice to survive without showing any signs of distress (FIG. 2D). DNase1/DNase1l3−/− mice co-expressing CSF3 with a control plasmid lacking DNase1 and DNase1l3 died within 5 days after gene delivery (FIG. 2D). The mortality in these mice was preceded by a rapidly progressing hypothermia, which was evidenced as a strong decrease in peripheral body temperature within 8 hours before exitus (FIG. 2E). Hypothermia was accompanied with hemolytic anemia shown by reddish plasma and urine and reduced blood hemoglobin (FIG. 2F and FIG. 2G). Abundant schistocytes in blood smears indicated that the hemolytic anemia was caused by erythrocyte fragmentation (FIG. 2H). Furthermore, we detected elevated plasma levels of lactate dehydrogenase (LDH), liver transaminases, and the renal injury markers blood urea nitrogen and creatinine, which indicated multiple organ damage (FIG. 2I, FIG. 6A, and FIG. 6B). Coexpression of DNase1 or DNase1l3 with CSF3 maintained the body temperature and integrity of erythrocytes and organs (FIG. 2E to FIG. 2I; FIG. 6A and FIG. 6B). In conclusion, these data indicate that either DNase1 or DNase1l3 is required to prevent host injury during chronic neutrophilia.

The histological analysis of DNase1/DNase1l3−/− mice with chronic neutrophilia showed intravascular hematoxylin-positive clots with entrapped erythrocytes that fully or partially occluded blood vessels in lungs, liver, and kidneys (FIGS. 3A and B; FIG. 6C and FIG. 6D). Expression of DNase1 or DNase1l3 in circulation prevented these vascular occlusions. The hematoxylin-positive clots showed an abundant light-violet staining pattern that was sporadically speckled with a dark-violet staining of individual leukocyte nuclei, suggesting that decondensed DNA is a main clot component (FIG. 3A). Given that nuclear breakdown and unfolding of tightly packed chromatin is a hallmark of NET-formation (15), we stained the hematoxylin-positive clots for NET-markers. We observed a robust staining with fluorescent double-stranded DNA-intercalating dyes and antibodies against chromatin (FIG. 7A). The co-localization of decondensed chromatin with the neutrophil granule-derived enzyme myeloperoxidase, antimicrobial cathelicidin peptides, and the NET-surrogate marker citrullinated histones confirmed that the clots were composed of NETs (FIG. 3C, FIG. 7B and FIG. 7C). To identify components of canonical thrombi, we stained NET-clots for fibrin and von Willebrand factor (vWF), a protein stored in the secretory vesicles of platelets and the vascular endothelium. NET-clots were very heterogeneous in their vWF and fibrin content (FIG. 3D and FIG. 3E). Cross-sections of NET-clots were covered on average with 46% of vWF, while 9% of NET-clots did not stain for vWF (FIG. 3E and FIG. 3F). Fibrin was largely absent and detected in less than 23% of the occluded vessels (FIG. 3E). These data are in line with findings that NETs serve as a fibrin-independent scaffold to immobilize platelets and erythrocytes in vitro (6). The absence of vWF and fibrin in some clots suggests that NETs may be sufficient for vascular occlusion. To corroborate this notion, we aimed to generate NET-clots from pure neutrophils in vitro. We isolated neutrophils from blood and induced NET-formation, while exposing the cells to shear forces to mimic blood flow. In this setup, we observed macroscopically visible and DNase-sensitive clots (FIG. 8A), which resembled the appearance of NET-clots within the murine vasculature (FIG. 8B). Now, we depleted platelets from the circulation and pharmacologically inhibited thrombin to block fibrin formation in CSF3-expressing DNase1/DNase1l3−/− mice. Unlike DNase1- or DNase1l3-expression, neither anti-thrombotic treatment could prevent mortality in these animals (FIG. 3H). Collectively, the data suggest that clots of NETs are sufficient to obstruct blood vessels during chronic neutrophilia in DNase1/DNase1l3−/− mice.

The formation of NET-clots in DNase1/DNase1l3−/− mice is associated with features of infection-induced thrombotic microangiopathies (TMAs) and disseminated intravascular coagulation in patients, including schistocytes, hemolytic anemia, and organ failure due to vascular occlusions. We analyzed plasma from TMA patients with hemolytic-uremic syndrome due to an infection with Shiga toxin-producing *Escherichia coli* [STEC-HUS, (16)]. Sepsis and septic shock was a frequent complication in these patients (17). NETs generated in vitro remained intact after exposure to patient plasma collected in the acute disease state, whereas plasma from patients in remission degraded NETs (FIG. 9A and FIG. 9B). The data indicate an acquired and temporary defect in NET-degradation, thus extending previous reports (18,19). Of note, the STEC-HUS patients were effectively treated with a regimen that included infusion of plasma from healthy donors (17), a source of DNases, which potentially restored NET-degradation.

Large aggregates of NETs are reportedly formed in the synovial fluid and pancreatic ducts of patients (21,22), but have not yet been described in other tissues. Therefore, we aimed to identify intravascular aggregates of NETs in patients with severe inflammatory diseases. We screened lung tissue collected at autopsy from patients with acute respiratory distress syndrome and/or sepsis (FIG. 10). We detected hematoxylin-positive clots in blood vessels of two septic patients (FIG. 11A and FIG. 11C). In both cases, clots were comprised of chromatin and MPO (FIG. 11B and FIG. 11D), indicating that NETs can form intravascular clots in human sepsis.

Septicemia is a potent and rapid trigger of intravascular NET-formation in mice (7). We therefore hypothesized that a defect in NET-degradation may aggravate the disease. Indeed, we observed that mice with a combined deficiency of DNase1 and DNase1l3, but not wild type mice, were highly susceptible to low doses lipopolysaccharide and heat-killed *E. coli* (FIG. 4A). Similar to neutrophilic DNase1/DNase1l3−/− mice, blood analysis of septic DNase1/DNase1l3−/− mice showed hemolytic anemia and hematuria (FIG. 4B and FIG. 4C), along with increased levels of plasma LDH and schistocytes in blood smears (FIG. 4D and FIG. 4E). Furthermore, we detected abundant partially or fully occluded blood vessels in the lung (FIG. 4F and FIG. 4G). Detailed analysis of partially occluded vessels revealed clots of NETs within the vascular lumen (FIG. 4H). In fully occluded vessels the NET-clots were congested with entrapped erythrocytes and leukocytes (FIG. 4I; FIG. 12A and FIG. 12B). Importantly, hepatic expression of DNase1 or DNase1l3 in DNase1/DNase1l3−/− mice prevented vascular occlusion and restored the wild type phenotype. Taken together, these data indicate that circulating DNase1 or DNase1l3 prevent the formation of NET-clots and host injury in septicemia.

In summary, while platelets and fibrin form hemostatic clots and pathological thrombi (23), our data introduces NET-clots as a non-canonical mechanism for vascular occlusion in inflammatory states. Similar to fibrin strands, NETs are ultra-large and stable molecules (6). At high concentrations, such as found in chronic neutrophilia or septicemia, intravascular NETs may form clots, which are sufficient in size to obstruct blood vessels and thus cause damage to erythrocytes and organs. To maintain blood and tissue integrity during inflammation, the host independently expresses DNase1 and DNase1l3 as a dual protection system against intravascular NETs. However, acquired and genetic defects in these host factors may delay the degradation of NETs and thus precipitate disease. Acquired defects may involve DNase1-inhibition by monomeric actin externalized from damaged tissue and inactivation of DNase1l3 by serum proteases (11). Mutations in DNase1 and DNase1l3 have been identified in patients and are associated with systemic lupus erythematosus (SLE), a systemic autoimmune disease (24,25). Interestingly, DNase1 and DNase1l3-deficient mice spontaneously develop SLE-like disease with age (13,26). NETs are composed of prominent autoantigens and neutrophils from SLE patients have an increased capacity to release NETs (27). A reduced clearance capacity may increase the half-life NETs and thus promote the autoimmune disease (10,27). In conclusion, defects in host DNases may bring forward the deleterious effects of NETs in a plethora of inflammatory diseases.

Consequently, DNase1- and DNase1l3-mediated NET-degradation provides attractive therapeutic opportunity for patients suffering from inflammatory conditions. To test whether DNase1 and DNase1l3 degrade NETs by the same or via distinct mechanisms, we cross-linked proteins in NETs using fixative. Fixed NETs were efficiently degraded by DNase1l3−/− sera, but were resistant to degradation by DNase1−/− sera (FIG. 13A and FIG. 13B). In line with these results, exposure of NETs to recombinant DNase1 or DNase1l3 showed that both DNases degrade naïve NETs (FIG. 13C and FIG. 13D), whereas fixed NETs are resistant to DNase1l3 activity (FIG. 13E and FIG. 13F). Collectively, these in vitro data suggest that DNase1 and DNase1l3 degrade NETs via distinct mechanisms.

Figure 14A:
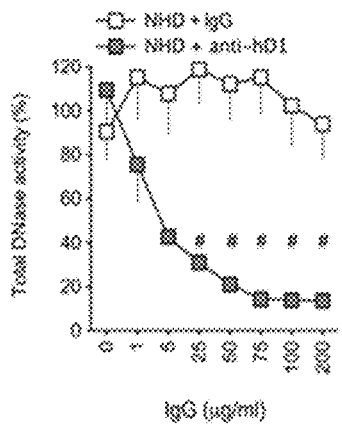
FIG. 14A-FIG. 14G provide DNase1 and DNase1l3 activity in the circulation of humans and mice.
Figure 14B:
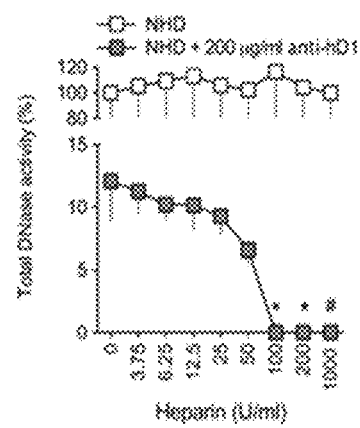
Figure 14C:
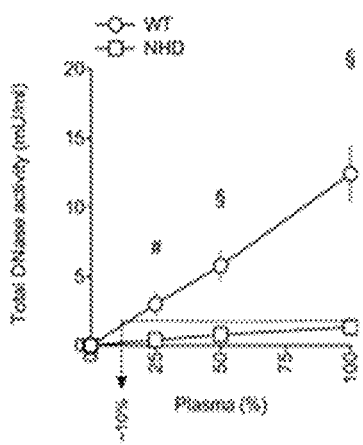
Figure 14D:
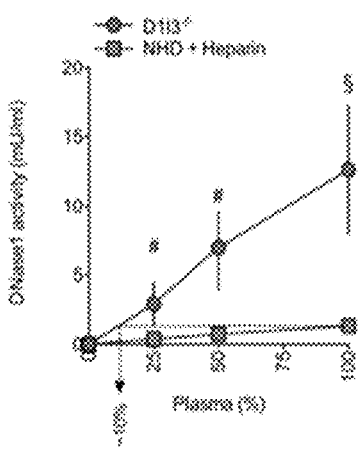
Figure 14E:
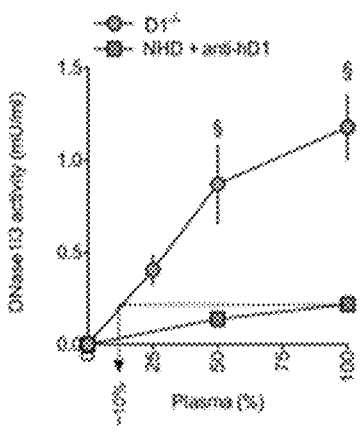
Figure 14F:
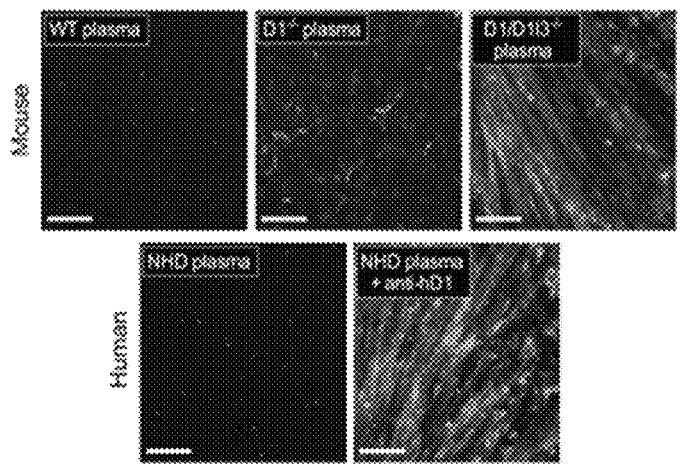
Figure 14G:
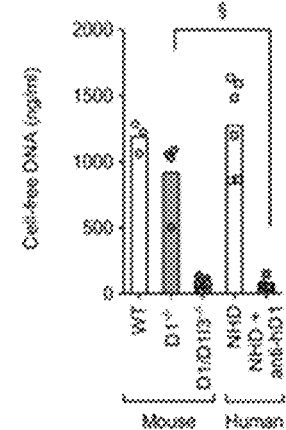

Finally, we compared the activity of DNase1 and DNase1l3 in the circulation of mice to humans. To discriminate DNase1 and DNase1l3 activity, we generated antibodies against human DNase1 (α-hDNase1), which block DNase1 activity in plasma from normal healthy donors (NHD) (FIG. 14A). Heparin is a known inhibitor of DNase1l3 and was used to block the DNA-degrading activity by DNase1l3 (FIG. 14B). Murine plasma showed approximately 10-fold higher total DNase activity (FIG. 14C), DNase1 activity (FIG. 14D), and DNase1l3 activity (FIG. 14E) than human plasma. Furthermore, DNase1l3 in murine plasma, but not in human plasma, degrades NETs efficiently (FIG. 14F and FIG. 14G). The data suggest that the concentration of DNase1l3 in human circulation is not sufficient to degrade NETs. Therefore, enabling DNase1l3-mediated NET-degradation in patients a novel and promising therapeutic strategy for inflammatory diseases.

Materials and Methods

Patient Plasma

Citrated plasma samples were obtained from patients during the STEC-HUS outbreak 2011 in Germany (16). The criteria for inclusion in our study were positive identification of STEC/enterohemorrhagic *E. coli* or bloody diarrhea, platelet count≤150×109/L or decreased by ≥25% in 1 week, evidence of hemolysis (LDH above the normal limit, haptoglobin below the normal limit, or the presence of schistocytes) and acute kidney injury stage≥1.

Human Tissue

Human tissues were fixed at room temperature overnight in 5% phosphate-buffered formalin. All tissues were collected at autopsy and originally submitted for diagnostic purposes to us and studied in accordance with national ethical principles. The cause of death of the patients is indicated in FIG. 10.

Mice

All mice were on a C57BL/6 genetic background. We crossed previously described DNase1−/− and DNase1-like 3−/− mice (26,28) to generate DNase1/DNase1l3−/− mice. This strain of DNase1−/− mice has been recently reported to contain an off-target mutation in the DNase1 overlapping gene Trap1/Hsp75, which encodes a mitochondrial chaperone (29). We therefore included an alternative DNase1−/− strain (30) to generate DNase1/DNase1l3−/− mice for control experiments (FIG. 15A-FIG. 15C)

Detection of DNase1 by Denaturing Polyacrylamide Gel Electrophoresis Zymography (DPZ)

We performed DPZ, as previously described with modifications (19). In brief, sodium dodecyl sulfate (SDS)-polyacrylamide gels were prepared with 4% (v/v) stacking gels without DNA and 10% (v/v) resolving gels containing 200 µg/ml of salmon testes DNA (Sigma-Aldrich, Germany). For the detection of DNase1, 0.5 µl of murine serum were mixed with 14.5 µl of water and 5 µl SDS gel-loading buffer (BioRad, Germany). The mixture was boiled for 5 minutes and loaded onto the gels. Electrophoresis was carried out at 120 V using Tris/glycine electrophoresis buffer (25 mM Tris, 192 mM glycine, 0.1% (w/v) SDS, pH 8.7). After electrophoresis, proteins were refolded by incubating the gels overnight at 37° C. in a refolding buffer containing 5% (w/v) milk powder, 10 mM Tris/HCl pH 7.8, 3 mM $CaCl_2$), 3 mM $MgCl_2$, 100 U/mL penicillin, and 100 µg/mL streptomycin. The gels were transferred to a refolding buffer without milk powder and incubated for additional 24 hours at 37° C. DNA was labeled fluorescently with 1×SYBR Safe (Thermo Scientific, Germany) and fluorescent images of gels were recorded using a fluorescence scanner (Molecular Imager FX, BioRad, Germany).

Detection of DNase1l3 by DPZ

For the detection of DNase1l3, 2 µl of serum were mixed with 12 µl of water, 5 µl SDS gelloading buffer, and 1 µl of beta-mercaptoethanol (BME, Sigma-Aldrich). BME reduces the disulfide bridges of DNase1, which causes its inactivation (11). The mixture was boiled for 5 minutes and loaded onto the gels. Electrophoresis was carried out as described for DNase1. SDS was removed by washing the gels with 10 mM Tris/HCl pH 7.8 for 30 minutes at 50° C. twice. The proteins were refolded by incubating the gels for 48 hours at 37° C. in a refolding buffer containing 10 mM Tris/HCl pH 7.8, 1 mM BME, 100 U/mL penicillin and 100 µg/mL streptomycin. The gels were then incubated for additional 48 hours at 37° C. in refolding buffer supplemented with 3 mM CaCl2 and 3 mM MnCl2. The addition of $Mn^{2+}$ is required to enable efficient degradation of protein-free DNA by DNase1l3 (11). DNA was labeled and imaged as described for DNase1.

Detection of Total DNase Activity by Single Radial Enzyme Diffusion (SRED) Assay To measure total DNase activity, we dissolved 55 µg/ml DNA from salmon testes in a buffer containing $Mn^{2+}$ (20 mM Tris-HCl pH 7.8, 10 mM MnCl2, 2 mM $CaCl_2$), and 2×SYBR Safe). The DNA solution was heated at 50° C. for 10 minutes and mixed with an equal volume of 2% ultrapure agarose (Thermo Scientific). The mixture was poured into plastic trays and stored at room temperature until solidification. Two µl of murine serum were loaded into wells of 1.0 mm diameter. Gels were incubated for 4 hours at 37° C. in a humid chamber. The DNA fluorescence of the gels was recorded with a fluorescence scanner.

In Vitro NET-Degradation Assay

NET-degradation was analyzed as previously described (19). Purified human neutrophils in serum-free DMEM were seeded to sterile 96-well plates (Falcon, BD Technologies, Germany) coated with 0.001% polylysine (Sigma) at a concentration of $5\times10^4$ cells per well. To induce NET-formation, neutrophils were activated with 100 nM phorbol 12-myristate 13-acetate (PMA; Sigma-Aldrich) for 4 h at 37° C. with 5% $CO_2$ and humidity. We added phosphate buffered saline (PBS) and stored the 96-well plates overnight at 4° C. NETs were washed with PBS, treated for 5 minutes with PBS containing 0.5% Triton X-100, and washed with PBS again. NETs were incubated with 10% murine serum or 10% citrated human plasma supplemented with 10 µM PPACK (Santa Cruz, Heidelberg, Germany) in HBSS with divalent cations (HBSS+; Thermo Scientific). NETs were allowed to be degraded for 3 hours at 37° C. with 5% CO2 and humidity. We discarded supernatants and stopped NET-degradation by adding 2% PFA in PBS for 1 hour at room temperature. PFA was discarded and non-degraded NETs were labeled fluorescently by adding 2 µM of the fluorescent DNA dye SytoxGreen (Thermo Scientific) in PBS. Images of fluorescently stained NETs were acquired with an inverted fluorescence microscope (Axiovert 200M, Zeiss, Germany). We quantified nondegraded NETs by recording the fluorescence intensity with a plate reader (Excitation: 485 nm; Emission: 535 nm) or by measuring the area coverage of NETs in microscopy pictures using ImageJ software (NIH, USA).

Preparation of In Vivo Expression Vectors

We used the pLIVE plasmid (Minis Bio, USA) to express proteins in mice. The vector enables a long-lasting and hepatocyte-specific expression of proteins. We generated pLIVE plasmids with murine DNase1, DNase1l3, and CSF3. For murine DNase1, a PCR of the cDNA (Genbank Accession Number NM010061) was performed using the pair of primers DNase1-F 5'-GTCGACATGCGGTA-CACAGG (SEQ ID NO:27) and DNase1-R 5'-CTCGAGTCAGATTTTTCTGAGTGTCA (SEQ ID NO:28) containing SalI and XhoI restriction sites. For DNase1l3, a PCR of the cDNA (Genbank Accession Number AF047355) was performed using the pair of primers DNase1l3-F 5'-GAAGTCCCAGGAATTCAAAGATGT (SEQ ID NO:29) and DNase1l3-R 5'-GCGTGATACCCGG-GAGCGATTG (SEQ ID NO:30) containing BamHI and SacI restriction sites. Both cDNAs were cloned using the T4 ligase (New England Biolabs, Germany) into the multi-cloning site (MCS) of the pLIVE vector, which was predigested with the appropriate enzymes. The pLIVE vector containing DNase1l3 was subjected to site-directed mutagenesis with the pair of primers mutDNase1l3-F 5'-AGTCGACTCCCGGCCACCATGTCCCTGCA (SEQ ID NO:31) and its complementary mutDNase1l13-R 5'-TGCAGGGACATGGTGGCCGGGAGTCGACT (SEQ ID NO:32) in order to match the consensus Kozak sequence and optimize protein expression. The generation of the pLIVE vector containing the cDNA of CSF3 was outsourced (Eurofins Genomics, Germany). The cDNA of CSF3 (Genbank Accession Number BC120761) was inserted in the MCS between restriction sites SalI and XhoI. Sequence of all the generated vectors was confirmed by double stranded DNA sequencing. As a control we used the parental pLIVE plasmid without additional inserts. All plasmids were purified using PureLink HiPure Plasmid Maxiprep Kit and potential contaminations of endotoxin were removed using High Capacity Endotoxin Removal Spin Columns (both Thermo Scientific).

In Vitro Expression of Murine DNase1 and DNase1l3

Plasmids containing the cDNA for DNase1 or DNase1l3, described elsewhere were transfected into Human Embryonic Kidney (HEK) cells with Lipofectamine 3000 (Thermo Scientific) in serum-free conditions with DMEM media (Thermo Scientific) supplemented with 10% KnockOut serum replacement (Thermo Scientific). After 72 hours, supernatants were collected, centrifuged at 500×g for 10 minutes, sterile filtered, and concentrated by ultracentrifugation with 3K columns (Amicon Ultra, Millipore, Darmstadt, Germany).

In Vivo Gene Expression

The pLIVE-plasmids containing DNase1, DNase1l3, CSF3, or empty control plasmids were administered to mice via hydrodynamic tail vein injection. In brief, 50 µg of plasmid were diluted in 0.9% saline in a volume equivalent to 10% of the body mass of the mouse. Mice were anaesthetized with isoflurane and the plasmid solution was then injected intravenously over 5 to 8 seconds via the tail vein. In rare cases, mice did not fully recover from the injection within the first 24 hours and these animals were excluded from the study. For coexpression studies, 50 µg of the CSF3-plasmid were mixed with 50 µg of the empty control plasmid, or the plasmids containing DNase1 and DNase1l3. The solution containing both plasmids was administered via hydrodynamic tail vein injection.

Chronic Neutrophilia

Female mice at 4 weeks or 8-12 weeks of age were injected with 50 µg of the pLIVE-plasmid containing CSF3 to induce G-CSF overexpression and neutrophilia. Mice were monitored every 8 hours during the first week after injection, and daily afterwards. Temperature was measured in the perianal area by a contactless infrared-thermometer (Etekcity, Germany). For survival studies, mice were euthanized and scored as "non-surviving" if the animals showed signs of distress (no spontaneous movement, closed eyes, occasional gasping). In all cases these signs of distress were accompanied with a rapidly progressing and severe hypothermia, defined as decrease in body temperature of 4° C. compared to the body temperature before the plasmid injection, and with hematuria. Non-hypothermic mice did not show any signs of distress and were euthanized at the end of the experiment. For organ, blood, and urine collection, we analyzed four groups of three D1/D1L3−/− mice. Mice in each group were injected with a mixture of CSF3 with empty plasma, DNase1, or DNase1l3. Each group of mice was euthanized for biosample collection, when the first animal of the group showed signs of distress, severe hypothermia, and hematuria. This time point was defined as "exitus" and occurred within 3 to 6 days after the injection.

Platelet Depletion

Mice received an intraperitoneal injection of 2 μg/g platelet-depleting antibody or isotype control antibody (both Emfret, Germany). This treatment depletes>95% of platelets from circulation. The treatment was started 24 hours after the injection of CSF3 and repeated every 48 hours until completion of the experiment.

Thrombin Inhibition

Powdered dabigatran etexilate (Pradaxa, Boehringer Ingelheim, Germany) was mixed with normal chow powder (Altromin, Germany) at a dose of 40 mg/g. Pellets were prepared by mixing the powder with distilled water and allowed to dry at room temperature. The feeding of dabigtran was started 24 hours after the injection of CSF3. WT mice fed with the dabigratan diet for 1 day showed a 6.48±1.19-fold (Mean±SD, N=4) increased activated partial thromboplastin time when compared to mice receiving normal chow without dabigratan (Student t-test; P<0.001).

Preparation of Bacteria for Septicemia

*Escherichia coli* (XEN 14, Perkin Elmer) was grown overnight in lysogeny broth media containing 50 μg/ml kanamycin. Bacteria were pelleted by centrifuging at 4000×g for 10 minutes, washed with and resuspended in PBS. Aliquots of $1.5 \times 10^9$ bacteria/ml were incubated at 70° C. for 15 minutes to heat-kill the bacteria. Aliquots stored at −20° C. until further use.

Septicemia

Male mice at 8-15 weeks of age received three daily intraperitoneal injections of 1 μg/g of LPS from *Salmonella enterica* serotype thyphimurium (Sigma-Aldrich) in 0.9% saline. Along with the third LPS injection, mice received an intravenous injection of 1.5×107 heat-killed *E. coli*/g. The shown survival time indicates the time after the injection of *E. coli*. Blood and organs were collected at the time of euthanasia. Insufficient biosamples were obtained from two animals (1×D1/D1L3−/−+Ctrl, 1×D1/D1L3−/−+DIL3) to perform the complete analysis shown in FIG. 4A-FIG. 4I. Mice were euthanized and scored as "non-surviving" if the animals showed signs of severe distress (irresponsiveness to touch). All non-surviving mice showed hematuria and paleness of extremities. All surviving mice were euthanized and scored as "surviving" 24 hours after the intravenous injection of heat-killed *E. coli*.

Murine Blood, Plasma, and Tissue Collection

Blood was collected by submandibular puncture or by the retroorbital sinus. Blood was collected into 200 μl serum tubes (Monovette; Sarstedt, Germany) and 200 μl EDTA tubes (GK 150, KABE labortechnik, Germany). Plasma was obtained by collecting the supernatant of blood after centrifugation at 3000×g for 15 minutes. Serum was obtained by allowing the blood to clot for 1 hour at room temperature followed by a centrifugation for 15 minutes at 3000×g. Serum and plasma samples were stored in aliquots at −20° C. until further use. For organ analysis, mice were perfused by intracardiac infusion of PBS. Organs were collected and fixed for 24 hours in 4% PFA at 4° C. Fixed organs were embedded in paraffin.

Analysis of Blood and Plasma

LDH, AST, ALT, creatinine and BUN in plasma were quantified by using standardized kits (Biotron Diagnostics, CA, USA) following the manufacturer instructions. Mouse G-CSF was quantified with a Quantikine ELISA Kit (R&D, United Kingdom). Hemoglobin in EDTA blood was quantified by an automated hemocytometer (Idexx ProCyte Dx Hematology Analyzer, Netherlands). To quantify neutrophils by FACS, whole blood was incubated on ice for 15 minutes with 0.2 μg of phycoerythrine-labelled anti-mouse CD11b (M1/70, Biolegend, Germany) and 0.5 μg of Alexa Fluor 488 anti-mouse Ly6G (1AB, Biolegend, Germany). The blood was then diluted with 0.5 ml PBS and analyzed with a FACSCalibur (BD Bioscience, USA). Blood smears of EDTA-anticoagulated blood were prepared on polylysine-coated slides (Hecht Assistant, Germany). After air-drying were incubated for 1 minute in methanol supplemented with 1 μM SytoxGreen on dry ice or stained with Giemsa using commercial kit (In Vitro Diagnostikum, Germany).

Immunofluorescence Stainings

Paraffin-embedded sections were de-waxed, rehydrated, and subjected to antigen retrieval for 25 minutes at 100° C. in citrate buffer (10 mM sodium citrate, 0.1% Tween, pH 6). Thereafter, sections were blocked for 30 minutes with 2.5% normal goat serum (Vector, United Kingdom) followed by incubation with a mouse-on-mouse blocking kit (Vector) for one hour. The sections were then incubated over night at 4° C. with 2 μg/ml of the primary antibody against MPO (A0398, Agilent, Germany), CRAMP (PA-CRLP-100, Innovagen, Sweden), citrullinated histone 3 (ab5103, Abcam, United Kingdom), fibrin [clone 59D8], or the complex of histone H2A, H2B, and DNA to detect chromatin (2). Sections were incubated with anti-rabbit and anti-mouse IgG antibodies conjugated with AlexaFluor488 or AlexaFluor555 (all Thermo Scientific) for 1 hour. After washing, DNA was labeled with 1 μg/ml DAPI for 2 minutes. Autofluorescence was quenched by a 25-minute incubation with Sudan Black (0.1% in 70% ethanol), and sections were mounted with Fluoromount G (Southern Biotech, USA). Images of fluorescently labeled sections were acquired with an inverted fluorescence microscope (Axiovert 200M, Zeiss, Germany) or a confocal microscope (TCS SPS, Leica, Germany). Images of NET-clots were quantified using software (ImageJ). A vWF or fibrin staining area of less than 3% of NET-clots was considered negative.

Immunohistochemistry

After antigen retrieval, deparaffinized sections were blocked for 30 minutes with 2.5% normal horse serum (Vector). The sections were incubated over night at 4° C. with 2 μg/ml of the primary antibody against neutrophil elastase (ab68672, Abcam). After washing, sections were stained using the anti-rabbit IgG-AP kit, (ImmPRESS, Vector) according to manufacturer's instruction. Sections were counterstained with hemalum (Merck, Germany) and mounted with Neo-Mount media (Merck). Images of stained sections were acquired with an inverted microscope (Axiovert 200M, Zeiss).

Generation of NET-Clots In Vitro

Purified human neutrophils were seeded to tissue culture plates at $3 \times 10^7$ cells/ml in DMEM supplemented with 2% BSA. The cells were activated with 0.1 μM PMA for 4 hours at 37° C., 5% $CO_2$ with humidity and rotating conditions (300 rpm). We used unstimulated neutrophils and neutrophils activated with PMA in the presence 10 U/ml recombinant human DNase1 (dornase alpha, Roche, Germany) as controls. NET-clots were fixed with 2% PFA overnight at 4° C. Fixed NET-clots were embedded in paraffin and sections were stained for NETs as described above.

Statistical Evaluation

Data are shown as mean±standard deviation. Statistical analysis was performed using Prism Software (GraphPad, USA) and included Student's t-test, one-way and two-way ANOVA followed by Bonferroni's multiple comparison test, and Log-rank test. Results were considered significant at $P<0.05$.

Movies

Chronic neutrophilia is tolerated in wild type mice. A movie generated shows the wild type mice one week after the injection of a CSF3-expression plasmid (CSF3) or a control plasmid lacking CSF3 (Ctrl). Both animals show normal behavior and no signs of distress.

Chronic neutrophilia causes distress in mice lacking DNase1 and DNase1l3. The movie shows DNase1/DNase1l3−/− mice co-expressing CSF3 with a control plasmid (CSF3/Ctrl), with DNase1 (CSF3/D1), or with DNase1l3 (CSF3/D1L3). Mice expressing circulatory DNases, DNase1 or DNase1l3, show normal behavior. Mice lacking circulatory DNases (CSF3/Ctrl) show signs of distress (no spontaneous movement, closed eyes, occasional gasping).

REFERENCES

1. V. Kumar, A. K. Abbas, N. Fausto, J. C. Aster, Acute and chronic inflammation. In Robbins & Cotran Pathologic Basis of Disease. (Elsevier Health Sciences, 2009), chap. 2.
2. V. Brinkmann, U. Reichard, C. Goosmann, B. Fauler, Y. Uhlemann, D. S. Weiss, Y. Weinrauch, A. Zychlinsky, Neutrophil extracellular traps kill bacteria. Science 303, 1532-1535 (2004).
3. P. Li, M. Li, M. R. Lindberg, M. J. Kennett, N. Xiong, Y. Wang, PAD4 is essential for antibacterial innate immunity mediated by neutrophil extracellular traps. J. Exp. Med. 207, 1853-1862 (2010).
4. V. Thammavongsa, D. M. Missiakas, O. Schneewind, *Staphylococcus aureus* degrades neutrophil extracellular traps to promote immune cell death. Science. 342, 863-866 (2013).
5. S. R. Clark, A. C. Ma, S. A. Tavener, B. McDonald, Z. Goodarzi, M. M. Kelly, K. D. Patel, S. Chakrabarti, E. McAvoy, G. D. Sinclair, E. M. Keys, E. Allen-Vercoe, R. Devinney, C. J. Doig, F. H. Green, P. Kubes, Platelet TLR4 activates neutrophil extracellular traps to ensnare bacteria in septic blood. Nat. Med. 13, 463-469 (2007).
6. T. A. Fuchs, A. Brill, D. Duerschmied, D. Schatzberg, M. Monestier, D. D. Myers, Jr., S. K. Wrobleski, T. W. Wakefield, J. H. Hartwig, D. D. Wagner, Extracellular DNA traps promote thrombosis. Proc. Natl. Acad. Sci. U.S.A. 107, 15880-15885 (2010).
7. A. Warnatsch, M. Ioannou, Q. Wang, V. Papayannopoulos, Neutrophil extracellular traps license macrophages for cytokine production in atherosclerosis. Science 349, 316-320 (2015).
8. B. Engelmann, S. Massberg, Thrombosis as an intravascular effector of innate immunity. Nat. Rev. Immunol. 13, 34-45 (2013).
9. S. K. Jorch, P. Kubes, An emerging role for neutrophil extracellular traps in noninfectious disease. Nat. Med. 23, 279-287 (2017).
10. A. Hakkim, B. G. Furnrohr, K. Amann, B. Laube, U. A. Abed, V. Brinkmann, M. Herrmann, R. E. Voll, A. Zychlinsky, Impairment of neutrophil extracellular trap degradation is associated with lupus nephritis. Proc. Natl. Acad. Sci. U.S.A. 107, 9813-9818 (2010).
11. M. Napirei, S. Ludwig, J. Mezrhab, T. Klockl, H. G. Mannherz, Murine serum nucleases—contrasting effects of plasmin and heparin on the activities of DNase1 and DNase1-like 3 (DNase1l3). FEBS J. 276, 1059-1073 (2009).
12. M. Napirei, A. Ricken, D. Eulitz, H. Knoop, H. G. Mannherz, Expression pattern of the deoxyribonuclease 1 gene: lessons from the Dnase1 knockout mouse. Biochem. J. 380, 929-937 (2004).
13. V. Sisirak, B. Sally, V. D'Agati, W. Martinez-Ortiz, Z. B. Ozcakar, J. David, A. Rashidfarrokhi, A. Yeste, C. Panea, A. S. Chida, M. Bogunovic, Ivanov, II, F. J. Quintana, I. Sanz, K. B. Elkon, M. Tekin, F. Yalcinkaya, T. J. Cardozo, R. M. Clancy, J. P. Buyon, B. Reizis, Digestion of Chromatin in Apoptotic Cell Microparticles Prevents Autoimmunity. Cell 166, 88-101 (2016).
14. M. Demers, D. S. Krause, D. Schatzberg, K. Martinod, J. R. Voorhees, T. A. Fuchs, D. T. Scadden, D. D. Wagner, Cancers predispose neutrophils to release extracellular DNA traps that contribute to cancer-associated thrombosis. Proc. Natl. Acad. Sci. U.S.A. 109, 13076-13081 (2012).
15. T. A. Fuchs, U. Abed, C. Goosmann, R. Hurwitz, I. Schulze, V. Wahn, Y. Weinrauch, V. Brinkmann, A. Zychlinsky, Novel cell death program leads to neutrophil extracellular traps. J. Cell Biol. 176, 231-241 (2007).
16. C. Frank, D. Werber, J. P. Cramer, M. Askar, M. Faber, M. an der Heiden, H. Bernard, A. Fruth, R. Prager, A. Spode, M. Wadl, A. Zoufaly, S. Jordan, M. J. Kemper, P. Follin, L. Muller, L. A. King, B. Rosner, U. Buchholz, K. Stark, G. Krause, HUS Investigation Team, Epidemic profile of Shiga-toxin-producing *Escherichia coli* O104: H4 outbreak in Germany. N. Engl. J. Med. 365, 1771-1780 (2011).
17. S. A. Braune, D. Wichmann, M. C. von Heinz, A. Nierhaus, H. Becker, T. N. Meyer, G. P. Meyer, M. Muller-Schulz, J. Fricke, A. de Weerth, W. W. Hoepker, J. Fiehler, T. Magnus, C. Gerloff, U. Panzer, R. A. Stahl, K. Wegscheider, S. Kluge. Clinical features of critically ill patients with Shiga toxin-induced hemolytic uremic syndrome. Crit. Care. Med. 41, 1702-1710 (2013).
18. M. Jimenez-Alcazar, M. Napirei, R. Panda, E. C. Kohler, J. A. Kremer Hovinga, H. G. Mannherz, S. Peine, T. Renne, B. Lammle, T. A. Fuchs, Impaired DNase1-mediated degradation of neutrophil extracellular traps is associated with acute thrombotic microangiopathies. J. Thromb. Haemost. 13, 732-742 (2015).
19. J. Leffler, Z. Prohaszka, B. Mikes, G. Sinkovits, K. Ciacma, P. Farkas, M. Reti, K. Kelen, G. S. Reusz, A. J. Szabo, M. Martin, A. M. Blom, Decreased neutrophil extracellular trap degradation in shiga toxin-associated haemolytic uraemic syndrome. J. Innate Immun. 9, 12-21 (2017).
20. M. Leppkes, C. Maueroder, S. Hirth, S. Nowecki, C. Gunther, U. Billmeier, S. Paulus, M. Biermann, L. E. Munoz, M. Hoffmann, D. Wildner, A. L. Croxford, A. Waisman, K. Mowen, D. E. Jenne, V. Krenn, J. Mayerle, M. M. Lerch, G. Schett, S. Wirtz, M. F. Neurath, M. Herrmann, C. Becker, Externalized decondensed neutro- 21. C. Schauer, C. Janko, L. E. Munoz, Y. Zhao, D. Kienhofer, B. Frey, M. Lell, B. Manger, J. Rech, E. Naschberger, R. Holmdahl, V. Krenn, T. Harrer, I. Jeremic, R. Bilyy, G. Schett, M. Hoffmann, M. Herrmann, Aggregated neutrophil extracellular traps limit inflammation by degrading cytokines and chemokines. Nat. Med. 20, 511-517 (2014).
22. V. Kumar, A. K. Abbas, N. Fausto, J. C. Aster, Hemodynamic disorders, thromboembolic disease, and shock. In Robbins & Cotran Pathologic Basis of Disease. (Elsevier Health Sciences, 2009), chap. 4.
23. M. Al-Mayouf, A. Sunker, R. Abdwani, S. A. Abrawi, F. Almurshedi, N. Alhashmi, A. Al Sonbul, W. Sewairi, A. Qari, E. Abdallah, E., M. Al-Owain, S. Al Motywee, H. Al-Rayes, M. Hashem, H. Khalak, L. Al-Jebali, F. S. Alkuraya. Loss-of-function variant in DNASE1L3 causes a familial form of systemic lupus erythematosus. Nat. Genet. 43, 1186-1188 (2011).
24. K. Yasutomo, T. Horiuchi, S. Kagami, H. Tsukamoto, C. Hashimura, M. Urushihara, Y. Kuroda. Mutation of DNASE1 in people with systemic lupus erythematosus. Nat. Genet. 28, 313-314 (2001).
25. M. Napirei, H. Karsunky, B. Zevnik, H. Stephan, H. G. Mannherz, T. Moroy, Features of systemic lupus erythematosus in Dnase1-deficient mice. Nat. Genet. 25, 177-181 (2000).
26. S. Gupta, M. J. Kaplan, The role of neutrophils and NETosis in autoimmune and renal diseases. Nat. Rev. Nephrol. 12, 402-413 (2016).
27. R. Mizuta, S. Araki, M. Furukawa, Y. Furukawa, S. Ebara, D. Shiokawa, K. Hayashi, S. Tanuma, D. Kitamura, DNase gamma is the effector endonuclease for internucleosomal DNA fragmentation in necrosis. PloS one 8, e80223 (2013).
28. J. Rossaint, J. M. Herter, H. Van Aken, M. Napirei, Y. Doring, C. Weber, O. Soehnlein, A. Zarbock, Synchronized integrin engagement and chemokine activation is crucial in neutrophil extracellular trap-mediated sterile inflammation. Blood 123, 2573-2584 (2014).
29. A. Bradley, K. Anastassiadis, A. Ayadi, J. F. Battey, C. Bell, M. C. Birling, J. Bottomley, S. D. Brown, A. Burger, C. J. Bult, W. Bushell, F. S. Collins, C. Desaintes, B. Doe, A. Economides, J. T. Eppig, R. H. Finnell, C. Fletcher, M. Fray, D. Frendewey, R. H. Friedel, F. G. Grosveld, J. Hansen, Y. Herault, G. Hicks, A. Horlein, R. Houghton, M. Hrabe de Angelis, D. Huylebroeck, V. Iyer, P. J. de Jong, J. A. Kadin, C. Kaloff, K. Kennedy, M. Koutsourakis, K. C. Lloyd, S. Marschall, J. Mason, C. McKerlie, M. P. McLeod, H. von Melchner, M. Moore, A. O. Mujica, A. Nagy, M. Nefedov, L. M. Nutter, G. Pavlovic, J. L. Peterson, J. Pollock, R. Ramirez-Solis, D. E. Rancourt, M. Raspa, J. E. Remade, M. Ringwald, B. Rosen, N. Rosenthal, J. Rossant, P. Ruiz Noppinger, E. Ryder, J. Z. Schick, F. Schnutgen, P. Schofield, C. Seisenberger, M. Selloum, E. M. Simpson, W. C. Skarnes, D. Smedley, W. L. Stanford, A. F. Stewart, K. Stone, K. Swan, H. Tadepally, L. Teboul, G. P. Tocchini-Valentini, D. Valenzuela, A. P. West, K. Yamamura, Y. Yoshinaga, W. Wurst, The mammalian gene function resource: the International Knockout Mouse Consortium. Mamm. Genome 23, 580-586 (2012).

Example 2: Development and Use of DNase1L3 and Variants for Therapy

Introduction

Uncontrolled inflammation causes a plethora of conditions (1). Neutrophil extracellular traps (NETs) are DNA filaments decorated with toxic proteins (2). NETs protect against microbial infection, but excessive NET formation triggers and exacerbates inflammatory and autoimmune diseases (3). DNase1 (D1), a DNA-degrading enzyme found in blood, has been widely used to disarm NETs in vitro and in vivo. Indeed, infusion of recombinant human D1, an FDA-approved drug (dornase alpha) for cystic fibrosis (CF), prevents the pathological effects of NETs in various disease models (3), supporting the use of D1 for prophylactic therapy.

DNase1-Like 3 is Novel Drug Candidate for NET-Associated Diseases

In Example 1, we found that in addition to D1, DNase1-like 3 (D1L3) also degrades NETs. Both enzymes maintain blood and tissue homeostasis during inflammatory responses. In brief, we showed that NETs are generated within blood vessels during neutrophilia, a hallmark of inflammation, under sterile as well as infectious conditions. D1 and D1L3 cleave NETs and thus prevent the aggregation of DNA-filaments of NETs to vascular clots. In the absence of D1 and D1L3, clots of NETs obstruct blood flow and cause organ damage and death. NET-clots are formed independently of platelets or fibrin and are therefore resistant to conventional anti-thrombotic therapy. Thus, we uncovered clots of NETs as a novel mechanism for vascular occlusion and D1L3 a new prophylactic therapy against NETs (see Example 1).

D1 and D1L3 belong, along with DNase1-like 1 (D1L1) and DNase1-like 2 (D1L2), to the DNase1-protein family (4). D1 and D1L3 are expressed in a variety of species including, humans, primates, and rodents. D1 is predominantly expressed in the gastrointestinal tract and exocrine glands (5), whereas hematopoietic cells, namely macrophages and dendritic cells produce D1L3 (6, 7). We found both DNases at low concentrations in serum of mice and humans (Example 1, FIG. 14), but the origin of D1 and D1L3 in circulation is unknown (7, 8). D1 preferentially cleaves protein-free DNA (e.g. bacterial DNA, plasmid DNA), whereas D1L3 targets chromatin, the complex of DNA and histones, which is commonly found in the nucleus of eukaryotic cells (7, 9, 10). D1 activity is inhibited upon binding to monomeric actin and sensitive to physiological salt concentrations (11-13). In addition, D1 is glycosylated at N40 (corresponds to N18 in the mature enzyme without signal peptide) and N128 (N106), which makes the enzyme resistant to inactivation by serum proteases (9). In contrast, D1L3 lacks glycosylation and actin-binding sites, which causes its susceptibility towards several proteases and resistance towards actin, respectively (9).

D1 was first discovered in body fluids of the gastrointestinal tract and urine, taking part in the digestion of DNA from food intake. We observed in the course of this disclosure that systemically administered DNase1 (e.g. through intraperitoneal or intravenous injection) has a relatively short half-life in circulation and is secreted in an enzymatically active form into the urine and, unexpectedly into bile. Its secretion into the bile fluid opens up the opportunity to target extracellular DNA and/or NETs in the biliary duct via systemic DNase1 therapy.

D1L3 was first described in the context of programmed cell death (14). D1L3 features two nuclear localization sites (NLS1, NLS2). NLS2 is embedded within a C-terminal tail that is unique to D1L3 and not present in D1. Both NLS target the enzyme to the nucleus during apoptosis (14). Indeed, intracellular D1L3 is required for fragmentation of nuclear DNA within apoptotic and necrotic cells in vivo (15). D1L3 requires its C-terminal tail to degrade extracellular DNA, namely lipid-encapsulated DNA, such as found in transfections, and chromatin within apoptotic bodies (7, 10). In transfections, cDNA and cationic lipids form a complex that penetrates through the plasma membrane of target cells. D1L3 interferes with transfections and the C-terminal tail is critical for this function (10). Apoptotic bodies, lipid vesicles filled with chromatin from apoptotic cells, are physiological substrates of D1L3 (7). Here, the C-terminal tail enables D1L3 to penetrate through lipid membranes of apoptotic bodies and degrade the chromatin load. Importantly, the C-terminal tail is also required for the degradation of lipid-free extracellular chromatin by D1L3 (7). The C-terminal tail is believed to be critical for the functions of D1L3 in the extracellular space.

While hD1 is effectively targeting NETs in animal models, mainly mice, it has shown limited or no therapeutic effect in clinical trials of CF (16) and emphysema (17), respectively. NETs are formed in CF (18), indicating that wild-type hD1 is not optimal for targeting NETs in patients. Hyperactive variants have been generated to circumvent the therapeutic limitations of D1, but their clinical manufacturing is challenging (12). Notably, NET-DNA contains histones and is structurally organized like chromatin (2). Thus, we speculated that the efficient degradation of chromatin is required for an optimal therapy against NETs.

A combinational therapy of hD1 and tissue plasminogen activator (tPA, alteplase) of emphysema patients has been described (17). The data are in line with our hypothesis because tPA enables D1 to degrade chromatin in vitro (19). U.S. Pat. No. 9,642,822, which is hereby incorporated by reference, further discloses combination therapy with tPA and D1 for therapeutic targeting of NETs (20). However, treatment with tPA is commonly associated with an increased risk of bleeding due to its fibrinolytic activity (17). D1L3 may provide a safer strategy for targeting NETs without putting patients at risk for bleeding, but a therapy with D1L3 protein has not been explored.

Engineering of DNase1 and DNase1-Like 3 Variants Through Amino Acid Transfer

In this Example we generated variants of D1 and D1L3 that are engineered for therapy against extracellular chromatin (including NETs). To design variants, we hypothesized that the capacity of human D1L3 to degrade chromatin is encoded by individual amino acids and/or amino acid sequences, which are absent in human D1. Furthermore, we speculated that transferring these individual amino acids and/or an amino acid sequence from human D1L3 to D1 generates hyperactive D1 variants with increased chromatin-degrading activity. Similarly, enzymatic properties (e.g. glycosylation) can be transferred from D1 to D1L3. To test our hypothesis, we employed conventional amino acid mutations and developed a novel building-block (BB) technology to engineer variants of DNases from the DNase1-protein family.

To produce variants of D1 and D1L3, we used in vitro expression systems [e.g. Chinese hamster ovary (CHO) cells, human embryonic kidney (HEK) cells, *Pichia pastoris*]. Enzymatic activity was characterized using the degradation of high-molecular weight (HMW)-DNA as a readout (FIG. 16). We chose two types of HMW-DNA: (a) double-stranded DNA (dsDNA) that was isolated from salmon testes. The degradation of HMW-dsDNA was analyzed by zymography; (b) chromatin of purified nuclei from HEK293 cells. To analyse its degradation, HMW-chromatin was first incubated with the DNase variants, followed by DNA isolation and visualization via agarose gel electrophoresis (AGE). Chromatin degradation was detected by low molecular weight (LMW)-DNA. In this setup, wild-type human D1 (SEQ ID NO: 1) has approximately 100-fold higher activity to degrade dsDNA than wild-type D1L3 (SEQ ID NO: 2), whereas wild-type D1L3 degrades chromatin with approximately 100-fold more efficiently than wild-type D1 (FIG. 16). We found synergistic effects of D1 and D1L3 in degrading chromatin, but not dsDNA. If D1 and D1L3 are mixed at a ratio of 10:1 or 1:1, we observed increased chromatin degradation, compared to each D1 or D1L3 alone (FIG. 16). Thus, we screened for D1 and/or D1L3 variants, which show increased chromatin and/or dsDNA degrading activity.

Selected D1 and D1L3 variants were further tested to degrade intravascular NETs, using an in vivo-expression system for members of the D1-protein family. See PCT/EP2018/051444, which is hereby incorporated by reference in its entirety. The system is based on two components, (a) an expression plasmid that enables the stable in vivo transfection of hepatocytes with cDNA of D1, D1L3, and variants thereof in recipient mice, and (b) Dnase1$^{-/-}$Dnase1l3$^{-/-}$ deficient mice, which are characterized by the absence of DNase activity in serum. In brief, the cDNA of candidate DNases is cloned into the hepatic expression vector. Next, the vector is co-expressed in Dnase1$^{-/-}$Dnase1l3$^{-/-}$ deficient mice along with the cDNA of murine Csf3, which encodes for the granulocyte colony-stimulating factor (G-CSF). The expression of Csf3 induces neutrophilia with concomitant intravascular NET-formation, which in turn causes the aggregation of undigested NETs within blood vessels and death in DNase1$^{-/-}$Dnase1l3$^{-/-}$ mice. To identify drug candidates, we screened for D1, D1L3, and variants thereof that efficiently degrade NETs and thus prevent morbidity and mortality in this model.

Results

Engineering DNase1 Variants Through Conventional Amino Acid Substitutions

Figure 17:
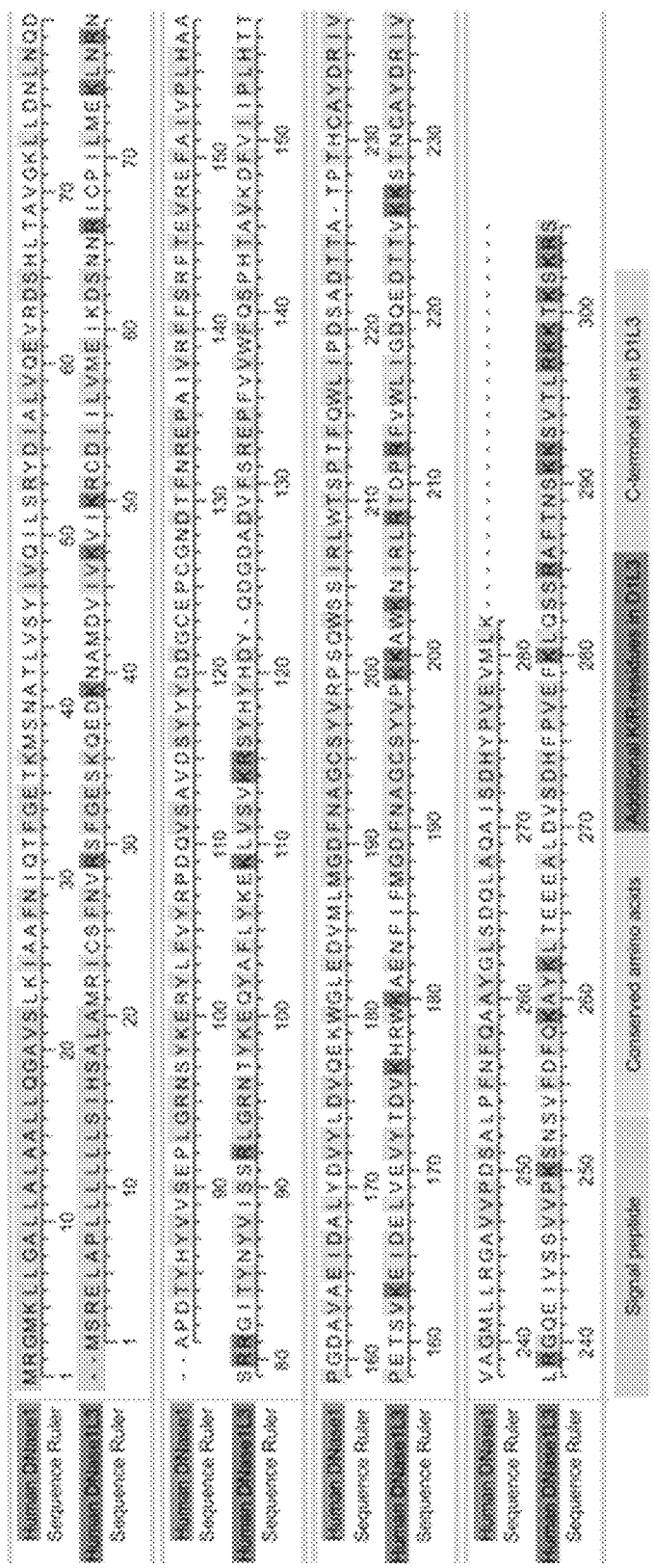
FIG. 17 shows an amino acid sequence alignment of human DNase1 (SEQ ID NO: 1) and human DNase1L3 (SEQ ID NO: 2). The signal peptide, conserved amino acids, additional arginine- and lysine-residues in variable regions of D1L3, and the C-terminal tail of D1L3 are highlighted. Sequence rulers indicate the amino acid position.
Figure 19:
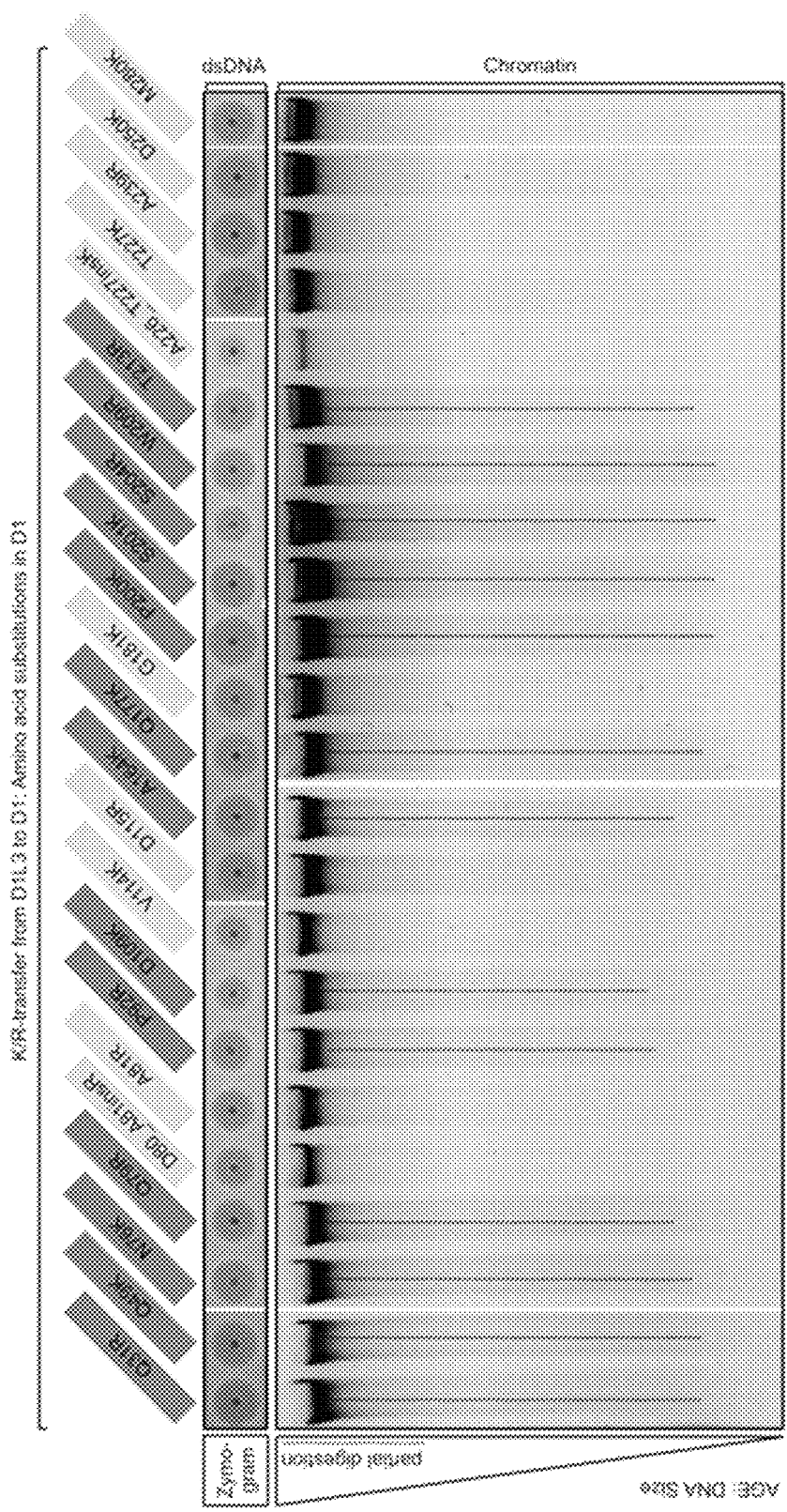
FIG. 19 shows the characterization of DNase1 variants with single arginine and lysine amino acid substitutions listed in FIG. 18. Zymography showed dsDNA degrading activity as dark circles. The dsDNA degrading activity correlates with the diameter. Agarose gel electrophoresis (AGE) of DNA isolated from digested chromatin shows a shift from high-molecular weight DNA to lower or low-molecular weight DNA that correlates with chromatin degrading activity. Amino acid substitutions that cause an increase in chromatin degrading activity are highlighted in blue. Samples without such effect are shown in light blue.
Figure 20:
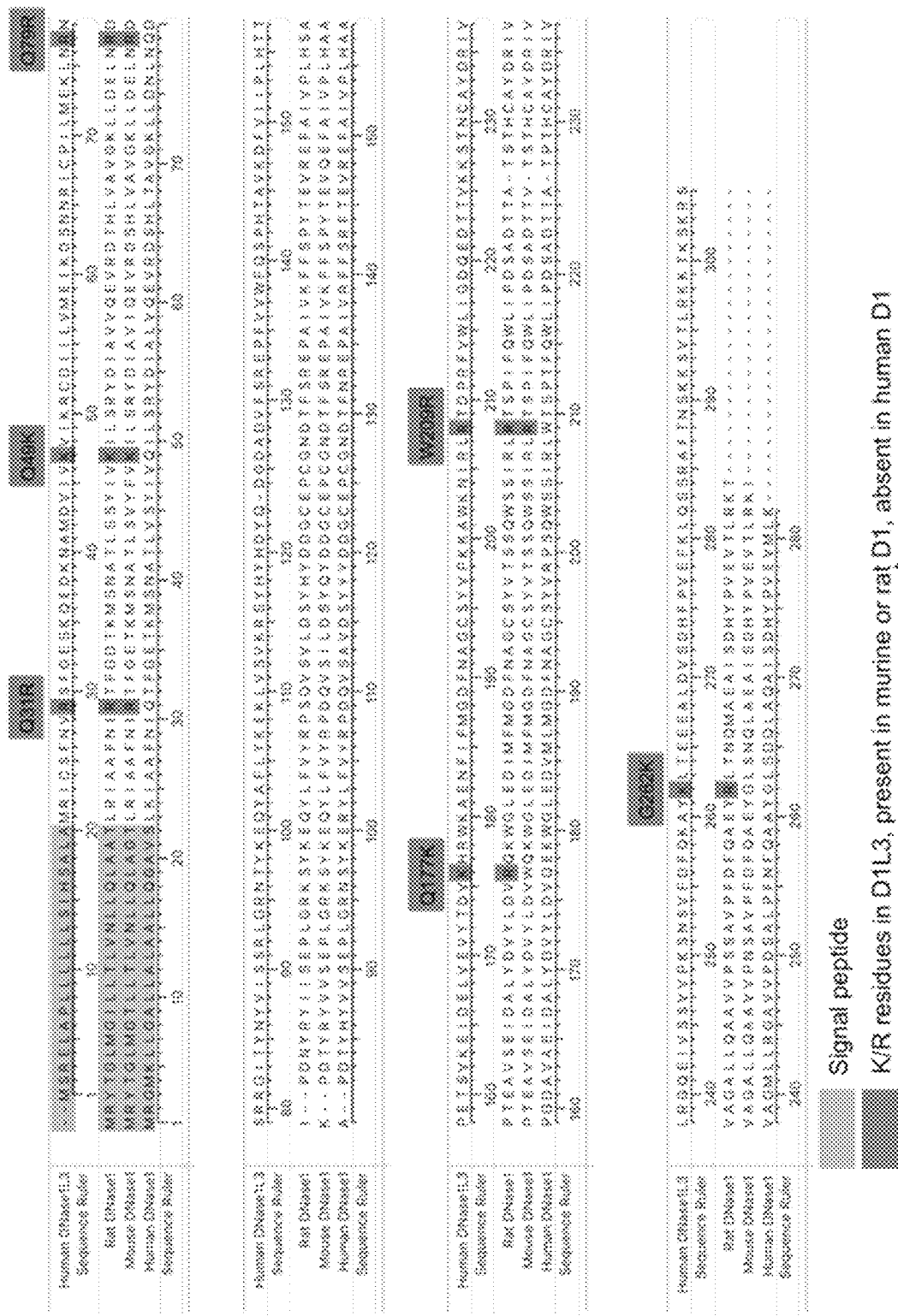
FIG. 20 shows the amino acid sequence alignment of human DNase1 (SEQ ID NO: 1), mouse DNase1 (SEQ ID NO: 3), rat DNase1 (SEQ ID NO: 4), and human DNase1L3 (SEQ ID NO: 2). Sequence rulers indicate the amino acid position. The signal peptides are highlighted in grey. Cationic amino acid residues (arginine: R, lysine: K) that are present in mouse/rat DNase1 and human DNase1L3, but not in human DNase1, are highlighted. Four such R/K-residues are shown in mouse DNase1 (Q31R, Q49K, Q79R, W209R). Rat DNase1 contains two additional R/K-residues (Q177K, G262K).
Figure 21A:
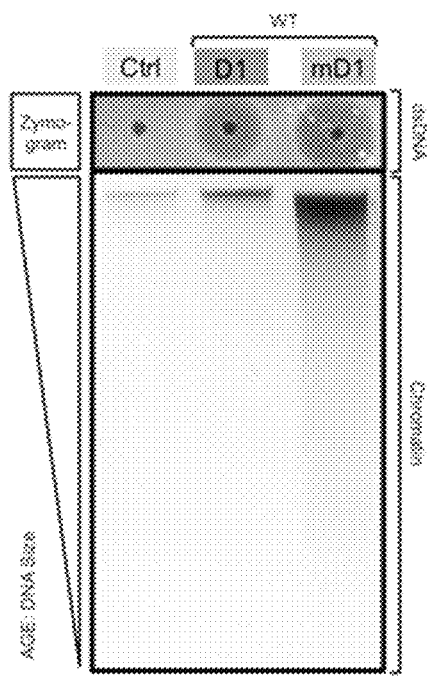
FIG. 21A-FIG. 21B shows a comparison between murine and human DNase1.
Figure 21B:
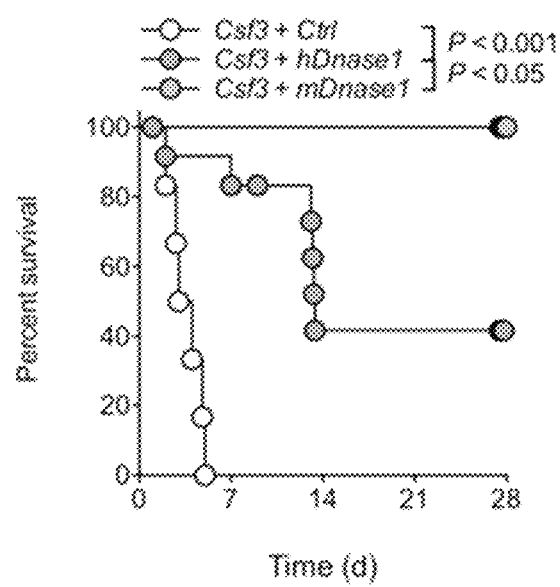
Figure 22B:
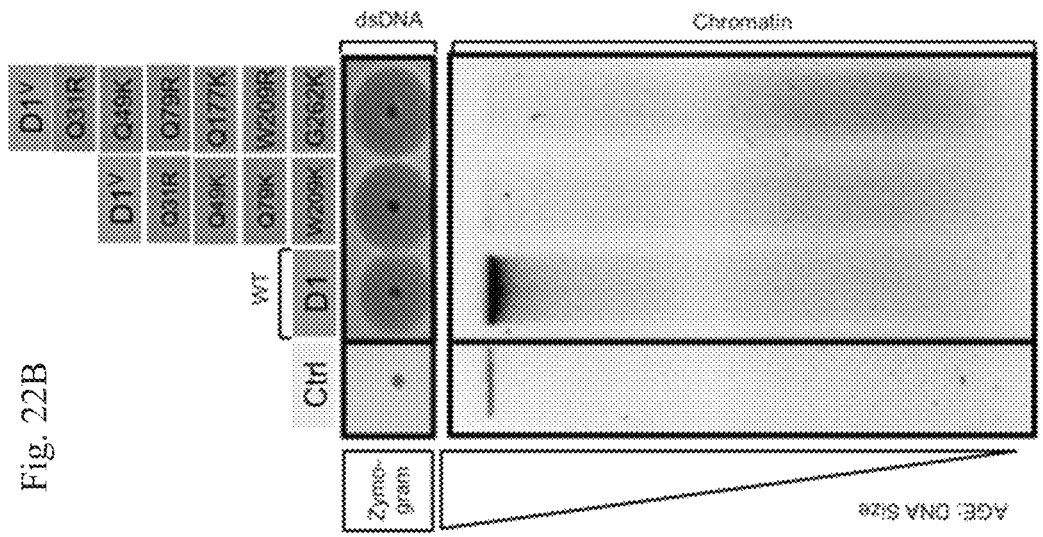
FIG. 22A-FIG. 22B shows the characterization of rodent-like human DNase1-variants in vivo and in vitro.
Figure 22A:
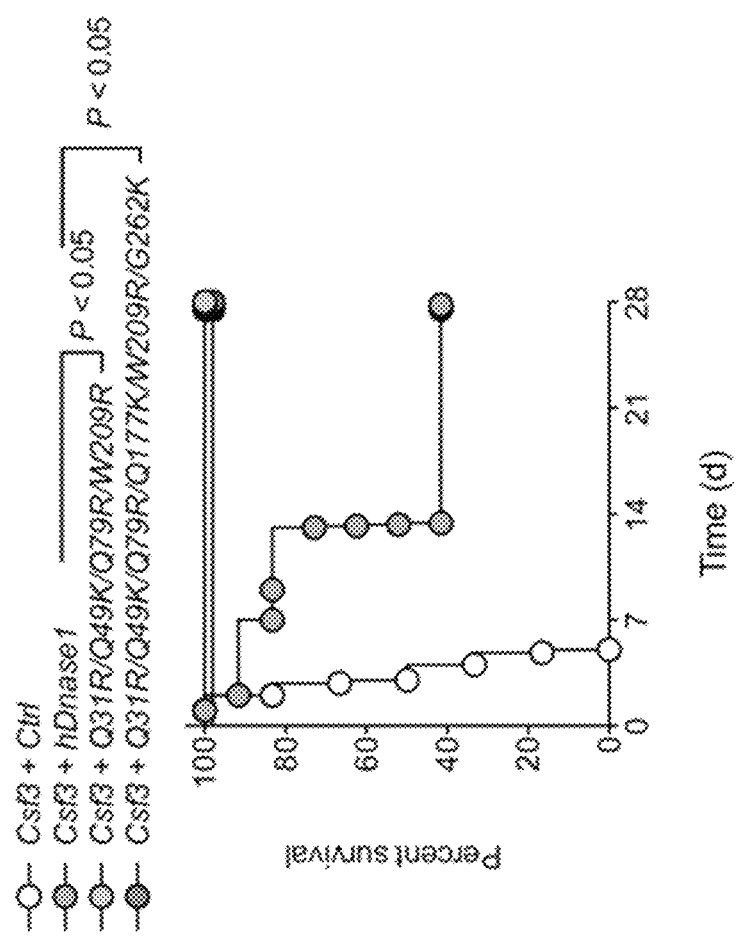
Figure 23:
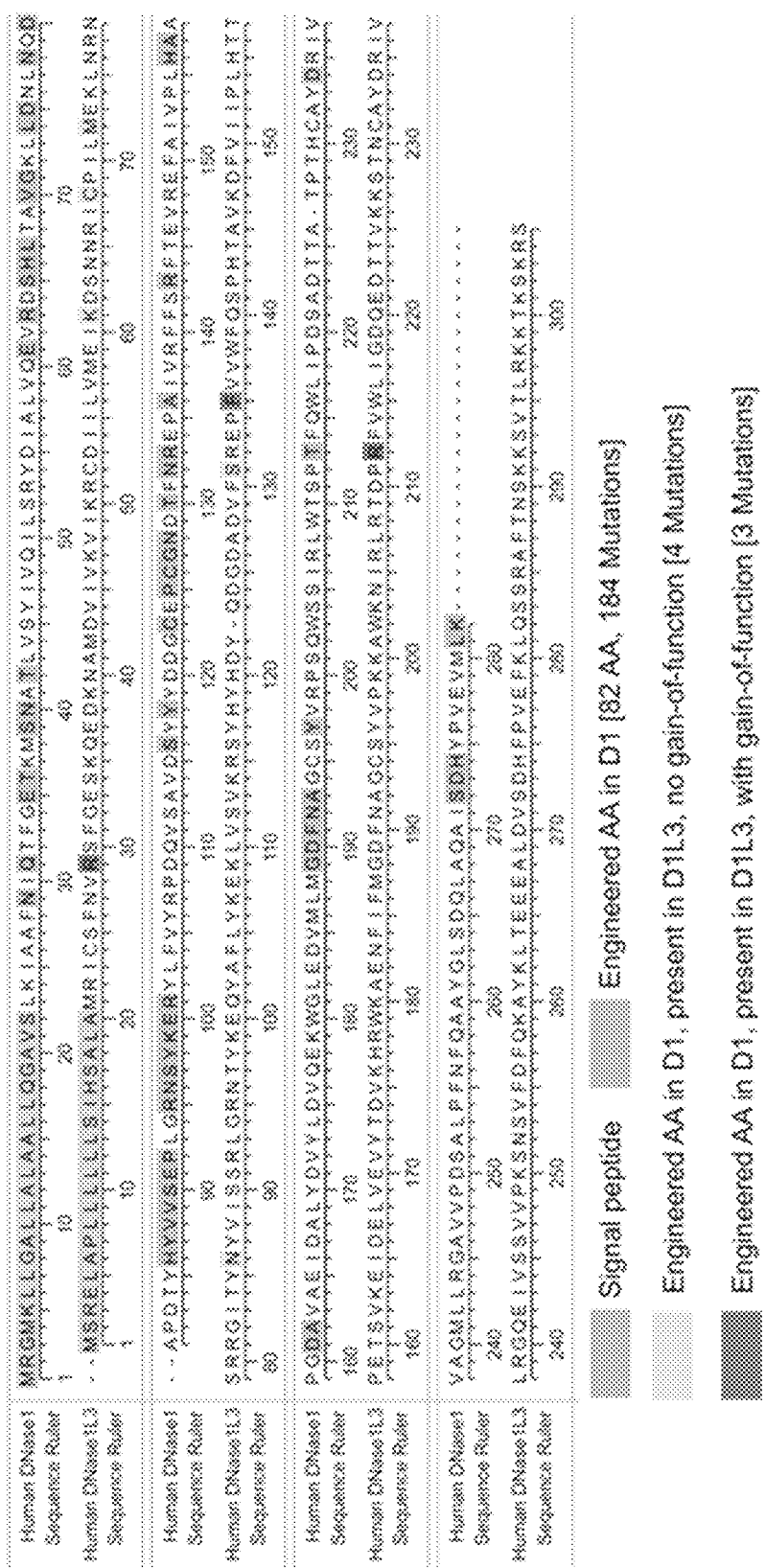
FIG. 23 shows the amino acid sequence alignment of human DNase1 (D1, SEQ ID NO: 1) and human DNase1L3 (D1L3, SEQ ID NO: 2). Sequence rulers demark the amino acid positions. Amino acids of D1 with published mutations are highlighted. Human D1L3 contains three mutations that are associated with a gain-of-function in human DNase1 (Q31R/T227K/A136F) and four mutations that are not linked to increased activity.
Figure 24B:
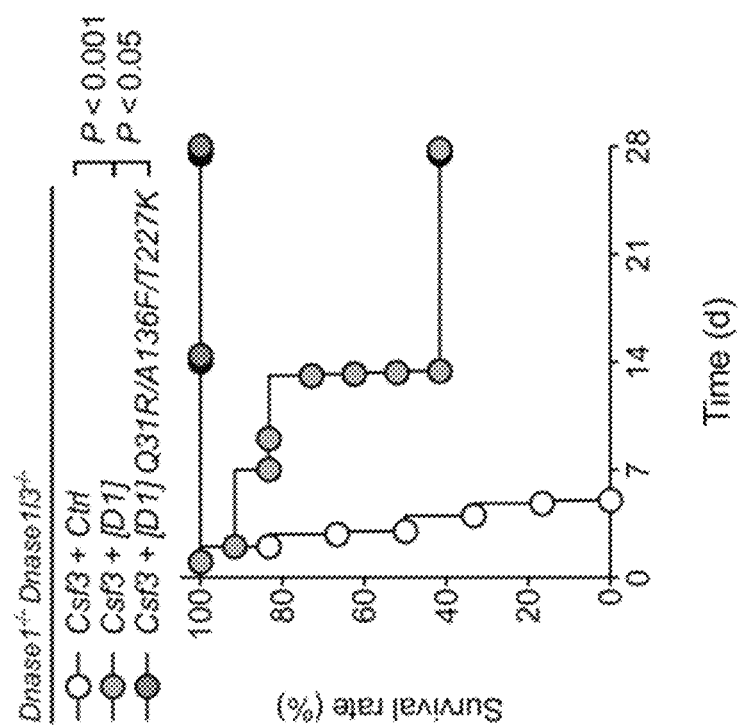
FIG. 24A-24B show the characterization of DNase1 variants (D1$^V$) with the mutations Q31R, T227K, and/or A136F.
Figure 24A:
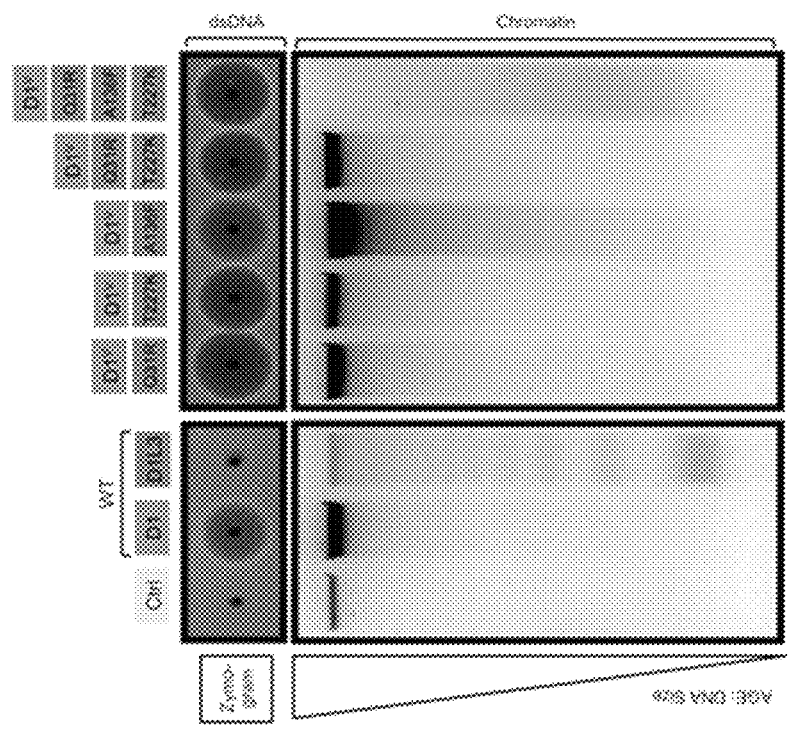
Figure 25:
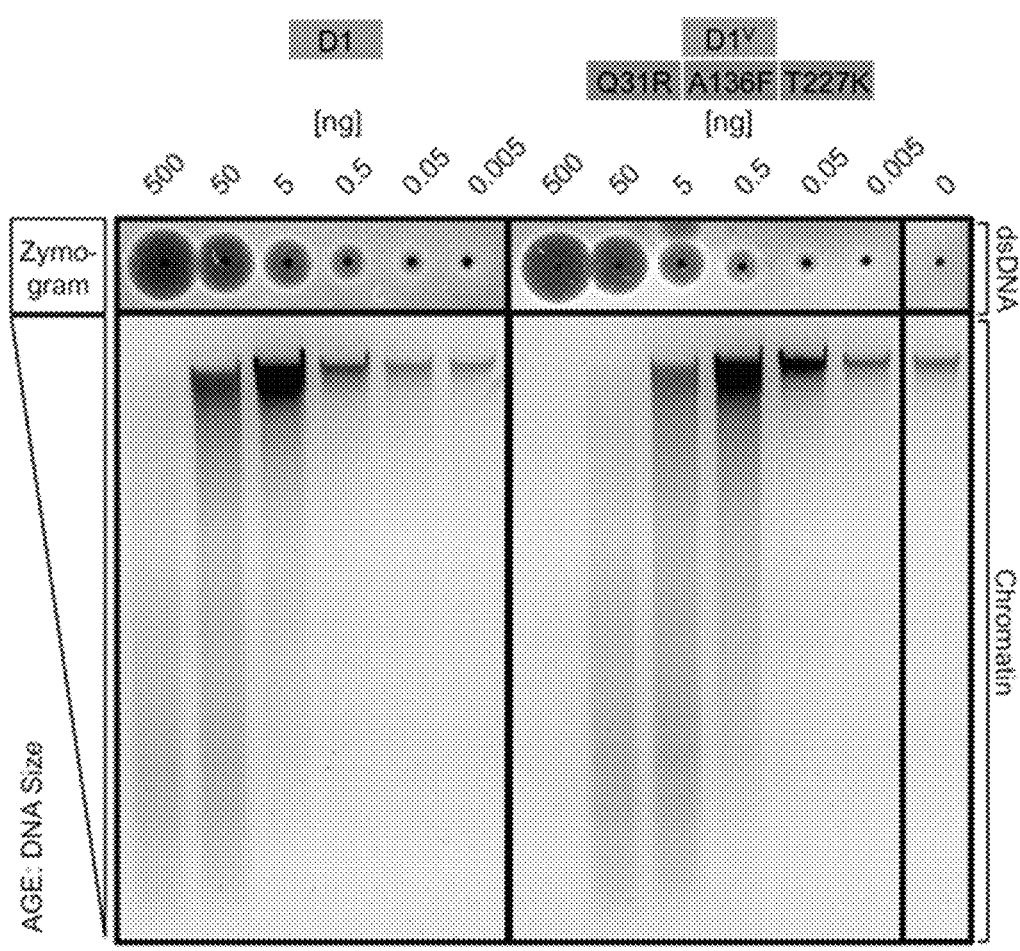
FIG. 25 shows a comparison of wild-type DNase1 (D1) and the DNase1-variants (D1$^V$) featuring the mutations Q31R/T227K/A136F. Purified proteins were analyzed at indicated amounts. Zymography showed dsDNA degrading activity as dark circles. The dsDNA degrading activity correlates with the diameter. Samples without activity show the loading well as small black spot (e.g. 0 ng). Agarose gel electrophoresis (AGE) of DNA isolated from digested chromatin shows a shift from high-molecular weight DNA to lower or low-molecular weight DNA that correlates with chromatin degrading activity. The DNase1-variant featuring the mutations Q31R/T227K/A136F degrades chromatin approximately 10-20-fold more efficiently than wild-type DNase1.
Figure 26:
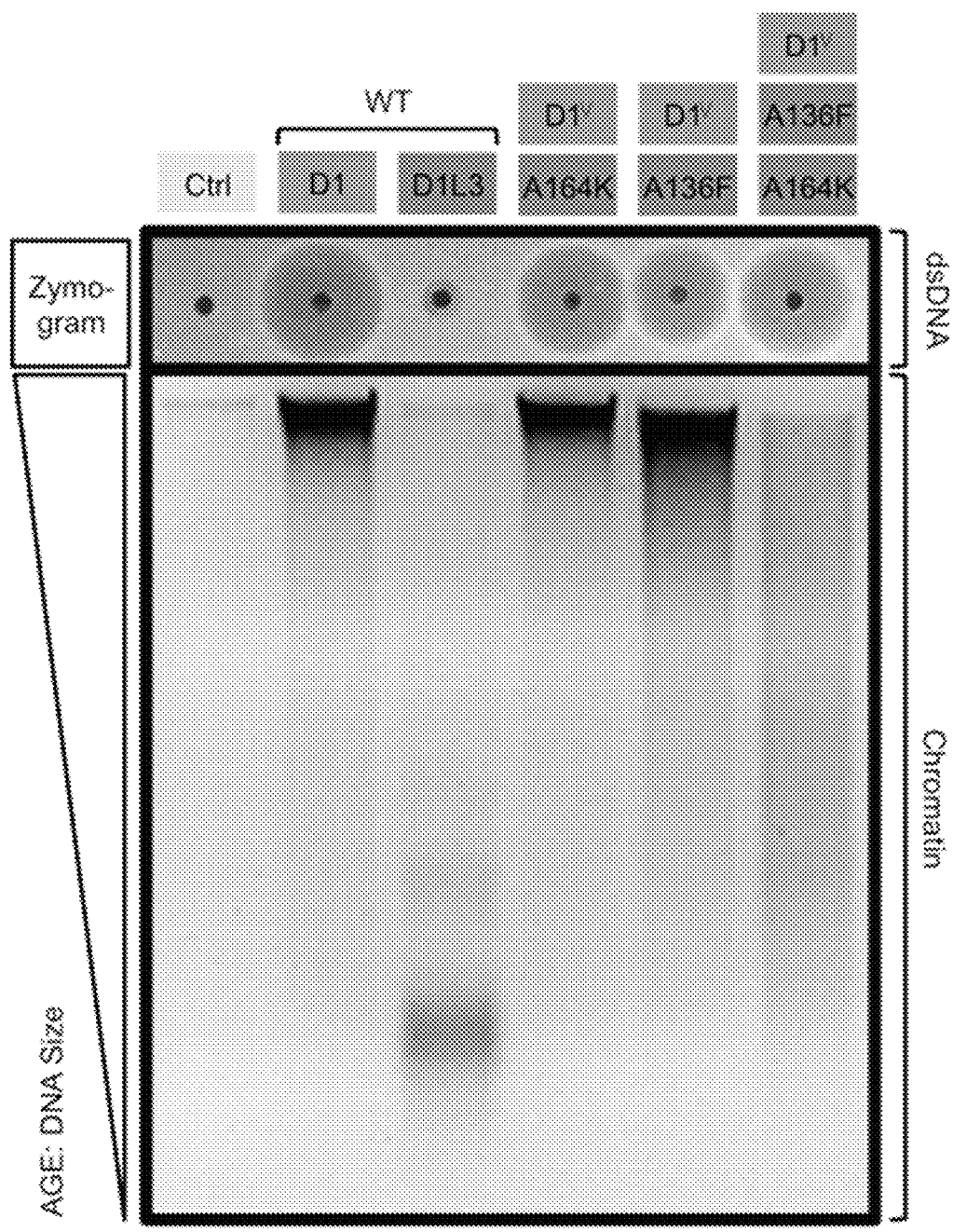
FIG. 26 shows a comparison of DNase1 variants (D1$^V$) with the amino acid mutations A164K, A136F, and A164K/A136F with wild-type DNase1 (D1) and wild-type (D1L3). Culture supernatants of transfected HEK cells were analyzed. Zymography showed dsDNA degrading activity as dark circles. The dsDNA degrading activity correlates with the diameter. Samples without activity show the loading well as small black spot (e.g. Ctrl). Agarose gel electrophoresis (AGE) of DNA isolated from digested chromatin shows a shift from high-molecular weight DNA to lower or low-molecular weight DNA that correlates with chromatin degrading activity. DNase1-variants featuring A136F/A164K degrades chromatin most efficiently.

Our central hypothesis is that the capacity of human D1L3 to degrade chromatin is mediated by amino acids that are not present in D1. Sequence alignment showed that 44% of the amino acids in human D1 and human D1L3 are identical (FIG. 17). We exclusively mutated only variable amino acids (56% non-shared amino acids) to generate D1 and DL3 variants.

D1L3 is a cationic protein with an isoelectric point of 9.35, whereas D1 and the other members are more basic proteins. We therefore speculated that the cationic nature of D1L3 enables the enzyme to degrade chromatin. Through sequence alignment, we identified 37 arginine or lysine residues in the variable amino acids, which are absent in D1 (FIG. 17). These amino acid residues are located at the amino acid positions 29 (position 9 with the signal peptide), 39 (9), 47 (7), 50 (30), 66 (46), 74 (54), 77 (57), 80 (60), 81 (61), 92 (72), 109 (89), 114 (94), 115 (95), 163 (143), 176 (156), 180 (160), 199 (179), 200 (180), 203 (183), 208 (188), 212 (192), 226 (206), 227 (207), 239 (219), 250 (230), 259 (239), 262 (242), 280 (260), 285 (265), 291 (271), 292 (272), 297 (277), 298 (278), 299 (279), 301 (281), 303 (283), 304 (284) with respect to SEQ ID NO: 2.

Twenty-six of these additional arginine or lysine residues in D1L3 correspond to the following amino acid positions in D1 (SEQ ID NO: 1): 31 (position 9 with the signal peptide), 41 (19), 49 (40), 52 (30), 68 (46), 76 (54), 79 (57), 81 (59), 92 (70), 109 (87), 114 (92), 115 (93), 164 (142), 177 (155), 181 (159), 200 (178), 201 (179), 204 (182), 209 (187), 213 (191), 227 (205), 239 (217), 250 (228), 259 (237), 262 (240), and 280 (260). In addition, D1L3 features 3 sites of insertions of arginine or lysine residues: R80, K226 and a C-terminal tail (after amino acid position 282 in SEQ ID NO: 2), which features 3 arginine and 6 lysine residues.

Figure 27A:
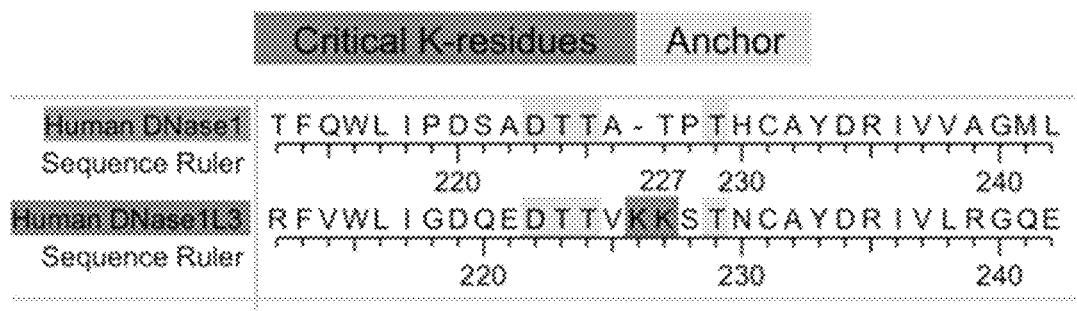
FIG. 27A-FIG. 27B shows development of a DNase1 variant with the mutation A226_T227insK.
Figure 27B:
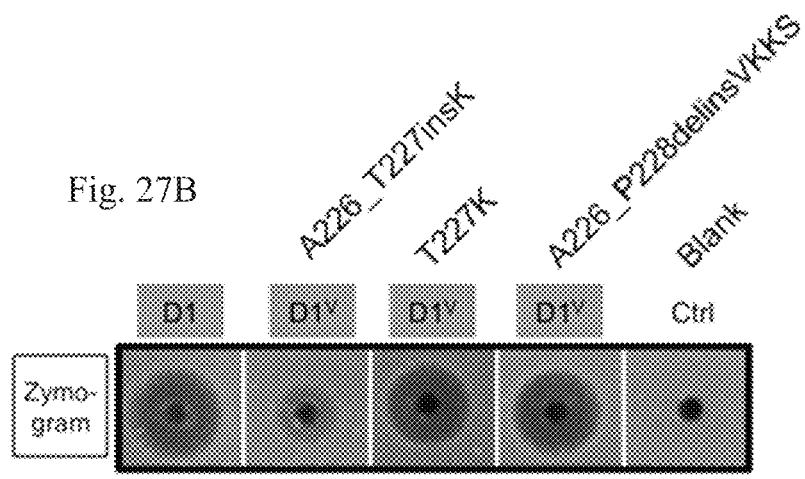
Figure 28:
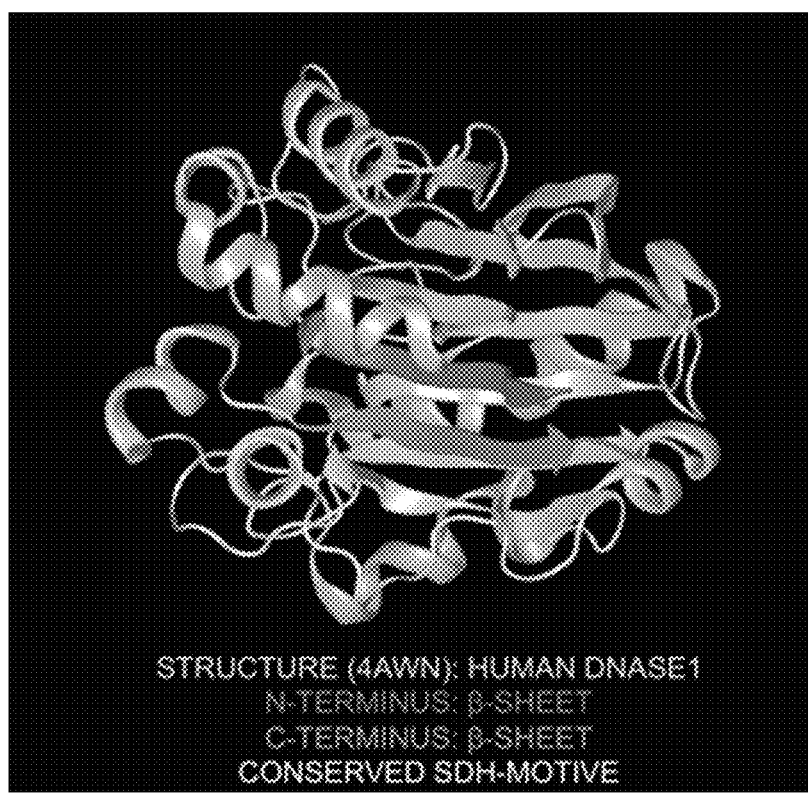
FIG. 28 shows the structure of human DNase1 [4AWN]. Highlighted are the N-terminal beta-sheet and the C-terminal beta-sheet and the motive S272/D273/H274, which is conserved among D1-protein family members.
Figure 33:
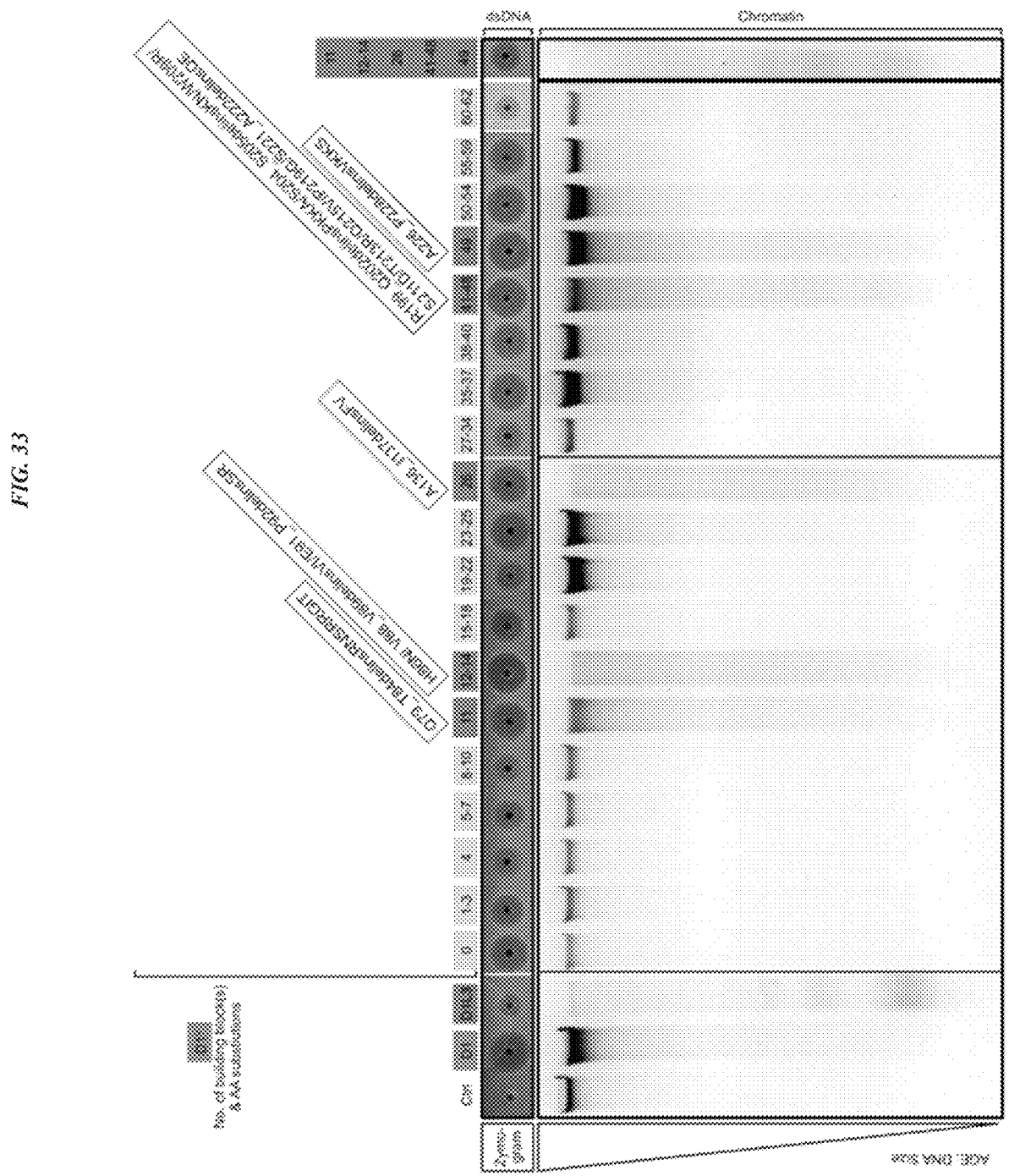
FIG. 33 shows characterization of DNase1 variants (D1$^V$) featuring building blocks from DNase1L3 (D1L3). Zymography showed dsDNA degrading activity as dark circles. The dsDNA degrading activity correlates with the diameter. Samples without activity show the loading well as small black spot (e.g. Ctrl). Agarose gel electrophoresis (AGE) of DNA isolated from digested chromatin shows a shift from high-molecular weight DNA to lower or low-molecular weight DNA that correlates with chromatin degrading activity. Building block substitutions that cause an increase in chromatin degrading activity are highlighted in dark shade. Samples without such effect are shown in light shade. A DNase1 variant featuring the combination of building blocks 11, 12-14, 26, 41-48, and 49 shows similar chromatin degrading activity than wild-type DNase1L3.
Figure 34A:
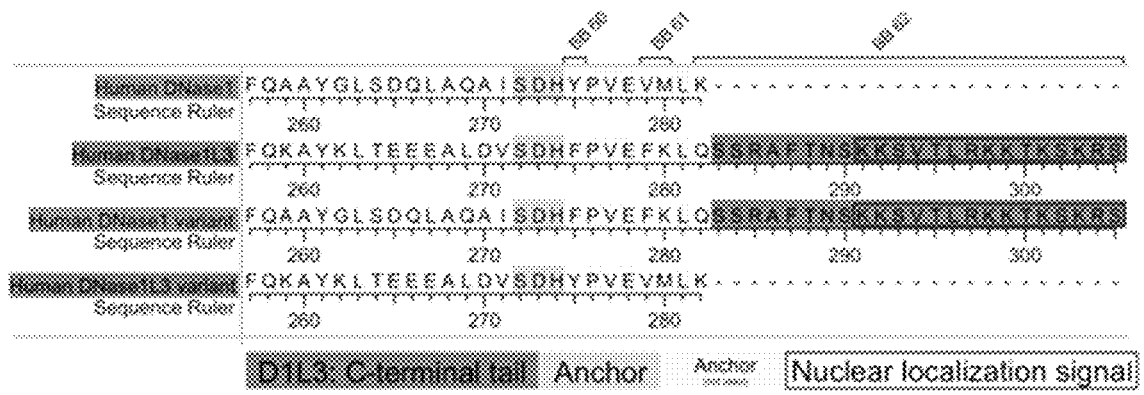
FIG. 34A-FIG. 34B shows the development of a DNase1L3 variant without the C-terminal tail of wild-type DNase1L3.
Figure 34B:
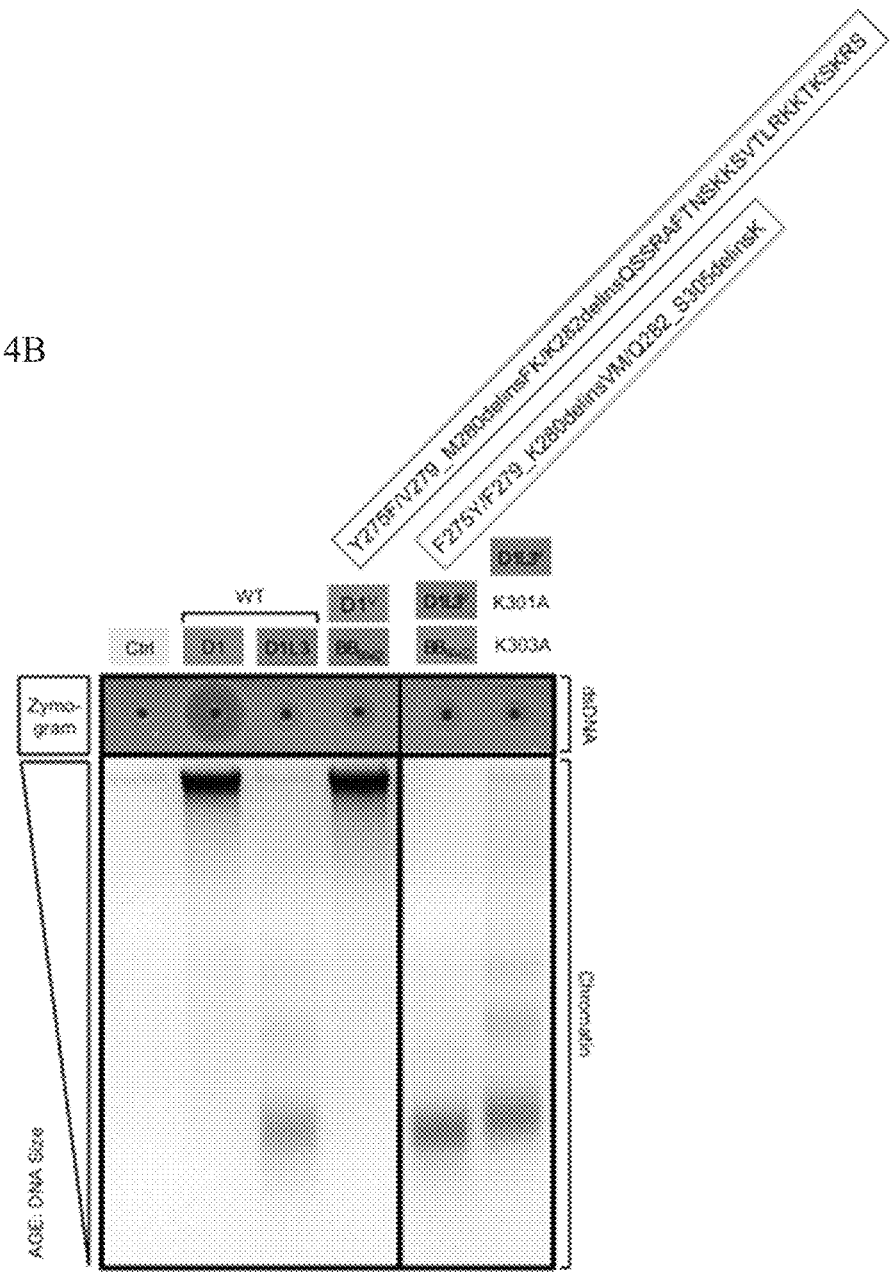
Figure 35A:
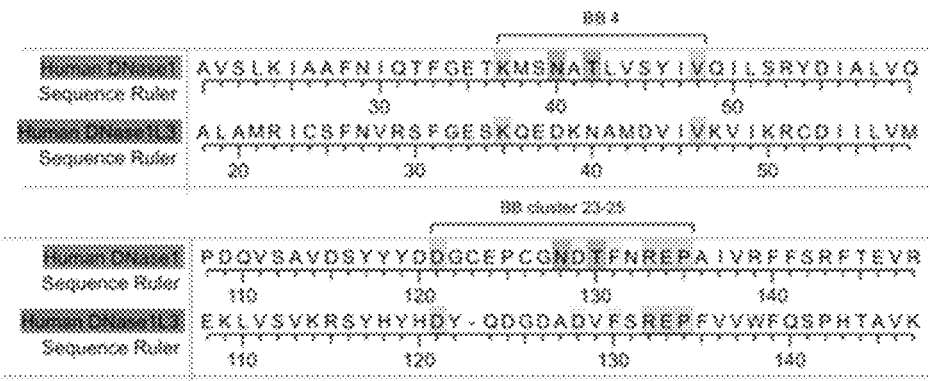
FIG. 35A-FIG. 35B shows the development of glycosylated DNase1L3 variants (D1L3$^V$).
Figure 35B:
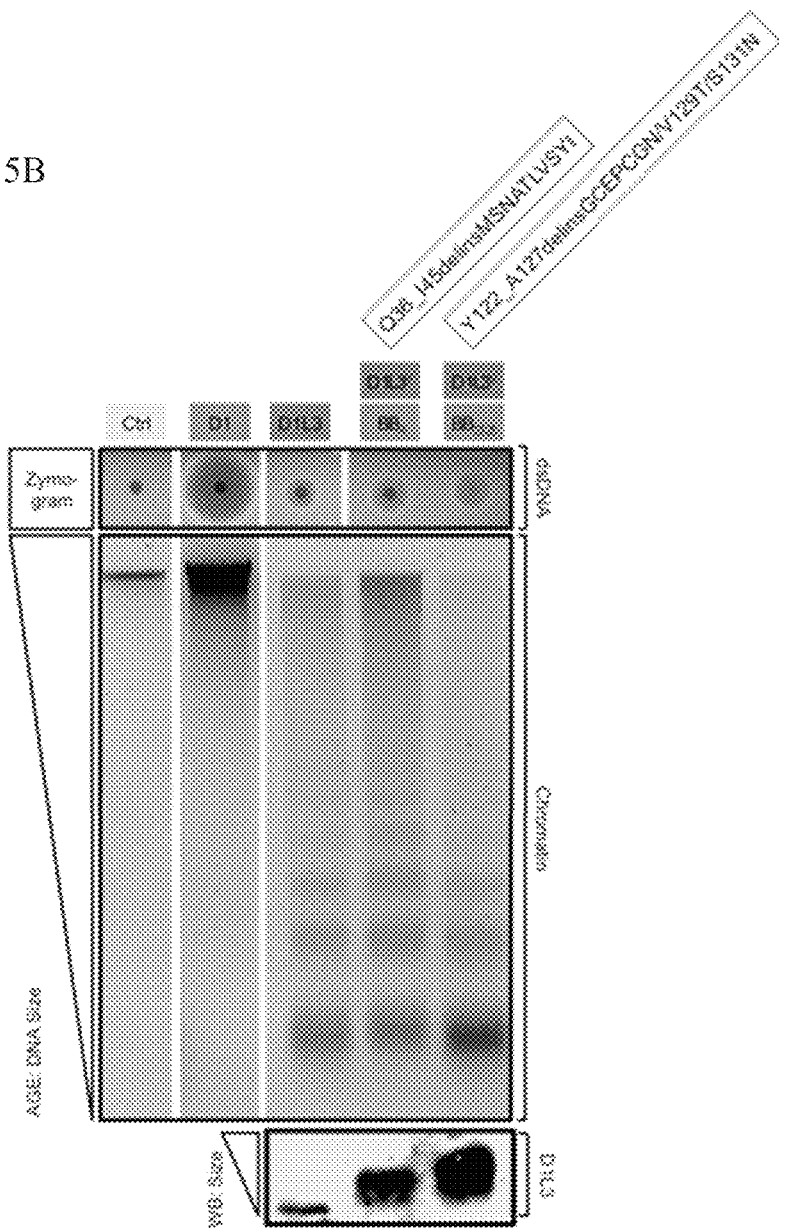

We aimed to transfer the arginine and lysine residues that are part of the core body of D1L3 to D1 by introducing the following mutations into wild-type D1 (FIG. 18): Q31R, A41K, Q49R, S52K, T68R, N76K, Q79R, D80_A81insR, A81R, P92R, D109K, V114K, D115R, A164K, Q177K, G181K, P200K, S201K, S204R, W209R, T213R, A226_T227insK, T227K, A239R, D250K, A259K, G262K, and K280M with respect to SEQ ID NO:1, thus generating 28 variants of D1.

In this Example, we were able to generate D1 variants that contain 23 of the 28 amino acid substitutions. We expressed the cDNA of these D1-variants in HEK293 cells and analyzed the dsDNA and chromatin degrading activity in the culture supernatants. We observed that the following amino acid modifications partially increased the chromatin degrading activity, while no major differences in dsDNA degradation were observed (FIG. 19): Q31R, Q49K, N76K, Q79R, P92R, D109K, A164K, Q177K, P200K, S201K, S204R, T213R. Interestingly, mouse and rat D1 (SEQ ID NO: 4), which share 79% and 78% of the amino acids of human D1, respectively, feature several of the analyzed amino acid substitutions, including Q31R, Q49K, and Q79K (FIG. 20). Analysis of supernatants from HEK293 cells expressing murine D1 and human D1 showed that murine D1 has an increased activity to degrade chromatin, when compared to human D1 (FIG. 21). We injected Dnase1$^{-/-}$Dnase1l3$^{-/-}$ mice with a mixture of Csf3 and murine D1 (mDnase1, SEQ ID NO: 3), human D1 (hDnase1, SEQ ID NO: 1), or an empty control plasmid (Ctrl). Mice receiving the control plasmid died within 7 days, whereas the expression of murine D1 provided a full protection for at least 28 days (FIG. 21). Unexpectedly, the expression of human D1 showed only a partial protection from death and more than half of the animals died within 14 days (FIG. 21), indicating that human D1 is less efficient in degrading intravascular NETs than murine D1. We now mutated Q31R, Q49K, Q79R, and W209R in human D1 to generate a murine-like D1-variant (SEQ ID NO: 5). A total of six mutations (Q31R, Q49K, Q79R, Q177K, W209R, G262K) were made to generate a rat-like D1-variant (SEQ ID NO: 6). Both rodent-like D1 variants were cloned into the hepatocyte expression vector and delivered along with Csf3 into Dnase1$^{-/-}$Dnase1l3$^{-/-}$ mice. We observed that gene therapy with the murine- and rat-like variant of D1 provided a full protection against NET-mediated vascular occlusions and death (FIG. 22). Importantly, in vitro expression of the rodent-like human D1-variants showed an increased activity to degrade chromatin (FIG. 22). Collectively, the data illustrate that (a) human D1 has a limited capacity to degrade NETs in vivo; (b) transferring multiple cationic amino acids from human D1L3 to human D1 generates hyperactive variants.

Several attempts have been made to generate hyperactive variants of D1 (6, 12, 13, 21-29). We found 184 mutations, which altered 82 of the 282 amino acids of wild-type human D1 (FIG. 23). Alignment of amino acid sequences of wild-type human D1 and human D1L3 revealed three gain-of-function mutations in human D1 that are already present in wild-type human D1L3 (FIG. 23): Q31R (corresponds to Q9R in D1 without signal peptide), T227K (T205K), and A136F (A114F). While the mutations Q31R and T227K may alter the DNA-binding properties of hD1 and thus cause hyperactivity, A136F confers resistance to inhibition by monomeric actin (21-24, 26, 29).

We designed a new D1-variant that carries the combination of Q31R/T227K/A136F (SEQ ID NO: 7) and compared its enzymatic activity to wild-type D1 (SEQ ID NO: 1), as well as to D1-variants carrying single mutations in Q31R, T227K, A136F, or a combined mutation in Q31R and T227K (SEQ ID NO: 8). We characterized the dsDNA and chromatin-degrading activity in the culture supernatants of transfected HEK293 cells. We observed no major differences in dsDNA-degrading activity with D1-variants carrying single or combinational mutations of Q31R and T227K (FIG. 24). Interestingly, chromatin was partially and fully degraded in A136F mutants and the combinational mutation of Q31R/T227K/A136F, respectively (FIG. 24). Next, we tested whether the Q31R/T227K/A136F variant of D1 is capable of preventing NET-mediated lethal vascular occlusions in neutrophilic Dnase1$^{-/-}$Dnase1l3$^{-/-}$. All mice receiving a control plasmid without DNases died, whereas all mice expressing the D1-variant (SEQ ID NO: 7) survived until the end of the experiment without showing signs of distress (FIG. 24). Using purified proteins, we observed that the triple amino acid substitution increases the chromatin degrading activity approximately 10-20 fold compared to wild-type D1 without detectable differences in dsDNA degrading activity (FIG. 25). Chromatin from nuclei and NETs contains actin (30, 31). The data suggest that chromatin degradation by D1 variants requires cationic amino acid substitutions as well as mutations that confer actin resistance—two features which are present in wild-type D1L3. To further corroborate this notion, we generated a D1 variant which features the combination of the mutations A164K and A136F (SEQ ID NO: 9). Indeed, we observed a strong increase in chromatin degrading activity in the D1 variant with both mutations (FIG. 26), supporting our hypothesis.

Development of Building Block Engineering of DNase1-Protein Family Members

D1L3 features three sites that contain additional amino acids: the C-terminal tail starting after Q282 ($NH_2$-SSRAFTNSKKSVTLRKKTKSKRS-COOH) (SEQ ID NO:33), and at two sites within the enzyme at S79/R80 and at K226 (FIG. 17). The 23 amino acids of the C-terminal tail of D1L3 have been attached to the C-terminus of D1 (10, 28). We observed that the insertion of an arginine-residue at position 226 of DNase1 (A226_T227insK) generated a D1-variant with reduced enzymatic activity to degrade dsDNA, while no such effect was observed with the substitution T227K (FIG. 27). Thus, an insertion of a K/R-residue goes along with a risk of reducing D1 function. The insertion of a charged amino acid may influence the local protein structure. Given that D1 is a globular enzyme that comprises one amino acid chain [FIG. 28, (27)], it is conceivable that such local alteration may render the whole enzyme inactive. Indeed, numerous non-conservative mutations throughout the D1 amino acid sequence inactivate the enzyme (12, 25, 26). We hypothesized that the transfer of local protein structures by implanting not only single arginine and lysine residues but also the neighboring amino acids sequences reduces the risk of inactivation. We searched within D1 and D1L3 for conserved amino acids in the vicinity of A226_T227insK that can be used as anchors for the insertion. We identified a D223/T224/T225 motif and a conserved T229 in D1 as N-terminal and C-terminal anchors, respectively (FIG. 27). We replaced 3 amino acids within D1 (ATP) with 4 amino acids, including K226, from D1L3 (VKKS) in silico. Expression of the cDNA of the new D1-variant (A226_P228delinsVKKS) in HEK239 cells revealed a functionally active enzyme with a similar dsDNA-degrading activity, when compared to wild-type D1

(FIG. 27). The data suggest that the variable amino acids between conserved amino acids are interchangeable between D1 and D1L3.

We conceptualized a building block-technology to transfer enzymatic properties from one member of the D1-protein family to another. The following cardinal steps characterize the technology (FIG. 29):
(1) Provide protein-protein alignment of donor and recipient DNase
(2) Identify variable amino acid or amino acid sequence for transfer (building block)
(3) Identify conserved amino acids in donor and recipient DNase that are located up and downstream of building block (anchors), respectively.
(4) Replace cDNA encoding for building block between C- and N-anchors in recipient DNase, with cDNA between the anchors in donor DNase.
(5) Synthesize cDNA of chimeric DNase, followed by in vitro/in vivo expression into a recipient organism that is preferably deficient in both donor and recipient DNase (e.g. CHO cells or Dnase1$^{-/-}$Dnase1l3$^{-/-}$ mice).

Engineering DNase1 Variants Through Building Block Technology

A multiple-species alignment of D1 and D1L3 from human, mouse, rat, and chimpanzee (FIG. 30), showed that N- and C-terminal anchors are conserved among these species. These anchor amino acids or amino acid sequences flank 62 building blocks of variable amino acids and amino acid sequences, which include the amino acid sequence in D1 (ATP) and D1L3 (VKKS) from the above-mentioned experiments as building blocks #49 (FIG. 31).

The transfer of these building blocks from D1L3 into D1 generates D1-variants with the following mutations (FIG. 31): 1M_S22delinsMSRELAPLLLLLLSIHSALA, L23_A27delinsMRICS, I30_T32delinsVRS, E35_T36delinsES, M38_I47delinsQEDKNAMDVI, Q49_S52delinsKVIK, Y54C, I56_Q60delinsIILVM, V62_R63delinsIK, S65_K72delinsSNNRICPI, L74_N76delinsMEK, Q79_T84delinsRNSRRGIT, H86N, V88_V89delinsVI, E91_P92delinsSR, N96_S97delinsNT, R101Q, L103A, V105L, R107_Q110delinsKEKL, A113_S116delinsVKRS, Y118H, D120H, G122_N128delinsYQDGDA, T130S, N132S, A136_I137delinsFV, R139W, F141_F144delinsQSPH, E146_E149delinsAVKD, A151V, V153I, A157_A158delinsTT, G160_A162delinsETS, A164K, A168E, Y170_D171delinsVE, L174T, Q177_K179delinsKHR, G181_L182delinsKA, D184_L187delinsNFIF, R199_Q202delinsPKKA, S204_S205delinsKN, W209R, S211D, T213R, Q215V, P219G, S221_A222delinsQE, A226_P228delinsVKKS, H230N, V238_A239delinsLR, M241_A246delinsQEIVSS, D250K, A252_P254delinsNSV, N256D, A259_A260delinsKA, G262K, S264 L267delinsTEEE, Q269_I271delinsLDV, Y275F, V279_M280delinsFK, and K282delinsQSSRAFTNSKKSVTLRKKTKSKRS.

The following D1L3-variants are generated if the building blocks are transferred from D1 to D1L3 (FIG. 31): M1_A20delinsMRGMKLLGALLALAALLQGAVS, M21_S25delinsLKIAA, V28_S30delinsIQT, E33_S34delinsET, Q36_I45delinsMSNATLVSYI, K47_K50delinsQILS, C52Y, I54_M58delinsIALVQ, I60_K61delinsVR, S63_I70delinsSHLTAVGK, M72_K74delinsLDN, R77_T84delinsQDAPDT, N86H, V88 I89delinsVV, S91_R92delinsEP, N96_T97delinsNS, Q101R, A103L, L105V, K107_L110delinsRPDQ, V113_S116delinsAVDS, H118Y, H120D, Y122_A127delinsGCEPCGN, V129T, S131N, I35F_136VdelinsAI, W138R, Q140_H143delinsFSRF, A145_D148delinsAVKD, V150A, I152A, T156_T157delinsAA, E159_S161delinsGDA, K163A, E167A, V169_E170delinsYD, T173L, K176_R178delinsQEK, K180_A181 delinsGL, N183_F186delinsDVML, P198_A201delinsRPSQ, K203_N204delinsSS, R208W, D210S, R212T, V214Q, G218P, Q220_E221delinsSA, V225_S228delinsATP, N230H, L238_R239delinsVA, Q241_S246delinsMLLRGA, K250D, N252_V254delinsALP, D256N, K259_A260delinsAA, K262G, T264_E267delinsSDQL, L269_V271delinsQAI, F275Y, F279_K280delinsVM, and Q282_S305delinsK.

Next, we conceptualized a sequential approach to engineer D1-variants with D1L3 activity that starts with the transfer of multiple adjacent building blocks (clusters), continues with the transfer of individual building blocks, and ends with a transfer of individual amino acids or the combination of multiple building blocks into new chimeric enzymes (FIG. 32). This approach reduces the number of D1-D1L3-chimera in the initial screening.

To test our method, we designed a total of 19 D1-variants comprising either individual building blocks or clusters of building block cluster from D1L3 (FIG. 31). These D1-variants feature the following amino acid mutations: 1M_S22delinsMSRELAPLLLLLLSIHSALA, L23_A27delinsMRICS/I30 T32delinsVRS/ E35_T36delinsES, M38_I47delinsQEDKNAMDVI, Q49_S52delinsKVIK/Y54C/I56_Q60delinsIILVM, V62_R63delinsIK/S65_K72delinsSNNRICPI/ L74_N76delinsMEK, Q79_T84delinsRNSRRGIT, H86N/ V88_V89delinsVI/E91_P92delinsSR, N96_S97delinsNT/ R101Q/L103A/V105L, R107_Q110delinsKEKL/ A113_S116delinsVKRS/Y118H/D120H, G122_N128delinsYQDGDA/T130S/N132S, A136_I137delinsFV, R139W/F141_F144delinsQSPH/ E146_E149delinsAVKD/A151V/V153I/ A157_A158delinsTT/G160_A162delinsETS/A164K, A168E/Y170_D171delinsVE/L174T, Q177_K179delinsKHR/G181_L182delinsKA/ D184_L187delinsNFIF, R199_Q202delinsPKKA/ S204_S205delinsKN/W209R/S211D/T213R/Q215V/ P219G/S221_A222delinsQE, A226_P228delinsVKKS, H230N/V238_A239delinsLR/M241_A246delinsQEIVSS/ D250K/A252_P254delinsNSV, N256D/ A259_A260delinsKA/G262K/S264_L267delinsTEEE/ Q269_I271delinsLDV, and Y275F/V279_M280delinsFK/ K282delinsQSSRAFTNSKKSVTLRKKTKSKRS.

Next, we cloned the cDNA into an expression vector, which was transfected into HEK293 cells. Analysis of the cell supernatants showed dsDNA degradation by all samples (FIG. 33). Furthermore, we observed that the transfer of building blocks (BB) 11 (see SEQ ID NO: 10), BB 12-14 (see SEQ ID NO: 11), BB 26 (see SEQ ID NO: 12), BB 41-48 (see SEQ ID NO: 13), and BB 49 (see SEQ ID NO: 14) from D1L3 to D1 resulted in enzymes with increased chromatin degrading activity. All these chimeric enzymes exhibited the same or more activity to degrade dsDNA substrates than wild-type D1. The building blocks 11 (RNSRRGI in SEQ ID NO: 2) and 49 (VKKS in SEQ ID NO: 2) from D1L3 contain R80/R81 and K227, respectively, which are not present in D1. The D1L3-BB cluster 41-48 (PKKAWKNIRLRTDPRFVWLIGDQE from SEQ ID NO:2) features 5 additional arginine and lysine residues than its counterpart in D1 (RPSQWSSIRLWTSPTFQWLIPDSA of SEQ ID NO:1). These additional cationic amino acids may be responsible for the hyperactivity. The D1-building blocks 12-14 and 26 contain the amino acid sequences H86 to R95 and A136 to V138 in SEQ ID NO: 1, which includes amino acid residues that are required for binding of the D1-inhibitor actin. Thus, replacement of these amino acid sequences with the respective building blocks from D1L3, which do not interact with actin, likely generates actin-resistant variants of D1. We now combined BB 11, 14, 26, 41-19 in one novel D1-variant (SEQ ID NO: 15). We observed that the combination of these gain-of-function BBs increased the chromatin degrading of the D1 variant to levels of wild-type D1L3 (FIG. 33). Thus, the BB technology provides a robust method to generate hyperactive D1 variants.

Engineering DNase1-Like 3 Variants Through Building Block Technology

The BB cluster 60 to 62 of D1L3 includes the amino acid from its C-terminal tail (FIG. 33). The tail starts after L281 (FIG. 34) and comprises the amino acid sequence QSSRAFTNSKKSVTLRKKTKSKRS (SEQ ID NO:40), which includes a bi-partite NLS. D1L3 requires the C-terminal tail to degrade DNA within lipid vesicles including transfection reagents and apoptotic bodies (7, 10, 28). Furthermore, the C-terminal tail is required for degradation of lipid- and cell-free chromatin by D1L3 (7). Both findings are based on a D1L3-variant that lacks the amino acids after Q282 and is thus inactive in degrading these substrates. Wilbert et al. attached the C-terminal extension of D1L3 to the C-terminus of D1 and thus transferred the capacity to degrade DNA within lipid vesicles to D1 (10, 28). Here, we employed our BB technology to transfer the C-terminus from D1L3 to D1 and vice versa. We used the conserved 5272/D273/H274 motif, which is located in front of the terminal beta-sheet in D1 (FIG. 28), as a N-anchor and exchanged the terminal 3 building blocks between D1 and D1L3 (FIG. 34). This approach generated a D1-variant that features the C-terminal extension of D1L3 due to the mutations Y275F/V279_M280delinsFK/K282delinsQSSRAFTNSKKSVTLRKKTKSKRS (SEQ ID NO: 16) and a truncated D1L3-variant due to the mutations F275Y/F279_K280delinsVM/Q282_S305delinsK (SEQ ID NO: 17). We expressed both variants and the wild-type enzymes in HEK293 cells and characterized the DNase activity in the supernatant. Unexpectedly, we observed that the D1-variant with the C-terminus of D1L3 did not degrade chromatin, while the D1L3-variant lacking the C-terminus of the wild-type enzyme was still able to cleave chromatin (FIG. 34). In fact, we observed an increased chromatin degrading activity with this D1L3 variant. To corroborate this finding, we tested whether the truncated variant of D1L3 in vivo and observed that its expression of protected from NET-mediated mortality of neutrophilic Dnase1$^{-/-}$ Dnase1l3$^{-/-}$ mice (FIG. 34). In conclusion, the deletion of the C-terminal does not inhibit, but rather increases the function of D1L3 to degrade lipid-free and cell-free chromatin.

Serum proteases, in particular plasmin, degrade D1L3, but not D1 (9). The sensitivity of D1L3 towards protease activity would limit its use in clinical practice. Glycosylated proteins display an increased protection against proteases (32). Using software analysis, we could not identify a known consensus sequence for glycosylation in human and murine D1L3. Software analysis of human D1 revealed 2 glycosylation sites, as observed both in silico and in vitro (9). We hypothesized that glycosylated variants of D1L3 may increase the half-life in circulation due to an improved resistance towards serum proteases. A glycosylation site requires a minimal consensus sequence of N-X-T/S. D1 contain two known N-glycosylation sites, N40 (N18 without signal peptide) and N128 [(N106 without signal peptide, (9)]. The amino acids of the D1-glycosylation sites N40-X-T42 and N128-X-T130 correspond to the D38-X-N40 and A127-X-V129 in D1L3. Thus, a glycosylated version of D1L3 needs to feature the amino acids mutations D38N, N40T, A127N, and V129T (see SEQ ID NO: 18). Instead of using conventional point mutations to insert these amino acid substitutions, we used BB technology to transfer the D1-glysylation sites N40-X-T42, which lies within BB4 (MSNATLVSY in SEQ ID NO: 1), and N128-X-T130, which lies within the BB cluster 23-25 (GCEPCGNDTFN in SEQ ID NO: 1), from D1 to D1L3 (FIG. 35). Thus, we generated two new D1L3 variants, which feature the mutations Q36_I45delinsMSNATLVSYI (SEQ ID NO: 19) and Y122_A127delinsGCEPCGN/V129T/S131N (SEQ ID NO: 20), respectively. We expressed these D1L3 variants along with the WT enzyme in HEK293 cells. Next, we analyzed the supernatant by Western Blot using a polyclonal antibody targeting an epitope in the C-terminal tail of the WT enzyme to detect the WT enzyme as well as the D1L3 variants. As expected the D1L3 variants showed bands of a higher molecular weight presumably to glycosylation, when compared to the WT enzyme (FIG. 35). D1L3 variant with glycosylation at N40 or N128 retained their chromatin degrading activity (FIG. 35). In conclusion, the data suggest that BB technology can be used to transfer the glycosylation sites from D1 to D1L3, which may generate D1L3 variants with increased protease-resistance and half-life in patients.

Therapy with DNase1-Like 3 and a Variant Thereof

Finally, we tested the therapeutic effects of D1L3 in vivo. Histological analysis of vascular clots of NETs show dense aggregates of chromatin (FIG. 36A), indicating that histone-free cleavage sites for D1 are rare in vivo. Thus, we hypothesized that an acute therapy with wild-type D1L3 is more effective in degrading intravascular NETs than wild-type D1. To test our hypothesis, we expressed Csf3 in Dnase1$^{-/-}$Dnase1l3$^{-/-}$ deficient mice to induce vascular clots of NETs. Importantly, preceding exitus, mice with vascular occlusions by NETs develop hematuria and hypothermia, which can be detected non-invasively. Therefore, the animal model allows identifying and hence selecting mice, which have formed NETs, to test drug candidates for an acute therapy against NETs (FIG. 36B). Here, we tested purified wild-type human D1 (dornase alpha; SEQ ID NO: 1), wild-type human D1L3 (SEQ ID NO: 2), and a hyperactive D1L3 variant [D1L3$^{V}$; (SEQ ID NO: 17)] for an acute therapy against NETs. We injected Csf3 into Dnase1$^{-/-}$ Dnase1l3$^{-/-}$ deficient mice. After 72 hours, the first individual animals started to develop hypothermia and hematuria. We used a drop in body temperature of 4° C. or more and the presence of red urine as inclusion criteria. Mice, which developed these phenotypes, were randomized into the different treatment groups. Animals received a single dose, intravenous injection via the tail vein of 1 mg/kg of D1, D1L3, or vehicle. After 30 minutes, the animals were euthanized to collect biosamples (blood and organs). Quantification of clots of NETs in the vasculature of lungs showed that NETs occluded blood vessels in mice receiving vehicle or D1 therapy (FIG. 36D). Importantly, mice injected with D1L3 and D1L3$^{V}$ showed no or few clot of NETs (FIG. 36D). In patients, circulating DNA has the size of DNA in mono-nucleosomes [180 base pairs, (33)], indicating that it is a degradation product of high-molecular weight DNA in chromatin. Circulating DNA is commonly used as a surrogate marker of intravascular NET formation, but can also derive from damaged and necrotic tissue (34). We quantified DNA in serum using a fluorescent DNA probe. We observed that the injection of D1L3 and D1L3$^V$, but not D1 or vehicle, caused a strong increase in levels of circulating DNA (FIG. 36E). Isolation and visualization of circulating DNA showed multimers 180 base pair fragments, indicating the presence of mono- and oligo-nucleosomes in serum from in mice receiving the D1L3 therapy (FIG. 36F). Mice receiving D1L3$^V$ showed only mono- and di-nucleosomes. The data confirm the hyperactivity of D1L3$^V$ in vivo. DNA isolates from serum of mice receiving D1 therapy showed faint DNA smears of various sizes, whereas no DNA could be isolated from serum of mice injected with vehicle (FIG. 36F). Thus, D1L3 may be used, not only for prophylaxis, but also for acute therapy of diseases that associated with NETs.

We further explored the therapeutic application of D1L3$^V$ in a model of ischemia-reperfusion injury (FIG. 37A). In brief, one testicle of male wild-type rats was subjected to testicular torsion as previously described by us (35). The procedure causes an ischemic tissue injury. After randomization and de-torsion of the testicle, the rats received three daily injections of vehicle dornase alpha (D1, 1 mg/kg), or a purified DNase1L3 variant (SEQ ID NO: 17, D1L3$^V$, 1 mg/kg). After 7 days the ischemic testicle and untreated testicle were collected. The therapy with the D1L3$^V$, but not saline or D1, significantly reduced the testicular atrophy (FIG. 37B). Moreover, therapy with the D1L3$^V$, but not saline or D1, substantially reduced the tissue injury and majority of animals no signs of injury (FIG. 37C). Collectively, the data identify D1L3 as a potent therapy against ischemia-reperfusion injury.

Drug Development of DNase1 Variants, DNase1-Like 3 and Variants

Nearly 70% of all protein therapeutics are produced using Chinese Hamster Ovary (CHO) (36). Indeed, wild-type DNase1 (dornase alpha) is produced in CHO cells. Despite significant advantages, cell line development and large-scale production in CHO still remains a huge challenge due a considerable degree of variability and no reliable methods for predicting or modeling cell growth characteristics (36). Importantly, CHO cells were not able to stably produce hyperactive variants of D1, which prevented their clinical manufacturing (12). The manufacturing properties of D1L3 are unknown. Thus, we developed stable CHO cell lines producing wild-type D1 (SEQ ID NO: 1), a hyperactive D1 variant (SEQ ID NO: 7), wild-type D1L3 (SEQ ID NO: 2) and a hyperactive D1L3 variant (SEQ ID NO: 17). We cultured the cell lines in bioreactors and observed a stable protein expression with wild-type D1 and the D1 variant, with the latter having strongly increased expression levels (FIG. 38), illustrating the feasibility of producing a hyperactive D1 variant in CHO. Unexpectedly, we observed only minor protein levels of wild-type D1L3 and the D1L3 variant (FIG. 38), pointing towards a major challenge for clinical manufacturing D1L3 and variants thereof.

Figure 38A:
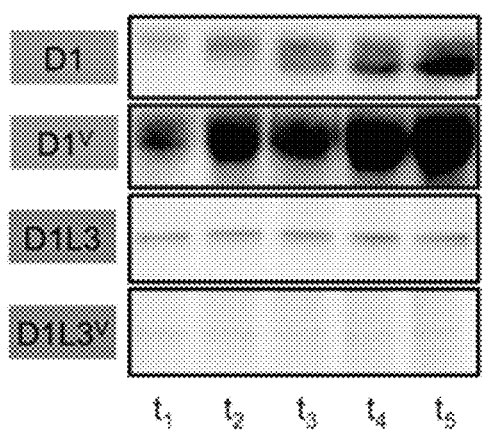
FIG. 38A-FIG. 38C shows the expression levels of DNase1, DNase1L3, and variants thereof (FIG. 38A) Stable pools of CHO cells producing wild-type DNase1 (D1), a variant thereof (D1$^V$, SEQ ID NO: 7), wild-type D1L3, and a variant thereof (D1L3$^V$, SEQ ID NO: 17) were cultured in bioreactors. Samples were collected periodically and analyzed by Western Blot. Expression of D1 and D1$^V$ was detected, but only low levels of D1L3 and D1L3$^V$.
Figure 38B:
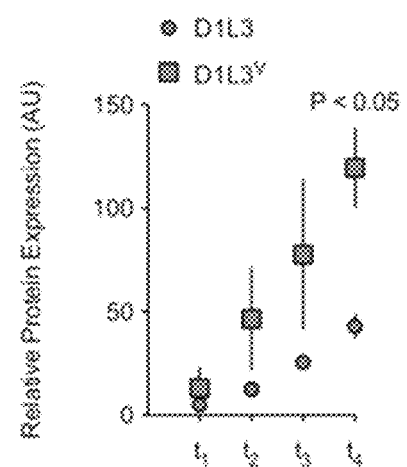
Figure 38C:
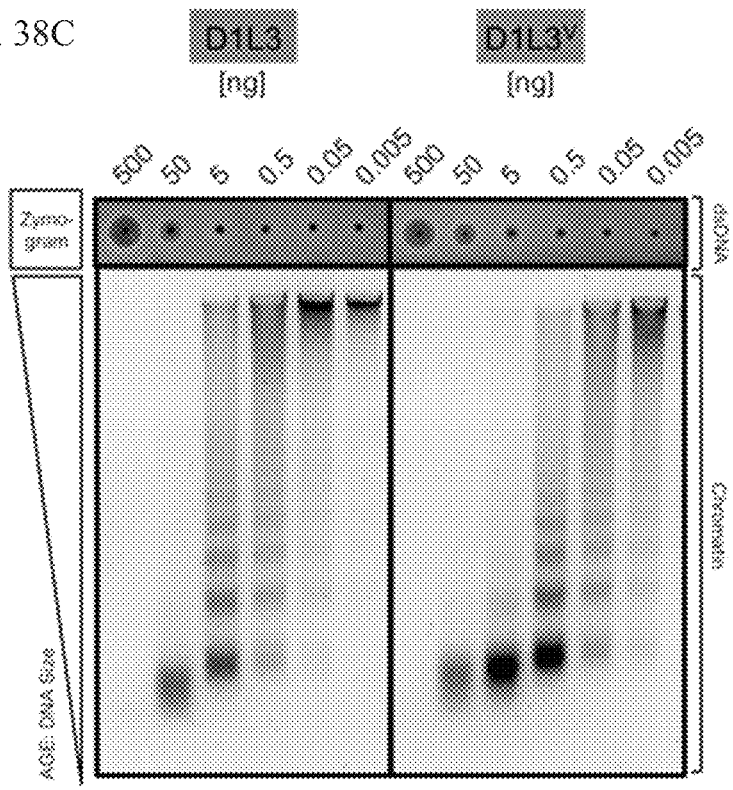

Due to high cell densities in large-scale bioreactors, cells compete for resources and undergo cellular stress leading to increased cell death called apoptosis, a cell death program used by multi-cellular organisms, including mammals (37). D1L3 targets DNA in apoptotic bodies (7). We speculated that the low levels of D1L3 are due to scavenging of the enzyme by these apoptotic vesicles. To overcome these limitations, we tested the production of D1, D1L3 and their variants using the microbial expression system, *Pichia pastoris*, an established, FDA approved and Generally Recognized As Safe (GRAS) organism with protein secretory abilities (38, 39). A key limitation of this approach is that proteins produced by *P. pastoris* are often hyperglycosylated and may result in enhanced immunogenicity (40). The composition of D1L3 and its variant are non-glycosylated and optimal for expression in *P. pastoris*. We mutated the glycosylation sites in D1 and its variant at N40S and N128S respectively to generate deglycosylated proteins (SEQ ID NO: 21, 23). Protein expression in *P. pastoris* is generally achieved by coupling proteins of interest to secretory signal peptides of various origins. We omitted this step to avoid the generation of immunogenic chimeric proteins. We speculated that the native signal peptide of D1 and/or D1L3 is recognized by *P. pastoris*. After codon-optimization was performed, we expressed the cDNA in *P. pastoris* (SEQ ID NO: 22, 24-26). We achieved expression of D1 and the D1 variant (not shown). Importantly, this approach furthermore enabled the expression of D1L3 and the D1L3 variant, with the latter showing increased expression levels (FIG. 38). We purified the proteins and confirmed that the D1L3 has increased activity (FIG. 38). In conclusion, the data suggest that using non-mammalian expression systems, such as *P. pastoris*, enables clinical manufacturing of D1L3 and variants thereof.

Discussion

Two DNA-degrading enzymes have been widely used therapeutically in experimental models and patients. Streptodornase, a secreted DNase from *Streptococcus* spp., has been tested in disease models of skin homograft, bladder clots, wound debridement, meningitis, DNase1 (including pancreatic DNase1) has been used therapeutically in experimental models of cancer, cystic fibrosis, lupus, thrombosis, stroke, sepsis, lung injury, atherosclerosis, viral infection, sickle cell disease, myocardial infarction, ear infection, wound healing, liver injury, endocarditis, liver infection, pancreatitis, primary graft dysfunction, limb ischemia reperfusion, kidney injury, blood clotting, asthma, alum-induced inflammation, hepatorenal injury. Streptodornase has also been used to treat patients with pleural exudations, hemotorax, intrabiliary blood clots, post pneumatic anemia, ulcers, otolaryngological conditions, oral infections, minor injuries, sinusitis, post-operative rhinoplasties, infertility, bladder catheter, wound cleaning, skin reaction test. Importantly, DNase1 has been tested therapeutically in patients with pneumococcal meningitis, gout, leg ulcers, cystic fibrosis, Kartegener's syndrome, asthma, lobar atelectasis, chronic bronchitis, bronchiectasis, lupus, primary, cilliary dyskinesia, bronchiolitis, empyema, pleural infections, cancer, dry eyes disease, lower respiratory tract infections, chronic hematomas, Alzheimer's disease, and obstructive pulmonary disease. In this example, we identified D1L3, variants thereof, as well as D1 variants as novel candidates for a DNase therapy (FIG. 39).

Methods

Detection of Chromatin Degrading Activity

To measure chromatin degrading activity, we mixed samples with nuclei isolated from HEK293 (1,500,000-3,000,000 per reaction), 20 mM Tris-HCl pH 7.4, 2 mM MgCl$_2$, 2 mM CaCl$_2$), 50 mM NaCl and protease inhibitors. After incubating the samples for 1 hour at 37° C., they were heated up to 65° C. for 10 minutes. We proceeded with DNA isolation using the QIAamp DNA Blood Mini Kit (Qiagen) according to the manufacturer's protocol. The eluent was then loaded onto an agarose gel and the DNA fragments were separated by gel electrophoresis. The DNA fluorescence of the gels was recorded with a fluorescence scanner. Further methods are described in Example 1.

REFERENCES

1. V. Kumar, A. K. Abbas, N. Fausto, J. C. Aster, in *Robbins & Cotran Pathologic Basis of Disease*. (Elsevier Health Sciences, 2009), chap. 2.
2. V. Brinkmann et al., Neutrophil extracellular traps kill bacteria. *Science* (New York, N.Y.) 303, 1532-1535 (2004).
3. T. A. Fuchs, A. Hakkim, C. F. Urban, in *Inflammation: Fundamental Mechanisms*, K. Ley, Ed. (World Scientific, 2018), chap. 6.
4. D. Shiokawa, S. Tanuma, Characterization of human DNase I family endonucleases and activation of DNase gamma during apoptosis. *Biochemistry* 40, 143-152 (2001).
5. M. Napirei, A. Ricken, D. Eulitz, H. Knoop, H. G. Mannherz, Expression pattern of the deoxyribonuclease 1 gene: lessons from the Dnase1 knockout mouse. *Biochem J* 380, 929-937 (2004).
6. W. F. Baron et al., Cloning and characterization of an actin-resistant DNase I-like endonuclease secreted by macrophages. *Gene* 215, 291-301 (1998).
7. V. Sisirak et al., Digestion of Chromatin in Apoptotic Cell Microparticles Prevents Autoimmunity. *Cell* 166, 88-101 (2016).
8. M. Jimenez-Alcazar et al., Impaired DNase1-mediated degradation of neutrophil extracellular traps is associated with acute thrombotic microangiopathies. *Journal of thrombosis and haemostasis: JTH* 13, 732-742 (2015).
9. M. Napirei, S. Ludwig, J. Mezrhab, T. Klockl, H. G. Mannherz, Murine serum nucleases—contrasting effects of plasmin and heparin on the activities of DNase1 and DNase1-like 3 (DNase1l3). *FEBS J* 276, 1059-1073 (2009).
10. A. Wilber, M. Lu, M. C. Schneider, Deoxyribonuclease I-like III is an inducible macrophage barrier to liposomal transfection. *Mol Ther* 6, 35-42 (2002).
11. W. Kabsch, H. G. Mannherz, D. Suck, E. F. Pai, K. C. Holmes, Atomic structure of the actin:DNase I complex. *Nature* 347, 37-44 (1990).
12. C. Lam et al., Taming hyperactive hDNase I: Stable inducible expression of a hyperactive salt- and actin-resistant variant of human deoxyribonuclease I in CHO cells. *Biotechnol Prog* 33, 523-533 (2017).
13. C. Q. Pan et al., Improved potency of hyperactive and actin-resistant human DNase I variants for treatment of cystic fibrosis and systemic lupus erythematosus. *J Biol Chem* 273, 18374-18381 (1998).
14. D. Shiokawa, Y. Shika, S. Tanuma, Identification of two functional nuclear localization signals in DNase gamma and their roles in its apoptotic DNase activity. *Biochem J* 376, 377-381 (2003).
15. R. Mizuta et al., DNase gamma is the effector endonuclease for internucleosomal DNA fragmentation in necrosis. *PLoS One* 8, e80223 (2013).
16. H. J. Fuchs et al., Effect of aerosolized recombinant human DNase on exacerbations of respiratory symptoms and on pulmonary function in patients with cystic fibrosis. The Pulmozyme Study Group. *N Engl J Med* 331, 637-642 (1994).
17. N. M. Rahman et al., Intrapleural use of tissue plasminogen activator and DNase in pleural infection. *N Engl J Med* 365, 518-526 (2011).
18. V. Papayannopoulos, D. Staab, A. Zychlinsky, Neutrophil elastase enhances sputum solubilization in cystic fibrosis patients receiving DNase therapy. *PLoS One* 6, e28526 (2011).
19. M. Napirei, S. Wulf, H. G. Mannherz, Chromatin breakdown during necrosis by serum Dnase1 and the plasminogen system. *Arthritis Rheum* 50, 1873-1883 (2004).
20. D. D. Wagner et al. (Children's Medical Center Corporation, Boston, Mass. (US), United States, 2017), vol. U.S. Pat. No. 9,642,822 B2.
21. R. A. Lazarus, C. Q. Pan. (Genentech Inc., United States, 2002), vol. U.S. Pat. No. 6,391,607 B1.
22. R. A. Lazarus, C. Q. Pan. (Genentech Inc., 2008), vol. U.S. Pat. No. 7,407,785 B2.
23. R. A. Lazarus, S. Shak, J. S. Ulmer. (Genentech Inc., 2001), vol. US 2001/0041360 A1.
24. C. Q. Pan, R. A. Lazarus, Hyperactivity of human DNase I variants. Dependence on the number of positively charged residues and concentration, length, and environment of DNA. *J Biol Chem* 273, 11701-11708 (1998).
25. C. Q. Pan, D. V. Sinicropi, R. A. Lazarus, Engineered properties and assays for human DNase I mutants. *Methods Mol Biol* 160, 309-321 (2001).
26. C. Q. Pan, J. S. Ulmer, A. Herzka, R. A. Lazarus, Mutational analysis of human DNase I at the DNA binding interface: implications for DNA recognition, catalysis, and metal ion dependence. *Protein Sci* 7, 628-636 (1998).
27. G. Parsiegla, C. Noguere, L. Santell, R. A. Lazarus, Y. Bourne, The structure of human DNase I bound to magnesium and phosphate ions points to a catalytic mechanism common to members of the DNase I-like superfamily. *Biochemistry* 51, 10250-10258 (2012).
28. M. C. Schneider, A. Wilber. (United States, 2004), vol. US 2004/0138156.
29. J. S. Ulmer et al., Engineering actin-resistant human DNase I for treatment of cystic fibrosis. *Proceedings of the National Academy of Sciences of the United States of America* 93, 8225-8229 (1996).
30. B. T. Bettinger, D. M. Gilbert, D. C. Amberg, Actin up in the nucleus. *Nat Rev Mol Cell Biol* 5, 410-415 (2004).
31. C. F. Urban et al., Neutrophil extracellular traps contain calprotectin, a cytosolic protein complex involved in host defense against *Candida albicans*. *PLoS Pathog* 5, e1000639 (2009).
32. D. Russell, N. J. Oldham, B. G. Davis, Site-selective chemical protein glycosylation protects from autolysis and proteolytic degradation. *Carbohydr Res* 344, 1508-1514 (2009).
33. T. A. Fuchs, J. A. Kremer Hovinga, D. Schatzberg, D. D. Wagner, B. Lammle, Circulating DNA and myeloperoxidase indicate disease activity in patients with thrombotic microangiopathies. *Blood* 120, 1157-1164 (2012).
34. M. Jimenez-Alcazar, N. Kim, T. A. Fuchs, Circulating Extracellular DNA: Cause or Consequence of Thrombosis? *Semin Thromb Hemost* 43, 553-561 (2017).
35. M. Boettcher et al., Degradation of Extracellular DNA by DNase1 Significantly Reduces Testicular Damage After Testicular Torsion in Rats. *Urology* 109, 223 e221-223 e227 (2017).
36. A. D. Bandaranayake, S. C. Almo, Recent advances in mammalian protein production. *FEBS letters* 588, 253-260 (2014).
37. Y. K. Han, Y. G. Kim, J. Y. Kim, G. M. Lee, Hyperosmotic stress induces autophagy and apoptosis in recombinant Chinese hamster ovary cell culture. *Biotechnology and bioengineering* 105, 1187-1192 (2010).
38. J. L. Cereghino, J. M. Cregg, Heterologous protein expression in the methylotrophic yeast *Pichia pastoris*. *FEMS microbiology reviews* 24, 45-66 (2000).
39. M. Ahmad, M. Hirz, H. Pichler, H. Schwab, Protein expression in *Pichia pastoris*: recent achievements and perspectives for heterologous protein production. *Applied microbiology and biotechnology* 98, 5301-5317 (2014).
40. R. Daly, M. T. Hearn, Expression of heterologous proteins in *Pichia pastoris*: a useful experimental tool in protein engineering and production. *Journal of molecular recognition: JMR* 18, 119-138 (2005).

```
Sequences of wild-type DNases
Human DNase1 (P24855), Amino acid sequence (Signal Peptide;
Mature Protein):
                                                SEQ ID NO: 1
MRGMKLLGALLALAALLQGAVSLKIAAFNIQTFGETKMSNATLVSYIVQILSRYDIAL

VQEVRDSHLTAVGKLLDNLNQDAPDTYHYVVSEPLGRNSYKERYLFVYRPDQVSAVDS

YYYDDGCEPCGNDTFNREPAIVRFFSRFTEVREFAIVPLHAAPGDAVAEIDALYDVYL

DVQEKWGLEDVMLMGDFNAGCSYVRPSQWSSIRLWTSPTFQWLIPDSADTTATPTHCA

YDRIVVAGMLLRGAVVPDSALPFNFQAAYGLSDQLAQAISDHYPVEVMLK

Human DNase1L3 (Q13609), Amino acid sequence (Signal Peptide;
Mature Protein):
                                                SEQ ID NO: 2
MSRELAPLLLLLLSIHSALAMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVFSREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVFDFQKAYKLTEEEALDVSDHFPVEFKLQSSRAFTNS

KKSVTLRKKTKSKRS

Murine DNase1 (P49183): Amino acid sequence (Signal Peptide;
Mature Protein):
                                                SEQ ID NO: 3
MRYTGLMGTLLTLVNLLQLAGTLRIAAFNIRTFGETKMSNATLSVYFVKILSRYDIAV

IQEVRDSHLVAVGKLLDELNRDKPDTYRYVVSEPLGRKSYKEQYLFVYRPDQVSILDS

YQYDDGCEPCGNDTFSREPAIVKFFSPYTEVQEFAIVPLHAAPTEAVSEIDALYDVYL

DVWQKWGLEDIMFMGDFNAGCSYVTSSQWSSIRLRTSPIFQWLIPDSADTTVTSTHCA

YDRIVVAGALLQAAVVPNSAVPFDFQAEYGLSNQLAEAISDHYPVEVTLRKI

Rat DNase1 (P21704), Amino acid sequence (Signal Peptide;
Mature Protein):
                                                SEQ ID NO: 4
MRYTGLMGILLTLVNLLQLAATLRIAAFNIRTFGDTKMSNATLSSYIVKILSRYDIAV

VQEVRDTHLVAVGKLLDELNRDIPDNYRYIISEPLGRKSYKEQYLFVYRPSQVSVLDS

YHYDDGCEPCGNDTFSREPAIVKFFSPYTEVREFAIVPLHSAPTEAVSEIDALYDVYL

DVRQKWGLEDIMFMGDFNAGCSYVTSSQWSSIRLRTSPIFQWLIPDSADTTATSTHCA

YDRIVVAGALLQAAVVPSSAVPFDFQAEYRLTNQMAEAISDHYPVEVTLRKT

Murine DNase1L3 (O55070): Amino acid sequence (Signal
Peptide; Mature Protein):
                                                SEQ ID NO: 34
MSLHPASPRLASLLLFILALHDTLALRLCSFNVRSFGASKKENHEAMDIIVKIIKRCD

LILLMEIKDSSNNICPMLMEKLNGNSRRSTTYNYVISSRLGRNTYKEQYAFVYKEKLV

SVKIKYHYHDYQDGDTDVFSREPFVVWFHSPFTAVKDFVIVPLHTTPETSVKEIDELV

DVYTDVRSQWKTENFIFMGDFNAGCSYVPKKAWQNIRLRTDPKFVWLIGDQEDTTVKK

STSCAYDRIVLCGQEIVNSVVPRSSGVFDFQKAYDLSEEEALDVSDHFPVEFKLQSSR

AFTNNRKSVSLKKRKKGNRS
```

Rat DNase1L3 (O89107): Amino acid sequence (Signal Peptide; Mature Protein):

SEQ ID NO: 35

MSLYPASPYLASLLLFILALHGALSLRLCSFNVRSFGESKKENHNAMDIIVKIIKRCD

LILLMEIKDSNNNICPMLMEKLNGNSRRSTTYNYVISSRLGRNTYKEQYAFLYKEKLV

SVKAKYLYHDYQDGDTDVFSREPFVVWFQAPFTAAKDFVIVPLHTTPETSVKEIDELA

DVYTDVRRRWKAENFIFMGDFNAGCSYVPKKAWKNIRLRTDPNFVWLIGDQEDTTVKK

STSCAYDRIVLRGQEIVNSVVPRSSGVFDFQKAYELSEEEALDVSDHFPVEFKLQSSR

AFTNSRKSVSLKKKKGSRS

Chimpanzee DNase1 (H2QAH1): Amino acid sequence (Signal Peptide; Mature Protein):

SEQ ID NO: 36

MRSMKLLGALLALAALLQGAVSLKIAAFNIQTFGETKMSNATLVSYIVQILSRYDIAL

VQEVRDSHLTAVGKLLDNLNQDAPDTYHYVVSEPLGRNSYKERYLFVYRPDQVSAVDS

YYYDDGCEPCGNDTFNREPAIVRFFSRFTEVREFAIVPLHAAPGDAVAEIDALYDVYL

DVQEKWGLEDVMLMGDFNAGCSYVRPSQWSSIRLRTSPAFQWLIPDSADTTATPTHCA

YDRIVVAGMLLQGAVVPDSALPFNFQAAYGLSDQLAQAISDHYPVEVMLK

Chimpanzee DNase1L3 (H2QMU7): Amino acid sequence (Signal Peptide; Mature Protein):

SEQ ID NO: 37

MSRELTPLLLLLLSIHSTLALRICSFNVRSFGESKQEDQNAMDVIVKVIKRCDIILVM

EIKDSNNRICPILMEKLNRNSRRGITYNYVISSRLGRNTYKEQYAFLYKEKLVSVKRS

YHYHDYQDGDADVFSREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVFDFQKAYKLTEEEALDVSDHFPVEFKLQSSRAFTNS

KKSVTLRKKTKSKRS

Human DNase1-like 1 (NM_006730): Amino acid sequence (Signal Peptide; Mature Protein):

SEQ ID NO: 38

MHYPTALLFLILANGAQAFRICAFNAQRLTLAKVAREQVMDTLVRILARCDIMVLQEV

VDSSGSAIPLLLRELNRFDGSGPYSTLSSPQLGRSTYMETYVYFYRSHKTQVLSSYVY

NDEDDVFAREPFVAQFSLPSNVLPSLVLVPLHTTPKAVEKELNALYDVFLEVSQHWQS

KDVILLGDFNADCASLTKKRLDKLELRTEPGFHWVIADGEDTTVRASTHCTYDRVVLH

GERCRSLLHTAAAFDFPTSFQLTEEEALNISDHYPVEVELKLSQAHSVQPLSLTVLLL

LSLLSPQLCPAA

Human DNase1-like 2 (NM_001374): Amino acid sequence (Signal Peptide; Mature Protein):

SEQ ID NO: 39

MGGPRALLAALWALEAAGTAALRIGAFNIQSFGDSKVSDPACGSIIAKILAGYDLALV

QEVRDPDLSAVSALMEQINSVSEHEYSFVSSQPLGRDQYKEMYLFVYRKDAVSVVDTY

LYPDPEDVFSREPFVVKFSAPGTGERAPPLPSRRALTPPPLPAAAQNLVLIPLHAAPH

QAVAEIDALYDVYLDVIDKWGTDDMLFLGDFNADCSYVRAQDWAAIRLRSSEVFKWLI

PDSADTTVGNSDCAYDRIVACGARLRRSLKPQSATVHDFQEEFGLDQTQALAISDHFP

VEVTLKFHR

C-terminal tail of human DNase1L3 Amino acid sequence:

SEQ ID NO: 33

SSRAFTNSKKSVTLRKKTKSKRS

Sequences of DNase1 variants
Amino acid sequence (Signal Peptide; Mature Protein):
SEQ ID NO: 5
MRGMKLLGALLALAALLQGAVSLKIAAFNIRTFGETKMSNATLVSYIVKILSRYDIAL

VQEVRDSHLTAVGKLLDNLNRDAPDTYHYVVSEPLGRNSYKERYLFVYRPDQVSAVDS

YYYDDGCEPCGNDTFNREPAIVRFFSRFTEVREFAIVPLHAAPGDAVAE DALYDVYL

DVQEKWGLEDVMLMGDFNAGCSYVRPSQWSSIRLRTSPTFQWLIPDSADTTATPTHCA

YDRIVVAGMLLRGAVVPDSALPFNFQAAYGLSDQLAQAISDHYPVEVMLK

Amino acid sequence (Signal Peptide; Mature Protein):
SEQ ID NO: 6
MRGMKLLGALLALAALLQGAVSLKIAAFNIRTFGETKMSNATLVSYIVKILSRYDIAL

VQEVRDSHLTAVGKLLDNLNRDAPDTYHYVVSEPLGRNSYKERYLFVYRPDQVSAVDS

YYYDDGCEPCGNDTFNREPAIVRFFSRFTEVREFAIVPLHAAPGDAVAEIDALYDVYL

DVKEKWGLEDVMLMGDFNAGCSYVRPSQWSSIRLRTSPTFQWLIPDSADTTATPTHCA

YDRIVVAGMLLRGAVVPDSALPFNFQAAYKLSDQLAQAISDHYPVEVMLK

Amino acid sequence (Signal Peptide; Mature Protein):
SEQ ID NO: 7
MRGMKLLGALLALAALLQGAVSLKIAAFNIRTFGETKMSNATLVSYIVQILSRYDIAL

VQEVRDSHLTAVGKLLDNLNQDAPDTYHYVVSEPLGRNSYKERYLFVYRPDQVSAVDS

YYYDDGCEPCGNDTFNREPFIVRFFSRFTEVREFAIVPLHAAPGDAVAEIDALYDVYL

DVQEKWGLEDVMLMGDFNAGCSYVRPSQWSSIRLWTSPTFQWLIPDSADTTAKPTHCA

YDRIVVAGMLLRGAVVPDSALPFNFQAAYGLSDQLAQAISDHYPVEVMLK

Amino acid sequence (Signal Peptide; Mature Protein):
SEQ ID NO: 8
MRGMKLLGALLALAALLQGAVSLKIAAFNIRTFGETKMSNATLVSYIVQILSRYDIAL

VQEVRDSHLTAVGKLLDNLNQDAPDTYHYVVSEPLGRNSYKERYLFVYRPDQVSAVDS

YYYDDGCEPCGNDTFNREPAIVRFFSRFTEVREFAIVPLHAAPGDAVAEIDALYDVYL

DVQEKWGLEDVMLMGDFNAGCSYVRPSQWSSIRLWTSPTFQWLIPDSADTTAKPTHCA

YDRIVVAGMLLRGAVVPDSALPFNFQAAYGLSDQLAQAISDHYPVEVMLK

Amino acid sequence (Signal Peptide; Mature Protein):
SEQ ID NO: 9
MRGMKLLGALLALAALLQGAVSLKIAAFNIQTFGETKMSNATLVSYIVQILSRYDIAL

VQEVRDSHLTAVGKLLDNLNQDAPDTYHYVVSEPLGRNSYKERYLFVYRPDQVSAVDS

YYYDDGCEPCGNDTFNREPFIVRFFSRFTEVREFAIVPLHAAPGDAVKEIDALYDVYL

DVQEKWGLEDVMLMGDFNAGCSYVRPSQWSSIRLWTSPTFQWLIPDSADTTATPTHCA

YDRIVVAGMLLRGAVVPDSALPFNFQAAYGLSDQLAQAISDHYPVEVMLK

Amino acid sequence (Signal Peptide; Mature Protein):
SEQ ID NO: 10
MRGMKLLGALLALAALLQGAVSLKIAAFNIQTFGETKMSNATLVSYIVQILSRYDIAL

VQEVRDSHLTAVGKLLDNLNRNSRRGITYHYVVSEPLGRNSYKERYLFVYRPDQVSAV

DSYYYDDGCEPCGNDTFNREPAIVRFFSRFTEVREFAIVPLHAAPGDAVAEIDALYDV

YLDVQEKWGLEDVMLMGDFNAGCSYVRPSQWSSIRLWTSPTFQWLIPDSADTTATPTH

CAYDRIVVAGMLLRGAVVPDSALPFNFQAAYGLSDQLAQAISDHYPVEVMLK

Amino acid sequence (Signal Peptide; Mature Protein):
SEQ ID NO: 11
MRGMKLLGALLALAALLQGAVSLKIAAFNIQTFGETKMSNATLVSYIVQILSRYDIAL

VQEVRDSHLTAVGKLLDNLNQDAPDTYNYVISSRLGRNSYKERYLFVYRPDQVSAVDS

YYYDDGCEPCGNDTFNREPAIVRFFSRFTEVREFAIVPLHAAPGDAVAEIDALYDVYL

```
DVQEKWGLEDVMLMGDFNAGCSYVRPSQWSSIRLWTSPTFQWLIPDSADTTATPTHCA

YDRIVVAGMLLRGAVVPDSALPFNFQAAYGLSDQLAQAISDHYPVEVMLK

Amino acid sequence (Signal Peptide; Mature Protein):
                                           SEQ ID NO: 12
MRGMKLLGALLALAALLQGAVSLKIAAFNIQTFGETKMSNATLVSYIVQILSRYDIAL

VQEVRDSHLTAVGKLLDNLNQDAPDTYHYVVSEPLGRNSYKERYLFVYRPDQVSAVDS

YYYDDGCEPCGNDTFNREPFVVRFFSRFTEVREFAIVPLHAAPGDAVAEIDALYDVYL

DVQEKWGLEDVMLMGDFNAGCSYVRPSQWSSIRLWTSPTFQWLIPDSADTTATPTHCA

YDRIVVAGMLLRGAVVPDSALPFNFQAAYGLSDQLAQAISDHYPVEVMLK

Amino acid sequence (Signal Peptide; Mature Protein):
                                           SEQ ID NO: 13
MRGMKLLGALLALAALLQGAVSLKIAAFNIQTFGETKMSNATLVSYIVQILSRYDIAL

VQEVRDSHLTAVGKLLDNLNQDAPDTYHYVVSEPLGRNSYKERYLFVYRPDQVSAVDS

YYYDDGCEPCGNDTFNREPAIVRFFSRFTEVREFAIVPLHAAPGDAVAEIDALYDVYL

DVQEKWGLEDVMLMGDFNAGCSYVPKKAWKNIRLRTDPRFVWLIGDQEDTTATPTHCA

YDRIVVAGMLLRGAVVPDSALPFNFQAAYGLSDQLAQAISDHYPVEVMLK

Amino acid sequence (Signal Peptide; Mature Protein):
                                           SEQ ID NO: 14
MRGMKLLGALLALAALLQGAVSLKIAAFNIQTFGETKMSNATLVSYIVQILSRYDIAL

VQEVRDSHLTAVGKLLDNLNQDAPDTYHYVVSEPLGRNSYKERYLFVYRPDQVSAVDS

YYYDDGCEPCGNDTFNREPAIVRFFSRFTEVREFAIVPLHAAPGDAVAEIDALYDVYL

DVQEKWGLEDVMLMGDFNAGCSYVRPSQWSSIRLWTSPTFQWLIPDSADTTVKKSTHC

AYDRIVVAGMLLRGAVVPDSALPFNFQAAYGLSDQLAQAISDHYPVEVMLK

Amino acid sequence (Signal Peptide; Mature Protein):
                                           SEQ ID NO: 15
MRGMKLLGALLALAALLQGAVSLKIAAFNIQTFGETKMSNATLVSYIVQILSRYDIAL

VQEVRDSHLTAVGKLLDNLNRNSRRGITYNYVISSRLGRNSYKERYLFVYRPDQVSAV

DSYYYDDGCEPCGNDTFNREPFVVRFFSRFTEVREFAIVPLHAAPGDAVAEIDALYDV

YLDVQEKWGLEDVMLMGDFNAGCSYVPKKAWKNIRLRTDPRFVWLIGDQEDTTVKKST

HCAYDRIVVAGMLLRGAVVPDSALPFNFQAAYGLSDQLAQAISDHYPVEVMLK

Amino acid sequence (Signal Peptide; Mature Protein):
                                           SEQ ID NO: 16
MRGMKLLGALLALAALLQGAVSLKIAAFNIQTFGETKMSNATLVSYIVQILSRYDIAL

VQEVRDSHLTAVGKLLDNLNQDAPDTYHYVVSEPLGRNSYKERYLFVYRPDQVSAVDS

YYYDDGCEPCGNDTFNREPAIVRFFSRFTEVREFAIVPLHAAPGDAVAEIDALYDVYL

DVQEKWGLEDVMLMGDFNAGCSYVRPSQWSSIRLWTSPTFQWLIPDSADTTATPTHCA

YDRIVVAGMLLRGAVVPDSALPFNFQAAYGLSDQLAQAISDHFPVEFKLQSSRAFTNS

KKSVTLRKKTKSKRS

Sequences of DNase1L3 variants
Amino acid sequence (Signal Peptide; Mature Protein):
                                           SEQ ID NO: 17
MSRELAPLLLLLLSIHSALAMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVFSREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVFDFQKAYKLTEEEALDVSDHYPVEVMLK
```

Amino acid sequence (Signal Peptide; Mature Protein):
SEQ ID NO: 18
<u>MSRELAPLLLLLLSIHSALA</u>MRICSFNVRSFGESKQENKTAMDVIVKVIKRCDIILVM

EIKDSNNRICPILMEKLNRNSRRGITYNYVISSRLGRNTYKEQYAFLYKEKLVSVKRS

YHYHDYQDGDNDTFSREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVFDFQKAYKLTEEEALDVSDHFPVEFKLQSSRAFTNS

KKSVTLRKKTKSKRS

Amino acid sequence (Signal Peptide; Mature Protein):
SEQ ID NO: 19
<u>MSRELAPLLLLLLSIHSALA</u>MRICSFNVRSFGESKMSNATLVSYIVKVIKRCDIILVM

EIKDSNNRICPILMEKLNRNSRRGITYNYVISSRLGRNTYKEQYAFLYKEKLVSVKRS

YHYHDYQDGDADVFSREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVFDFQKAYKLTEEEALDVSDHFPVEFKLQSSRAFTNS

KKSVTLRKKTKSKRS

Amino acid sequence (Signal Peptide; Mature Protein):
SEQ ID NO: 20
<u>MSRELAPLLLLLLSIHSALA</u>MRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDGCEPCGNDTFNREPFVVWFQSPHTAVKDFVIIPLHTTPETSVKEIDELVEVYT

DVKHRWKAENFIFMGDFNAGCSYVPKKAWKNIRLRTDPRFVWLIGDQEDTTVKKSTNC

AYDRIVLRGQEIVSSVVPKSNSVFDFQKAYKLTEEEALDVSDHFPVEFKLQSSRAFTN

SKKSVTLRKKTKSKRS

Sequences used in *Pichia pastoris*
Amino acid sequence (Signal Peptide; Mature Protein):
SEQ ID NO: 21
<u>MRGMKLLGALLALAALLQGAVS</u>LKIAAFNIQTFGETKMSSATLVSYIVQILSRYDIAL

VQEVRDSHLTAVGKLLDNLNQDAPDTYHYVVSEPLGRNSYKERYLFVYRPDQVSAVDS

YYYDDGCEPCGSDTFNREPAIVRFFSRFTEVREFAIVPLHAAPGDAVAEIDALYDVYL

DVQEKWGLEDVMLMGDFNAGCSYVRPSQWSSIRLWTSPTFQWLIPDSADTTATPTHCA

YDRIVVAGMLLRGAVVPDSALPFNFQAAYGLSDQLAQAISDHYPVEVMLK

Codon-optimized cDNA of SEQ ID NO: 21 (Start codon, Signal
peptide):
SEQ ID NO: 22
<u>ATG</u><u>AGAGGTATGAAGCTCCTTGGTGCCCTCCTGGCTCTCGCTGCTCTCCTCCAAGGAG</u>

<u>CAGTTTCT</u>CTAAAGATTGCTGCTTTCAATATTCAAACCTTTGGCGAGACTAAAATGTC

CTCGGCAACATTAGTATCTTACATTGTTCAGATCCTTTCTCGTTACGACATAGCTTTG

GTCCAGGAGGTTAGAGACTCCCACTTGACTGCCGTCGGTAAGCTGCTAGACAATCTTA

ACCAAGACGCACCTGACACCTACCACTACGTTGTTAGTGAGCCTCTCGGTAGAAACTC

CTACAAGGAGAGATACCTATTTGTCTACCGTCCAGATCAGGTGTCTGCTGTGGACTCT

TACTACTATGACGACGGTTGTGAACCTTGTGGTTCAGACACCTTCAACAGAGAACCAG

CTATCGTTAGATTTTTCTCCAGATTCACCGAGGTCAGAGAGTTCGCCATCGTTCCATT

GCACGCTGCGCCTGGAGATGCAGTGGCCGAAATTGACGCTCTCTATGATGTCTACCTG

GACGTTCAGGAAAAATGGGGTCTAGAAGATGTTATGCTGATGGGAGACTTCAACGCTG

GTTGCTCTTACGTTAGGCCATCTCAATGGTCAAGCATCAGACTATGGACTTCCCCAAC

-continued
```
GTTCCAATGGCTTATTCCTGACTCCGCTGATACTACCGCCACTCCCACTCATTGTGCA

TATGACAGAATTGTTGTCGCTGGTATGCTACTGCGTGGAGCTGTCGTACCAGATTCTG

CTCTGCCATTTAACTTCCAAGCCGCATATGGTCTTTCTGACCAACTGGCTCAAGCCAT

CTCTGATCACTACCCTGTGGAAGTTATGCTTAAG
```

Amino acid sequence (Signal Peptide; Mature Protein):
SEQ ID NO: 23

<u>MRGMKLLGALLALAALLQGAVS</u>LKIAAFNIRTFGETKMSSATLVSYIVQILSRYDIAL

VQEVRDSHLTAVGKLLDNLNQDAPDTYHYVVSEPLGRNSYKERYLFVYRPDQVSAVDS

YYYDDGCEPCGSDTFNREPFIVRFFSRFTEVREFAIVPLHAAPGDAVAEIDALYDVYL

DVQEKWGLEDVMLMGDFNAGCSYVRPSQWSSIRLWTSPTFQWLIPDSADTTAKPTHCA

YDRIVVAGMLLRGAVVPDSALPFNFQAAYGLSDQLAQAISDHYPVEVMLK

Codon-optimized cDNA of SEQ ID NO: 23 (Start codon, Signal peptide):
SEQ ID NO: 24

<u>ATG</u><u>AGAGGTATGAAGCTCCTTGGTGCCCTCCTGGCTCTCGCTGCTCTCCTCCAAGGAG</u>

<u>CAGTTTCT</u>CTAAAGATTGCTGCTTTCAATATTAGAACCTTTGGCGAGACTAAAATGTC

CTCGGCAACATTAGTATCTTACATTGTTCAGATCCTTTCTCGTTACGACATAGCTTTG

GTCCAGGAGGTTAGAGACTCCCACTTGACTGCCGTCGGTAAGCTGCTAGACAATCTTA

ACCAAGACGCACCTGACACCTACCACTACGTTGTTAGTGAGCCTCTCGGTAGAAACTC

CTACAAGGAGAGATACCTATTTGTCTACCGTCCAGATCAGGTGTCTGCTGTGGACTCT

TACTACTATGACGACGGTTGTGAACCTTGTGGTTCAGACACCTTCAACAGAGAACCAT

TCATCGTTAGATTTTTCTCCAGATTCACCGAGGTCAGAGAGTTCGCCATCGTTCCATT

GCACGCTGCGCCTGGAGATGCAGTGGCCGAAATTGACGCTCTCTATGATGTCTACCTG

GACGTTCAGGAAAAATGGGGTCTAGAAGATGTTATGCTGATGGGAGACTTCAACGCTG

GTTGCTCTTACGTTAGGCCATCTCAATGGTCAAGCATCGACTATGGACTTCCCCAAC

GTTCCAATGGCTTATTCCTGACTCCGCTGATACTACCGCCAAGCCCACTCATTGTGCA

TATGACAGAATTGTTGTCGCTGGTATGCTACTGCGTGGAGCTGTCGTACCAGATTCTG

CTCTGCCATTTAACTTCCAAGCCGCATATGGTCTTTCTGACCAACTGGCTCAAGCCAT

CTCTGATCACTACCCTGTGGAAGTTATGCTTAAG

Codon-optimized cDNA of SEQ ID NO: 2 (Start codon, Signal peptide):
SEQ ID NO: 25

<u>ATG</u><u>TCTAGAGAGCTTGCTCCACTCCTCCTACTCCTTCTTAGTATCCACTCTGCACTCG</u>

<u>CC</u>ATGAGAATTTGTAGCTTCAATGTAAGATCCTTCGGTGAATCTAAGCAGGAGGACAA

AAACGCTATGGACGTTATTGTGAAGGTCATTAAGAGATGTGATATCATTCTAGTTATG

GAGATCAAGGACTCTAACAACAGAATTTGCCCCATCCTTATGGAAAAGCTGAATAGAA

ACTCTAGAAGAGGAATTACTTACAACTACGTTATCTCTTCTAGGCTGGGTAGAAACAC

TTACAAGGAGCAATATGCATTTCTATACAAGGAAAAGCTAGTTTCCGTTAAGCGTTCT

TACCACTATCATGACTACCAAGACGGCGATGCTGACGTTTTCTCCAGAGAACCATTCG

TTGTTTGGTTTCAGTCTCCTCACACCGCTGTTAAGGACTTCGTGATTATCCCACTACA

CACTACGCCAGAAACCTCTGTCAAGGAAATAGATGAACTTGTTGAAGTTTACACCGAC

GTGAAGCACAGATGGAAGGCCGAGAATTTCATTTTCATGGGTGATTTCAACGCCGGAT

GCTCATATGTCCCTAAAAAGGCTTGGAAAACATCCGTTTGAGAACCGATCCTAGATT

TGTCTGGCTCATCGGTGACCAAGAGGACACCACAGTCAAAAAGTCTACCAACTGTGCT

TACGACAGAATTGTTCTGCGTGGTCAGGAGATTGTTTCATCTGTTGTCCCAAAGTCCA

-continued

```
ACTCCGTCTTTGATTTCCAAAAGGCTTACAAACTGACTGAGGAGGAAGCTTTAGACGT

GTCCGACCACTTCCCTGTAGAGTTTAAGCTGCAATCCTCCAGAGCATTCACTAACTCT

AAAAAGTCAGTCACTTTGCGTAAAAAGACTAAGTCTAAGAGATCG
```

Codon-optimized cDNA of SEQ ID NO: 17 (Start codon, Signal peptide):
SEQ ID NO: 26

```
ATGTCTAGAGAGCTTGCTCCACTCCTCCTACTCCTTCTTAGTATCCACTCTGCACTCG

CCATGAGAATTTGTAGCTTCAATGTAAGATCCTTCGGTGAATCTAAGCAGGAGGACAA

AAACGCTATGGACGTTATTGTGAAGGTCATTAAGAGATGTGATATCATTCTAGTTATG

GAGATCAAGGACTCTAACAACAGAATTTGCCCCATCCTTATGGAAAAGCTGAATAGAA

ACTCTAGAAGAGGAATTACTTACAACTACGTTATCTCTTCTAGGCTGGGTAGAAACAC

TTACAAGGAGCAATATGCATTTCTATACAAGGAAAAGCTAGTTTCCGTTAAGCGTTCT

TACCACTATCATGACTACCAAGACGGCGATGCTGACGTTTTCTCCAGAGAACCATTCG

TTGTTTGGTTTCAGTCTCCTCACACCGCTGTTAAGGACTTCGTGATTATCCCACTACA

CACTACGCCAGAAACCTCTGTCAAGGAAATAGATGAACTTGTTGAAGTTTACACCGAC

GTGAAGCACAGATGGAAGGCCGAGAATTTCATTTTCATGGGTGATTTCAACGCCGGAT

GCTCATATGTCCCTAAAAAGGCTTGGAAAAACATCCGTTTGAGAACCGATCCTAGATT

TGTCTGGCTCATCGGTGACCAAGAGGACACCACAGTCAAAAAGTCTACCAACTGTGCT

TACGACAGAATTGTTCTGCGTGGTCAGGAGATTGTTTCATCTGTTGTCCCAAAGTCCA

ACTCCGTCTTTGATTTCCAAAAGGCTTACAAACTGACTGAGGAGGAAGCTTTAGACGT

GTCCGACCACTACCCTGTAGAGGTCATGTTGAAG
```

---

What is claimed is:

1. A method for treating a human subject having an intravascular accumulation of neutrophil extracellular traps (NETs), the method comprising administering to said subject an effective amount of a heterologous polynucleotide encoding a DNase 1-like 3 (D1L3) enzyme comprising an amino acid sequence having at least 90% sequence identity to amino acids 21 to 305 of SEQ ID NO: 2, wherein the subject has a condition selected from:
   a severe inflammatory disease selected from acute respiratory distress syndrome (ARDS), sepsis, and a viral infection;
   partially or fully occluded blood vessels;
   thrombotic microangiopathy (TMA);
   disseminated intravascular coagulation (DIC);
   venous thromboembolism;
   leukemia; and
   tumor metastasis.

2. The method of claim 1, wherein the D1L3 enzyme comprises an amino acid sequence having at least 95% sequence identity to amino acids 21 to 305 of the amino acid sequence of SEQ ID NO: 2.

3. The method of claim 1, wherein the D1L3 enzyme comprises a deletion of NLS2.

4. The method of claim 1, wherein the D1L3 enzyme comprises a deletion of all or part of the C-terminal tail defined by SEQ ID NO: 33.

5. The method of claim 1, wherein the heterologous polynucleotide encoding the D1L3 enzyme is administered by intradermal, intramuscular, subcutaneous, intraperitoneal, intravenous, or intraarterial administration.

6. The method of claim 5, wherein the polynucleotide is RNA.

7. The method of claim 5, wherein the polynucleotide is DNA.

8. The method of claim 7, wherein the D1L3 polynucleotide is delivered with a viral vector.

9. The method of claim 1, wherein the subject further has neutrophilia.

10. The method of claim 1, wherein the subject has a severe inflammatory disease.

11. The method of claim 10, wherein the subject has sepsis.

12. The method of claim 10, wherein the subject has acute respiratory distress syndrome (ARDS).

13. The method of claim 10, wherein the subject has a viral infection.

14. The method of claim 1, wherein the subject has partially or fully occluded blood vessels.

15. The method of claim 14, wherein the partially or fully occluded blood vessels are in the lung.

16. The method of claim 14, wherein the occlusions comprise entrapped erythrocytes and leukocytes.

17. The method of claim 1, wherein the subject has thrombotic microangiopathy (TMA).

18. The method of claim 1, wherein the subject has disseminated intravascular coagulation (DIC).

19. The method of claim 1, wherein the subject has venous thromboembolism.

20. The method of claim 1, wherein the subject has leukemia.

21. The method of claim 1, wherein the subject has tumor metastasis.

22. The method of claim 1, wherein the administration results in higher levels of circulating mono- and di-nucleosomes.

* * * * *